US006667387B1

(12) United States Patent
De Leys

(10) Patent No.: US 6,667,387 B1
(45) Date of Patent: Dec. 23, 2003

(54) HCV CORE PEPTIDES

(75) Inventor: Robert De Leys, Grimbergen (BE)

(73) Assignee: N.V. Innogenetics S.A., Ghent (BE)

( * ) Notice: Subject to any disclaimer, the term of this patent is extended or adjusted under 35 U.S.C. 154(b) by 0 days.

(21) Appl. No.: 09/576,824

(22) Filed: May 23, 2000

Related U.S. Application Data

(62) Division of application No. 08/723,425, filed on Sep. 30, 1996, which is a division of application No. 08/146,028, filed as application No. PCT/EP93/00517 on Mar. 6, 1992.

(51) Int. Cl.[7] ............................ C07K 5/00; G01N 33/53
(52) U.S. Cl. ....................................... 530/300; 435/7.1
(58) Field of Search ................................. 530/350, 300; 435/7.2

(56) References Cited

U.S. PATENT DOCUMENTS

| | | | |
|---|---|---|---|
| 4,833,071 A | 5/1989 | Wang et al. | |
| 5,001,049 A | 3/1991 | Klein et al. | |
| 5,075,211 A | 12/1991 | Cosand et al. | ................. 435/5 |
| 5,443,965 A | * 8/1995 | Reyes et al. | ................. 435/693 |
| 5,574,132 A | 11/1996 | Lacroix | ....................... 530/323 |
| 5,843,639 A | * 12/1998 | Reyes et al. | .................... 435/5 |

FOREIGN PATENT DOCUMENTS

| | | |
|---|---|---|
| CA | 2036463 | 8/1991 |
| CA | 2111108 | 12/1992 |
| CA | 2126693 | 7/1993 |
| EP | 22571 | 1/1981 |
| EP | 0 278 940 | 8/1988 |
| EP | 318 216 A1 | 5/1989 |
| EP | 0 345 375 | 12/1989 |
| EP | 0 379 949 | 8/1990 |
| EP | 0 388 232 | 9/1990 |
| EP | 0 438 332 | 7/1991 |
| EP | 0 422 394 | 8/1991 |
| EP | 442 394 A2 | 8/1991 |
| EP | 0 448 095 | 8/1991 |
| EP | 445 423 A2 | 9/1991 |
| EP | 445 801 | 9/1991 |
| EP | 0 445 801 A2 | 9/1991 |
| EP | 451 891 A2 | 10/1991 |
| EP | 0 461 462 | 12/1991 |
| EP | 0 468 527 | 1/1992 |
| EP | 471 356 A1 | 2/1992 |
| EP | 479 376 A1 | 4/1992 |
| EP | 0 484 787 | 5/1992 |
| EP | 485 209 A1 | 5/1992 |
| EP | 0 489 968 | 6/1992 |
| EP | 501 557 A1 | 9/1992 |
| EP | 516 859 A1 | 12/1992 |
| EP | 525 910 A1 | 2/1993 |
| EP | 536 838 A2 | 4/1993 |
| EP | 214 709 B1 | 9/1993 |
| EP | 278 148 B1 | 11/1994 |
| WO | 84/03506 | 9/1984 |
| WO | WO 89/04669 | 6/1989 |
| WO | WO 90/11089 | 10/1990 |
| WO | WO 91/15516 | 10/1991 |
| WO | WO 92/03458 | 3/1992 |
| WO | WO 93/18054 | 9/1993 |
| WO | WO 93/10239 | 8/1994 |

OTHER PUBLICATIONS

Munekata et al, "Epitope–Mapping of Hepatitis C Virus Containing Protein," Peptide Chemistry, Proceedings of the 28th Symposium on Peptide Chemistry, Osaka, Oct. 25–27, 1990, pp 211–214; Y. Shimonishi (Ed), Protein Research Foundation, Osaka (1991).
De Leys et al., Journal of Virology, vol. 64, No. 3, p. 1207–1216, Mar. 1990, "Isolation and Partial Characterization of an Unusual Human Immunodeficiency Retrovirus from Two Persons of West–Central African Origin".
R. Von Gruenigen et al., Biol. Chem. Hoppe–Seyler, vol. 372, pp. 163–172, Mar. 1991, "Enzyme Immunoassay with Captured Hapten".
Database WPI, Week 9146, Derwent Publications Ltd., London, GB, AN 91–337496 & SU, A, 1 612 264 (Bioorg Chem Inst) Dec. 7, 1990.
R. Von Gruenigen et al, Journal of Immunological Methods, 125 (1989) 143–146, "Epitope Analysis: Biotinylated Short Peptides As Inhibitors of Anti–Peptide Antibody".
K. R. Anumula et al., Journal of Immunological Methods, 135 (1990)199–208, "Immunologic Methods for Quantitative Estimation of Small Peptides and Their Application to Bradykinin".
D.E. Pollet et al., Clinial Chemistry, 37, No. 6 (1991) 1024–1025 "Development of a Screening Elisa and a Confirmatory Assay for Hepatitis C Antibodies Based on Synthetic Peptides", Abstract No. 0547.
Fischer and Howden, J. Immunoassay, 11:311–327 (1990).
Rosen et al., Vaccines 87, Cold spring Harbor Laboratory, 1987, "Detection of Antibodies to HIV Using Synthetic Peptides Derived from the gp41 Envelope Protein".
Gnann et al., J. Virol., 61:2630–2641, 1987.
Gnann et al., J. Infect. Dis., 156:261–267, 1987.
Oldstone et al., J. Virol. 65:1727–1734, 1991.
Cerino, 1991, J. Immunol. 147:2692–2696.
Choo, 1991, PNAS 88: 2451–2455.
Fieser, PNAS (Dec. 1987) 84(23):8568–72.
Geysen, Journal of Molecular recognition (Feb. 1988) 9(1):32–42.

* cited by examiner

*Primary Examiner*—Jeffrey Fredman
*Assistant Examiner*—Prabha Chunduru
(74) *Attorney, Agent, or Firm*—Nixon & Vanderhye, P.C.

(57) ABSTRACT

This invention is directed toward a peptide corresponding to an immunologically important viral epitope. Specifically, the peptide corresponds to an immunodominant epitope identified in the gp41 region of the human immunodeficiency virus type 1 (HIV-1), strain Ant70. This peptide has the following amino acid sequence: $NH_2$-Leu-Trp-Gly-Cys-Lys-Gly-Lys-Leu-Val-Cys-$CO_2H$. The invention also relates to the use of this peptide, particularly when biotinylated in the form of complexes of streptavidin-biotinylated peptides or of avidin-biotinylated peptides, for the in vitro determination of HIV-1-specific antibodies.

50 Claims, 57 Drawing Sheets

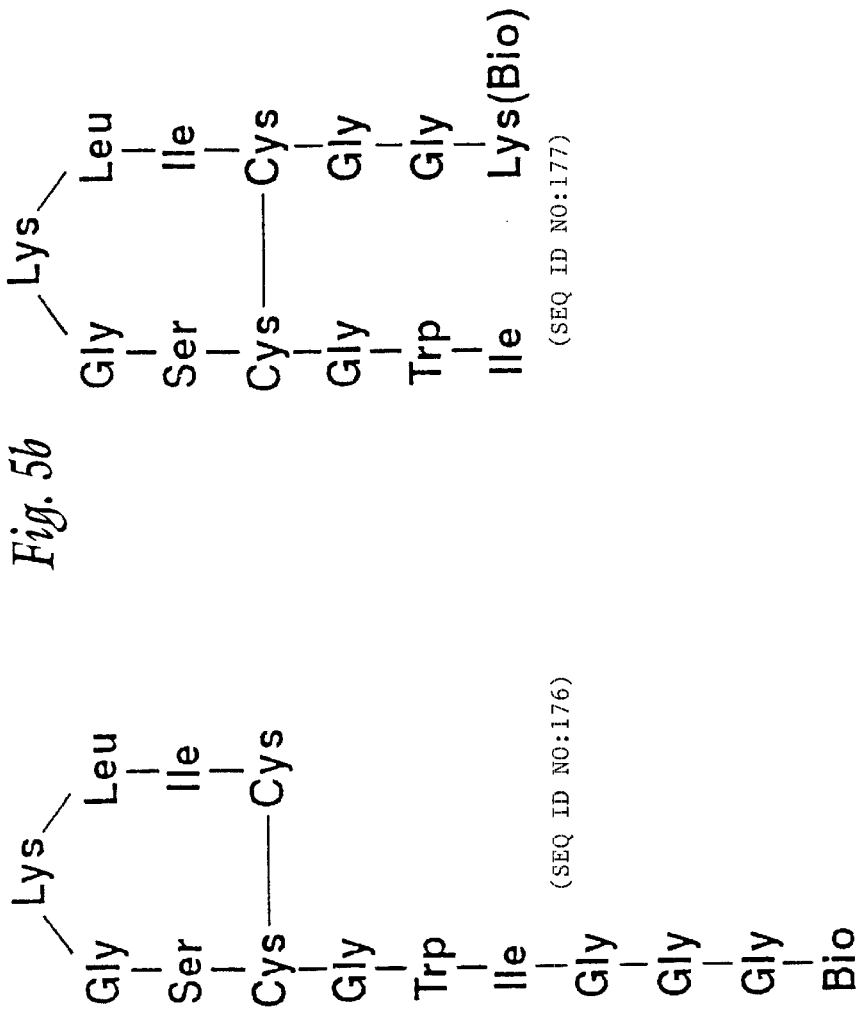
Fig. 5a  N-terminally biotinylated TM peptide
Fig. 5b  C-terminally biotinylated TM peptide

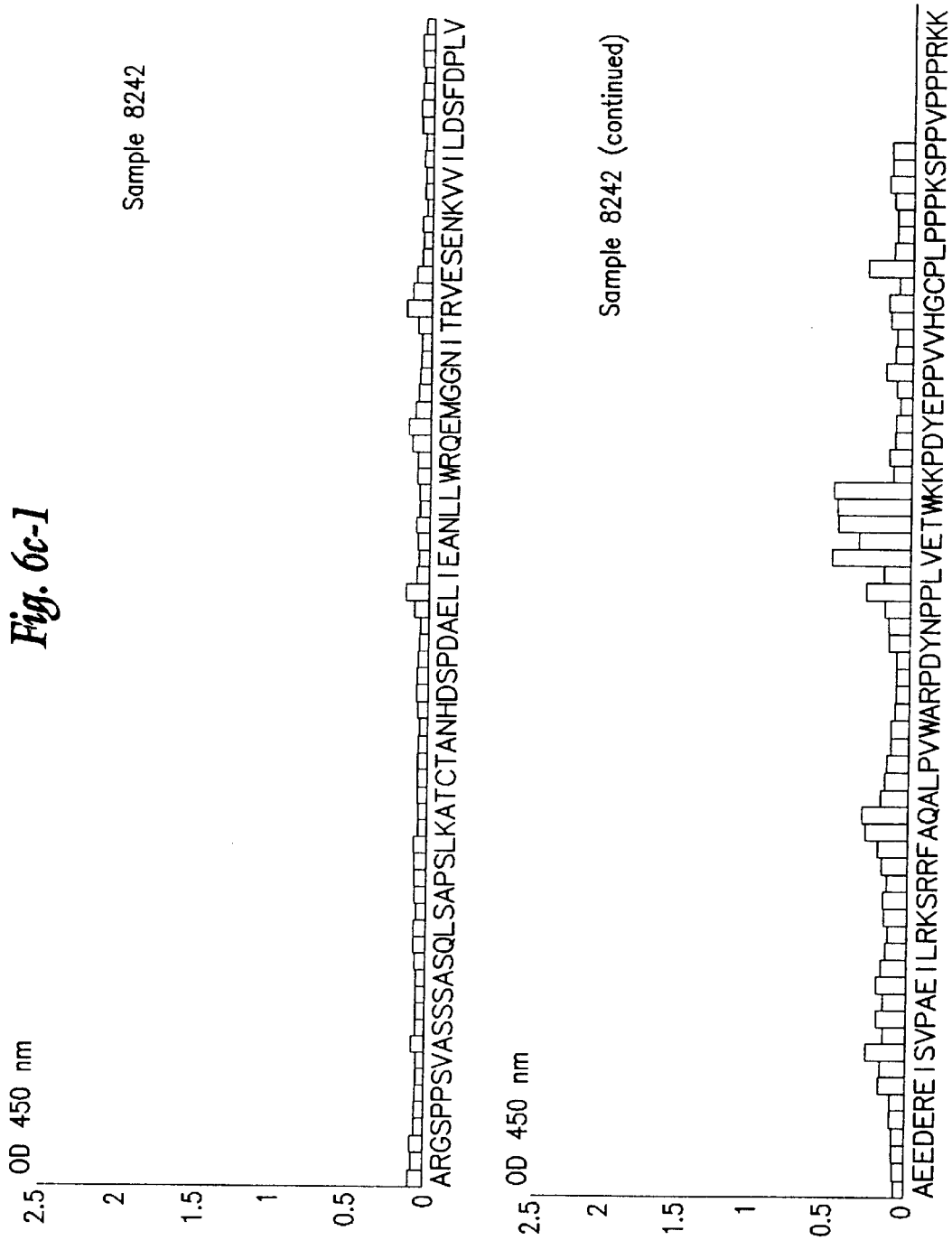

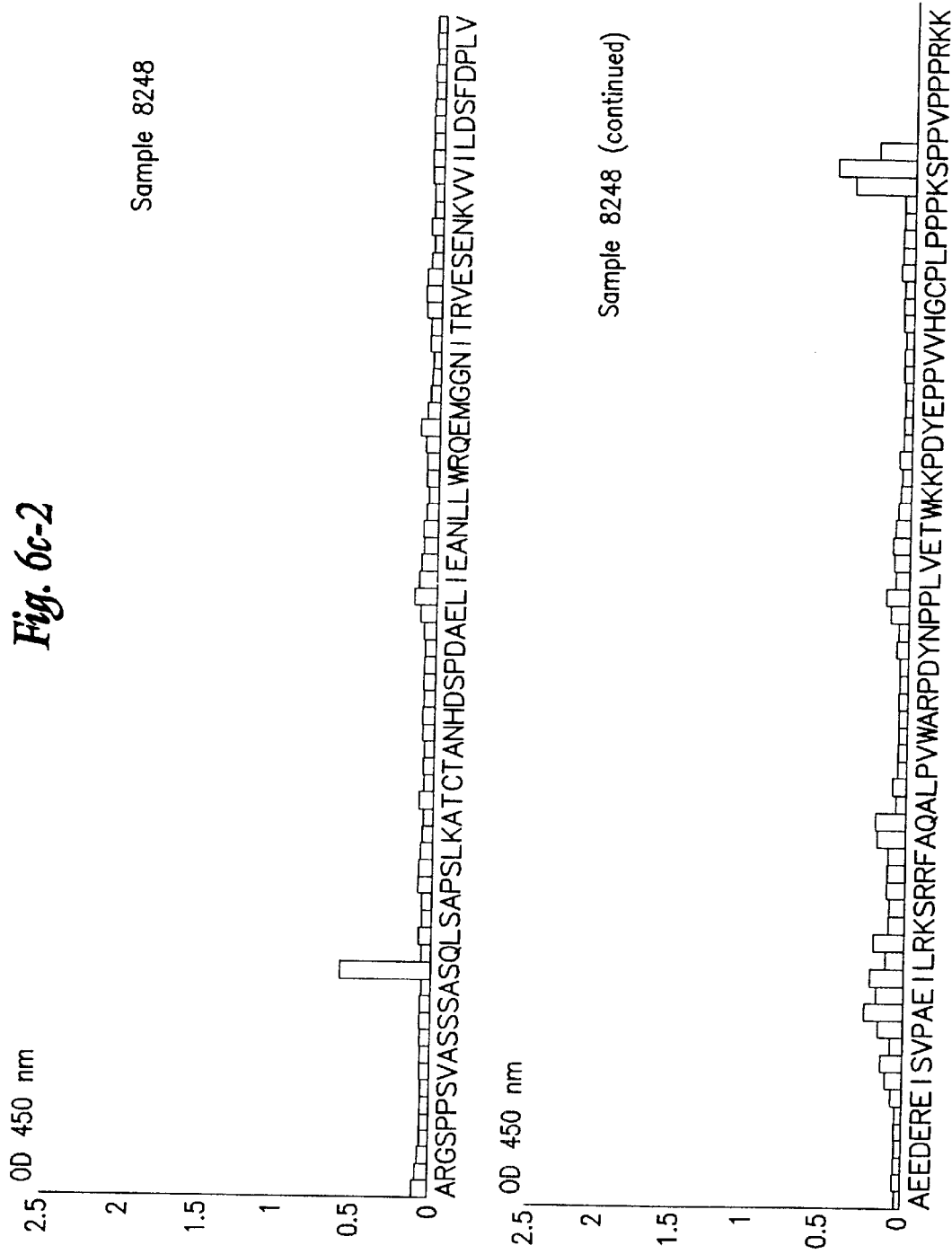

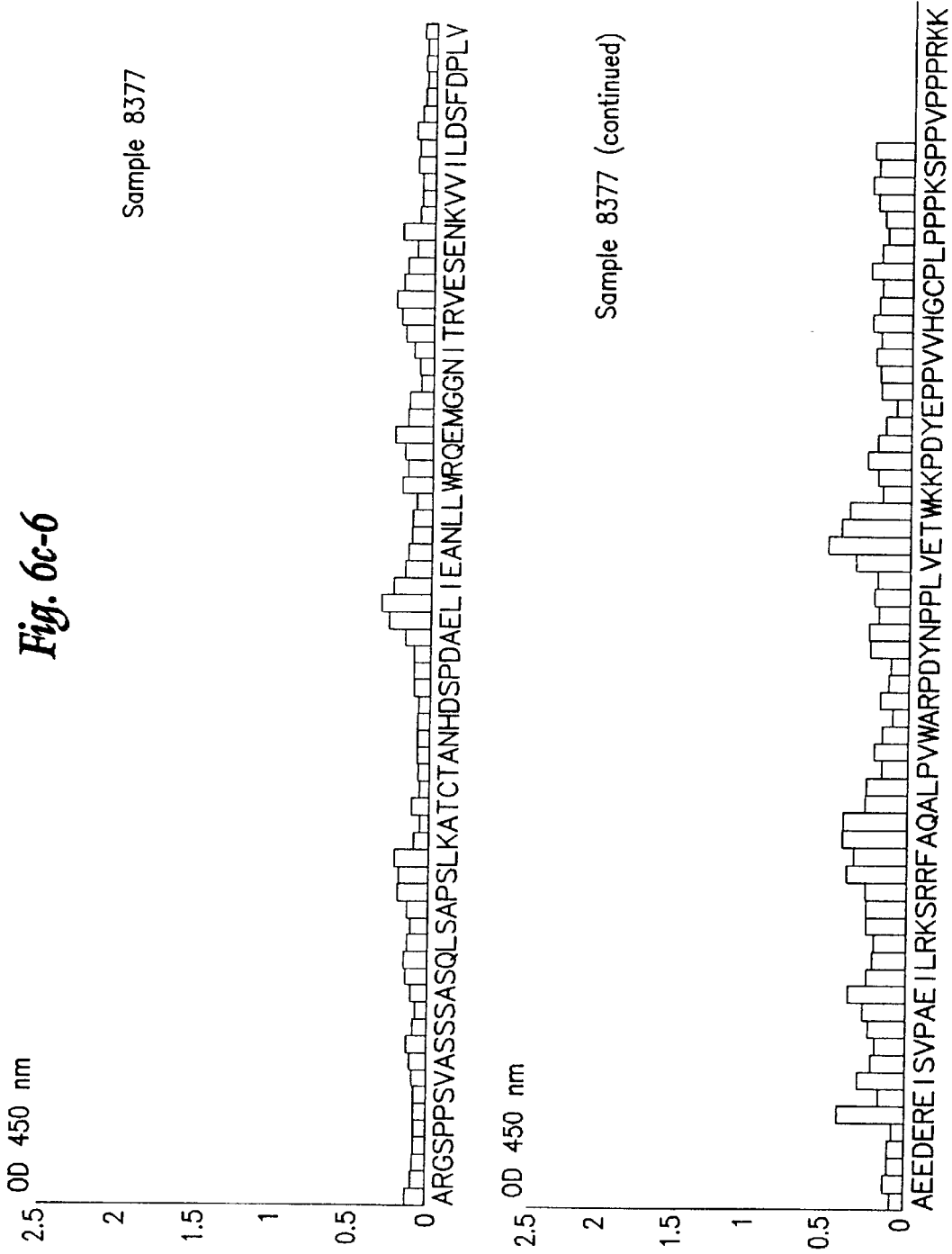

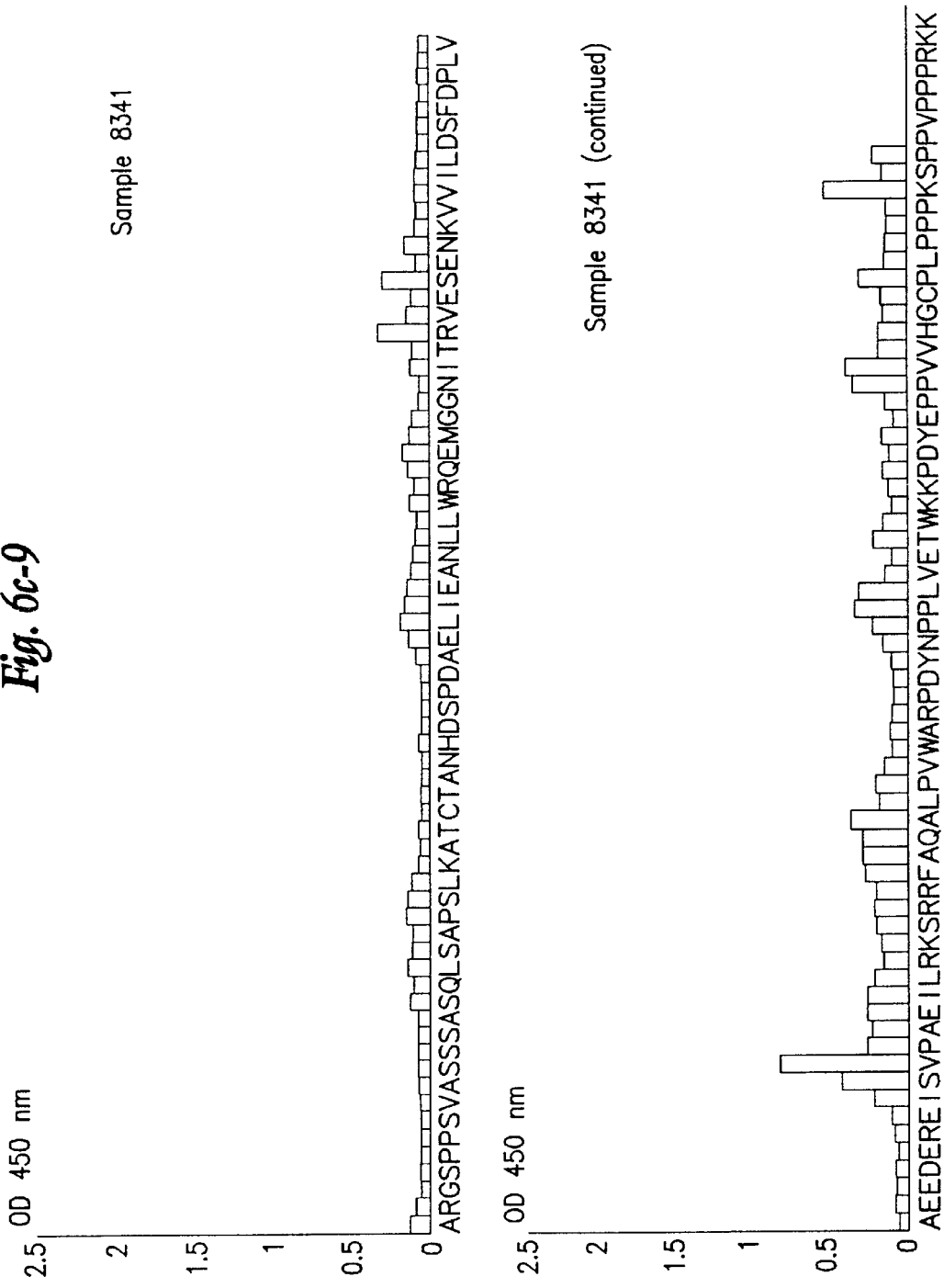

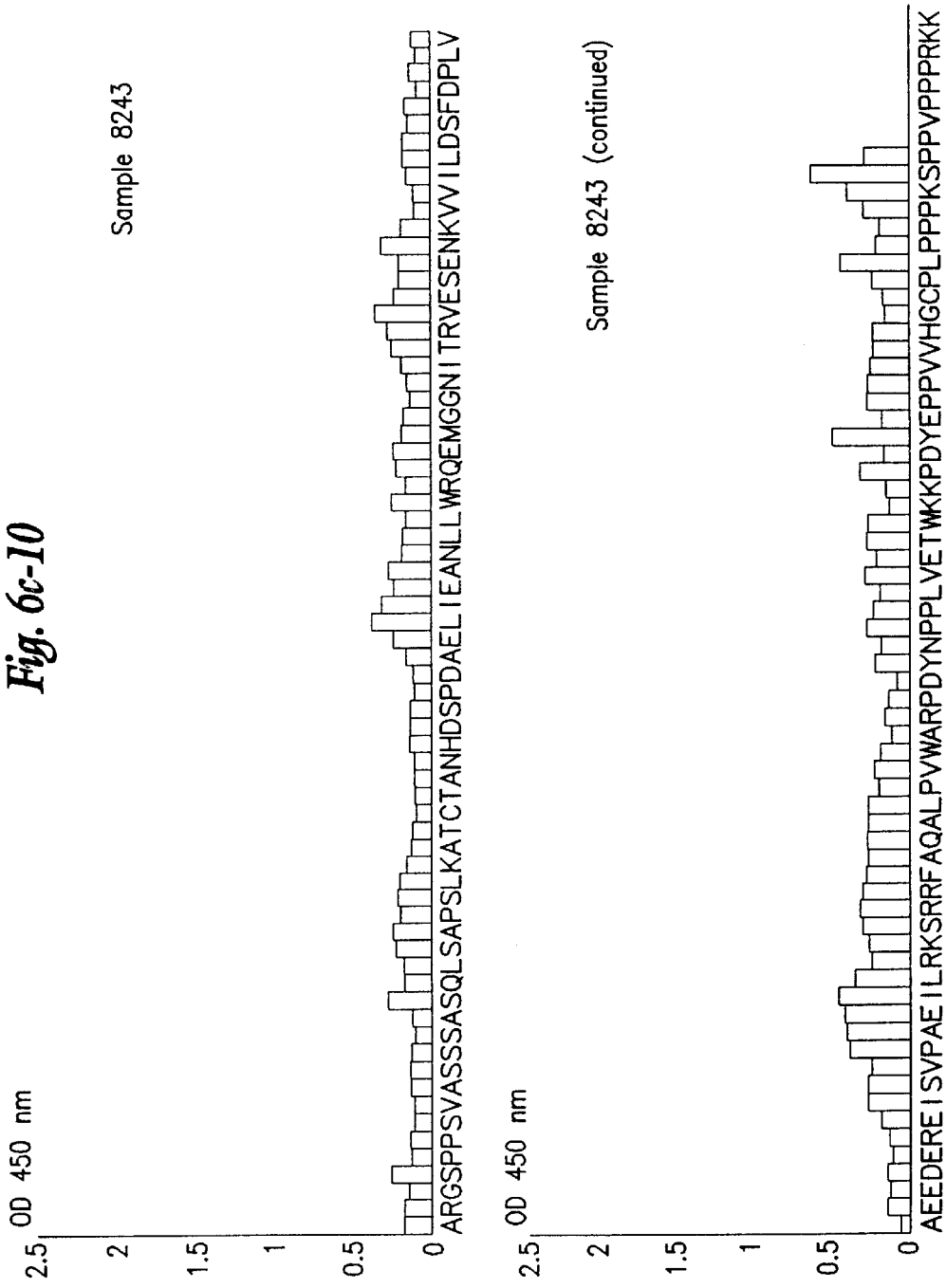

Fig. 7a-1

Peptide I   MSTIPKPQRKTKRNTNRRPQ                    (SEQ ID NO:453)
Peptide II      PQRKTKRNTNRRPQDVKFPG                (SEQ ID NO:454)
Peptide III            RNTNRRPQDVKFPGGGQIVG         (SEQ ID NO:455)

| Peptide I | Peptide II | Peptide III |
|---|---|---|
| (SEQ ID NO:) | (SEQ ID NO:) | (SEQ ID NO:) |
| (178) MSTIPKPQR | (184) PQRKTKRNT | (190) RNTNRRPQD |
| (179) STIPKPQRK | (185) QRKTKRNTN | (191) NTNRRPQDV |
| (180) TIPKPQRKT | (186) RKTKRNTNR | (192) TNRRPQDVK |
| (181) IPKPQRKTK | (187) KTKRNTNRR | (193) NRRPQDVKF |
| (182) PKPQRKTKR | (188) TKRNTNRRP | (194) RRPQDVKFP |
| (183) KPQRKTKRN | (189) KRNTNRRPQ | (195) RPQDVKFPG |
| (184) PQRKTKRNT | (190) RNTNRRPQD | (196) PQDVKFPGG |
| (185) QRKTKRNTN | (191) NTNRRPQDV | (197) QDVKFPGGG |
| (186) RKTKRNTNR | (192) TNRRPQDVK | (198) DVKFPGGGQ |
| (187) KTKRNTNRR | (193) NRRPQDVKF | (199) VKFPGGGQI |
| (188) TKRNTNRRP | (194) RRPQDVKFP | (200) KFPGGGQIV |
| (189) KRNTNRRPQ | (195) RPQDVKFPG | (201) FPGGGQIVG |

Fig. 7a-2

```
Core 5       PGGGQIVGGVYLLPRRGPRL          (SEQ ID NO:456)
Peptide IV   LPRRGPRLGVRATRKTSERS          (SEQ ID NO:457)
Peptide V    (SEQ ID NO:458) TRKTSERSQPRGRRQPIPKV
Peptide VI   (SEQ ID NO:459) RRQPIPKVRRPEGRTWAQPG
```

| Core 5 (SEQ ID NO:) | | Peptide IV (SEQ ID NO:) | | Peptide V (SEQ ID NO:) | | Peptides VI (SEQ ID NO:) | |
|---|---|---|---|---|---|---|---|
| (202) | PGGGQIVGG | (214) | LPRRGPRLG | (226) | TRKTSERSQ | (238) | RRQPIPKVR |
| (203) | GGGQIVGGV | (215) | PRRGPRLGV | (227) | RKTSERSQP | (239) | RQPIPKVRR |
| (204) | GGQIVGGVY | (216) | RRGPRLGVR | (228) | KTSERSQPR | (240) | QPIPKVRRP |
| (205) | GQIVGGVYL | (217) | RGPRLGVRA | (229) | TSERSQPRG | (241) | PIPKVRRPE |
| (206) | QIVGGVYLL | (218) | GPRLGVRAT | (230) | SERSQPRGR | (242) | IPKVRRPEG |
| (207) | IVGGVYLLP | (219) | PRLGVRATR | (231) | ERSQPRGRR | (243) | PKVRRPEGR |
| (208) | VGGVYLLPR | (220) | RLGVRATRK | (232) | RSQPRGRRQ | (244) | KVRRPEGRT |
| (209) | GGVYLLPRR | (221) | LGVRATRKT | (233) | SQPRGRRQP | (245) | VRRPEGRTW |
| (210) | GVYLLPRRG | (222) | GVRATRKTS | (234) | QPRGRRQPI | (246) | RRPEGRTWA |
| (211) | VYLLPRRGP | (223) | VRATRKTSE | (235) | PRGRRQPIP | (247) | RPEGRTWAQ |
| (212) | YLLPRRGPR | (224) | RATRKTSER | (236) | RGRRQPIPK | (248) | PEGRTWAQP |
| (213) | LLPRRGPRL | (225) | ATRKTSERS | (237) | GRRQPIPKV | (249) | EGRTWAQPG |

Fig. 7b-1

HCV1  LSGKPAIIPDREVLYREFDE           (SEQ ID NO:460)
HCV2  IIPDREVLYREFDEMEECSQ           (SEQ ID NO:461)
HCV3  VLYREFDEMEECSQHLPYIE           (SEQ ID NO:462)
HCV4  DEMEECSQHLPYIEQGMMLA           (SEQ ID NO:463)
HCV5  SQHLPYIEQGMMLAEQFKQK           (SEQ ID NO:464)
HCV6  IEQGMMLAEQFKQKALGLLQ           (SEQ ID NO:465)

| HCV1 | HCV2 | HCV3 | HCV4 | HCV5 | HCV6 |
|---|---|---|---|---|---|
| (SEQ ID NO:) | (SEQ ID NO:) | (SEQ ID NO:) | (SEQ ID NO:) | (SEQ ID NO:) | (SEQ ID NO:) |
| (258) 263LSGKPAIIP | | | | | |
| (259) 264SGKPAIIPD | | | | | |
| (260) 265GKPAIIPDR | | | | | |
| (261) 266KPAIIPDRE | | | | | |
| (262) 267PAIIPDREV | | | | | |
| (263) 268AIIPDREVL | | | | | |
| (264) 269IIPDREVLY | 264IIPDREVLY | | | | |
| (265) 270IPDREVLYR | 265IPDREVLYR | | | | |
| (266) 271PDREVLYRE | 266PDREVLYRE | | | | |
| (267) 272DREVLYREF | 267DREVLYREF | | | | |
| (268) 273REVLYREFD | 268REVLYREFD | | | | |
| (269) 274EVLYREFDE | 269EVLYREFDE | | | | |
|      | 270VLYREFDEM | 270VLYREFDEM | | | |
|      | 271LYREFDEME | 271LYREFDEME | | | |
|      | 272YREFDEMEE | 272YREFDEMEE | | | |
|      | 273REFDEMEEC | 273REFDEMEEC | | | |
|      | 274EFDEMEECS | 274EFDEMEECS | | | |
|      | 275FDEMEECSQ | 275FDEMEECSQ | | | |
|      |            | 276DEMEECSQH | 276DEMEECSQH | | |
|      |            | 277EMEECSQHL | 277EMEECSQHL | | |
|      |            | 278MEECSQHLP | 278MEECSQHLP | | |
|      |            | 279EECSQHLPY | 279EECSQHLPY | | |
|      |            | 280ECSQHLPYI | 280ECSQHLPYI | | |
|      |            | 281CSQHLPYIE | 281CSQHLPYIE | | |
|      |            |            | 282SQHLPYIEQ | 282SQHLPYIEQ | |
|      |            |            | 283QHLPYIEQG | 283QHLPYIEQG | |
|      |            |            | 284HLPYIEQGM | 284HLPYIEQGM | |
|      |            |            | 285LPYIEQGMM | 285LPYIEQGMM | |
|      |            |            | 286PYIEQGMML | 286PYIEQGMML | |
|      |            |            | 287YIEQGMMLA | 287YIEQGMMLA | |
|      |            |            |            | 288IEQGMMLAE | 288IEQGMMLAE |
|      |            |            |            | 289EQGMMLAEQ | 289EQGMMLAEQ |
|      |            |            |            | 290QGMMLAEQF | 290QGMMLAEQF |
|      |            |            |            | 291GMMLAEQFK | 291GMMLAEQFK |
|      |            |            |            | 292MMLAEQFKQ | 292MMLAEQFKQ |
|      |            |            |            | 293MLAEQFKQK | 293MLAEQFKQK |
|      |            |            |            |            | 294LAEQFKQKA |
|      |            |            |            |            | 295AEQFKQKAL |
|      |            |            |            |            | 296EQFKQKALG |
|      |            |            |            |            | 297QFKQKALGL |
|      |            |            |            |            | 298FKQKALGLL |
|      |            |            |            |            | 299KQKALGLLQ |

Fig. 7b-2

HCV7    LAEQFKQKALGLLQTASRQA (SEQ ID NO:466)
HCV8    QKALGLLQTASRQAEVIAPA (SEQ ID NO:467)
HCV9    LQTASRQAEVIAPAVQTNWQ (SEQ ID NO:468)

HCV7

| (SEQ ID NO:) | |
|---|---|
| (294) | LAEQFKQKA |
| (295) | AEQFKQKAL |
| (296) | EQFKQKALG |
| (297) | QFKQKALGL |
| (298) | FKQKALGLL |
| (299) | KQKALGLLQ |
| (300) | QKALGLLQT |
| (301) | KALGLLQTA |
| (302) | ALGLLQTAS |
| (303) | LGLLQTASR |
| (304) | GLLQTASRQ |
| (305) | LLQTASRQA |

HCV8

| (SEQ ID NO:) | |
|---|---|
| (300) | QKALGLLQT |
| (301) | KALGLLQTA |
| (302) | ALGLLQTAS |
| (303) | LGLLQTASR |
| (304) | GLLQTASRQ |
| (305) | LLQTASRQA |
| (306) | LQTASRQAE |
| (307) | QTASRQAEV |
| (308) | TASRQAEVI |
| (309) | ASRQAEVIA |
| (310) | SRQAEVIAP |
| (311) | RQAEVIAPA |

HCV9

| (SEQ ID NO:) | |
|---|---|
| (306) | LQTASRQAE |
| (307) | QTASRQAEV |
| (308) | TASRQAEVI |
| (309) | ASRQAEVIA |
| (310) | SRQAEVIAP |
| (311) | RQAEVIAPA |
| (312) | QAEVIAPAV |
| (313) | AEVIAPAVQ |
| (314) | EVIAPAVQT |
| (315) | VIAPAVQTN |
| (316) | IAPAVQTNW |
| (317) | APAVQTNWQ |

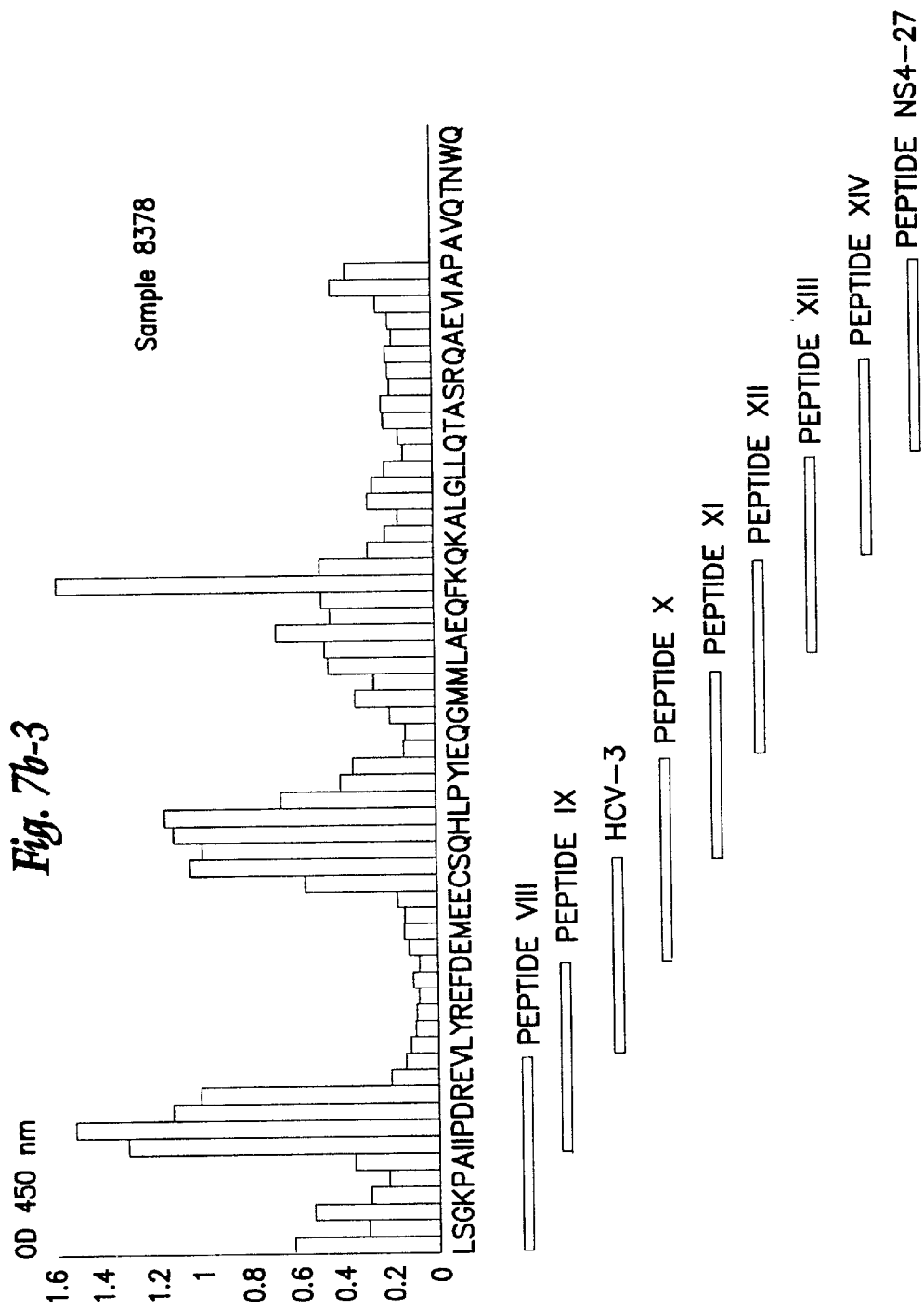

Fig. 7c-1

NS5-21  GNITRYESENKVVILDSFDP (SEQ ID NO:469)
NS5-23         VILDSFDPLVAEEDEREISV (SEQ ID NO:470)
NS5-25                 EDEREISVPAEILRKSRRFA (SEQ ID NO:471)
NS5-27                         (SEQ ID NO:472) LRKSRRFAQALPVWARPDYN
NS5-29                                 (SEQ ID NO:473) VWARPDYNPPLVETWKKPDY

| NS5-21 | NS5-23 | NS5-25 | NS5-27 | NS5-29 |
|---|---|---|---|---|
| SEQ ID NO: | SEQ ID NO: | SEQ ID NO: | SEQ ID NO: | SEQ ID NO: |
| 318 GNITRYESE | 330 VILDSFDPL | 342 EDEREISVP | 354 LRKSRRFAQ | 366 VWARPDYNP |
| 319 NITRYESEN | 331 ILDSFDPLV | 343 DEREISVPA | 355 RKSRRFAQA | 367 WARPDYNPP |
| 320 ITRYESENK | 332 LDSFDPLVA | 344 EREISVPAE | 356 KSRRFAQAL | 368 ARPDYNPPL |
| 321 TRYESENKV | 333 DSFDPLVAE | 345 REISVPAEI | 357 SRRFAQALP | 369 RPDYNPPLV |
| 322 RYESENKVV | 334 SFDPLVAEE | 346 EISVPAEIL | 358 RRFAQALPV | 370 PDYNPPLVE |
| 323 YESENKVVI | 335 FDPLVAEED | 347 ISVPAEILR | 359 RFAQALPVW | 371 DYNPPLVET |
| 324 ESENKVVIL | 336 DPLVAEEDE | 348 SVPAEILRK | 360 FAQALPVWA | 372 YNPPLVETW |
| 325 SENKVVILD | 337 PLVAEEDER | 349 VPAEILRKS | 361 AQALPVWAR | 373 NPPLVETWK |
| 326 ENKVVILDS | 338 LVAEEDERE | 350 PAEILRKSR | 362 QALPVWARP | 374 PPLVETWKK |
| 327 NKVVILDSF | 339 VAEEDEREI | 351 AEILRKSRR | 363 ALPVWARPD | 375 PLVETWKKP |
| 328 KVVILDSFD | 340 AEEDEREIS | 352 EILRKSRRF | 364 LPVWARPDY | 376 LVETWKKPD |
| 329 VVILDSFDP | 341 EEDEREISV | 353 ILRKSRRFA | 365 PVWARPDYN | 377 VETWKKPDY |

Fig. 7c-2

NS5-31    ETWKKPDYEPPVVHGCPLPP (SEQ ID NO:474)
NS5-33    VHGCPLPPPKSPPVPPPRKK (SEQ ID NO:475)

NS5-31

| (SEQ ID NO:) | |
|---|---|
| 378 | ETWKKPDYE |
| 379 | TWKKPDYEP |
| 380 | WKKPDYEPP |
| 381 | KKPDYEPPV |
| 382 | KPDYEPPVV |
| 383 | PDYEPPVVH |
| 384 | DYEPPVVHG |
| 385 | YEPPVVHGC |
| 386 | EPPVVHGCP |
| 387 | PPVVHGCPL |
| 388 | PVVHGCPLP |
| 389 | VVHGCPLPP |

NS5-33

| (SEQ ID NO:) | |
|---|---|
| 390 | VHGCPLPPK |
| 391 | HGCPLPPKS |
| 392 | GCPLPPKSP |
| 393 | CPLPPKSPP |
| 394 | PLPPKSPPV |
| 395 | LPPKSPPVP |
| 396 | PPKSPPVPP |
| 397 | PKSPPVPPP |
| 398 | KSPPVPPPR |
| 399 | SPPVPPPRK |
| 400 | PPVPPPRKK |

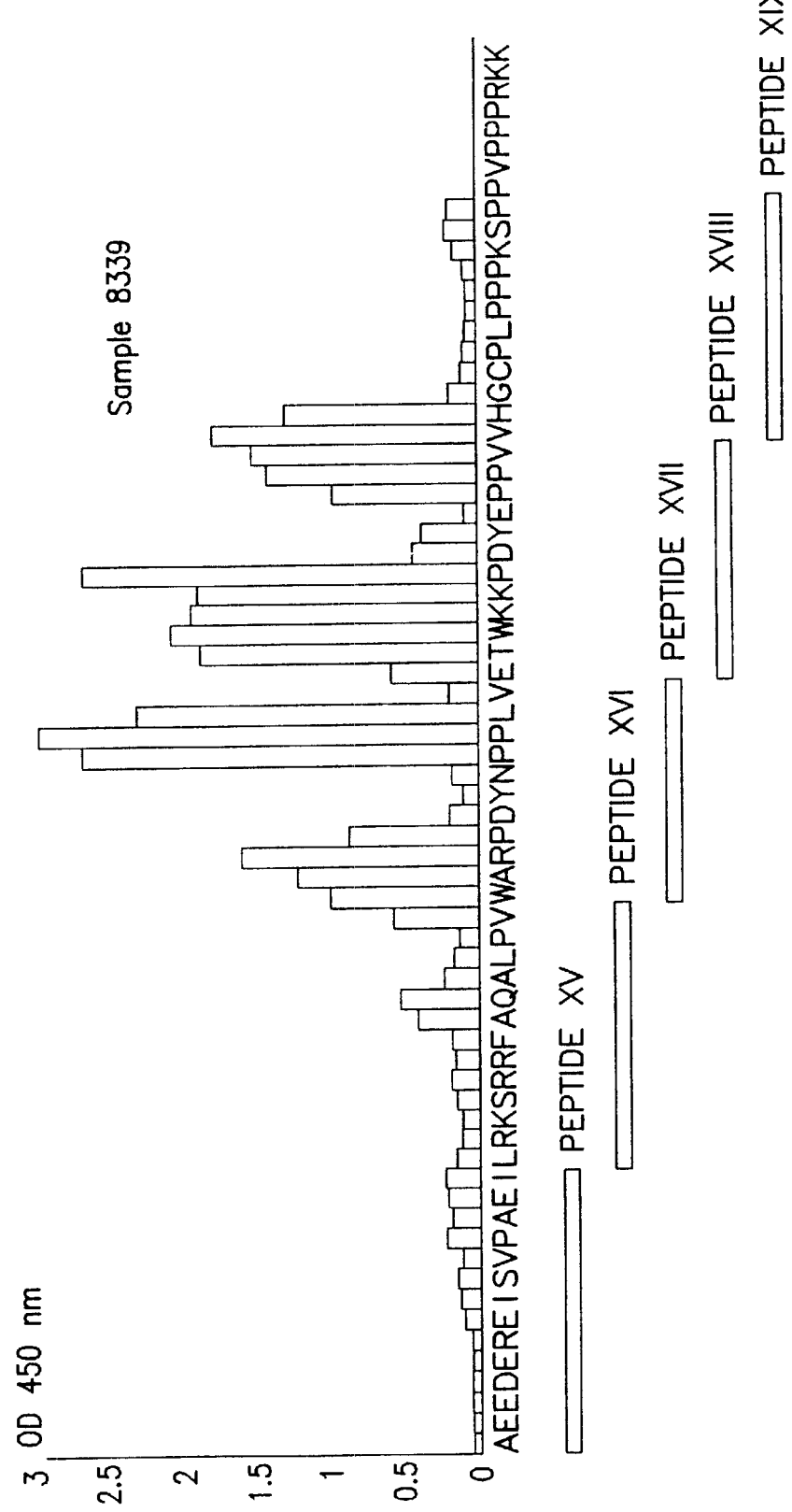

Fig. 11

| Peptide | Sequence |
|---|---|
| NS4-a | GALVAFKIMSGEVPSTEDLV (SEQ ID NO:445) |
| NS4-b | VPSTEDLVNLLPAILSPGAL (SEQ ID NO:446) |
| NS4-c | AILSPGALVVGVVCAAILRR (SEQ ID NO:447) |
| NS4-d | VCAAILRRHVGPGEGAVQWM (SEQ ID NO:448) |
| NS4-e | GEGAVQWMNRLIAFASRGNH (SEQ ID NO:449) |

Fig. 12

| Peptide (SEQ ID NO:) | Amino Acid Sequence |
|---|---|
| Epi-152 (450) | Bio-GG- I P D R E V L Y R G G K K P D Y E P P V G G R R P Q D V K F P<br>　　　　　　　└─NS4 epitope 1─┘　└─NS5 epitope 5─┘　└─Core epitope 2─┘ |
| Epi-33B3A (451) | Bio-GG- W A R P D Y N P P G G Q F K Q K A L G L G S G V Y L L P R R G<br>　　　　　└─NS5 epitope 3─┘　└─NS4 epitope 3B─┘　└─Core epitope 3A─┘ |
| Epi-4B2A6 (452) | Bio-GG- R G R R Q P I P K G G S Q H L P Y I E Q S G P V V H G C P L P<br>　　　　　└─Core epitope 4B─┘　└─NS4 epitope 2A─┘　└─NS5 epitope 6─┘ |

Synthesis of peptide sequence

Cleavage and side-chain deprotection

Oxidation and dimerization

Fig. 17A

```
         PRE-        FIRST
       IMMUNE      BLEEDING
      13.01.92    07.04.92     B
                               L
                               A
RABBIT  3 3 3 3   3 3 3 3      N
  No    2 2 2 2   2 2 2 2      K
        5 6 7 8   5 6 7 8
```

- XXc - 1
- XXc - 2
- XXe - 1
- XXe - 2
- XXf - 1
- XXf - 2
- XXg - 1
- XXg - 2

RABBIT 325, 326: XXb-2-MAP
RABBIT 327, 328: XXg-2-MAP

Fig. 17B

```
         PRE-        FIRST
       IMMUNE      BLEEDING
      13.01.92    07.04.92     B
                               L
                               A
RABBIT  3 3 3 3   3 3 3 3      N
  No    2 2 2 2   2 2 2 2      K
        5 6 7 8   5 6 7 8
```

- XXb - 1
- XXb - 2
- XXd - 1
- XXd - 2
- XXa - 1
- XXa - 2
- XXh - 1
- XXh - 2

RABBIT 325, 326: XXb-2-MAP
RABBIT 327, 328: XXg-2-MAP

SEQUENCE LISTING

```
<160> NUMBER OF SEQ ID NOS: 600

<210> SEQ ID NO 1
<211> LENGTH: 11
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (11)
<223> OTHER INFORMATION: modified site

<400> SEQUENCE: 1

Xaa Ile Trp Gly Cys Ser Gly Lys Ile Cys Xaa
  1               5                  10

<210> SEQ ID NO 2
<211> LENGTH: 20
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (20)
<223> OTHER INFORMATION: modified site

<400> SEQUENCE: 2

Xaa Ile Trp Gly Cys Ser Gly Lys Leu Ile Cys Thr Thr Ala Val Pro
```

-continued

```
                1               5              10              15

Asn Ala Ser Xaa
            20

<210> SEQ ID NO 3
<211> LENGTH: 21
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (21)
<223> OTHER INFORMATION: modified site

<400> SEQUENCE: 3

Xaa Glu Arg Tyr Leu Lys Asp Gln Gln Leu Leu Gly Ile Trp Gly Cys
 1               5                  10                  15

Gly Lys Leu Ile Xaa
            20

<210> SEQ ID NO 4
<211> LENGTH: 18
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (18)
<223> OTHER INFORMATION: modified site

<400> SEQUENCE: 4

Xaa Leu Gln Ala Arg Ile Leu Ala Val Glu Arg Tyr Leu Lys Asp Gln
 1               5                  10                  15

Leu Xaa

<210> SEQ ID NO 5
<211> LENGTH: 12
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (12)
<223> OTHER INFORMATION: modified site

<400> SEQUENCE: 5

Xaa Leu Trp Gly Cys Lys Gly Lys Leu Val Cys Xaa
 1               5                  10

<210> SEQ ID NO 6
<211> LENGTH: 24
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (24)
<223> OTHER INFORMATION: modified site

<400> SEQUENCE: 6
```

```
Xaa Asp Gln Gln Leu Leu Gly Ile Trp Gly Cys Ser Gly Lys His Ile
 1               5                  10                  15

Thr Thr Asn Val Pro Trp Asn Xaa
                20
```

<210> SEQ ID NO 7
<211> LENGTH: 24
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (24)
<223> OTHER INFORMATION: modified site

<400> SEQUENCE: 7

```
Xaa Asn Asn Thr Arg Lys Ser Ile His Ile Gly Pro Gly Arg Ala Phe
 1               5                  10                  15

Thr Thr Gly Glu Ile Ile Gly Xaa
                20
```

<210> SEQ ID NO 8
<211> LENGTH: 36
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (36)
<223> OTHER INFORMATION: modified site

<400> SEQUENCE: 8

```
Xaa Cys Thr Arg Pro Asn Asn Asn Thr Arg Lys Ser Ile His Ile Gly
 1               5                  10                  15

Gly Arg Ala Phe Tyr Thr Thr Gly Glu Ile Ile Gly Asp Ile Arg Gln
                20                  25                  30

Ala His Cys Xaa
            35
```

<210> SEQ ID NO 9
<211> LENGTH: 24
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (24)
<223> OTHER INFORMATION: modified site

<400> SEQUENCE: 9

```
Xaa Asn Asn Thr Arg Lys Ser Ile Tyr Ile Gly Pro Gly Arg Ala Phe
 1               5                  10                  15

Thr Thr Gly Arg Ile Ile Gly Xaa
                20
```

<210> SEQ ID NO 10
<211> LENGTH: 24
<212> TYPE: PRT
<213> ORGANISM: Human immunodeficiency virus
<220> FEATURE:
<221> NAME/KEY: VARIANT

```
<222> LOCATION: (1)
<223> OTHER INFORMATION: modified site
<221> NAME/KEY: VARIANT
<222> LOCATION: (24)
<223> OTHER INFORMATION: modified site

<400> SEQUENCE: 10

Xaa Asn Asn Thr Thr Arg Ser Ile His Ile Gly Pro Gly Arg Ala Phe
  1               5                  10                  15

Ala Thr Gly Asp Ile Ile Gly Xaa
            20

<210> SEQ ID NO 11
<211> LENGTH: 24
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (24)
<223> OTHER INFORMATION: modified site

<400> SEQUENCE: 11

Xaa Tyr Asn Lys Arg Lys Arg Ile His Ile Gly Pro Gly Arg Ala Phe
  1               5                  10                  15

Thr Thr Lys Asn Ile Ile Gly Xaa
            20

<210> SEQ ID NO 12
<211> LENGTH: 25
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (25)
<223> OTHER INFORMATION: modified site

<400> SEQUENCE: 12

Xaa Asn Asn Thr Arg Lys Ser Ile Thr Lys Gly Pro Gly Arg Val Ile
  1               5                  10                  15

Tyr Ala Thr Gly Gln Ile Ile Gly Xaa
            20                  25

<210> SEQ ID NO 13
<211> LENGTH: 24
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (24)
<223> OTHER INFORMATION: modified site

<400> SEQUENCE: 13

Xaa Asn Asn Thr Arg Arg Gly Ile His Phe Gly Pro Gly Gln Ala Leu
  1               5                  10                  15

Tyr Thr Thr Gly Ile Val Gly Xaa
            20

<210> SEQ ID NO 14
```

```
<211> LENGTH: 26
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (26)
<223> OTHER INFORMATION: modified site

<400> SEQUENCE: 14

Xaa Asn Asn Thr Arg Lys Ser Ile Arg Ile Gln Arg Gly Pro Gly Arg
 1               5                  10                  15

Ala Phe Val Thr Ile Gly Lys Ile Gly Xaa
             20                  25

<210> SEQ ID NO 15
<211> LENGTH: 24
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (24)
<223> OTHER INFORMATION: modified site

<400> SEQUENCE: 15

Xaa Gln Asn Thr Arg Gln Arg Thr Pro Ile Gly Leu Gly Gln Ser Leu
 1               5                  10                  15

Tyr Thr Thr Arg Ser Arg Ser Xaa
             20

<210> SEQ ID NO 16
<211> LENGTH: 23
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (23)
<223> OTHER INFORMATION: modified site

<400> SEQUENCE: 16

Xaa Gln Ile Asp Ile Gln Glu Met Arg Ile Gly Pro Met Ala Trp Tyr
 1               5                  10                  15

Ser Met Gly Ile Gly Gly Xaa
             20

<210> SEQ ID NO 17
<211> LENGTH: 25
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (25)
<223> OTHER INFORMATION: modified site

<400> SEQUENCE: 17

Xaa Asn Asn Thr Arg Arg Gly Ile His Met Gly Trp Gly Arg Thr Phe
 1               5                  10                  15
```

Tyr Ala Thr Gly Glu Ile Ile Gly Xaa
            20              25

<210> SEQ ID NO 18
<211> LENGTH: 38
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (38)
<223> OTHER INFORMATION: modified site

<400> SEQUENCE: 18

Xaa Arg Asp Asn Trp Arg Ser Glu Leu Tyr Lys Tyr Lys Val Val Lys
 1               5                  10                  15

Ile Glu Pro Leu Gly Val Ala Pro Thr Lys Ala Lys Arg Arg Val Val
            20                  25                  30

Gln Arg Glu Lys Arg Xaa
        35

<210> SEQ ID NO 19
<211> LENGTH: 12
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (12)
<223> OTHER INFORMATION: modified site

<400> SEQUENCE: 19

Xaa Ser Trp Gly Cys Ala Phe Arg Gln Val Cys Xaa
 1               5                  10

<210> SEQ ID NO 20
<211> LENGTH: 22
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 20

Xaa Lys Tyr Leu Gln Asp Gln Ala Arg Leu Asn Ser Trp Gly Cys Ala
 1               5                  10                  15

Phe Arg Gln Val Cys Xaa
            20

<210> SEQ ID NO 21
<211> LENGTH: 25
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (25)
<223> OTHER INFORMATION: modified site

```
<400> SEQUENCE: 21

Xaa Asn Lys Thr Val Leu Pro Ile Thr Phe Met Ser Gly Phe Lys Phe
 1               5                  10                  15

His Ser Gln Pro Val Ile Asn Lys Xaa
            20                  25

<210> SEQ ID NO 22
<211> LENGTH: 24
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (24)
<223> OTHER INFORMATION: modified site

<400> SEQUENCE: 22

Xaa Asn Lys Thr Val Val Pro Ile Thr Leu Met Ser Gly Leu Val Phe
 1               5                  10                  15

His Ser Gln Pro Ile Asn Lys Xaa
            20

<210> SEQ ID NO 23
<211> LENGTH: 24
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (24)
<223> OTHER INFORMATION: modified site

<400> SEQUENCE: 23

Xaa Asn Lys Thr Val Leu Pro Val Thr Ile Met Ser Gly Leu Val Phe
 1               5                  10                  15

His Ser Gln Pro Ile Asn Asp Xaa
            20

<210> SEQ ID NO 24
<211> LENGTH: 12
<212> TYPE: PRT
<213> ORGANISM: Chimpanzee Immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (12)
<223> OTHER INFORMATION: modified site

<400> SEQUENCE: 24

Xaa Leu Trp Gly Cys Ser Gly Lys Ala Val Cys Xaa
 1               5                  10

<210> SEQ ID NO 25
<211> LENGTH: 12
<212> TYPE: PRT
<213> ORGANISM: Simian immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (12)
```

<223> OTHER INFORMATION: modified site

<400> SEQUENCE: 25

Xaa Ser Trp Gly Cys Ala Trp Lys Gln Val Cys Xaa
 1               5                   10

<210> SEQ ID NO 26
<211> LENGTH: 12
<212> TYPE: PRT
<213> ORGANISM: Simian immunodeficiency virus
<220> FEATURE:
<221> NAME/KEY: VARIANT
<222> LOCATION: (1)
<223> OTHER INFORMATION: modified site
<221> NAME/KEY: VARIANT
<222> LOCATION: (12)
<223> OTHER INFORMATION: modified site

<400> SEQUENCE: 26

Xaa Gln Trp Gly Cys Ser Trp Ala Gln Val Cys Xaa
 1               5                   10

<210> SEQ ID NO 27
<211> LENGTH: 24
<212> TYPE: PRT
<213> ORGANISM: Human T-cell lymphotropic virus
<220> FEATURE:
<221> NAME/KEY: VARIANT
<222> LOCATION: (1)
<223> OTHER INFORMATION: modified site
<221> NAME/KEY: VARIANT
<222> LOCATION: (24)
<223> OTHER INFORMATION: modified site

<400> SEQUENCE: 27

Xaa Val Leu Tyr Ser Pro Asn Val Ser Val Pro Ser Ser Ser Thr
 1               5                   10                  15

Leu Leu Tyr Pro Ser Leu Ala Xaa
                20

<210> SEQ ID NO 28
<211> LENGTH: 23
<212> TYPE: PRT
<213> ORGANISM: Human T-cell lymphotropic virus
<220> FEATURE:
<221> NAME/KEY: VARIANT
<222> LOCATION: (1)
<223> OTHER INFORMATION: modified site
<221> NAME/KEY: VARIANT
<222> LOCATION: (23)
<223> OTHER INFORMATION: modified site

<400> SEQUENCE: 28

Xaa Tyr Thr Cys Ile Val Cys Ile Asp Arg Ala Ser Leu Ser Thr Trp
 1               5                   10                  15

His Val Leu Tyr Ser Pro Xaa
                20

<210> SEQ ID NO 29
<211> LENGTH: 24
<212> TYPE: PRT
<213> ORGANISM: Human T-cell lymphotropic virus
<220> FEATURE:
<221> NAME/KEY: VARIANT
<222> LOCATION: (1)
<223> OTHER INFORMATION: modified site
<221> NAME/KEY: VARIANT
<222> LOCATION: (24)
<223> OTHER INFORMATION: modified site -continued

<400> SEQUENCE: 29

```
Xaa Asn Ser Leu Ile Leu Pro Pro Phe Ser Leu Ser Pro Val Pro Thr
  1               5                  10                  15

Leu Gly Ser Arg Ser Arg Arg Xaa
             20
```

<210> SEQ ID NO 30
<211> LENGTH: 38
<212> TYPE: PRT
<213> ORGANISM: Human T-cell lymphotropic virus
<220> FEATURE:
<221> NAME/KEY: VARIANT
<222> LOCATION: (1)
<223> OTHER INFORMATION: modified site
<221> NAME/KEY: VARIANT
<222> LOCATION: (38)
<223> OTHER INFORMATION: modified site

<400> SEQUENCE: 30

```
Xaa Asp Ala Pro Gly Tyr Asp Pro Ile Trp Phe Leu Asn Thr Glu Pro
  1               5                  10                  15

Ser Gln Leu Pro Pro Thr Ala Pro Pro Leu Leu Pro His Ser Asn Leu
             20                  25                  30

Asp His Ile Leu Glu Xaa
         35
```

<210> SEQ ID NO 31
<211> LENGTH: 33
<212> TYPE: PRT
<213> ORGANISM: Human T-cell lymphotropic virus
<220> FEATURE:
<221> NAME/KEY: VARIANT
<222> LOCATION: (1)
<223> OTHER INFORMATION: modified site
<221> NAME/KEY: VARIANT
<222> LOCATION: (33)
<223> OTHER INFORMATION: modified site

<400> SEQUENCE: 31

```
Xaa Gln Tyr Ala Ala Gln Asn Arg Arg Gly Leu Asp Leu Leu Phe Trp
  1               5                  10                  15

Glu Gln Gly Gly Leu Cys Lys Ala Leu Gln Glu Gln Cys Arg Phe Pro
             20                  25                  30

Xaa
```

<210> SEQ ID NO 32
<211> LENGTH: 33
<212> TYPE: PRT
<213> ORGANISM: Human T-cell lymphotropic virus
<220> FEATURE:
<221> NAME/KEY: VARIANT
<222> LOCATION: (1)
<223> OTHER INFORMATION: modified site
<221> NAME/KEY: VARIANT
<222> LOCATION: (33)
<223> OTHER INFORMATION: modified site

<400> SEQUENCE: 32

```
Xaa Pro Pro Pro Pro Ser Ser Pro Thr His Asp Pro Pro Asp Ser Asp
  1               5                  10                  15

Pro Gln Ile Pro Pro Pro Tyr Val Glu Pro Thr Ala Pro Gln Val Leu
             20                  25                  30

Xaa
```

<210> SEQ ID NO 33
<211> LENGTH: 20
<212> TYPE: PRT
<213> ORGANISM: Human T-cell lymphotropic virus
<220> FEATURE:
<221> NAME/KEY: VARIANT
<222> LOCATION: (1)
<223> OTHER INFORMATION: modified site
<221> NAME/KEY: VARIANT
<222> LOCATION: (20)
<223> OTHER INFORMATION: modified site

<400> SEQUENCE: 33

Xaa Lys Lys Pro Asn Arg Gln Gly Leu Gly Tyr Tyr Ser Pro Ser Tyr
 1               5                  10                  15

Asn Asp Pro Xaa
            20

<210> SEQ ID NO 34
<211> LENGTH: 38
<212> TYPE: PRT
<213> ORGANISM: Human T-cell lymphotropic virus
<220> FEATURE:
<221> NAME/KEY: VARIANT
<222> LOCATION: (1)
<223> OTHER INFORMATION: modified site
<221> NAME/KEY: VARIANT
<222> LOCATION: (38)
<223> OTHER INFORMATION: modified site

<400> SEQUENCE: 34

Xaa Asp Ala Pro Gly Tyr Asp Pro Leu Trp Phe Ile Thr Ser Glu Pro
 1               5                  10                  15

Thr Gln Pro Pro Pro Thr Ser Pro Pro Leu Val His Asp Ser Asp Leu
            20                  25                  30

Glu His Val Leu Thr Xaa
        35

<210> SEQ ID NO 35
<211> LENGTH: 40
<212> TYPE: PRT
<213> ORGANISM: Human T-cell lymphotropic virus
<220> FEATURE:
<221> NAME/KEY: VARIANT
<222> LOCATION: (1)
<223> OTHER INFORMATION: modified site
<221> NAME/KEY: VARIANT
<222> LOCATION: (40)
<223> OTHER INFORMATION: modified site

<400> SEQUENCE: 35

Xaa Tyr Ser Cys Met Val Cys Val Asp Arg Ser Ser Leu Ser Ser Trp
 1               5                  10                  15

His Val Leu Tyr Thr Pro Asn Ile Ser Ile Pro Gln Gln Thr Ser Ser
            20                  25                  30

Arg Thr Ile Leu Phe Pro Ser Xaa
        35                  40

<210> SEQ ID NO 36
<211> LENGTH: 32
<212> TYPE: PRT
<213> ORGANISM: Human T-cell lymphotropic virus
<220> FEATURE:
<221> NAME/KEY: VARIANT
<222> LOCATION: (1)
<223> OTHER INFORMATION: modified site
<221> NAME/KEY: VARIANT
<222> LOCATION: (32)
<223> OTHER INFORMATION: modified site

<400> SEQUENCE: 36

Xaa Pro Thr Thr Thr Pro Pro Pro Pro Pro Ser Pro Glu Ala
 1               5                  10                  15

His Val Pro Pro Pro Tyr Val Glu Pro Thr Thr Thr Gln Cys Phe Xaa
             20                  25                  30

<210> SEQ ID NO 37
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 37

Xaa Met Ser Thr Ile Pro Lys Pro Gln Arg Lys Thr Lys Arg Asn Thr
 1               5                  10                  15

Asn Arg Arg Pro Gln Xaa
             20

<210> SEQ ID NO 38
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 38

Xaa Pro Gln Arg Lys Thr Lys Arg Asn Thr Asn Arg Arg Pro Gln Asp
 1               5                  10                  15

Val Lys Phe Pro Gly Xaa
             20

<210> SEQ ID NO 39
<211> LENGTH: 13
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (13)
<223> OTHER INFORMATION: modified site

<400> SEQUENCE: 39

Xaa Gln Arg Lys Thr Lys Arg Asn Thr Asn Arg Arg Xaa
 1               5                  10

<210> SEQ ID NO 40
<211> LENGTH: 22
<212> TYPE: PRT
<213> ORGANISM: Hepatitis C virus
<220> FEATURE:
<221> NAME/KEY: VARIANT
<222> LOCATION: (1)

```
<223> OTHER INFORMATION: modified site
<221> NAME/KEY: VARIANT
<222> LOCATION: (22)
<223> OTHER INFORMATION: modified site

<400> SEQUENCE: 40

Xaa Arg Asn Thr Asn Arg Arg Pro Gln Asp Val Lys Phe Pro Gly Gly
 1               5                  10                  15

Gly Gln Ile Val Gly Xaa
            20

<210> SEQ ID NO 41
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 41

Xaa Leu Pro Arg Arg Gly Pro Arg Leu Gly Val Arg Ala Thr Arg Lys
 1               5                  10                  15

Thr Ser Glu Arg Ser Xaa
            20

<210> SEQ ID NO 42
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 42

Xaa Val Gly Gly Val Tyr Leu Leu Pro Arg Arg Gly Pro Arg Leu Gly
 1               5                  10                  15

Val Arg Ala Thr Arg Xaa
            20

<210> SEQ ID NO 43
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 43

Xaa Thr Arg Lys Thr Ser Glu Arg Ser Gln Pro Arg Gly Arg Arg Gln
 1               5                  10                  15

Pro Ile Pro Lys Val Xaa
            20

<210> SEQ ID NO 44
<211> LENGTH: 22
```

<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 44

Xaa Arg Ser Gln Pro Arg Gly Arg Arg Gln Pro Ile Pro Lys Val Arg
 1               5                  10                  15

Arg Pro Glu Gly Arg Xaa
            20

<210> SEQ ID NO 45
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 45

Xaa Arg Arg Gln Pro Ile Pro Lys Val Arg Arg Pro Glu Gly Arg Thr
 1               5                  10                  15

Trp Ala Gln Pro Gly Xaa
            20

<210> SEQ ID NO 46
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 46

Xaa Gly Arg Thr Trp Ala Gln Pro Gly Tyr Pro Trp Pro Leu Tyr Gly
 1               5                  10                  15

Asn Glu Gly Cys Gly Xaa
            20

<210> SEQ ID NO 47
<211> LENGTH: 32
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (32)
<223> OTHER INFORMATION: modified site

<400> SEQUENCE: 47

Xaa Met Ser Thr Ile Pro Gln Arg Lys Thr Lys Arg Asn Thr Asn Arg
 1               5                  10                  15

Arg Pro Gln Asp Val Lys Phe Pro Gly Gly Gly Gln Ile Val Gly Xaa

-continued

```
            20                  25                  30

<210> SEQ ID NO 48
<211> LENGTH: 42
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (42)
<223> OTHER INFORMATION: modified site

<400> SEQUENCE: 48

Xaa Gly Gly Val Tyr Leu Leu Pro Arg Arg Gly Pro Arg Leu Gly Val
  1               5                  10                  15

Arg Arg Ala Thr Arg Lys Thr Ser Glu Arg Ser Gln Pro Arg Gly Arg
            20                  25                  30
Arg Gln Pro Ile Pro Lys Val Arg Arg Xaa
        35                  40

<210> SEQ ID NO 49
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 49

Xaa Leu Ser Gly Lys Pro Ala Ile Ile Pro Asp Arg Glu Val Leu Tyr
  1               5                  10                  15

Arg Glu Phe Asp Glu Xaa
            20

<210> SEQ ID NO 50
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 50

Xaa Ile Ile Pro Asp Arg Glu Val Leu Tyr Arg Glu Phe Asp Glu Met
  1               5                  10                  15

Glu Glu Cys Ser Gln Xaa
            20

<210> SEQ ID NO 51
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
```

<223> OTHER INFORMATION: modified site

<400> SEQUENCE: 51

Xaa Val Leu Tyr Arg Glu Phe Asp Glu Met Glu Glu Cys Ser Gln His
 1               5                  10                  15

Leu Pro Tyr Ile Glu Xaa
            20

<210> SEQ ID NO 52
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 52

Xaa Asp Glu Met Glu Glu Cys Ser Gln His Leu Pro Tyr Ile Glu Gln
 1               5                  10                  15

Gly Met Met Leu Ala Xaa
            20

<210> SEQ ID NO 53
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 53

```
Xaa Ser Gln His Leu Pro Tyr Ile Glu Gln Gly Met Met Leu Ala Glu
  1               5                  10                  15

Gln Phe Lys Gln Lys Xaa
             20
```

<210> SEQ ID NO 54
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 54

```
Xaa Ile Glu Gln Gly Met Met Leu Ala Glu Gln Phe Lys Gln Lys Ala
  1               5                  10                  15

Leu Gly Leu Leu Gln Xaa
             20
```

<210> SEQ ID NO 55
<211> LENGTH: 22
<212> TYPE: PRT
<213> ORGANISM: Hepatitis C virus
<220> FEATURE:

```
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 55

Xaa Leu Ala Glu Gln Phe Lys Gln Lys Ala Leu Gly Leu Leu Gln Thr
 1               5                  10                  15

Ala Ser Arg Gln Ala Xaa
            20

<210> SEQ ID NO 56
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 56

Xaa Gln Lys Ala Leu Gly Leu Leu Gln Thr Ala Ser Arg Gln Ala Glu
 1               5                  10                  15

Val Ile Ala Pro Ala Xaa
            20

<210> SEQ ID NO 57
<211> LENGTH: 33
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (33)
<223> OTHER INFORMATION: modified site

<400> SEQUENCE: 57

Xaa Ser Gln His Leu Pro Tyr Ile Glu Gln Glu Met Leu Ala Glu Gln
 1               5                  10                  15

Phe Lys Gln Lys Ala Leu Gly Leu Leu Gln Thr Ala Ser Arg Gln Ala
            20                  25                  30
    Xaa

<210> SEQ ID NO 58
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 58

Xaa Gly Glu Gly Ala Val Gln Trp Met Asn Arg Leu Ile Ala Phe Ala
 1               5                  10                  15

Ser Arg Gly Asn His Xaa
            20
```

```
<210> SEQ ID NO 59
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 59

Xaa Glu Asp Glu Arg Glu Ile Ser Val Pro Ala Glu Ile Leu Arg Lys
 1               5                  10                  15

Ser Arg Arg Phe Ala Xaa
            20

<210> SEQ ID NO 60
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 60

Xaa Leu Arg Lys Ser Arg Arg Phe Ala Gln Ala Leu Pro Val Trp Ala
 1               5                  10                  15

Arg Pro Asp Tyr Asn Xaa
            20

<210> SEQ ID NO 61
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 61

Xaa Val Trp Ala Arg Pro Asp Tyr Asn Pro Pro Leu Val Glu Thr Trp
 1               5                  10                  15

Lys Lys Pro Asp Tyr Xaa
            20

<210> SEQ ID NO 62
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 62

Xaa Glu Thr Trp Lys Lys Pro Asp Tyr Glu Pro Pro Val Val His Gly
```

```
                1               5               10              15

Cys Pro Leu Pro Pro Xaa
                20

<210> SEQ ID NO 63
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 63

Xaa Val His Gly Cys Pro Leu Pro Pro Pro Lys Ser Pro Pro Val Pro
 1               5                   10                  15

Pro Pro Arg Lys Lys Xaa
                20

<210> SEQ ID NO 64
<211> LENGTH: 39
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (39)
<223> OTHER INFORMATION: modified site

<400> SEQUENCE: 64

Xaa Glu Asp Glu Arg Glu Ile Ser Val Pro Ala Glu Ile Leu Arg Lys
 1               5                   10                  15

Ser Arg Lys Ser Arg Arg Phe Ala Gln Ala Leu Pro Val Trp Ala Arg
                20                  25                  30

Pro Asp Tyr Asp Tyr Asn Xaa
                35

<210> SEQ ID NO 65
<211> LENGTH: 36
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (36)
<223> OTHER INFORMATION: modified site

<400> SEQUENCE: 65

Xaa Gly Glu Thr Tyr Thr Ser Gly Gly Ala Ala Ser His Thr Thr Ser
 1               5                   10                  15

Thr Leu Ala Ser Leu Phe Ser Pro Gly Ala Ser Gln Arg Ile Gln Leu
                20                  25                  30

Val Asn Thr Xaa
        35

<210> SEQ ID NO 66
<211> LENGTH: 24
<212> TYPE: PRT
<213> ORGANISM: Hepatitis C virus
```

```
<220> FEATURE:
<221> NAME/KEY: VARIANT
<222> LOCATION: (1)
<223> OTHER INFORMATION: modified site
<221> NAME/KEY: VARIANT
<222> LOCATION: (24)
<223> OTHER INFORMATION: modified site

<400> SEQUENCE: 66

Xaa Gly Glu Thr Tyr Thr Ser Gly Gly Ala Ala Ser His Thr Thr Ser
 1               5                  10                  15

Thr Leu Ala Ser Leu Phe Ser Xaa
            20

<210> SEQ ID NO 67
<211> LENGTH: 26
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (26)
<223> OTHER INFORMATION: modified site

<400> SEQUENCE: 67

Xaa Ser His Thr Thr Ser Thr Leu Ala Ser Leu Phe Ser Pro Gly Ala
 1               5                  10                  15

Ser Gln Arg Ile Gln Leu Val Asn Thr Xaa
            20                  25

<210> SEQ ID NO 68
<211> LENGTH: 36
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (36)
<223> OTHER INFORMATION: modified site

<400> SEQUENCE: 68

Xaa Gly His Thr Arg Val Ser Gly Gly Ala Ala Ala Ser Asp Thr Arg
 1               5                  10                  15

Gly Leu Val Ser Leu Phe Ser Pro Gly Ser Ala Gln Lys Ile Gln Leu
            20                  25                  30

Val Asn Thr Xaa
        35

<210> SEQ ID NO 69
<211> LENGTH: 24
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (24)
<223> OTHER INFORMATION: modified site

<400> SEQUENCE: 69

Xaa Gly His Thr Arg Val Ser Gly Gly Ala Ala Ala Ser Asp Thr Arg
 1               5                  10                  15
```

-continued

```
Gly Leu Val Ser Leu Phe Ser Xaa
             20

<210> SEQ ID NO 70
<211> LENGTH: 26
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (26)
<223> OTHER INFORMATION: modified site

<400> SEQUENCE: 70

Xaa Ala Ser Asp Thr Arg Gly Leu Val Ser Leu Phe Ser Pro Gly Ser
  1               5                  10                  15

Ala Gln Lys Ile Gln Leu Val Asn Thr Xaa
             20                  25

<210> SEQ ID NO 71
<211> LENGTH: 36
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (36)
<223> OTHER INFORMATION: modified site

<400> SEQUENCE: 71

Xaa Gly His Thr Arg Val Thr Gly Gly Val Gln Gly His Val Thr Cys
  1               5                  10                  15

Thr Leu Thr Ser Leu Phe Arg Pro Gly Ala Ser Gln Lys Ile Gln Leu
             20                  25                  30

Val Asn Thr Xaa
         35

<210> SEQ ID NO 72
<211> LENGTH: 24
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (24)
<223> OTHER INFORMATION: modified site

<400> SEQUENCE: 72

Xaa Gly His Thr Arg Val Thr Gly Gly Val Gln Gly His Val Thr Cys
  1               5                  10                  15

Thr Leu Thr Ser Leu Phe Arg Xaa
             20

<210> SEQ ID NO 73
<211> LENGTH: 26
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
```

```
<222> LOCATION: (26)
<223> OTHER INFORMATION: modified site

<400> SEQUENCE: 73

Xaa Gly His Val Thr Cys Thr Leu Thr Ser Leu Phe Arg Pro Gly Ala
 1               5                   10                  15

Ser Gln Lys Ile Gln Leu Val Asn Thr Xaa
            20                  25

<210> SEQ ID NO 74
<211> LENGTH: 36
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (36)
<223> OTHER INFORMATION: modified site

<400> SEQUENCE: 74

Xaa Gly His Thr His Val Thr Gly Gly Arg Val Ala Ser Ser Thr Gln
 1               5                   10                  15

Ser Leu Val Ser Trp Leu Ser Gln Gly Pro Ser Gln Lys Ile Gln Leu
            20                  25                  30

Val Asn Thr Xaa
        35

<210> SEQ ID NO 75
<211> LENGTH: 24
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (24)
<223> OTHER INFORMATION: modified site

<400> SEQUENCE: 75

Xaa Gly His Thr His Val Thr Gly Gly Arg Val Ala Ser Ser Thr Gln
 1               5                   10                  15

Ser Leu Val Ser Trp Leu Ser Xaa
            20

<210> SEQ ID NO 76
<211> LENGTH: 26
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (26)
<223> OTHER INFORMATION: modified site

<400> SEQUENCE: 76

Xaa Ala Ser Ser Thr Gln Ser Leu Val Ser Trp Leu Ser Gln Gly Pro
 1               5                   10                  15

Ser Gln Lys Ile Gln Leu Val Asn Thr Xaa
            20                  25

<210> SEQ ID NO 77
```

-continued

<211> LENGTH: 36
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (26)
<223> OTHER INFORMATION: modified site

<400> SEQUENCE: 77

Xaa Gly Asp Thr His Val Thr Gly Gly Ala Gln Ala Lys Thr Thr Asn
1 5 10 15

Arg Leu Val Ser Met Phe Ala Ser Gly Pro Ser Gln Lys Ile Gln Leu
20 25 30

Ile Asn Thr Xaa
35

<210> SEQ ID NO 78
<211> LENGTH: 24
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (24)
<223> OTHER INFORMATION: modified site

<400> SEQUENCE: 78

Xaa Gly Asp Thr His Val Thr Gly Gly Ala Gln Ala Lys Thr Thr Asn
1 5 10 15

Arg Leu Val Ser Met Phe Ala Xaa
20

<210> SEQ ID NO 79
<211> LENGTH: 26
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (26)
<223> OTHER INFORMATION: modified site

<400> SEQUENCE: 79

Xaa Ala Lys Thr Thr Asn Arg Leu Val Ser Met Phe Ala Ser Gly Pro
1 5 10 15

Ser Gln Lys Ile Gln Leu Ile Asn Thr Xaa
20 25

<210> SEQ ID NO 80
<211> LENGTH: 36
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (36)
<223> OTHER INFORMATION: modified site

<400> SEQUENCE: 80

Xaa Ala Glu Thr Tyr Thr Ser Gly Gly Asn Ala Gly His Thr Met Thr
 1               5                  10                  15

Gly Ile Val Arg Phe Phe Ala Pro Gly Pro Lys Gln Asn Val His Leu
            20                  25                  30

Ile Asn Thr Xaa
            35

<210> SEQ ID NO 81
<211> LENGTH: 24
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (24)
<223> OTHER INFORMATION: modified site

<400> SEQUENCE: 81

Xaa Ala Glu Thr Tyr Thr Ser Gly Gly Asn Ala Gly His Thr Met Thr
 1               5                  10                  15

Gly Ile Val Arg Phe Phe Ala Xaa
            20

<210> SEQ ID NO 82
<211> LENGTH: 26
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (26)
<223> OTHER INFORMATION: modified site

<400> SEQUENCE: 82

Xaa Gly His Thr Met Thr Gly Ile Val Arg Phe Phe Ala Pro Gly Pro
 1               5                  10                  15

Lys Gln Asn Val His Leu Ile Asn Thr Xaa
            20                  25

<210> SEQ ID NO 83
<211> LENGTH: 36
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (36)
<223> OTHER INFORMATION: modified site

<400> SEQUENCE: 83

Xaa Ala Glu Thr Ile Val Ser Gly Gly Gln Ala Ala Arg Ala Met Ser
 1               5                  10                  15

Gly Leu Val Ser Leu Phe Thr Pro Gly Ala Lys Gln Asn Ile Gln Leu
            20                  25                  30

Ile Asn Thr Xaa
            35

<210> SEQ ID NO 84
<211> LENGTH: 24
<212> TYPE: PRT

-continued

```
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (24)
<223> OTHER INFORMATION: modified site

<400> SEQUENCE: 84

Xaa Ala Glu Thr Ile Val Ser Gly Gly Gln Ala Ala Arg Ala Met Ser
  1               5                  10                  15

Gly Leu Val Ser Leu Phe Thr Xaa
             20

<210> SEQ ID NO 85
<211> LENGTH: 26
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (26)
<223> OTHER INFORMATION: modified site

<400> SEQUENCE: 85

Xaa Ala Arg Ala Met Ser Gly Leu Val Ser Leu Phe Thr Pro Gly Ala
  1               5                  10                  15

Lys Gln Asn Ile Gln Leu Ile Asn Thr Xaa
             20                  25

<210> SEQ ID NO 86
<211> LENGTH: 36
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (36)
<223> OTHER INFORMATION: modified site

<400> SEQUENCE: 86

Xaa Ala Glu Thr Tyr Thr Thr Gly Gly Ser Thr Ala Arg Thr Thr Gln
  1               5                  10                  15

Gly Leu Val Ser Leu Phe Ser Arg Gly Ala Lys Gln Asp Ile Gln Leu
             20                  25                  30

Ile Asn Thr Xaa
         35

<210> SEQ ID NO 87
<211> LENGTH: 24
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (24)
<223> OTHER INFORMATION: modified site

<400> SEQUENCE: 87

Xaa Ala Glu Thr Tyr Thr Thr Gly Gly Ser Thr Ala Arg Thr Thr Gln
  1               5                  10                  15
```

Gly Leu Val Ser Leu Phe Ser Xaa
            20

<210> SEQ ID NO 88
<211> LENGTH: 26
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (26)
<223> OTHER INFORMATION: modified site

<400> SEQUENCE: 88

Xaa Ala Arg Thr Thr Gln Gly Leu Val Ser Leu Phe Ser Arg Gly Ala
 1               5                  10                  15

Lys Gln Asp Ile Gln Leu Ile Asn Thr Xaa
            20                  25

<210> SEQ ID NO 89
<211> LENGTH: 36
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (36)
<223> OTHER INFORMATION: modified site

<400> SEQUENCE: 89

Xaa Ala Gln Thr His Thr Val Gly Gly Ser Thr Ala His Asn Ala Arg
 1               5                  10                  15

Thr Leu Thr Gly Met Phe Ser Leu Gly Ala Arg Gln Lys Ile Gln Leu
            20                  25                  30
Ile Asn Thr Xaa
        35

<210> SEQ ID NO 90
<211> LENGTH: 24
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (24)
<223> OTHER INFORMATION: modified site

<400> SEQUENCE: 90

Xaa Ala Gln Thr His Thr Val Gly Gly Ser Thr Ala His Asn Ala Arg
 1               5                  10                  15

Thr Leu Thr Gly Met Phe Ser Xaa
            20

<210> SEQ ID NO 91
<211> LENGTH: 26
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (26)
<223> OTHER INFORMATION: modified site

<400> SEQUENCE: 91

Xaa Ala His Asn Ala Arg Thr Leu Thr Gly Met Phe Ser Leu Gly Ala
 1               5                  10                  15

Arg Gln Lys Ile Gln Leu Ile Asn Thr Xaa
            20                  25

<210> SEQ ID NO 92
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 92

Xaa Val Asn Gln Arg Ala Val Val Ala Pro Asp Lys Glu Val Leu Tyr
 1               5                  10                  15

Glu Ala Phe Asp Glu Xaa
            20

<210> SEQ ID NO 93
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 93

Xaa Val Ala Pro Asp Lys Glu Val Leu Tyr Glu Ala Phe Asp Glu Met
 1               5                  10                  15

Glu Glu Cys Ala Ser Xaa
            20

<210> SEQ ID NO 94
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 94

Xaa Asp Glu Met Glu Glu Cys Ala Ser Arg Ala Ala Leu Ile Glu Glu
 1               5                  10                  15

Gly Gln Arg Ile Ala Xaa
            20

<210> SEQ ID NO 95
<211> LENGTH: 22
<212> TYPE: PRT
<213> ORGANISM: Hepatitis C virus

```
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 95

Xaa Ala Ser Arg Ala Ala Leu Ile Glu Glu Gly Gln Arg Ile Ala Glu
 1               5                  10                  15

Met Leu Lys Ser Lys Xaa
            20

<210> SEQ ID NO 96
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 96

Xaa Ile Glu Glu Gly Gln Arg Ile Ala Glu Met Leu Lys Ser Lys Ile
 1               5                  10                  15

Gln Gly Leu Leu Gln Xaa
            20

<210> SEQ ID NO 97
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 97

Xaa Ile Ala Glu Met Leu Lys Ser Lys Ile Gln Gly Leu Leu Gln Gln
 1               5                  10                  15

Ala Ser Lys Gln Ala Xaa
            20

<210> SEQ ID NO 98
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 98

Xaa Ser Lys Ile Gln Gly Leu Leu Gln Gln Ala Ser Lys Gln Ala Gln
 1               5                  10                  15

Asp Ile Gln Pro Ala Xaa
            20
```

```
<210> SEQ ID NO 99
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 99

Xaa Arg Ser Asp Leu Glu Pro Ser Ile Pro Ser Glu Tyr Met Leu Pro
 1               5                  10                  15

Lys Lys Arg Phe Pro Xaa
            20

<210> SEQ ID NO 100
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 100

Xaa Met Leu Pro Lys Lys Arg Phe Pro Pro Ala Leu Pro Ala Trp Ala
 1               5                  10                  15

Arg Pro Asp Tyr Asn Xaa
            20

<210> SEQ ID NO 101
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 101

Xaa Ala Trp Ala Arg Pro Asp Tyr Asn Pro Pro Leu Val Glu Ser Trp
 1               5                  10                  15

Lys Arg Pro Asp Tyr Xaa
            20

<210> SEQ ID NO 102
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 102

Xaa Glu Ser Trp Lys Arg Pro Asp Tyr Gln Pro Ala Thr Val Ala Gly
```

```
            1               5               10              15

Cys Ala Leu Pro Pro Xaa
                    20

<210> SEQ ID NO 103
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 103

Xaa Val Ala Gly Cys Ala Leu Pro Pro Lys Lys Thr Pro Thr Pro
 1               5               10              15

Pro Pro Arg Arg Arg Xaa
                    20

<210> SEQ ID NO 104
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 104

Xaa Leu Gly Gly Lys Pro Ala Ile Val Pro Asp Lys Glu Val Leu Tyr
 1               5               10              15

Gln Gln Tyr Asp Glu Xaa
                    20

<210> SEQ ID NO 105
<211> LENGTH: 22
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (22)
<223> OTHER INFORMATION: modified site

<400> SEQUENCE: 105

Xaa Ser Gln Ala Ala Pro Tyr Ile Glu Gln Ala Gln Val Ile Ala His
 1               5               10              15

Gln Phe Lys Glu Lys Xaa
                    20

<210> SEQ ID NO 106
<211> LENGTH: 24
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (24)
```

<223> OTHER INFORMATION: modified site

<400> SEQUENCE: 106

Xaa Ile Ala His Gln His Gln Phe Lys Glu Lys Val Leu Gly Leu Leu
 1               5                  10                  15

Gln Arg Ala Thr Gln Gln Gln Xaa
            20

<210> SEQ ID NO 107
<211> LENGTH: 33
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (33)
<223> OTHER INFORMATION: modified site

<400> SEQUENCE: 107

Xaa Ile Pro Asp Arg Glu Val Leu Tyr Arg Gly Gly Lys Lys Pro Asp
 1               5                  10                  15

Tyr Glu Pro Pro Val Gly Gly Arg Arg Pro Gln Asp Val Lys Phe Pro
            20                  25                  30

Xaa

<210> SEQ ID NO 108
<211> LENGTH: 33
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (33)
<223> OTHER INFORMATION: modified site

<400> SEQUENCE: 108

Xaa Trp Ala Arg Pro Asp Tyr Asn Pro Pro Gly Gly Gln Phe Lys Gln
 1               5                  10                  15

Lys Ala Leu Gly Leu Gly Ser Gly Val Tyr Leu Leu Pro Arg Arg Gly
            20                  25                  30

Xaa

<210> SEQ ID NO 109
<211> LENGTH: 33
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site
<221> NAME/KEY: VARIANT
<222> LOCATION: (33)
<223> OTHER INFORMATION: modified site

<400> SEQUENCE: 109

Xaa Arg Gly Arg Arg Gln Pro Ile Pro Lys Gly Gly Ser Gln His Leu
 1               5                  10                  15

Pro Tyr Ile Glu Gln Ser Gly Pro Val Val His Gly Cys Pro Leu Pro
            20                  25                  30

Xaa

```
<210> SEQ ID NO 110
<211> LENGTH: 12
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site : Ac
<221> NAME/KEY: VARIANT
<222> LOCATION: (12)
<223> OTHER INFORMATION: modified site : NH2

<400> SEQUENCE: 110

Xaa Ile Trp Gly Cys Ser Gly Lys Leu Ile Cys Xaa
 1               5                  10

<210> SEQ ID NO 111
<211> LENGTH: 15
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site : Bio
<221> NAME/KEY: VARIANT
<222> LOCATION: (15)
<223> OTHER INFORMATION: modified site : NH2

<400> SEQUENCE: 111

Xaa Gly Gly Gly Ile Trp Gly Cys Ser Gly Lys Leu Ile Cys Xaa
 1               5                  10                  15

<210> SEQ ID NO 112
<211> LENGTH: 12
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site : Ac
<221> NAME/KEY: VARIANT
<222> LOCATION: (12)
<223> OTHER INFORMATION: modified site : NH2

<400> SEQUENCE: 112

Xaa Ser Trp Gly Cys Ala Phe Arg Gln Val Cys Xaa
 1               5                  10

<210> SEQ ID NO 113
<211> LENGTH: 15
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site : Bio
<221> NAME/KEY: VARIANT
<222> LOCATION: (15)
<223> OTHER INFORMATION: modified site : NH2

<400> SEQUENCE: 113

Xaa Gly Gly Gly Ser Trp Gly Cys Ala Phe Arg Gln Val Cys Xaa
 1               5                  10                  15

<210> SEQ ID NO 114
<211> LENGTH: 25
<212> TYPE: PRT
<213> ORGANISM: Human immunodeficiency virus
<220> FEATURE:
<221> NAME/KEY: VARIANT
```

<222> LOCATION: (1)
<223> OTHER INFORMATION: modified site : Ac
<221> NAME/KEY: VARIANT
<222> LOCATION: (25)
<223> OTHER INFORMATION: modified site : NH2

<400> SEQUENCE: 114

Xaa Tyr Asn Lys Arg Lys Arg Ile His Ile Gly Pro Gly Arg Ala Phe
 1               5                  10                  15

Tyr Thr Thr Lys Asn Ile Ile Gly Xaa
            20                  25

<210> SEQ ID NO 115
<211> LENGTH: 26
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site : Bio
<221> NAME/KEY: VARIANT
<222> LOCATION: (26)
<223> OTHER INFORMATION: modified site : NH2

<400> SEQUENCE: 115

Xaa Gly Gly Tyr Asn Lys Arg Lys Arg Ile His Ile Gly Pro Gly Arg
 1               5                  10                  15

Ala Phe Thr Thr Lys Asn Ile Ile Gly Xaa
            20                  25

<210> SEQ ID NO 116
<211> LENGTH: 20
<212> TYPE: PRT
<213> ORGANISM: Hepatitis C virus

<400> SEQUENCE: 116

Ser Gln His Leu Pro Tyr Ile Glu Gln Gly Met Met Leu Ala Glu Gln
 1               5                  10                  15

Phe Lys Gln Lys
            20

<210> SEQ ID NO 117
<211> LENGTH: 20
<212> TYPE: PRT
<213> ORGANISM: Hepatitis C virus

<400> SEQUENCE: 117

Leu Arg Lys Ser Arg Arg Phe Ala Gln Ala Leu Pro Val Trp Ala Arg
 1               5                  10                  15

Pro Asp Tyr Asn
            20

<210> SEQ ID NO 118
<211> LENGTH: 19
<212> TYPE: PRT
<213> ORGANISM: Hepatitis C virus

<400> SEQUENCE: 118

Pro Gln Arg Lys Thr Lys Arg Asn Thr Asn Arg Arg Pro Gln Asp Val
 1               5                  10                  15

Lys Phe Gly

<210> SEQ ID NO 119
<211> LENGTH: 20

-continued

```
<212> TYPE: PRT
<213> ORGANISM: Hepatitis C virus

<400> SEQUENCE: 119

Arg Asn Thr Asn Arg Arg Pro Gln Asp Val Lys Phe Pro Gly Gly Gly
  1               5                  10                  15

Gln Ile Val Gly
            20

<210> SEQ ID NO 120
<211> LENGTH: 20
<212> TYPE: PRT
<213> ORGANISM: Hepatitis C virus

<400> SEQUENCE: 120

Thr Arg Lys Thr Ser Glu Arg Ser Gln Pro Arg Gly Arg Arg Gln Pro
  1               5                  10                  15

Ile Pro Lys Val
            20

<210> SEQ ID NO 121
<211> LENGTH: 20
<212> TYPE: PRT
<213> ORGANISM: Hepatitis C virus

<400> SEQUENCE: 121

Ile Ile Pro Asp Arg Glu Val Leu Tyr Arg Glu Phe Asp Glu Met Glu
  1               5                  10                  15

Glu Cys Ser Gln
            20

<210> SEQ ID NO 122
<211> LENGTH: 20
<212> TYPE: PRT
<213> ORGANISM: Hepatitis C virus

<400> SEQUENCE: 122

Glu Thr Trp Lys Lys Pro Asp Tyr Glu Pro Pro Val Val His Gly Cys
  1               5                  10                  15

Pro Leu Pro Pro
            20

<210> SEQ ID NO 123
<211> LENGTH: 21
<212> TYPE: PRT
<213> ORGANISM: Hepatitis C virus
<220> FEATURE:
<221> NAME/KEY: VARIANT
<222> LOCATION: (1)
<223> OTHER INFORMATION: modified site : NH2
<221> NAME/KEY: VARIANT
<222> LOCATION: (21)
<223> OTHER INFORMATION: modified site : CONH2

<400> SEQUENCE: 123

Xaa Met Ser Thr Ile Pro Lys Pro Gln Arg Lys Thr Lys Arg Asn Thr
  1               5                  10                  15

Asn Arg Pro Gln Xaa
            20

<210> SEQ ID NO 124
<211> LENGTH: 24
<212> TYPE: PRT
<213> ORGANISM: Hepatitis C virus
```

```
<220> FEATURE:
<221> NAME/KEY: VARIANT
<222> LOCATION: (1)
<223> OTHER INFORMATION: modified site : NH2
<221> NAME/KEY: VARIANT
<222> LOCATION: (23)
<223> OTHER INFORMATION: modified site : Lys (Bio)
<221> NAME/KEY: VARIANT
<222> LOCATION: (24)
<223> OTHER INFORMATION: modified site : CONH2

<400> SEQUENCE: 124

Xaa Met Ser Thr Ile Pro Lys Pro Gln Arg Lys Thr Lys Arg Asn Thr
 1               5                  10                  15

Asn Arg Pro Gln Gly Gly Xaa Xaa
            20

<210> SEQ ID NO 125
<211> LENGTH: 34
<212> TYPE: PRT
<213> ORGANISM: Hepatitis C virus

<400> SEQUENCE: 125

Gly Glu Thr Tyr Thr Ser Gly Gly Ala Ala Ser His Thr Thr Ser Thr
 1               5                  10                  15

Leu Ala Ser Leu Phe Ser Pro Gly Ala Ser Gln Arg Ile Gln Leu Val
            20                  25                  30

Asn Thr

<210> SEQ ID NO 126
<211> LENGTH: 34
<212> TYPE: PRT
<213> ORGANISM: Hepatitis C virus

<400> SEQUENCE: 126

Gly His Thr Arg Val Ser Gly Gly Ala Ala Ala Ser Asp Thr Arg Gly
 1               5                  10                  15

Leu Val Ser Leu Phe Ser Pro Gly Ser Ala Gln Lys Ile Gln Leu Val
            20                  25                  30

Asn Thr

<210> SEQ ID NO 127
<211> LENGTH: 34
<212> TYPE: PRT
<213> ORGANISM: Hepatitis C virus

<400> SEQUENCE: 127

Gly His Thr Arg Val Thr Gly Gly Val Gln Gly His Val Thr Cys Thr
 1               5                  10                  15

Leu Thr Ser Leu Phe Arg Pro Gly Ala Ser Gln Lys Ile Gln Leu Val
            20                  25                  30

Asn Thr

<210> SEQ ID NO 128
<211> LENGTH: 34
<212> TYPE: PRT
<213> ORGANISM: Hepatitis C virus

<400> SEQUENCE: 128

Gly His Thr His Val Thr Gly Gly Arg Val Ala Ser Ser Thr Gln Ser
 1               5                  10                  15

Leu Val Ser Trp Leu Ser Gln Gly Pro Ser Gln Lys Ile Gln Leu Val
```

```
                         20                  25                  30

Asn Thr

<210> SEQ ID NO 129
<211> LENGTH: 34
<212> TYPE: PRT
<213> ORGANISM: Hepatitis C virus

<400> SEQUENCE: 129

Gly Asp Thr His Val Thr Gly Gly Ala Gln Ala Lys Thr Thr Asn Arg
 1               5                  10                  15

Leu Val Ser Met Phe Ala Ser Gly Pro Ser Gln Lys Ile Gln Leu Ile
                 20                  25                  30

Asn Thr

<210> SEQ ID NO 130
<211> LENGTH: 34
<212> TYPE: PRT
<213> ORGANISM: Hepatitis C virus

<400> SEQUENCE: 130

Ala Glu Thr Tyr Thr Ser Gly Gly Asn Ala Gly His Thr Met Thr Gly
 1               5                  10                  15

Ile Val Arg Phe Phe Ala Pro Gly Pro Lys Gln Asn Val His Leu Ile
                 20                  25                  30

Asn Thr

<210> SEQ ID NO 131
<211> LENGTH: 34
<212> TYPE: PRT
<213> ORGANISM: Hepatitis C virus

<400> SEQUENCE: 131

Ala Glu Thr Ile Val Ser Gly Gly Gln Ala Ala Arg Ala Met Ser Gly
 1               5                  10                  15

Leu Val Ser Leu Phe Thr Pro Gly Ala Lys Gln Asn Ile Gln Leu Ile
                 20                  25                  30

Asn Thr

<210> SEQ ID NO 132
<211> LENGTH: 34
<212> TYPE: PRT
<213> ORGANISM: Hepatitis C virus

<400> SEQUENCE: 132

Ala Glu Thr Tyr Thr Thr Gly Gly Ser Thr Ala Arg Thr Thr Gln Gly
 1               5                  10                  15

Leu Val Ser Leu Phe Ser Arg Gly Ala Lys Gln Asp Ile Gln Leu Ile
                 20                  25                  30

Asn Thr

<210> SEQ ID NO 133
<211> LENGTH: 20
<212> TYPE: PRT
<213> ORGANISM: Hepatitis C virus

<400> SEQUENCE: 133

Met Ser Thr Ile Pro Lys Pro Gln Arg Lys Thr Lys Arg Asn Thr Asn
 1               5                  10                  15
```

-continued

Arg Arg Pro Gln
        20

<210> SEQ ID NO 134
<211> LENGTH: 15
<212> TYPE: PRT
<213> ORGANISM: Hepatitis C virus

<400> SEQUENCE: 134

Pro Lys Pro Gln Arg Lys Thr Lys Arg Asn Thr Asn Arg Arg Pro
 1               5                  10                  15

<210> SEQ ID NO 135
<211> LENGTH: 20
<212> TYPE: PRT
<213> ORGANISM: Hepatitis C virus

<400> SEQUENCE: 135

Arg Asn Thr Asn Arg Arg Pro Gln Asp Val Lys Phe Pro Gly Gly Gly
 1               5                  10                  15

Gln Ile Val Gly
        20

<210> SEQ ID NO 136
<211> LENGTH: 32
<212> TYPE: PRT
<213> ORGANISM: Hepatitis C virus

<400> SEQUENCE: 136

Met Ser Thr Ile Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
                20                  25                  30

<210> SEQ ID NO 137
<211> LENGTH: 20
<212> TYPE: PRT
<213> ORGANISM: Hepatitis C virus

<400> SEQUENCE: 137

Val Gly Gly Val Tyr Leu Leu Pro Arg Arg Gly Pro Arg Leu Gly Val
 1               5                  10                  15

Arg Ala Thr Arg
        20

<210> SEQ ID NO 138
<211> LENGTH: 20
<212> TYPE: PRT
<213> ORGANISM: Hepatitis C virus

<400> SEQUENCE: 138

Leu Pro Arg Arg Gly Pro Arg Leu Gly Val Arg Ala Thr Arg Lys Thr
 1               5                  10                  15

Ser Glu Arg Ser
        20

<210> SEQ ID NO 139
<211> LENGTH: 20
<212> TYPE: PRT
<213> ORGANISM: Hepatitis C virus

<400> SEQUENCE: 139

Thr Arg Lys Thr Ser Glu Arg Ser Gln Pro Arg Gly Arg Arg Gln Pro

```
                   1               5                  10                  15
Ile Pro Glu Val
            20

<210> SEQ ID NO 140
<211> LENGTH: 20
<212> TYPE: PRT
<213> ORGANISM: Hepatitis C virus

<400> SEQUENCE: 140

Arg Ser Gln Pro Arg Gly Arg Gln Pro Ile Pro Glu Val Arg Arg
  1               5                  10                  15
Pro Glu Gly Arg
            20

<210> SEQ ID NO 141
<211> LENGTH: 39
<212> TYPE: PRT
<213> ORGANISM: Hepatitis C virus

<400> SEQUENCE: 141

Gly Gly Val Tyr Leu Leu Pro Arg Arg Gly Pro Arg Leu Gly Val Arg
  1               5                  10                  15
Ala Thr Arg Lys Thr Ser Glu Arg Ser Gln Pro Arg Gly Arg Gln
            20                  25                  30
Pro Ile Pro Lys Val Arg Arg
            35

<210> SEQ ID NO 142
<211> LENGTH: 20
<212> TYPE: PRT
<213> ORGANISM: Hepatitis C virus

<400> SEQUENCE: 142

Ser Gln His Leu Pro Tyr Ile Glu Gln Gly Met Met Leu Ala Glu Gln
  1               5                  10                  15
Phe Lys Gln Lys
            20

<210> SEQ ID NO 143
<211> LENGTH: 20
<212> TYPE: PRT
<213> ORGANISM: Hepatitis C virus

<400> SEQUENCE: 143

Leu Ala Glu Gln Phe Lys Gln Lys Ala Leu Gly Leu Leu Gln Thr Ala
  1               5                  10                  15
Ser Arg Gln Ala
            20

<210> SEQ ID NO 144
<211> LENGTH: 32
<212> TYPE: PRT
<213> ORGANISM: Hepatitis C virus

<400> SEQUENCE: 144

Ser Gln His Leu Pro Tyr Ile Glu Gln Gly Met Met Leu Ala Glu Gln
  1               5                  10                  15
Phe Lys Gln Lys Ala Leu Gly Leu Leu Gln Thr Ala Ser Arg Gln Ala
            20                  25                  30
```

```
<210> SEQ ID NO 145
<211> LENGTH: 20
<212> TYPE: PRT
<213> ORGANISM: Hepatitis C virus

<400> SEQUENCE: 145

Glu Asp Glu Arg Glu Ile Ser Val Pro Ala Glu Ile Leu Arg Lys Ser
 1               5                  10                  15

Arg Arg Phe Ala
            20

<210> SEQ ID NO 146
<211> LENGTH: 20
<212> TYPE: PRT
<213> ORGANISM: Hepatitis C virus

<400> SEQUENCE: 146

Leu Arg Lys Ser Arg Arg Phe Ala Gln Ala Leu Pro Val Trp Ala Arg
 1               5                  10                  15

Pro Asp Tyr Asn
            20

<210> SEQ ID NO 147
<211> LENGTH: 32
<212> TYPE: PRT
<213> ORGANISM: Hepatitis C virus

<400> SEQUENCE: 147

Glu Asp Glu Arg Glu Ile Ser Val Pro Ala Glu Ile Leu Arg Lys Ser
 1               5                  10                  15

Arg Arg Phe Ala Gln Ala Leu Pro Val Trp Ala Arg Pro Asp Tyr Asn
            20                  25                  30

<210> SEQ ID NO 148
<211> LENGTH: 20
<212> TYPE: PRT
<213> ORGANISM: Hepatitis C virus

<400> SEQUENCE: 148

Leu Ser Gly Lys Pro Ala Ile Ile Pro Asp Arg Glu Val Leu Tyr Arg
 1               5                  10                  15

Glu Phe Asp Glu
            20

<210> SEQ ID NO 149
<211> LENGTH: 20
<212> TYPE: PRT
<213> ORGANISM: Hepatitis C virus

<400> SEQUENCE: 149

Val Asn Gln Arg Ala Val Val Ala Pro Asp Lys Glu Val Leu Tyr Glu
 1               5                  10                  15

Ala Phe Asp Glu
            20

<210> SEQ ID NO 150
<211> LENGTH: 20
<212> TYPE: PRT
<213> ORGANISM: Hepatitis C virus

<400> SEQUENCE: 150

Ser Gln His Leu Pro Tyr Ile Glu Gln Gly Met Met Leu Ala Glu Gln
 1               5                  10                  15
```

```
Phe Lys Gln Lys
        20

<210> SEQ ID NO 151
<211> LENGTH: 20
<212> TYPE: PRT
<213> ORGANISM: Hepatitis C virus

<400> SEQUENCE: 151

Ala Ser Arg Ala Ala Leu Ile Glu Glu Gly Gln Arg Ile Ala Glu Met
 1               5                  10                  15

Leu Lys Ser Lys
        20

<210> SEQ ID NO 152
<211> LENGTH: 20
<212> TYPE: PRT
<213> ORGANISM: Hepatitis C virus

<400> SEQUENCE: 152

Leu Ala Glu Gln Phe Lys Gln Lys Ala Leu Gly Leu Leu Gln Thr Ala
 1               5                  10                  15

Ser Arg Gln Ala
        20

<210> SEQ ID NO 153
<211> LENGTH: 20
<212> TYPE: PRT
<213> ORGANISM: Hepatitis C virus

<400> SEQUENCE: 153

Ile Ala Glu Met Leu Lys Ser Lys Ile Gln Gly Leu Leu Gln Gln Ala
 1               5                  10                  15

Ser Lys Gln Ala
        20

<210> SEQ ID NO 154
<211> LENGTH: 23
<212> TYPE: PRT
<213> ORGANISM: Human immunodeficiency virus

<400> SEQUENCE: 154

Asn Asn Thr Arg Lys Ser Ile His Ile Gly Pro Gly Arg Ala Phe Tyr
 1               5                  10                  15

Thr Thr Gly Glu Ile Ile Gly
            20

<210> SEQ ID NO 155
<211> LENGTH: 23
<212> TYPE: PRT
<213> ORGANISM: Human immunodeficiency virus

<400> SEQUENCE: 155

Asn Asn Thr Arg Lys Ser Ile Tyr Ile Gly Pro Gly Arg Ala Phe His
 1               5                  10                  15

Thr Thr Gly Arg Ile Ile Gly
            20

<210> SEQ ID NO 156
<211> LENGTH: 23
<212> TYPE: PRT
<213> ORGANISM: Human immunodeficiency virus
```

```
<400> SEQUENCE: 156

Asn Asn Thr Thr Arg Ser Ile His Ile Gly Pro Gly Arg Ala Phe Tyr
  1               5                  10                  15

Ala Thr Gly Asp Ile Ile Gly
             20

<210> SEQ ID NO 157
<211> LENGTH: 23
<212> TYPE: PRT
<213> ORGANISM: Human immunodeficiency virus

<400> SEQUENCE: 157

Tyr Asn Lys Arg Lys Arg Ile His Ile Gly Pro Gly Arg Ala Phe Tyr
  1               5                  10                  15

Thr Thr Lys Asn Ile Ile Gly
             20

<210> SEQ ID NO 158
<211> LENGTH: 23
<212> TYPE: PRT
<213> ORGANISM: Human immunodeficiency virus

<400> SEQUENCE: 158

Asn Asn Thr Arg Lys Ser Ile Thr Lys Gly Pro Gly Arg Val Ile Tyr
  1               5                  10                  15

Ala Thr Gly Gln Ile Ile Gly
             20

<210> SEQ ID NO 159
<211> LENGTH: 22
<212> TYPE: PRT
<213> ORGANISM: Human immunodeficiency virus

<400> SEQUENCE: 159

Asn Asn Thr Arg Arg Gly Ile His Phe Gly Pro Gly Gln Ala Leu Tyr
  1               5                  10                  15

Thr Thr Gly Ile Val Gly
             20

<210> SEQ ID NO 160
<211> LENGTH: 24
<212> TYPE: PRT
<213> ORGANISM: Human immunodeficiency virus

<400> SEQUENCE: 160

Asn Asn Thr Arg Lys Ser Ile Arg Ile Gln Arg Gly Pro Gly Arg Ala
  1               5                  10                  15

Phe Val Thr Ile Gly Lys Ile Gly
             20

<210> SEQ ID NO 161
<211> LENGTH: 22
<212> TYPE: PRT
<213> ORGANISM: Human immunodeficiency virus

<400> SEQUENCE: 161

Gln Asn Thr Arg Gln Arg Thr Pro Ile Gly Leu Gly Gln Ser Leu Tyr
  1               5                  10                  15

Thr Thr Arg Ser Arg Ser
             20
```

<210> SEQ ID NO 162
<211> LENGTH: 21
<212> TYPE: PRT
<213> ORGANISM: Human immunodeficiency virus

<400> SEQUENCE: 162

Gln Ile Asp Ile Gln Glu Met Arg Ile Gly Pro Met Ala Trp Tyr Ser
 1               5                  10                  15

Met Gly Ile Gly Gly
            20

<210> SEQ ID NO 163
<211> LENGTH: 23
<212> TYPE: PRT
<213> ORGANISM: Human immunodeficiency virus

<400> SEQUENCE: 163

Asn Asn Thr Arg Arg Gly Ile His Met Gly Trp Gly Arg Thr Phe Tyr
 1               5                  10                  15

Ala Thr Gly Glu Ile Ile Gly
            20

<210> SEQ ID NO 164
<211> LENGTH: 22
<212> TYPE: PRT
<213> ORGANISM: Human immunodeficiency virus

<400> SEQUENCE: 164

Asn Lys Thr Val Val Pro Ile Thr Leu Met Ser Gly Leu Val Phe His
 1               5                  10                  15

Ser Gln Pro Ile Asn Lys
            20

<210> SEQ ID NO 165
<211> LENGTH: 22
<212> TYPE: PRT
<213> ORGANISM: Human immunodeficiency virus

<400> SEQUENCE: 165

Asn Lys Thr Val Leu Pro Val Thr Ile Met Ser Gly Leu Val Phe His
 1               5                  10                  15

Ser Gln Pro Ile Asn Asp
            20

<210> SEQ ID NO 166
<211> LENGTH: 25
<212> TYPE: PRT
<213> ORGANISM: Human T-cell lymphotropic virus
<220> FEATURE:
<221> NAME/KEY: VARIANT
<222> LOCATION: (1)
<223> OTHER INFORMATION: modified site : Bio

<400> SEQUENCE: 166

Xaa Gly Gly Val Leu Tyr Ser Pro Asn Val Ser Val Pro Ser Ser Ser
 1               5                  10                  15

Ser Thr Leu Leu Tyr Pro Ser Leu Ala
            20                  25

<210> SEQ ID NO 167
<211> LENGTH: 24
<212> TYPE: PRT
<213> ORGANISM: Human T-cell lymphotropic virus -continued

```
<220> FEATURE:
<221> NAME/KEY: VARIANT
<222> LOCATION: (1)
<223> OTHER INFORMATION: modified site : Bio

<400> SEQUENCE: 167

Xaa Gly Gly Tyr Thr Cys Ile Val Cys Ile Asp Arg Ala Ser Leu Ser
 1               5                  10                  15

Thr Trp His Val Leu Tyr Ser Pro
            20

<210> SEQ ID NO 168
<211> LENGTH: 25
<212> TYPE: PRT
<213> ORGANISM: Human T-cell lymphotropic virus
<220> FEATURE:
<221> NAME/KEY: VARIANT
<222> LOCATION: (1)
<223> OTHER INFORMATION: modified site

<400> SEQUENCE: 168

Xaa Gly Gly Asn Ser Leu Ile Leu Pro Pro Phe Ser Leu Ser Pro Val
 1               5                  10                  15

Pro Thr Leu Gly Ser Arg Ser Arg Arg
            20                  25

<210> SEQ ID NO 169
<211> LENGTH: 39
<212> TYPE: PRT
<213> ORGANISM: Human T-cell lymphotropic virus
<220> FEATURE:
<221> NAME/KEY: VARIANT
<222> LOCATION: (1)
<223> OTHER INFORMATION: modified site : Bio

<400> SEQUENCE: 169

Xaa Gly Gly Asp Ala Pro Gly Tyr Asp Pro Ile Trp Phe Leu Asn Thr
 1               5                  10                  15

Glu Pro Ser Gln Leu Pro Pro Thr Ala Pro Pro Leu Leu Pro His Ser
            20                  25                  30

Asn Leu Asp His Ile Leu Glu
        35

<210> SEQ ID NO 170
<211> LENGTH: 34
<212> TYPE: PRT
<213> ORGANISM: Human T-cell lymphotropic virus
<220> FEATURE:
<221> NAME/KEY: VARIANT
<222> LOCATION: (1)
<223> OTHER INFORMATION: modified site : Bio

<400> SEQUENCE: 170

Xaa Gly Gly Gln Tyr Ala Ala Gln Asn Arg Arg Gly Leu Asp Leu Leu
 1               5                  10                  15

Phe Trp Glu Gln Gly Gly Leu Cys Lys Ala Leu Gln Glu Gln Cys Arg
            20                  25                  30

Phe Pro

<210> SEQ ID NO 171
<211> LENGTH: 34
<212> TYPE: PRT
<213> ORGANISM: Human T-cell lymphotropic virus
<220> FEATURE:
<221> NAME/KEY: VARIANT
```

```
<222> LOCATION: (1)
<223> OTHER INFORMATION: modified site : Bio

<400> SEQUENCE: 171

Xaa Gly Gly Pro Pro Pro Pro Ser Ser Pro Thr His Asp Pro Pro Asp
  1               5                  10                  15

Ser Asp Pro Gln Ile Pro Pro Pro Tyr Val Glu Pro Thr Ala Pro Gln
             20                  25                  30

Val Leu

<210> SEQ ID NO 172
<211> LENGTH: 21
<212> TYPE: PRT
<213> ORGANISM: Human T-cell lymphotropic virus
<220> FEATURE:
<221> NAME/KEY: VARIANT
<222> LOCATION: (1)
<223> OTHER INFORMATION: modified site : Bio

<400> SEQUENCE: 172

Xaa Gly Gly Lys Lys Pro Asn Arg Gln Gly Leu Gly Tyr Tyr Ser Pro
  1               5                  10                  15

Ser Tyr Asn Asp Pro
             20

<210> SEQ ID NO 173
<211> LENGTH: 39
<212> TYPE: PRT
<213> ORGANISM: Human T-cell lymphotropic virus
<220> FEATURE:
<221> NAME/KEY: VARIANT
<222> LOCATION: (1)
<223> OTHER INFORMATION: modified site

<400> SEQUENCE: 173

Xaa Gly Gly Asp Ala Pro Gly Tyr Asp Pro Leu Trp Phe Ile Thr Ser
  1               5                  10                  15

Glu Pro Thr Gln Pro Pro Pro Thr Ser Pro Pro Leu Val His Asp Ser
             20                  25                  30

Asp Leu Glu His Val Leu Thr
         35

<210> SEQ ID NO 174
<211> LENGTH: 41
<212> TYPE: PRT
<213> ORGANISM: Human T-cell lymphotropic virus
<220> FEATURE:
<221> NAME/KEY: VARIANT
<222> LOCATION: (1)
<223> OTHER INFORMATION: modified site : Bio

<400> SEQUENCE: 174

Xaa Gly Gly Tyr Ser Cys Met Val Cys Val Asp Arg Ser Ser Leu Ser
  1               5                  10                  15

Ser Trp His Val Leu Tyr Thr Pro Asn Ile Ser Ile Pro Gln Gln Thr
             20                  25                  30

Ser Ser Arg Thr Ile Leu Phe Pro Ser
         35                  40

<210> SEQ ID NO 175
<211> LENGTH: 33
<212> TYPE: PRT
<213> ORGANISM: Human T-cell lymphotropic virus
```

```
<220> FEATURE:
<221> NAME/KEY: VARIANT
<222> LOCATION: (1)
<223> OTHER INFORMATION: modified site : Bio

<400> SEQUENCE: 175

Xaa Gly Gly Pro Thr Thr Thr Pro Pro Pro Pro Pro Pro Ser Pro
 1               5                  10                  15

Glu Ala His Val Pro Pro Pro Tyr Val Glu Pro Thr Thr Thr Gln Cys
             20                  25                  30

Phe

<210> SEQ ID NO 176
<211> LENGTH: 14
<212> TYPE: PRT
<213> ORGANISM: Human immunodeficiency virus
<220> FEATURE:
<221> NAME/KEY: VARIANT
<222> LOCATION: (1)
<223> OTHER INFORMATION: modified site : Bio

<400> SEQUENCE: 176

Xaa Gly Gly Gly Ile Trp Gly Cys Ser Gly Lys Leu Ile Cys
 1               5                  10

<210> SEQ ID NO 177
<211> LENGTH: 13
<212> TYPE: PRT
<213> ORGANISM: Human immunodeficiency virus
<220> FEATURE:
<221> NAME/KEY: VARIANT
<222> LOCATION: (13)
<223> OTHER INFORMATION: modified site : Lys (Bio)

<400> SEQUENCE: 177

Ile Trp Gly Cys Ser Gly Lys Leu Ile Cys Gly Gly Xaa
 1               5                  10

<210> SEQ ID NO 178
<211> LENGTH: 9
<212> TYPE: PRT
<213> ORGANISM: Hepatitis C virus

<400> SEQUENCE: 178

Met Ser Thr Ile Pro Lys Pro Gln Arg
 1               5

<210> SEQ ID NO 179
<211> LENGTH: 9
<212> TYPE: PRT
<213> ORGANISM: Hepatitis C virus

<400> SEQUENCE: 179

Ser Thr Ile Pro Lys Pro Gln Arg Lys
 1               5

<210> SEQ ID NO 180
<211> LENGTH: 9
<212> TYPE: PRT
<213> ORGANISM: Hepatitis C virus

<400> SEQUENCE: 180

Thr Ile Pro Lys Pro Gln Arg Lys Thr
 1               5
```

<210> SEQ ID NO 181
<211> LENGTH: 9
<212> TYPE: PRT
<213> ORGANISM: Hepatitis C virus

<400> SEQUENCE: 181

Ile Pro Lys Pro Gln Arg Lys Thr Lys
 1               5

<210> SEQ ID NO 182
<211> LENGTH: 9
<212> TYPE: PRT
<213> ORGANISM: Hepatitis C virus

<400> SEQUENCE: 182

Pro Lys Pro Gln Arg Lys Thr Lys Arg
 1               5

<210> SEQ ID NO 183
<211> LENGTH: 9
<212> TYPE: PRT
<213> ORGANISM: Hepatitis C virus

<400> SEQUENCE: 183

Lys Pro Gln Arg Lys Thr Lys Arg Asn
 1               5

<210> SEQ ID NO 184
<211> LENGTH: 9
<212> TYPE: PRT
<213> ORGANISM: Hepatitis C virus

<400> SEQUENCE: 184

Pro Gln Arg Lys Thr Lys Arg Asn Thr
 1               5

<210> SEQ ID NO 185
<211> LENGTH: 9
<212> TYPE: PRT
<213> ORGANISM: Hepatitis C virus

<400> SEQUENCE: 185

Gln Arg Lys Thr Lys Arg Asn Thr Asn
 1               5

<210> SEQ ID NO 186
<211> LENGTH: 9
<212> TYPE: PRT
<213> ORGANISM: Hepatitis C virus

<400> SEQUENCE: 186

Arg Lys Thr Lys Arg Asn Thr Asn Arg
 1               5

<210> SEQ ID NO 187
<211> LENGTH: 9
<212> TYPE: PRT
<213> ORGANISM: Hepatitis C virus

<400> SEQUENCE: 187

Lys Thr Lys Arg Asn Thr Asn Arg Arg
 1               5

<210> SEQ ID NO 188
<211> LENGTH: 9
<212> TYPE: PRT
<213> ORGANISM: Hepatitis C virus

<400> SEQUENCE: 188

Thr Lys Arg Asn Thr Asn Arg Arg Pro
 1               5

<210> SEQ ID NO 189
<211> LENGTH: 9
<212> TYPE: PRT
<213> ORGANISM: Hepatitis C virus

<400> SEQUENCE: 189

Lys Arg Asn Thr Asn Arg Arg Pro Gln
 1               5

<210> SEQ ID NO 190
<211> LENGTH: 9
<212> TYPE: PRT
<213> ORGANISM: Hepatitis C virus

<400> SEQUENCE: 190

Arg Asn Thr Asn Arg Arg Pro Gln Asp
 1               5

<210> SEQ ID NO 191
<211> LENGTH: 9
<212> TYPE: PRT
<213> ORGANISM: Hepatitis C virus

<400> SEQUENCE: 191

Asn Thr Asn Arg Arg Pro Gln Asp Val
 1               5

<210> SEQ ID NO 192
<211> LENGTH: 9
<212> TYPE: PRT
<213> ORGANISM: Hepatitis C virus

<400> SEQUENCE: 192

Thr Asn Arg Arg Pro Gln Asp Val Lys
 1               5

<210> SEQ ID NO 193
<211> LENGTH: 9
<212> TYPE: PRT
<213> ORGANISM: Hepatitis C virus

<400> SEQUENCE: 193

Asn Arg Arg Pro Gln Asp Val Lys Phe
 1               5

<210> SEQ ID NO 194
<211> LENGTH: 9
<212> TYPE: PRT
<213> ORGANISM: Hepatitis C virus

<400> SEQUENCE: 194

Arg Arg Pro Gln Asp Val Lys Phe Pro
 1               5

<210> SEQ ID NO 195

-continued

```
<211> LENGTH: 9
<212> TYPE: PRT
<213> ORGANISM: Hepatitis C virus

<400> SEQUENCE: 195

Arg Pro Gln Asp Val Lys Phe Pro Gly
1 5

<210> SEQ ID NO 196
<211> LENGTH: 9
<212> TYPE: PRT
<213> ORGANISM: Hepatitis C virus

<400> SEQUENCE: 196

Pro Gln Asp Val Lys Phe Pro Gly Gly
1 5

<210> SEQ ID NO 197
<211> LENGTH: 9
<212> TYPE: PRT
<213> ORGANISM: Hepatitis C virus

<400> SEQUENCE: 197

Gln Asp Val Lys Phe Pro Gly Gly Gly
1 5

<210> SEQ ID NO 198
<211> LENGTH: 9
<212> TYPE: PRT
<213> ORGANISM: Hepatitis C virus

<400> SEQUENCE: 198

Asp Val Lys Phe Pro Gly Gly Gly Gln
1 5

<210> SEQ ID NO 199
<211> LENGTH: 9
<212> TYPE: PRT
<213> ORGANISM: Hepatitis C virus

<400> SEQUENCE: 199

Val Lys Phe Pro Gly Gly Gly Gln Ile
1 5

<210> SEQ ID NO 200
<211> LENGTH: 9
<212> TYPE: PRT
<213> ORGANISM: Hepatitis C virus

<400> SEQUENCE: 200

Lys Phe Pro Gly Gly Gly Gln Ile Val
1 5

<210> SEQ ID NO 201
<211> LENGTH: 9
<212> TYPE: PRT
<213> ORGANISM: Hepatitis C virus

<400> SEQUENCE: 201

Phe Pro Gly Gly Gly Gln Ile Val Gly
1 5

<210> SEQ ID NO 202
<211> LENGTH: 9
<212> TYPE: PRT

<213> ORGANISM: Hepatitis C virus

<400> SEQUENCE: 202

Pro Gly Gly Gly Gln Ile Val Gly Gly
1 5

<210> SEQ ID NO 203
<211> LENGTH: 9
<212> TYPE: PRT
<213> ORGANISM: Hepatitis C virus

<400> SEQUENCE: 203

Gly Gly Gly Gln Ile Val Gly Gly Val
1 5

<210> SEQ ID NO 204
<211> LENGTH: 9
<212> TYPE: PRT
<213> ORGANISM: Hepatitis C virus

<400> SEQUENCE: 204

Gly Gly Gln Ile Val Gly Gly Val Tyr
1 5

<210> SEQ ID NO 205
<211> LENGTH: 9
<212> TYPE: PRT
<213> ORGANISM: Hepatitis C virus

<400> SEQUENCE: 205

Gly Gln Ile Val Gly Gly Val Tyr Leu
1 5

<210> SEQ ID NO 206
<211> LENGTH: 9
<212> TYPE: PRT
<213> ORGANISM: Hepatitis C virus

<400> SEQUENCE: 206

Gln Ile Val Gly Gly Val Tyr Leu Leu
1 5

<210> SEQ ID NO 207
<211> LENGTH: 9
<212> TYPE: PRT
<213> ORGANISM: Hepatitis C virus

<400> SEQUENCE: 207

Ile Val Gly Gly Val Tyr Leu Leu Pro
1 5

<210> SEQ ID NO 208
<211> LENGTH: 9
<212> TYPE: PRT
<213> ORGANISM: Hepatitis C virus

<400> SEQUENCE: 208

Val Gly Gly Val Tyr Leu Leu Pro Arg
1 5

<210> SEQ ID NO 209
<211> LENGTH: 9
<212> TYPE: PRT
<213> ORGANISM: Hepatitis C virus

```
<400> SEQUENCE: 209

Gly Gly Val Tyr Leu Leu Pro Arg Arg
  1               5

<210> SEQ ID NO 210
<211> LENGTH: 9
<212> TYPE: PRT
<213> ORGANISM: Hepatitis C virus

<400> SEQUENCE: 210

Gly Val Tyr Leu Leu Pro Arg Arg Gly
  1               5

<210> SEQ ID NO 211
<211> LENGTH: 9
<212> TYPE: PRT
<213> ORGANISM: Hepatitis C virus

<400> SEQUENCE: 211

Val Tyr Leu Leu Pro Arg Arg Gly Pro
  1               5

<210> SEQ ID NO 212
<211> LENGTH: 9
<212> TYPE: PRT
<213> ORGANISM: Hepatitis C virus

<400> SEQUENCE: 212

Tyr Leu Leu Pro Arg Arg Gly Pro Arg
  1               5

<210> SEQ ID NO 213
<211> LENGTH: 9
<212> TYPE: PRT
<213> ORGANISM: Hepatitis C virus

<400> SEQUENCE: 213

Leu Leu Pro Arg Arg Gly Pro Arg Leu
  1               5

<210> SEQ ID NO 214
<211> LENGTH: 9
<212> TYPE: PRT
<213> ORGANISM: Hepatitis C virus

<400> SEQUENCE: 214

Leu Pro Arg Arg Gly Pro Arg Leu Gly
  1               5

<210> SEQ ID NO 215
<211> LENGTH: 9
<212> TYPE: PRT
<213> ORGANISM: Hepatitis C virus

<400> SEQUENCE: 215

Pro Arg Arg Gly Pro Arg Leu Gly Val
  1               5

<210> SEQ ID NO 216
<211> LENGTH: 9
<212> TYPE: PRT
<213> ORGANISM: Hepatitis C virus

<400> SEQUENCE: 216
```

Arg Arg Gly Pro Arg Leu Gly Val Arg
1               5

<210> SEQ ID NO 217
<211> LENGTH: 9
<212> TYPE: PRT
<213> ORGANISM: Hepatitis C virus

<400> SEQUENCE: 217

Arg Gly Pro Arg Leu Gly Val Arg Ala
1               5

<210> SEQ ID NO 218
<211> LENGTH: 9
<212> TYPE: PRT
<213> ORGANISM: Hepatitis C virus

<400> SEQUENCE: 218

Gly Pro Arg Leu Gly Val Arg Ala Thr
1               5

<210> SEQ ID NO 219
<211> LENGTH: 9
<212> TYPE: PRT
<213> ORGANISM: Hepatitis C virus

<400> SEQUENCE: 219

Pro Arg Leu Gly Val Arg Ala Thr Arg
1               5

<210> SEQ ID NO 220
<211> LENGTH: 9
<212> TYPE: PRT
<213> ORGANISM: Hepatitis C virus

<400> SEQUENCE: 220

Arg Leu Gly Val Arg Ala Thr Arg Lys
1               5

<210> SEQ ID NO 221
<211> LENGTH: 9
<212> TYPE: PRT
<213> ORGANISM: Hepatitis C virus

<400> SEQUENCE: 221

Leu Gly Val Arg Ala Thr Arg Lys Thr
1               5

<210> SEQ ID NO 222
<211> LENGTH: 9
<212> TYPE: PRT
<213> ORGANISM: Hepatitis C virus

<400> SEQUENCE: 222

Gly Val Arg Ala Thr Arg Lys Thr Ser
1               5

<210> SEQ ID NO 223
<211> LENGTH: 9
<212> TYPE: PRT
<213> ORGANISM: Hepatitis C virus

<400> SEQUENCE: 223

Val Arg Ala Thr Arg Lys Thr Ser Glu
1               5

<210> SEQ ID NO 224
<211> LENGTH: 9
<212> TYPE: PRT
<213> ORGANISM: Hepatitis C virus

<400> SEQUENCE: 224

Arg Ala Thr Arg Lys Thr Ser Glu Arg
 1               5

<210> SEQ ID NO 225
<211> LENGTH: 9
<212> TYPE: PRT
<213> ORGANISM: Hepatitis C virus

<400> SEQUENCE: 225

Ala Thr Arg Lys Thr Ser Glu Arg Ser
 1               5

<210> SEQ ID NO 226
<211> LENGTH: 9
<212> TYPE: PRT
<213> ORGANISM: Hepatitis C virus

<400> SEQUENCE: 226

Thr Arg Lys Thr Ser Glu Arg Ser Gln
 1               5

<210> SEQ ID NO 227
<211> LENGTH: 9
<212> TYPE: PRT
<213> ORGANISM: Hepatitis C virus

<400> SEQUENCE: 227

Arg Lys Thr Ser Glu Arg Ser Gln Pro
 1               5

<210> SEQ ID NO 228
<211> LENGTH: 9
<212> TYPE: PRT
<213> ORGANISM: Hepatitis C virus

<400> SEQUENCE: 228

Lys Thr Ser Glu Arg Ser Gln Pro Arg
 1               5

<210> SEQ ID NO 229
<211> LENGTH: 9
<212> TYPE: PRT
<213> ORGANISM: Hepatitis C virus

<400> SEQUENCE: 229

Thr Ser Glu Arg Ser Gln Pro Arg Gly
 1               5

<210> SEQ ID NO 230
<211> LENGTH: 9
<212> TYPE: PRT
<213> ORGANISM: Hepatitis C virus

<400> SEQUENCE: 230

Ser Glu Arg Ser Gln Pro Arg Gly Arg
 1               5

<210> SEQ ID NO 231
<211> LENGTH: 9
<212> TYPE: PRT
<213> ORGANISM: Hepatitis C virus

<400> SEQUENCE: 231

Glu Arg Ser Gln Pro Arg Gly Arg Arg
 1               5

<210> SEQ ID NO 232
<211> LENGTH: 9
<212> TYPE: PRT
<213> ORGANISM: Hepatitis C virus

<400> SEQUENCE: 232

Arg Ser Gln Pro Arg Gly Arg Arg Gln
 1               5

<210> SEQ ID NO 233
<211> LENGTH: 9
<212> TYPE: PRT
<213> ORGANISM: Hepatitis C virus

<400> SEQUENCE: 233

Ser Gln Pro Arg Gly Arg Arg Gln Pro
 1               5

<210> SEQ ID NO 234
<211> LENGTH: 9
<212> TYPE: PRT
<213> ORGANISM: Hepatitis C virus

<400> SEQUENCE: 234

Gln Pro Arg Gly Arg Arg Gln Pro Ile
 1               5

<210> SEQ ID NO 235
<211> LENGTH: 9
<212> TYPE: PRT
<213> ORGANISM: Hepatitis C virus

<400> SEQUENCE: 235

Pro Arg Gly Arg Arg Gln Pro Ile Pro
 1               5

<210> SEQ ID NO 236
<211> LENGTH: 9
<212> TYPE: PRT
<213> ORGANISM: Hepatitis C virus

<400> SEQUENCE: 236

Arg Gly Arg Arg Gln Pro Ile Pro Lys
 1               5

<210> SEQ ID NO 237
<211> LENGTH: 9
<212> TYPE: PRT
<213> ORGANISM: Hepatitis C virus

<400> SEQUENCE: 237

Gly Arg Arg Gln Pro Ile Pro Lys Val
 1               5

<210> SEQ ID NO 238
<211> LENGTH: 9

<212> TYPE: PRT
<213> ORGANISM: Hepatitis C virus

<400> SEQUENCE: 238

Arg Arg Gln Pro Ile Pro Lys Val Arg
 1               5

<210> SEQ ID NO 239
<211> LENGTH: 9
<212> TYPE: PRT
<213> ORGANISM: Hepatitis C virus

<400> SEQUENCE: 239

Arg Gln Pro Ile Pro Lys Val Arg Arg
 1               5

<210> SEQ ID NO 240
<211> LENGTH: 9
<212> TYPE: PRT
<213> ORGANISM: Hepatitis C virus

<400> SEQUENCE: 240

Gln Pro Ile Pro Lys Val Arg Arg Pro
 1               5

<210> SEQ ID NO 241
<211> LENGTH: 9
<212> TYPE: PRT
<213> ORGANISM: Hepatitis C virus

<400> SEQUENCE: 241

Pro Ile Pro Lys Val Arg Arg Pro Glu
 1               5

<210> SEQ ID NO 242
<211> LENGTH: 9
<212> TYPE: PRT
<213> ORGANISM: Hepatitis C virus

<400> SEQUENCE: 242

Ile Pro Lys Val Arg Arg Pro Glu Gly
 1               5

<210> SEQ ID NO 243
<211> LENGTH: 9
<212> TYPE: PRT
<213> ORGANISM: Hepatitis C virus

<400> SEQUENCE: 243

Pro Lys Val Arg Arg Pro Glu Gly Arg
 1               5

<210> SEQ ID NO 244
<211> LENGTH: 9
<212> TYPE: PRT
<213> ORGANISM: Hepatitis C virus

<400> SEQUENCE: 244

Lys Val Arg Arg Pro Glu Gly Arg Thr
 1               5

<210> SEQ ID NO 245
<211> LENGTH: 9
<212> TYPE: PRT
<213> ORGANISM: Hepatitis C virus

<400> SEQUENCE: 245

Val Arg Arg Pro Glu Gly Arg Thr Trp
 1               5

<210> SEQ ID NO 246
<211> LENGTH: 9
<212> TYPE: PRT
<213> ORGANISM: Hepatitis C virus

<400> SEQUENCE: 246

Arg Arg Pro Glu Gly Arg Thr Trp Ala
 1               5

<210> SEQ ID NO 247
<211> LENGTH: 9
<212> TYPE: PRT
<213> ORGANISM: Hepatitis C virus

<400> SEQUENCE: 247

Arg Pro Glu Gly Arg Thr Trp Ala Gln
 1               5

<210> SEQ ID NO 248
<211> LENGTH: 9
<212> TYPE: PRT
<213> ORGANISM: Hepatitis C virus

<400> SEQUENCE: 248

Pro Glu Gly Arg Thr Trp Ala Gln Pro
 1               5

<210> SEQ ID NO 249
<211> LENGTH: 9
<212> TYPE: PRT
<213> ORGANISM: Hepatitis C virus

<400> SEQUENCE: 249

Glu Gly Arg Thr Trp Ala Gln Pro Gly
 1               5

<210> SEQ ID NO 250
<211> LENGTH: 9
<212> TYPE: PRT
<213> ORGANISM: Hepatitis C virus

<400> SEQUENCE: 250

Gly Arg Thr Trp Ala Gln Pro Gly Tyr
 1               5

<210> SEQ ID NO 251
<211> LENGTH: 9
<212> TYPE: PRT
<213> ORGANISM: Hepatitis C virus

<400> SEQUENCE: 251

Arg Thr Trp Ala Gln Pro Gly Tyr Pro
 1               5

<210> SEQ ID NO 252
<211> LENGTH: 9
<212> TYPE: PRT
<213> ORGANISM: Hepatitis C virus

<400> SEQUENCE: 252

```
Thr Trp Ala Gln Pro Gly Tyr Pro Trp
 1               5
```

<210> SEQ ID NO 253
<211> LENGTH: 9
<212> TYPE: PRT
<213> ORGANISM: Hepatitis C virus

<400> SEQUENCE: 253

```
Trp Ala Gln Pro Gly Tyr Pro Trp Pro
 1               5
```

<210> SEQ ID NO 254
<211> LENGTH: 9
<212> TYPE: PRT
<213> ORGANISM: Hepatitis C virus

<400> SEQUENCE: 254

```
Ala Gln Pro Gly Tyr Pro Trp Pro Leu
 1               5
```

<210> SEQ ID NO 255
<211> LENGTH: 9
<212> TYPE: PRT
<213> ORGANISM: Hepatitis C virus

<400> SEQUENCE: 255

```
Gln Pro Gly Tyr Pro Trp Pro Leu Tyr
 1               5
```

<210> SEQ ID NO 256
<211> LENGTH: 9
<212> TYPE: PRT
<213> ORGANISM: Hepatitis C virus

<400> SEQUENCE: 256

```
Pro Gly Tyr Pro Trp Pro Leu Tyr Gly
 1               5
```

<210> SEQ ID NO 257
<211> LENGTH: 9
<212> TYPE: PRT
<213> ORGANISM: Hepatitis C virus

<400> SEQUENCE: 257

```
Gly Tyr Pro Trp Pro Leu Tyr Gly Asn
 1               5
```

<210> SEQ ID NO 258
<211> LENGTH: 9
<212> TYPE: PRT
<213> ORGANISM: Hepatitis C virus

<400> SEQUENCE: 258

```
Leu Ser Gly Lys Pro Ala Ile Ile Pro
 1               5
```

<210> SEQ ID NO 259
<211> LENGTH: 9
<212> TYPE: PRT
<213> ORGANISM: Hepatitis C virus

<400> SEQUENCE: 259

```
Ser Gly Lys Pro Ala Ile Ile Pro Asp
```

-continued 1 5

<210> SEQ ID NO 260
<211> LENGTH: 9
<212> TYPE: PRT
<213> ORGANISM: Hepatitis C virus

<400> SEQUENCE: 260

Gly Lys Pro Ala Ile Ile Pro Asp Arg
1 5

<210> SEQ ID NO 261
<211> LENGTH: 9
<212> TYPE: PRT
<213> ORGANISM: Hepatitis C virus

<400> SEQUENCE: 261

Lys Pro Ala Ile Ile Pro Asp Arg Glu
1 5

<210> SEQ ID NO 262
<211> LENGTH: 9
<212> TYPE: PRT
<213> ORGANISM: Hepatitis C virus

<400> SEQUENCE: 262

Pro Ala Ile Ile Pro Asp Arg Glu Val
1 5

<210> SEQ ID NO 263
<211> LENGTH: 9
<212> TYPE: PRT
<213> ORGANISM: Hepatitis C virus

<400> SEQUENCE: 263

Ala Ile Ile Pro Asp Arg Glu Val Leu
1 5

<210> SEQ ID NO 264
<211> LENGTH: 9
<212> TYPE: PRT
<213> ORGANISM: Hepatitis C virus

<400> SEQUENCE: 264

Ile Ile Pro Asp Arg Glu Val Leu Tyr
1 5

<210> SEQ ID NO 265
<211> LENGTH: 9
<212> TYPE: PRT
<213> ORGANISM: Hepatitis C virus

<400> SEQUENCE: 265

Ile Pro Asp Arg Glu Val Leu Tyr Arg
1 5

<210> SEQ ID NO 266
<211> LENGTH: 9
<212> TYPE: PRT
<213> ORGANISM: Hepatitis C virus

<400> SEQUENCE: 266

Pro Asp Arg Glu Val Leu Tyr Arg Glu
1 5

<210> SEQ ID NO 267
<211> LENGTH: 9
<212> TYPE: PRT
<213> ORGANISM: Hepatitis C virus

<400> SEQUENCE: 267

Asp Arg Glu Val Leu Tyr Arg Glu Phe
 1               5

<210> SEQ ID NO 268
<211> LENGTH: 9
<212> TYPE: PRT
<213> ORGANISM: Hepatitis C virus

<400> SEQUENCE: 268

Arg Glu Val Leu Tyr Arg Glu Phe Asp
 1               5

<210> SEQ ID NO 269
<211> LENGTH: 9
<212> TYPE: PRT
<213> ORGANISM: Hepatitis C virus

<400> SEQUENCE: 269

Glu Val Leu Tyr Arg Glu Phe Asp Glu
 1               5

<210> SEQ ID NO 270
<211> LENGTH: 9
<212> TYPE: PRT
<213> ORGANISM: Hepatitis C virus

<400> SEQUENCE: 270

Val Leu Tyr Arg Glu Phe Asp Glu Met
 1               5

<210> SEQ ID NO 271
<211> LENGTH: 9
<212> TYPE: PRT
<213> ORGANISM: Hepatitis C virus

<400> SEQUENCE: 271

Leu Tyr Arg Glu Phe Asp Glu Met Glu
 1               5

<210> SEQ ID NO 272
<211> LENGTH: 9
<212> TYPE: PRT
<213> ORGANISM: Hepatitis C virus

<400> SEQUENCE: 272

Tyr Arg Glu Phe Asp Glu Met Glu Glu
 1               5

<210> SEQ ID NO 273
<211> LENGTH: 9
<212> TYPE: PRT
<213> ORGANISM: Hepatitis C virus

<400> SEQUENCE: 273

Arg Glu Phe Asp Glu Met Glu Glu Cys
 1               5

<210> SEQ ID NO 274

```
<211> LENGTH: 9
<212> TYPE: PRT
<213> ORGANISM: Hepatitis C virus

<400> SEQUENCE: 274

Glu Phe Asp Glu Met Glu Glu Cys Ser
 1               5

<210> SEQ ID NO 275
<211> LENGTH: 9
<212> TYPE: PRT
<213> ORGANISM: Hepatitis C virus

<400> SEQUENCE: 275

Phe Asp Glu Met Glu Glu Cys Ser Gln
 1               5

<210> SEQ ID NO 276
<211> LENGTH: 9
<212> TYPE: PRT
<213> ORGANISM: Hepatitis C virus

<400> SEQUENCE: 276

Asp Glu Met Glu Glu Cys Ser Gln His
 1               5

<210> SEQ ID NO 277
<211> LENGTH: 9
<212> TYPE: PRT
<213> ORGANISM: Hepatitis C virus

<400> SEQUENCE: 277

Glu Met Glu Glu Cys Ser Gln His Leu
 1               5

<210> SEQ ID NO 278
<211> LENGTH: 9
<212> TYPE: PRT
<213> ORGANISM: Hepatitis C virus

<400> SEQUENCE: 278

Met Glu Glu Cys Ser Gln His Leu Pro
 1               5

<210> SEQ ID NO 279
<211> LENGTH: 9
<212> TYPE: PRT
<213> ORGANISM: Hepatitis C virus

<400> SEQUENCE: 279

Glu Glu Cys Ser Gln His Leu Pro Tyr
 1               5

<210> SEQ ID NO 280
<211> LENGTH: 9
<212> TYPE: PRT
<213> ORGANISM: Hepatitis C virus

<400> SEQUENCE: 280

Glu Cys Ser Gln His Leu Pro Tyr Ile
 1               5

<210> SEQ ID NO 281
<211> LENGTH: 9
<212> TYPE: PRT
```

-continued

<213> ORGANISM: Hepatitis C virus

<400> SEQUENCE: 281

Cys Ser Gln His Leu Pro Tyr Ile Glu
1 5

<210> SEQ ID NO 282
<211> LENGTH: 9
<212> TYPE: PRT
<213> ORGANISM: Hepatitis C virus

<400> SEQUENCE: 282

Ser Gln His Leu Pro Tyr Ile Glu Gln
1 5

<210> SEQ ID NO 283
<211> LENGTH: 9
<212> TYPE: PRT
<213> ORGANISM: Hepatitis C virus

<400> SEQUENCE: 283

Gln His Leu Pro Tyr Ile Glu Gln Gly
1 5

<210> SEQ ID NO 284
<211> LENGTH: 9
<212> TYPE: PRT
<213> ORGANISM: Hepatitis C virus

<400> SEQUENCE: 284

His Leu Pro Tyr Ile Glu Gln Gly Met
1 5

<210> SEQ ID NO 285
<211> LENGTH: 9
<212> TYPE: PRT
<213> ORGANISM: Hepatitis C virus

<400> SEQUENCE: 285

Leu Pro Tyr Ile Glu Gln Gly Met Met
1 5

<210> SEQ ID NO 286
<211> LENGTH: 9
<212> TYPE: PRT
<213> ORGANISM: Hepatitis C virus

<400> SEQUENCE: 286

Pro Tyr Ile Glu Gln Gly Met Met Leu
1 5

<210> SEQ ID NO 287
<211> LENGTH: 9
<212> TYPE: PRT
<213> ORGANISM: Hepatitis C virus

<400> SEQUENCE: 287

Tyr Ile Glu Gln Gly Met Met Leu Ala
1 5

<210> SEQ ID NO 288
<211> LENGTH: 9
<212> TYPE: PRT
<213> ORGANISM: Hepatitis C virus

```
<400> SEQUENCE: 288

Ile Glu Gln Gly Met Met Leu Ala Glu
 1               5

<210> SEQ ID NO 289
<211> LENGTH: 9
<212> TYPE: PRT
<213> ORGANISM: Hepatitis C virus

<400> SEQUENCE: 289

Glu Gln Gly Met Met Leu Ala Glu Gln
 1               5

<210> SEQ ID NO 290
<211> LENGTH: 9
<212> TYPE: PRT
<213> ORGANISM: Hepatitis C virus

<400> SEQUENCE: 290

Gln Gly Met Met Leu Ala Glu Gln Phe
 1               5

<210> SEQ ID NO 291
<211> LENGTH: 9
<212> TYPE: PRT
<213> ORGANISM: Hepatitis C virus

<400> SEQUENCE: 291

Gly Met Met Leu Ala Glu Gln Phe Lys
 1               5

<210> SEQ ID NO 292
<211> LENGTH: 9
<212> TYPE: PRT
<213> ORGANISM: Hepatitis C virus

<400> SEQUENCE: 292

Met Met Leu Ala Glu Gln Phe Lys Gln
 1               5

<210> SEQ ID NO 293
<211> LENGTH: 9
<212> TYPE: PRT
<213> ORGANISM: Hepatitis C virus

<400> SEQUENCE: 293

Met Leu Ala Glu Gln Phe Lys Gln Lys
 1               5

<210> SEQ ID NO 294
<211> LENGTH: 9
<212> TYPE: PRT
<213> ORGANISM: Hepatitis C virus

<400> SEQUENCE: 294

Leu Ala Glu Gln Phe Lys Gln Lys Ala
 1               5

<210> SEQ ID NO 295
<211> LENGTH: 9
<212> TYPE: PRT
<213> ORGANISM: Hepatitis C virus

<400> SEQUENCE: 295
```

-continued

```
Ala Glu Gln Phe Lys Gln Lys Ala Leu
 1               5

<210> SEQ ID NO 296
<211> LENGTH: 9
<212> TYPE: PRT
<213> ORGANISM: Hepatitis C virus

<400> SEQUENCE: 296

Glu Gln Phe Lys Gln Lys Ala Leu Gly
 1               5

<210> SEQ ID NO 297
<211> LENGTH: 9
<212> TYPE: PRT
<213> ORGANISM: Hepatitis C virus

<400> SEQUENCE: 297

Gln Phe Lys Gln Lys Ala Leu Gly Leu
 1               5

<210> SEQ ID NO 298
<211> LENGTH: 9
<212> TYPE: PRT
<213> ORGANISM: Hepatitis C virus

<400> SEQUENCE: 298

Phe Lys Gln Lys Ala Leu Gly Leu Leu
 1               5

<210> SEQ ID NO 299
<211> LENGTH: 9
<212> TYPE: PRT
<213> ORGANISM: Hepatitis C virus

<400> SEQUENCE: 299

Lys Gln Lys Ala Leu Gly Leu Leu Gln
 1               5

<210> SEQ ID NO 300
<211> LENGTH: 9
<212> TYPE: PRT
<213> ORGANISM: Hepatitis C virus

<400> SEQUENCE: 300

Gln Lys Ala Leu Gly Leu Leu Gln Thr
 1               5

<210> SEQ ID NO 301
<211> LENGTH: 9
<212> TYPE: PRT
<213> ORGANISM: Hepatitis C virus

<400> SEQUENCE: 301

Lys Ala Leu Gly Leu Leu Gln Thr Ala
 1               5

<210> SEQ ID NO 302
<211> LENGTH: 9
<212> TYPE: PRT
<213> ORGANISM: Hepatitis C virus

<400> SEQUENCE: 302

Ala Leu Gly Leu Leu Gln Thr Ala Ser
 1               5
```

<210> SEQ ID NO 303
<211> LENGTH: 9
<212> TYPE: PRT
<213> ORGANISM: Hepatitis C virus

<400> SEQUENCE: 303

Leu Gly Leu Leu Gln Thr Ala Ser Arg
 1               5

<210> SEQ ID NO 304
<211> LENGTH: 9
<212> TYPE: PRT
<213> ORGANISM: Hepatitis C virus

<400> SEQUENCE: 304

Gly Leu Leu Gln Thr Ala Ser Arg Gln
 1               5

<210> SEQ ID NO 305
<211> LENGTH: 9
<212> TYPE: PRT
<213> ORGANISM: Hepatitis C virus

<400> SEQUENCE: 305

Leu Leu Gln Thr Ala Ser Arg Gln Ala
 1               5

<210> SEQ ID NO 306
<211> LENGTH: 9
<212> TYPE: PRT
<213> ORGANISM: Hepatitis C virus

<400> SEQUENCE: 306

Leu Gln Thr Ala Ser Arg Gln Ala Glu
 1               5

<210> SEQ ID NO 307
<211> LENGTH: 9
<212> TYPE: PRT
<213> ORGANISM: Hepatitis C virus

<400> SEQUENCE: 307

Gln Thr Ala Ser Arg Gln Ala Glu Val
 1               5

<210> SEQ ID NO 308
<211> LENGTH: 9
<212> TYPE: PRT
<213> ORGANISM: Hepatitis C virus

<400> SEQUENCE: 308

Thr Ala Ser Arg Gln Ala Glu Val Ile
 1               5

<210> SEQ ID NO 309
<211> LENGTH: 9
<212> TYPE: PRT
<213> ORGANISM: Hepatitis C virus

<400> SEQUENCE: 309

Ala Ser Arg Gln Ala Glu Val Ile Ala
 1               5

<210> SEQ ID NO 310
<211> LENGTH: 9
<212> TYPE: PRT
<213> ORGANISM: Hepatitis C virus

<400> SEQUENCE: 310

Ser Arg Gln Ala Glu Val Ile Ala Pro
 1               5

<210> SEQ ID NO 311
<211> LENGTH: 9
<212> TYPE: PRT
<213> ORGANISM: Hepatitis C virus

<400> SEQUENCE: 311

Arg Gln Ala Glu Val Ile Ala Pro Ala
 1               5

<210> SEQ ID NO 312
<211> LENGTH: 9
<212> TYPE: PRT
<213> ORGANISM: Hepatitis C virus

<400> SEQUENCE: 312

Gln Ala Glu Val Ile Ala Pro Ala Val
 1               5

<210> SEQ ID NO 313
<211> LENGTH: 9
<212> TYPE: PRT
<213> ORGANISM: Hepatitis C virus

<400> SEQUENCE: 313

Ala Glu Val Ile Ala Pro Ala Val Gln
 1               5

<210> SEQ ID NO 314
<211> LENGTH: 9
<212> TYPE: PRT
<213> ORGANISM: Hepatitis C virus

<400> SEQUENCE: 314

Glu Val Ile Ala Pro Ala Val Gln Thr
 1               5

<210> SEQ ID NO 315
<211> LENGTH: 9
<212> TYPE: PRT
<213> ORGANISM: Hepatitis C virus

<400> SEQUENCE: 315

Val Ile Ala Pro Ala Val Gln Thr Asn
 1               5

<210> SEQ ID NO 316
<211> LENGTH: 9
<212> TYPE: PRT
<213> ORGANISM: Hepatitis C virus

<400> SEQUENCE: 316

Ile Ala Pro Ala Val Gln Thr Asn Trp
 1               5

<210> SEQ ID NO 317
<211> LENGTH: 9

-continued

<212> TYPE: PRT
<213> ORGANISM: Hepatitis C virus

<400> SEQUENCE: 317

Ala Pro Ala Val Gln Thr Asn Trp Gln
1 5

<210> SEQ ID NO 318
<211> LENGTH: 9
<212> TYPE: PRT
<213> ORGANISM: Hepatitis C virus

<400> SEQUENCE: 318

Gly Asn Ile Thr Arg Tyr Glu Ser Glu
1 5

<210> SEQ ID NO 319
<211> LENGTH: 9
<212> TYPE: PRT
<213> ORGANISM: Hepatitis C virus

<400> SEQUENCE: 319

Asn Ile Thr Arg Tyr Glu Ser Glu Asn
1 5

<210> SEQ ID NO 320
<211> LENGTH: 9
<212> TYPE: PRT
<213> ORGANISM: Hepatitis C virus

<400> SEQUENCE: 320

Ile Thr Arg Tyr Glu Ser Glu Asn Lys
1 5

<210> SEQ ID NO 321
<211> LENGTH: 9
<212> TYPE: PRT
<213> ORGANISM: Hepatitis C virus

<400> SEQUENCE: 321

Thr Arg Tyr Glu Ser Glu Asn Lys Val
1 5

<210> SEQ ID NO 322
<211> LENGTH: 9
<212> TYPE: PRT
<213> ORGANISM: Hepatitis C virus

<400> SEQUENCE: 322

Arg Tyr Glu Ser Glu Asn Lys Val Val
1 5

<210> SEQ ID NO 323
<211> LENGTH: 9
<212> TYPE: PRT
<213> ORGANISM: Hepatitis C virus

<400> SEQUENCE: 323

Tyr Glu Ser Glu Asn Lys Val Val Ile
1 5

<210> SEQ ID NO 324
<211> LENGTH: 9
<212> TYPE: PRT
<213> ORGANISM: Hepatitis C virus

```
<400> SEQUENCE: 324

Glu Ser Glu Asn Lys Val Val Ile Leu
  1               5

<210> SEQ ID NO 325
<211> LENGTH: 9
<212> TYPE: PRT
<213> ORGANISM: Hepatitis C virus

<400> SEQUENCE: 325

Ser Glu Asn Lys Val Val Ile Leu Asp
  1               5

<210> SEQ ID NO 326
<211> LENGTH: 9
<212> TYPE: PRT
<213> ORGANISM: Hepatitis C virus

<400> SEQUENCE: 326

Glu Asn Lys Val Val Ile Leu Asp Ser
  1               5

<210> SEQ ID NO 327
<211> LENGTH: 9
<212> TYPE: PRT
<213> ORGANISM: Hepatitis C virus

<400> SEQUENCE: 327

Asn Lys Val Val Ile Leu Asp Ser Phe
  1               5

<210> SEQ ID NO 328
<211> LENGTH: 9
<212> TYPE: PRT
<213> ORGANISM: Hepatitis C virus

<400> SEQUENCE: 328

Lys Val Val Ile Leu Asp Ser Phe Asp
  1               5

<210> SEQ ID NO 329
<211> LENGTH: 9
<212> TYPE: PRT
<213> ORGANISM: Hepatitis C virus

<400> SEQUENCE: 329

Val Val Ile Leu Asp Ser Phe Asp Pro
  1               5

<210> SEQ ID NO 330
<211> LENGTH: 9
<212> TYPE: PRT
<213> ORGANISM: Hepatitis C virus

<400> SEQUENCE: 330

Val Ile Leu Asp Ser Phe Asp Pro Leu
  1               5

<210> SEQ ID NO 331
<211> LENGTH: 9
<212> TYPE: PRT
<213> ORGANISM: Hepatitis C virus

<400> SEQUENCE: 331
```

Ile Leu Asp Ser Phe Asp Pro Leu Val
 1               5

<210> SEQ ID NO 332
<211> LENGTH: 9
<212> TYPE: PRT
<213> ORGANISM: Hepatitis C virus

<400> SEQUENCE: 332

Leu Asp Ser Phe Asp Pro Leu Val Ala
 1               5

<210> SEQ ID NO 333
<211> LENGTH: 9
<212> TYPE: PRT
<213> ORGANISM: Hepatitis C virus

<400> SEQUENCE: 333

Asp Ser Phe Asp Pro Leu Val Ala Glu
 1               5

<210> SEQ ID NO 334
<211> LENGTH: 9
<212> TYPE: PRT
<213> ORGANISM: Hepatitis C virus

<400> SEQUENCE: 334

Ser Phe Asp Pro Leu Val Ala Glu Glu
 1               5

<210> SEQ ID NO 335
<211> LENGTH: 9
<212> TYPE: PRT
<213> ORGANISM: Hepatitis C virus

<400> SEQUENCE: 335

Phe Asp Pro Leu Val Ala Glu Glu Asp
 1               5

<210> SEQ ID NO 336
<211> LENGTH: 9
<212> TYPE: PRT
<213> ORGANISM: Hepatitis C virus

<400> SEQUENCE: 336

Asp Pro Leu Val Ala Glu Glu Asp Glu
 1               5

<210> SEQ ID NO 337
<211> LENGTH: 9
<212> TYPE: PRT
<213> ORGANISM: Hepatitis C virus

<400> SEQUENCE: 337

Pro Leu Val Ala Glu Glu Asp Glu Arg
 1               5

<210> SEQ ID NO 338
<211> LENGTH: 9
<212> TYPE: PRT
<213> ORGANISM: Hepatitis C virus

<400> SEQUENCE: 338

Leu Val Ala Glu Glu Asp Glu Arg Glu

```
                   1               5

<210> SEQ ID NO 339
<211> LENGTH: 9
<212> TYPE: PRT
<213> ORGANISM: Hepatitis C virus

<400> SEQUENCE: 339

Val Ala Glu Glu Asp Glu Arg Glu Ile
  1               5

<210> SEQ ID NO 340
<211> LENGTH: 9
<212> TYPE: PRT
<213> ORGANISM: Hepatitis C virus

<400> SEQUENCE: 340

Ala Glu Glu Asp Glu Arg Glu Ile Ser
  1               5

<210> SEQ ID NO 341
<211> LENGTH: 9
<212> TYPE: PRT
<213> ORGANISM: Hepatitis C virus

<400> SEQUENCE: 341

Glu Glu Asp Glu Arg Glu Ile Ser Val
  1               5

<210> SEQ ID NO 342
<211> LENGTH: 9
<212> TYPE: PRT
<213> ORGANISM: Hepatitis C virus

<400> SEQUENCE: 342

Glu Asp Glu Arg Glu Ile Ser Val Pro
  1               5

<210> SEQ ID NO 343
<211> LENGTH: 9
<212> TYPE: PRT
<213> ORGANISM: Hepatitis C virus

<400> SEQUENCE: 343

Asp Glu Arg Glu Ile Ser Val Pro Ala
  1               5

<210> SEQ ID NO 344
<211> LENGTH: 9
<212> TYPE: PRT
<213> ORGANISM: Hepatitis C virus

<400> SEQUENCE: 344

Glu Arg Glu Ile Ser Val Pro Ala Glu
  1               5

<210> SEQ ID NO 345
<211> LENGTH: 9
<212> TYPE: PRT
<213> ORGANISM: Hepatitis C virus

<400> SEQUENCE: 345

Arg Glu Ile Ser Val Pro Ala Glu Ile
  1               5
```

```
<210> SEQ ID NO 346
<211> LENGTH: 9
<212> TYPE: PRT
<213> ORGANISM: Hepatitis C virus

<400> SEQUENCE: 346

Glu Ile Ser Val Pro Ala Glu Ile Leu
 1               5

<210> SEQ ID NO 347
<211> LENGTH: 9
<212> TYPE: PRT
<213> ORGANISM: Hepatitis C virus

<400> SEQUENCE: 347

Ile Ser Val Pro Ala Glu Ile Leu Arg
 1               5

<210> SEQ ID NO 348
<211> LENGTH: 9
<212> TYPE: PRT
<213> ORGANISM: Hepatitis C virus

<400> SEQUENCE: 348

Ser Val Pro Ala Glu Ile Leu Arg Lys
 1               5

<210> SEQ ID NO 349
<211> LENGTH: 9
<212> TYPE: PRT
<213> ORGANISM: Hepatitis C virus

<400> SEQUENCE: 349

Val Pro Ala Glu Ile Leu Arg Lys Ser
 1               5

<210> SEQ ID NO 350
<211> LENGTH: 9
<212> TYPE: PRT
<213> ORGANISM: Hepatitis C virus

<400> SEQUENCE: 350

Pro Ala Glu Ile Leu Arg Lys Ser Arg
 1               5

<210> SEQ ID NO 351
<211> LENGTH: 9
<212> TYPE: PRT
<213> ORGANISM: Hepatitis C virus

<400> SEQUENCE: 351

Ala Glu Ile Leu Arg Lys Ser Arg Arg
 1               5

<210> SEQ ID NO 352
<211> LENGTH: 9
<212> TYPE: PRT
<213> ORGANISM: Hepatitis C virus

<400> SEQUENCE: 352

Glu Ile Leu Arg Lys Ser Arg Arg Phe
 1               5

<210> SEQ ID NO 353
```

```
<211> LENGTH: 9
<212> TYPE: PRT
<213> ORGANISM: Hepatitis C virus

<400> SEQUENCE: 353

Ile Leu Arg Lys Ser Arg Arg Phe Ala
 1               5

<210> SEQ ID NO 354
<211> LENGTH: 9
<212> TYPE: PRT
<213> ORGANISM: Hepatitis C virus

<400> SEQUENCE: 354

Leu Arg Lys Ser Arg Arg Phe Ala Gln
 1               5

<210> SEQ ID NO 355
<211> LENGTH: 9
<212> TYPE: PRT
<213> ORGANISM: Hepatitis C virus

<400> SEQUENCE: 355

Arg Lys Ser Arg Arg Phe Ala Gln Ala
 1               5

<210> SEQ ID NO 356
<211> LENGTH: 9
<212> TYPE: PRT
<213> ORGANISM: Hepatitis C virus

<400> SEQUENCE: 356

Lys Ser Arg Arg Phe Ala Gln Ala Leu
 1               5

<210> SEQ ID NO 357
<211> LENGTH: 9
<212> TYPE: PRT
<213> ORGANISM: Hepatitis C virus

<400> SEQUENCE: 357

Ser Arg Arg Phe Ala Gln Ala Leu Pro
 1               5

<210> SEQ ID NO 358
<211> LENGTH: 9
<212> TYPE: PRT
<213> ORGANISM: Hepatitis C virus

<400> SEQUENCE: 358

Arg Arg Phe Ala Gln Ala Leu Pro Val
 1               5

<210> SEQ ID NO 359
<211> LENGTH: 9
<212> TYPE: PRT
<213> ORGANISM: Hepatitis C virus

<400> SEQUENCE: 359

Arg Phe Ala Gln Ala Leu Pro Val Trp
 1               5

<210> SEQ ID NO 360
<211> LENGTH: 9
<212> TYPE: PRT
```

-continued

<213> ORGANISM: Hepatitis C virus

<400> SEQUENCE: 360

Phe Ala Gln Ala Leu Pro Val Trp Ala
1 5

<210> SEQ ID NO 361
<211> LENGTH: 9
<212> TYPE: PRT
<213> ORGANISM: Hepatitis C virus

<400> SEQUENCE: 361

Ala Gln Ala Leu Pro Val Trp Ala Arg
1 5

<210> SEQ ID NO 362
<211> LENGTH: 9
<212> TYPE: PRT
<213> ORGANISM: Hepatitis C virus

<400> SEQUENCE: 362

Gln Ala Leu Pro Val Trp Ala Arg Pro
1 5

<210> SEQ ID NO 363
<211> LENGTH: 9
<212> TYPE: PRT
<213> ORGANISM: Hepatitis C virus

<400> SEQUENCE: 363

Ala Leu Pro Val Trp Ala Arg Pro Asp
1 5

<210> SEQ ID NO 364
<211> LENGTH: 9
<212> TYPE: PRT
<213> ORGANISM: Hepatitis C virus

<400> SEQUENCE: 364

Leu Pro Val Trp Ala Arg Pro Asp Tyr
1 5

<210> SEQ ID NO 365
<211> LENGTH: 9
<212> TYPE: PRT
<213> ORGANISM: Hepatitis C virus

<400> SEQUENCE: 365

Pro Val Trp Ala Arg Pro Asp Tyr Asn
1 5

<210> SEQ ID NO 366
<211> LENGTH: 9
<212> TYPE: PRT
<213> ORGANISM: Hepatitis C virus

<400> SEQUENCE: 366

Val Trp Ala Arg Pro Asp Tyr Asn Pro
1 5

<210> SEQ ID NO 367
<211> LENGTH: 9
<212> TYPE: PRT
<213> ORGANISM: Hepatitis C virus

```
<400> SEQUENCE: 367

Trp Ala Arg Pro Asp Tyr Asn Pro Pro
 1               5

<210> SEQ ID NO 368
<211> LENGTH: 9
<212> TYPE: PRT
<213> ORGANISM: Hepatitis C virus

<400> SEQUENCE: 368

Ala Arg Pro Asp Tyr Asn Pro Pro Leu
 1               5

<210> SEQ ID NO 369
<211> LENGTH: 9
<212> TYPE: PRT
<213> ORGANISM: Hepatitis C virus

<400> SEQUENCE: 369

Arg Pro Asp Tyr Asn Pro Pro Leu Val
 1               5

<210> SEQ ID NO 370
<211> LENGTH: 9
<212> TYPE: PRT
<213> ORGANISM: Hepatitis C virus

<400> SEQUENCE: 370

Pro Asp Tyr Asn Pro Pro Leu Val Glu
 1               5

<210> SEQ ID NO 371
<211> LENGTH: 9
<212> TYPE: PRT
<213> ORGANISM: Hepatitis C virus

<400> SEQUENCE: 371

Asp Tyr Asn Pro Pro Leu Val Glu Thr
 1               5

<210> SEQ ID NO 372
<211> LENGTH: 9
<212> TYPE: PRT
<213> ORGANISM: Hepatitis C virus

<400> SEQUENCE: 372

Tyr Asn Pro Pro Leu Val Glu Thr Trp
 1               5

<210> SEQ ID NO 373
<211> LENGTH: 9
<212> TYPE: PRT
<213> ORGANISM: Hepatitis C virus

<400> SEQUENCE: 373

Asn Pro Pro Leu Val Glu Thr Trp Lys
 1               5

<210> SEQ ID NO 374
<211> LENGTH: 9
<212> TYPE: PRT
<213> ORGANISM: Hepatitis C virus

<400> SEQUENCE: 374
```

```
Pro Pro Leu Val Glu Thr Trp Lys Lys
 1               5
```

<210> SEQ ID NO 375
<211> LENGTH: 9
<212> T

```
<210> SEQ ID NO 382
<211> LENGTH: 9
<212> TYPE: PRT
<213> ORGANISM: Hepatitis C virus

<400> SEQUENCE: 382

Lys Pro Asp Tyr Glu Pro Pro Val Val
 1               5

<210> SEQ ID NO 383
<211> LENGTH: 9
<212> TYPE: PRT
<213> ORGANISM: Hepatitis C virus

<400> SEQUENCE: 383

Lys Pro Asp Tyr Glu Pro Pro Val Val
 1               5

<210> SEQ ID NO 384
<211> LENGTH: 9
<212> TYPE: PRT
<213> ORGANISM: Hepatitis C virus

<400> SEQUENCE: 384

Asp Tyr Glu Pro Pro Val Val His Gly
 1               5

<210> SEQ ID NO 385
<211> LENGTH: 9
<212> TYPE: PRT
<213> ORGANISM: Hepatitis C virus

<400> SEQUENCE: 385

Tyr Glu Pro Pro Val Val His Gly Cys
 1               5

<210> SEQ ID NO 386
<211> LENGTH: 9
<212> TYPE: PRT
<213> ORGANISM: Hepatitis C virus

<400> SEQUENCE: 386

Glu Pro Pro Val Val His Gly Cys Pro
 1               5

<210> SEQ ID NO 387
<211> LENGTH: 9
<212> TYPE: PRT
<213> ORGANISM: Hepatitis C virus

<400> SEQUENCE: 387

Pro Pro Val Val His Gly Cys Pro Leu
 1               5

<210> SEQ ID NO 388
<211> LENGTH: 9
<212> TYPE: PRT
<213> ORGANISM: Hepatitis C virus

<400> SEQUENCE: 388

Pro Val Val His Gly Cys Pro Leu Pro
 1               5
```

```
<210> SEQ ID NO 389
<211> LENGTH: 9
<212> TYPE: PRT
<213> ORGANISM: Hepatitis C virus

<400> SEQUENCE: 389

Val Val His Gly Cys Pro Leu Pro Pro
  1               5

<210> SEQ ID NO 390
<211> LENGTH: 9
<212> TYPE: PRT
<213> ORGANISM: Hepatitis C virus

<400> SEQUENCE: 390

Val His Gly Cys Pro Leu Pro Pro Pro
  1               5

<210> SEQ ID NO 391
<211> LENGTH: 9
<212> TYPE: PRT
<213> ORGANISM: Hepatitis C virus

<400> SEQUENCE: 391

His Gly Cys Pro Leu Pro Pro Pro Lys
  1               5

<210> SEQ ID NO 392
<211> LENGTH: 9
<212> TYPE: PRT
<213> ORGANISM: Hepatitis C virus

<400> SEQUENCE: 392

Gly Cys Pro Leu Pro Pro Pro Lys Ser
  1               5

<210> SEQ ID NO 393
<211> LENGTH: 9
<212> TYPE: PRT
<213> ORGANISM: Hepatitis C virus

<400> SEQUENCE: 393

Cys Pro Leu Pro Pro Pro Lys Ser Pro
  1               5

<210> SEQ ID NO 394
<211> LENGTH: 9
<212> TYPE: PRT
<213> ORGANISM: Hepatitis C virus

<400> SEQUENCE: 394

Pro Leu Pro Pro Pro Lys Ser Pro Pro
  1               5

<210> SEQ ID NO 395
<211> LENGTH: 9
<212> TYPE: PRT
<213> ORGANISM: Hepatitis C virus

<400> SEQUENCE: 395

Leu Pro Pro Pro Lys Ser Pro Pro Val
  1               5

<210> SEQ ID NO 396
<211> LENGTH: 9
```

```
<212> TYPE: PRT
<213> ORGANISM: Hepatitis C virus

<400> SEQUENCE: 396

Pro Pro Pro Lys Ser Pro Pro Val Pro

```
<400> SEQUENCE: 402

Xaa Met Ser Thr Ile Pro Lys Pro Gln Arg Lys Thr Lys Arg Asn Thr
 1               5                  10                  15

Asn Arg Arg Pro Gln Asp Val Lys Phe Pro Gly Gly Gly Gln Ile Val
             20                  25                  30

Gly Xaa

<210> SEQ ID NO 403
<211> LENGTH: 41
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (41)
<223> OTHER INFORMATION: Xaa = modified site : when present, represents
      an amino acid, OH-group, NH2-group, or a linkage involving these
      two groups

<400> SEQUENCE: 403

Xaa Gly Gly Val Tyr Leu Leu Pro Arg Arg Gly Pro Arg Leu Gly Val
 1               5                  10                  15

Arg Ala Thr Arg Lys Thr Ser Glu Arg Ser Gln Pro Arg Gly Arg Arg
             20                  25                  30

Gln Pro Ile Pro Lys Val Arg Arg Xaa
         35                  40

<210> SEQ ID NO 404
<211> LENGTH: 34
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (34)
<223> OTHER INFORMATION: Xaa = modified site : when present, represents
      an amino acid, OH-group, NH2-group, or a linkage involving these
      two groups

<400> SEQUENCE: 404

Xaa Ser Gln His Leu Pro Tyr Ile Glu Gln Gly Met Met Leu Ala Glu
 1               5                  10                  15

Gln Phe Lys Gln Lys Ala Leu Gly Leu Leu Gln Thr Ala Ser Arg Gln
             20                  25                  30

Ala Xaa

<210> SEQ ID NO 405
<211> LENGTH: 34
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminuss
<221> NAME/KEY: VARIANT
<222> LOCATION: (34)
<223> OTHER INFORMATION: Xaa = modified site : when present, represents
      an amino acid, OH-group, NH2-group, or a linkage involving these
      two groups
```

-continued

<400> SEQUENCE: 405

Xaa Glu Asp Glu Arg Glu Ile Ser Val Pro Ala Glu Ile Leu Arg Lys
1               5                   10                  15

Ser Arg Arg Phe Ala Gln Ala Leu Pro Val Trp Ala Arg Pro Asp Tyr
            20                  25                  30

Asn Xaa

<210> SEQ ID NO 406
<211> LENGTH: 22
<212> TYPE: PRT
<213> ORGANISM: Hepatitis C virus

<400> SEQUENCE: 406

Gly Glu Thr Tyr Thr Ser Gly Gly Ala Ala Ser His Thr Thr Ser Thr
1               5                   10                  15

Leu Ala Ser Leu Phe Ser
            20

<210> SEQ ID NO 407
<211> LENGTH: 24
<212> TYPE: PRT
<213> ORGANISM: Hepatitis C virus

<400> SEQUENCE: 407

Ser His Thr Thr Ser Thr Leu Ala Ser Leu Phe Ser Pro Gly Ala Ser
1               5                   10                  15

Gln Arg Ile Gln Leu Val Asn Thr
            20

<210> SEQ ID NO 408
<211> LENGTH: 22
<212> TYPE: PRT
<213> ORGANISM: Hepatitis C virus

<400> SEQUENCE: 408

Gly His Thr Arg Val Ser Gly Gly Ala Ala Ser Asp Thr Arg Gly
1               5                   10                  15

Leu Val Ser Leu Phe Ser
            20

<210> SEQ ID NO 409
<211> LENGTH: 24
<212> TYPE: PRT
<213> ORGANISM: Hepatitis C virus

<400> SEQUENCE: 409

Ala Ser Asp Thr Arg Gly Leu Val Ser Leu Phe Ser Pro Gly Ser Ala
1               5                   10                  15

Gln Lys Ile Gln Leu Val Asn Thr
            20

<210> SEQ ID NO 410
<211> LENGTH: 22
<212> TYPE: PRT
<213> ORGANISM: Hepatitis C virus

<400> SEQUENCE: 410

Gly His Thr Arg Val Thr Gly Gly Val Gln Gly His Val Thr Cys Thr
1               5                   10                  15

Leu Thr Ser Leu Phe Arg
            20

<210> SEQ ID NO 411
<211> LENGTH: 24
<212> TYPE: PRT
<213> ORGANISM: Hepatitis C virus

<400> SEQUENCE: 411

Gly His Val Thr Cys Thr Leu Thr Ser Leu Phe Arg Pro Gly Ala Ser
 1               5                  10                  15

Gln Lys Ile Gln Leu Val Asn Thr
            20

<210> SEQ ID NO 412
<211> LENGTH: 22
<212> TYPE: PRT
<213> ORGANISM: Hepatitis C virus

<400> SEQUENCE: 412

Gly His Thr His Val Thr Gly Gly Arg Val Ala Ser Ser Thr Gln Ser
 1               5                  10                  15

Leu Val Ser Trp Leu Ser
            20

<210> SEQ ID NO 413
<211> LENGTH: 24
<212> TYPE: PRT
<213> ORGANISM: Hepatitis C virus

<400> SEQUENCE: 413

Ala Ser Ser Thr Gln Ser Leu Val Ser Trp Leu Ser Gln Gly Pro Ser
 1               5                  10                  15

Gln Lys Ile Gln Leu Val Asn Thr
            20

<210> SEQ ID NO 414
<211> LENGTH: 22
<212> TYPE: PRT
<213> ORGANISM: Hepatitis C virus

<400> SEQUENCE: 414

Gly Asp Thr His Val Thr Gly Gly Ala Gln Ala Lys Thr Thr Asn Arg
 1               5                  10                  15

Leu Val Ser Met Phe Ala
            20

<210> SEQ ID NO 415
<211> LENGTH: 24
<212> TYPE: PRT
<213> ORGANISM: Hepatitis C virus

<400> SEQUENCE: 415

Ala Lys Thr Thr Asn Arg Leu Val Ser Met Phe Ala Ser Gly Pro Ser
 1               5                  10                  15

Gln Lys Ile Gln Leu Ile Asn Thr
            20

<210> SEQ ID NO 416
<211> LENGTH: 22
<212> TYPE: PRT
<213> ORGANISM: Hepatitis C virus

<400> SEQUENCE: 416

-continued

Ala Glu Thr Tyr Thr Ser Gly Gly Asn Ala Gly His Thr Met Thr Gly
 1               5                  10                  15

Ile Val Arg Phe Phe Ala
            20

<210> SEQ ID NO 417
<211> LENGTH: 24
<212> TYPE: PRT
<213> ORGANISM: Hepatitis C virus

<400> SEQUENCE: 417

Gly His Thr Met Thr Gly Ile Val Arg Phe Phe Ala Pro Gly Pro Lys
 1               5                  10                  15

Gln Asn Val His Leu Ile Asn Thr
            20

<210> SEQ ID NO 418
<211> LENGTH: 22
<212> TYPE: PRT
<213> ORGANISM: Hepatitis C virus

<400> SEQUENCE: 418

Ala Glu Thr Ile Val Ser Gly Gly Gln Ala Ala Arg Ala Met Ser Gly
 1               5                  10                  15

Leu Val Ser Leu Phe Thr
            20

<210> SEQ ID NO 419
<211> LENGTH: 24
<212> TYPE: PRT
<213> ORGANISM: Hepatitis C virus

<400> SEQUENCE: 419

Ala Arg Ala Met Ser Gly Leu Val Ser Leu Phe Thr Pro Gly Ala Lys
 1               5                  10                  15

Gln Asn Ile Gln Leu Ile Asn Thr
            20

<210> SEQ ID NO 420
<211> LENGTH: 22
<212> TYPE: PRT
<213> ORGANISM: Hepatitis C virus

<400> SEQUENCE: 420

Ala Glu Thr Tyr Thr Thr Gly Gly Ser Thr Ala Arg Thr Thr Gln Gly
 1               5                  10                  15

Leu Val Ser Leu Phe Ser
            20

<210> SEQ ID NO 421
<211> LENGTH: 24
<212> TYPE: PRT
<213> ORGANISM: Hepatitis C virus

<400> SEQUENCE: 421

Ala Arg Thr Thr Gln Gly Leu Val Ser Leu Phe Ser Arg Gly Ala Lys
 1               5                  10                  15

Gln Asp Ile Gln Leu Ile Asn Thr
            20

<210> SEQ ID NO 422
<211> LENGTH: 6

-continued

<212> TYPE: PRT
<213> ORGANISM: Hepatitis C virus

<400> SEQUENCE: 422

Pro Gln Arg Lys Thr Lys
1 5

<210> SEQ ID NO 423
<211> LENGTH: 7
<212> TYPE: PRT
<213> ORGANISM: Hepatitis C virus

<400> SEQUENCE: 423

Lys Thr Lys Arg Asn Thr Asn
1 5

<210> SEQ ID NO 424
<211> LENGTH: 7
<212> TYPE: PRT
<213> ORGANISM: Hepatitis C virus

<400> SEQUENCE: 424

Pro Gln Asp Val Lys Phe Pro
1 5

<210> SEQ ID NO 425
<211> LENGTH: 6
<212> TYPE: PRT
<213> ORGANISM: Hepatitis C virus

<400> SEQUENCE: 425

Tyr Leu Leu Pro Arg Arg
1 5

<210> SEQ ID NO 426
<211> LENGTH: 7
<212> TYPE: PRT
<213> ORGANISM: Hepatitis C virus

<400> SEQUENCE: 426

Pro Arg Arg Gly Pro Arg Leu
1 5

<210> SEQ ID NO 427
<211> LENGTH: 7
<212> TYPE: PRT
<213> ORGANISM: Hepatitis C virus

<400> SEQUENCE: 427

Arg Leu Gly Val Arg Ala Thr
1 5

<210> SEQ ID NO 428
<211> LENGTH: 7
<212> TYPE: PRT
<213> ORGANISM: Hepatitis C virus

<400> SEQUENCE: 428

Ser Gln Pro Arg Gly Arg Arg
1 5

<210> SEQ ID NO 429
<211> LENGTH: 7
<212> TYPE: PRT
<213> ORGANISM: Hepatitis C virus

```
<400> SEQUENCE: 429

Arg Arg Gln Pro Ile Pro Lys
  1               5

<210> SEQ ID NO 430
<211> LENGTH: 6
<212> TYPE: PRT
<213> ORGANISM: Hepatitis C virus

<400> SEQUENCE: 430

Arg Thr Trp Ala Gln Pro
  1               5

<210> SEQ ID NO 431
<211> LENGTH: 8
<212> TYPE: PRT
<213> ORGANISM: Hepatitis C virus

<400> SEQUENCE: 431

Gln Pro Gly Tyr Pro Trp Pro Leu
  1               5

<210> SEQ ID NO 432
<211> LENGTH: 6
<212> TYPE: PRT
<213> ORGANISM: Hepatitis C virus

<400> SEQUENCE: 432

Pro Asp Arg Glu Val Leu
  1               5

<210> SEQ ID NO 433
<211> LENGTH: 6
<212> TYPE: PRT
<213> ORGANISM: Hepatitis C virus

<400> SEQUENCE: 433

His Leu Pro Tyr Ile Glu
  1               5

<210> SEQ ID NO 434
<211> LENGTH: 8
<212> TYPE: PRT
<213> ORGANISM: Hepatitis C virus

<400> SEQUENCE: 434

Tyr Ile Glu Gln Gly Met Met Leu
  1               5

<210> SEQ ID NO 435
<211> LENGTH: 7
<212> TYPE: PRT
<213> ORGANISM: Hepatitis C virus

<400> SEQUENCE: 435

Ala Glu Gln Phe Lys Gln Lys
  1               5

<210> SEQ ID NO 436
<211> LENGTH: 6
<212> TYPE: PRT
<213> ORGANISM: Hepatitis C virus

<400> SEQUENCE: 436
```

Lys Gln Lys Ala Leu Gly
 1               5

<210> SEQ ID NO 437
<211> LENGTH: 7
<212> TYPE: PRT
<213> ORGANISM: Hepatitis C virus

<400> SEQUENCE: 437

Leu Gly Leu Leu Gln Thr Ala
 1               5

<210> SEQ ID NO 438
<211> LENGTH: 7
<212> TYPE: PRT
<213> ORGANISM: Hepatitis C virus

<400> SEQUENCE: 438

Pro Ala Glu Ile Leu Arg Lys
 1               5

<210> SEQ ID NO 439
<211> LENGTH: 7
<212> TYPE: PRT
<213> ORGANISM: Hepatitis C virus

<400> SEQUENCE: 439

Glu Ile Leu Arg Lys Ser Arg
 1               5

<210> SEQ ID NO 440
<211> LENGTH: 7
<212> TYPE: PRT
<213> ORGANISM: Hepatitis C virus

<400> SEQUENCE: 440

Gln Ala Leu Pro Val Trp Ala
 1               5

<210> SEQ ID NO 441
<211> LENGTH: 6
<212> TYPE: PRT
<213> ORGANISM: Hepatitis C virus

<400> SEQUENCE: 441

Pro Asp Tyr Asn Pro Pro
 1               5

<210> SEQ ID NO 442
<211> LENGTH: 7
<212> TYPE: PRT
<213> ORGANISM: Hepatitis C virus

<400> SEQUENCE: 442

Leu Val Glu Thr Trp Lys Lys
 1               5

<210> SEQ ID NO 443
<211> LENGTH: 6
<212> TYPE: PRT
<213> ORGANISM: Hepatitis C virus

<400> SEQUENCE: 443

Asp Tyr Glu Pro Pro Val

-continued

```
                 1               5

<210> SEQ ID NO 444
<211> LENGTH: 5
<212> TYPE: PRT
<213> ORGANISM: Hepatitis C virus

<400> SEQUENCE: 444

His Gly Cys Pro Leu
 1               5

<210> SEQ ID NO 445
<211> LENGTH: 20
<212> TYPE: PRT
<213> ORGANISM: Hepatitis C virus

<400> SEQUENCE: 445

Gly Ala Leu Val Ala Phe Lys Ile Met Ser Gly Glu Val Pro Ser Thr
 1               5                  10                  15

Glu Asp Leu Val
            20

<210> SEQ ID NO 446
<211> LENGTH: 20
<212> TYPE: PRT
<213> ORGANISM: Hepatitis C virus

<400> SEQUENCE: 446

Val Pro Ser Thr Glu Asp Leu Val Asn Leu Leu Pro Ala Ile Leu Ser
 1               5                  10                  15

Pro Gly Ala Leu
            20

<210> SEQ ID NO 447
<211> LENGTH: 20
<212> TYPE: PRT
<213> ORGANISM: Hepatitis C virus

<400> SEQUENCE: 447

Ala Ile Leu Ser Pro Gly Ala Leu Val Val Gly Val Val Cys Ala Ala
 1               5                  10                  15

Ile Leu Arg Arg
            20

<210> SEQ ID NO 448
<211> LENGTH: 20
<212> TYPE: PRT
<213> ORGANISM: Hepatitis C virus

<400> SEQUENCE: 448

Val Cys Ala Ala Ile Leu Arg Arg His Val Gly Pro Gly Glu Gly Ala
 1               5                  10                  15

Val Gln Trp Met
            20

<210> SEQ ID NO 449
<211> LENGTH: 20
<212> TYPE: PRT
<213> ORGANISM: Hepatitis C virus

<400> SEQUENCE: 449

Gly Glu Gly Ala Val Gln Trp Met Asn Arg Leu Ile Ala Phe Ala Ser
 1               5                  10                  15
```

-continued

Arg Gly Asn His
            20

<210> SEQ ID NO 450
<211> LENGTH: 34
<212> TYPE: PRT
<213> ORGANISM: Hepatitis C virus

<400> SEQUENCE: 450

Gly Gly Ile Pro Asp Arg Glu Val Leu Tyr Arg Gly Gly Lys Lys Pro
 1               5                  10                  15

Asp Thr Tyr Glu Pro Pro Val Gly Gly Arg Arg Pro Gln Asp Val Lys
            20                  25                  30

Phe Pro

<210> SEQ ID NO 451
<211> LENGTH: 33
<212> TYPE: PRT
<213> ORGANISM: Hepatitis C virus

<400> SEQUENCE: 451

Gly Gly Trp Ala Arg Pro Asp Tyr Asn Pro Pro Gly Gly Gln Phe Lys
 1               5                  10                  15

Gln Lys Ala Leu Gly Leu Gly Ser Gly Val Tyr Leu Leu Pro Arg Arg
            20                  25                  30

Gly

<210> SEQ ID NO 452
<211> LENGTH: 33
<212> TYPE: PRT
<213> ORGANISM: Hepatitis C virus

<400> SEQUENCE: 452

Gly Gly Arg Gly Arg Arg Gln Pro Ile Pro Lys Gly Gly Ser Gln His
 1               5                  10                  15

Leu Pro Tyr Ile Glu Gln Ser Gly Pro Val Val His Gly Cys Pro Leu
            20                  25                  30

Pro

<210> SEQ ID NO 453
<211> LENGTH: 36
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (36)
<223> OTHER INFORMATION: Xaa = modified site : when present, represents
      an amino acid, OH-group, NH2-group, or a linkage involving these
      two groups

<400> SEQUENCE: 453

Ala Gly Glu Thr Tyr Thr Ser Gly Gly Ala Ala Ser His Thr Thr Ser
 1               5                  10                  15

Thr Leu Ala Ser Leu Phe Ser Pro Gly Ala Ser Gln Arg Ile Gln Leu
            20                  25                  30

Val Asn Thr Glx
            35

```
<210> SEQ ID NO 454
<211> LENGTH: 36
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (36)
<223> OTHER INFORMATION: Xaa = modified site : when present, represents
      an amino acid, OH-group, NH2-group, or a linkage involving these
      two groups

<400> SEQUENCE: 454

Ala Gly His Thr Arg Val Ser Gly Gly Ala Ala Ala Ser Asp Thr Arg
 1               5                  10                  15

Gly Leu Val Ser Leu Phe Ser Pro Gly Ser Ala Gln Lys Ile Gln Leu
            20                  25                  30

Val Asn Thr Glx
         35

<210> SEQ ID NO 455
<211> LENGTH: 36
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (36)
<223> OTHER INFORMATION: Xaa = modified site : when present, represents
      an amino acid, OH-group, NH2-group, or a linkage involving these
      two groups

<400> SEQUENCE: 455

Ala Gly His Thr Arg Val Thr Gly Gly Val Gln Gly His Val Thr Cys
 1               5                  10                  15

Thr Leu Thr Ser Leu Phe Arg Pro Gly Ala Ser Gln Lys Ile Gln Leu
            20                  25                  30

Val Asn Thr Glx
         35

<210> SEQ ID NO 456
<211> LENGTH: 36
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (36)
<223> OTHER INFORMATION: Xaa = modified site : when present, represents
      an amino acid, OH-group, NH2-group, or a linkage involving these
      two groups

<400> SEQUENCE: 456

Ala Gly His Thr His Val Thr Gly Gly Arg Val Ala Ser Ser Thr Gln
 1               5                  10                  15

Ser Leu Val Ser Trp Leu Ser Gln Gly Pro Ser Gln Lys Ile Gln Leu
            20                  25                  30

Val Asn Thr Glx
```

```
<210> SEQ ID NO 457
<211> LENGTH: 36
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (1)
<223> OTHER INFORMATION: Xaa = modified site : when present, represents
      anamino acid, OH-group, NH2-group, or a linkage involving these
      two groups

<400> SEQUENCE: 457

Ala Gly Asp Thr His Val Thr Gly Gly Ala Gln Ala Lys Thr Thr Asn
 1               5                  10                  15

Arg Leu Val Ser Met Phe Ala Ser Gly Pro Ser Gln Lys Ile Gln Leu
            20                  25                  30

Ile Asn Thr Glx
        35

<210> SEQ ID NO 458
<211> LENGTH: 36
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (36)
<223> OTHER INFORMATION: Xaa = modified site : when present, represents
      an amino acid, OH-group, NH2-group, or a linkage involving these
      two groups

<400> SEQUENCE: 458

Ala Ala Glu Thr Tyr Thr Ser Gly Gly Asn Ala Gly His Thr Met Thr
 1               5                  10                  15

Gly Ile Val Arg Phe Phe Ala Pro Gly Pro Lys Gln Asn Val His Leu
            20                  25                  30

Ile Asn Thr Glx
        35

<210> SEQ ID NO 459
<211> LENGTH: 36
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (36)
<223> OTHER INFORMATION: Xaa = modified site : when present, represents
      an amino acid, OH-group, NH2-group, or a linkage involving these
      two groups

<400> SEQUENCE: 459

Ala Ala Glu Thr Ile Val Ser Gly Gly Gln Ala Ala Arg Ala Met Ser
 1               5                  10                  15

Gly Leu Val Ser Leu Phe Thr Pro Gly Ala Lys Gln Asn Ile Gln Leu
            20                  25                  30
```

Ile Asn Thr Glx
        35

<210> SEQ ID NO 460
<211> LENGTH: 36
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (36)
<223> OTHER INFORMATION: Xaa = modified site : when present, represents
      an amino acid, OH-group, NH2-group, or a linkage involving these
      two groups

<400> SEQUENCE: 460

Ala Ala Glu Thr Tyr Thr Thr Gly Gly Ser Thr Ala Arg Thr Thr Gln
 1               5                  10                  15

Gly Leu Val Ser Leu Phe Ser Arg Gly Ala Lys Gln Asp Ile Gln Leu
            20                  25                  30

Ile Asn Thr Glx
        35

<210> SEQ ID NO 461
<211> LENGTH: 24
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (24)
<223> OTHER INFORMATION: Xaa = modified site : when present, represents
      an amino acid, OH-group, NH2-group, or a linkage involving these
      two groups

<400> SEQUENCE: 461

Ala Gly Glu Thr Tyr Thr Ser Gly Gly Ala Ala Ser His Thr Thr Ser
 1               5                  10                  15

Thr Leu Ala Ser Leu Phe Ser Glx
            20

<210> SEQ ID NO 462
<211> LENGTH: 26
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (26)
<223> OTHER INFORMATION: Xaa = modified site : when present, represents
      an amino acid, OH-group, NH2-group, or a linkage involving these
      two groups

<400> SEQUENCE: 462

Ala Ser His Thr Thr Ser Thr Leu Ala Ser Leu Phe Ser Pro Gly Ala
 1               5                  10                  15

Ser Gln Arg Ile Gln Leu Val Asn Thr Glx
            20                  25

```
<210> SEQ ID NO 463
<211> LENGTH: 24
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (24)
<223> OTHER INFORMATION: Xaa = modified site : when present, represents
      an amino acid, OH-group, NH2-group, or a linkage involving these
      two groups

<400> SEQUENCE: 463

Ala Gly His Thr Arg Val Ser Gly Gly Ala Ala Ala Ser Asp Thr Arg
  1               5                  10                  15

Gly Leu Val Ser Leu Phe Ser Glx
              20

<210> SEQ ID NO 464
<211> LENGTH: 26
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (26)
<223> OTHER INFORMATION: Xaa = modified site : when present, represents
      an amino acid, OH-group, NH2-group, or a linkage involving these
      two groups

<400> SEQUENCE: 464

Ala Ala Ser Asp Thr Arg Gly Leu Val Ser Leu Phe Ser Pro Gly Ser
  1               5                  10                  15

Ala Gln Lys Ile Gln Leu Val Asn Thr Glx
              20                  25

<210> SEQ ID NO 465
<211> LENGTH: 24
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (24)
<223> OTHER INFORMATION: Xaa = modified site : when present, represents
      an amino acid, OH-group, NH2-group, or a linkage involving these
      two groups

<400> SEQUENCE: 465

Ala Gly His Thr Arg Val Thr Gly Gly Val Gln Gly His Val Thr Cys
  1               5                  10                  15

Thr Leu Thr Ser Leu Phe Arg Glx
              20

<210> SEQ ID NO 466
<211> LENGTH: 26
<212> TYPE: PRT
<213> ORGANISM: Hepatitis C virus
<220> FEATURE:
<221> NAME/KEY: VARIANT
```

```
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (26)
<223> OTHER INFORMATION: Xaa = modified site : when present, represents
      an amino acid, OH-group, NH2-group, or a linkage involving these
      two groups

<400> SEQUENCE: 466

Ala Gly His Val Thr Cys Thr Leu Thr Ser Leu Phe Arg Pro Gly Ala
 1               5                  10                  15

Ser Gln Lys Ile Gln Leu Val Asn Thr Glx
            20                  25

<210> SEQ ID NO 467
<211> LENGTH: 24
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (24)
<223> OTHER INFORMATION: Xaa = modified site : when present, represents
      an amino acid, OH-group, NH2-group, or a linkage involving these
      two groups

<400> SEQUENCE: 467

Ala Gly His Thr His Val Thr Gly Gly Arg Val Ala Ser Ser Thr Gln
 1               5                  10                  15

Ser Leu Val Ser Trp Leu Ser Glx
            20

<210> SEQ ID NO 468
<211> LENGTH: 26
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (26)
<223> OTHER INFORMATION: Xaa = modified site : when present, represents
      an amino acid, OH-group, NH2-group, or a linkage involving these
      two groups

<400> SEQUENCE: 468

Ala Ala Ser Ser Thr Gln Ser Leu Val Ser Trp Leu Ser Gln Gly Pro
 1               5                  10                  15

Ser Gln Lys Ile Gln Leu Val Asn Thr Glx
            20                  25

<210> SEQ ID NO 469
<211> LENGTH: 24
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (24)
<223> OTHER INFORMATION: Xaa = modified site : when present, represents
      an amino acid, OH-group, NH2-group, or a linkage involving these
``` two groups

<400> SEQUENCE: 469

Ala Gly Asp Thr His Val Thr Gly Gly Ala Gln Ala Lys Thr Thr Asn
 1               5                  10                  15

Arg Leu Val Ser Met Phe Ala Glx
            20

<210> SEQ ID NO 470
<211> LENGTH: 26
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (26)
<223> OTHER INFORMATION: Xaa = modified site : when present, represents
      an amino acid, OH-group, NH2-group, or a linkage involving these
      two groups

<400> SEQUENCE: 470

Ala Ala Lys Thr Thr Asn Arg Leu Val Ser Met Phe Ala Ser Gly Pro
 1               5                  10                  15

Ser Gln Lys Ile Gln Leu Ile Asn Thr Glx
            20                  25

<210> SEQ ID NO 471
<211> LENGTH: 24
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (24)
<223> OTHER INFORMATION: Xaa = modified site : when present, represents
      an amino acid, OH-group, NH2-group, or a linkage involving these
      two groups

<400> SEQUENCE: 471

Ala Ala Glu Thr Tyr Thr Ser Gly Gly Asn Ala Gly His Thr Met Thr
 1               5                  10                  15

Gly Ile Val Arg Phe Phe Ala Glx
            20

<210> SEQ ID NO 472
<211> LENGTH: 26
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (26)
<223> OTHER INFORMATION: Xaa = modified site : when present, represents
      an amino acid, OH-group, NH2-group, or a linkage involving these
      two groups

<400> SEQUENCE: 472

Ala Gly His Thr Met Thr Gly Ile Val Arg Phe Phe Ala Pro Gly Pro
 1               5                  10                  15

Lys Gln Asn Val His Leu Ile Asn Thr Glx
            20                  25

<210> SEQ ID NO 473
<211> LENGTH: 24
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminuss
<221> NAME/KEY: VARIANT
<222> LOCATION: (24)
<223> OTHER INFORMATION: Xaa = modified site : when present, represents
      an amino acid, OH-group, NH2-group, or a linkage involving these
      two groups

<400> SEQUENCE: 473

Ala Ala Glu Thr Ile Val Ser Gly Gly Gln Ala Ala Arg Ala Met Ser
 1               5                  10                  15

Gly Leu Val Ser Leu Phe Thr Glx
            20

<210> SEQ ID NO 474
<211> LENGTH: 26
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (26)
<223> OTHER INFORMATION: Xaa = modified site : when present, represents
      an amino acid, OH-group, NH2-group, or a linkage involving these
      two groups

<400> SEQUENCE: 474

Ala Ala Arg Ala Met Ser Gly Leu Val Ser Leu Phe Thr Pro Gly Ala
 1               5                  10                  15

Lys Gln Asn Ile Gln Leu Ile Asn Thr Glx
            20                  25

<210> SEQ ID NO 475
<211> LENGTH: 24
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (24)
<223> OTHER INFORMATION: Xaa = modified site : when present, represents
      an amino acid, OH-group, NH2-group, or a linkage involving these
      two groups

<400> SEQUENCE: 475

Ala Ala Glu Thr Tyr Thr Thr Gly Gly Ser Thr Ala Arg Thr Thr Gln
 1               5                  10                  15

Gly Leu Val Ser Leu Phe Ser Glx
            20

<210> SEQ ID NO 476
<211> LENGTH: 26
<212> TYPE: PRT

```
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (26)
<223> OTHER INFORMATION: Xaa = modified site : when present, represents
      an amino acid, OH-group, NH2-group, or a linkage involving these
      two groups

<400> SEQUENCE: 476

Ala Ala Arg Thr Thr Gln Gly Leu Val Ser Leu Phe Ser Arg Gly Ala
  1               5                  10                  15

Lys Gln Asp Ile Gln Leu Ile Asn Thr Glx
             20                  25

<210> SEQ ID NO 477
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 477

Ala Ile Pro Lys Pro Gln Arg Lys Thr Lys Glx
  1               5                  10

<210> SEQ ID NO 478
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 478

Ala Pro Lys Pro Gln Arg Lys Thr Lys Arg Glx
  1               5                  10

<210> SEQ ID NO 479
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 479
```

```
Ala Lys Pro Gln Arg Lys Thr Lys Arg Asn Glx
  1               5                  10
```

<210> SEQ ID NO 480
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 480

```
Ala Pro Gln Arg Lys Thr Lys Arg Asn Thr Glx
  1               5                  10
```

<210> SEQ ID NO 481
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 481

```
Ala Gln Arg Lys Thr Lys Arg Asn Thr Asn Glx
  1               5                  10
```

<210> SEQ ID NO 482
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 482

```
Ala Arg Lys Thr Lys Arg Asn Thr Asn Arg Glx
  1               5                  10
```

<210> SEQ ID NO 483
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)

```
<223> OTHER INFORMATION: Xaa = modified site : when present, represents
     an amino acid, OH-group, NH2-group, or a linkage involving these
     two groups

<400> SEQUENCE: 483

Ala Lys Thr Lys Arg Asn Thr Asn Arg Arg Glx
 1               5                  10

<210> SEQ ID NO 484
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
     an amino acid, amino group, or chemically modified amino terminus
<221> NAME/KEY: VARIANT
<222> LOCATION: (11)
<223> OTHER INFORMATION: Xaa = modified site : when present, represents
     an amino acid, OH-group, NH2-group, or a linkage involving these
     two groups

<400> SEQUENCE: 484

Ala Thr Lys Arg Asn Thr Asn Arg Arg Pro Glx
 1               5                  10

<210> SEQ ID NO 485
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
     an amino acid, amino group, or chemically modified amino terminus
<221> NAME/KEY: VARIANT
<222> LOCATION: (11)
<223> OTHER INFORMATION: Xaa = modified site : when present, represents
     an amino acid, OH-group, NH2-group, or a linkage involving these
     two groups

<400> SEQUENCE: 485

Ala Arg Arg Pro Gln Asp Val Lys Phe Pro Glx
 1               5                  10

<210> SEQ ID NO 486
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
     an amino acid, amino group, or chemically modified amino terminus
<221> NAME/KEY: VARIANT
<222> LOCATION: (11)
<223> OTHER INFORMATION: Xaa = modified site : when present, represents
     an amino acid, OH-group, NH2-group, or a linkage involv-ing these
     two groups

<400> SEQUENCE: 486

Ala Arg Pro Gln Asp Val Lys Phe Pro Gly Glx
 1               5                  10

<210> SEQ ID NO 487
<211> LENGTH: 11
<212> TYPE: PRT
<213> ORGANISM: Hepatitis C virus
<220> FEATURE:
<221> NAME/KEY: VARIANT
```

```
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 487

Ala Pro Gln Asp Val Lys Phe Pro Gly Gly Glx
 1               5                  10

<210> SEQ ID NO 488
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 488

Ala Gln Asp Val Lys Phe Pro Gly Gly Gly Glx
 1               5                  10

<210> SEQ ID NO 489
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 489

Ala Asp Val Lys Phe Pro Gly Gly Gly Gln Glx
 1               5                  10

<210> SEQ ID NO 490
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 490

Ala Gly Gly Val Tyr Leu Leu Pro Arg Arg Glx
 1               5                  10

<210> SEQ ID NO 491
```

```
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involv-ing these
      two groups

<400> SEQUENCE: 491

Ala Gly Val Tyr Leu Leu Pro Arg Arg Gly Glx
 1               5                  10

<210> SEQ ID NO 492
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 492

Ala Val Tyr Leu Leu Pro Arg Arg Gly Pro Glx
 1               5                  10

<210> SEQ ID NO 493
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 493

Ala Tyr Leu Leu Pro Arg Arg Gly Pro Arg Glx
 1               5                  10

<210> SEQ ID NO 494
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 494
```

Ala Leu Leu Pro Arg Arg Gly Pro Arg Leu Glx
 1               5                  10

<210> SEQ ID NO 495
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 495

Ala Leu Pro Arg Arg Gly Pro Arg Leu Gly Glx
 1               5                  10

<210> SEQ ID NO 496
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 496

Ala Pro Arg Arg Gly Pro Arg Leu Gly Val Glx
 1               5                  10

<210> SEQ ID NO 497
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 497

Ala Gly Pro Arg Leu Gly Val Arg Ala Thr Glx
 1               5                  10

<210> SEQ ID NO 498
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents an amino acid, OH-group, NH2-group, or a linkage involving these
two groups

<400> SEQUENCE: 498

Ala Pro Arg Leu Gly Val Arg Ala Thr Arg Glx
 1               5                  10

<210> SEQ ID NO 499
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 499

Ala Arg Leu Gly Val Arg Ala Thr Arg Lys Glx
 1               5                  10

<210> SEQ ID NO 500
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 500

Ala Glu Arg Ser Gln Pro Arg Gly Arg Arg Glx
 1               5                  10

<210> SEQ ID NO 501
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 501

Ala Arg Ser Gln Pro Arg Gly Arg Arg Gln Glx
 1               5                  10

<210> SEQ ID NO 502
<211> LENGTH: 11
<212> TYPE: PRT
<213> ORGANISM: Hepatitis C virus
<220> FEATURE:
<221> NAME/KEY: VARIANT
<222> LOCATION: (1)

```
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 502

Ala Ser Gln Pro Arg Gly Arg Arg Gln Pro Glx
 1               5                  10

<210> SEQ ID NO 503
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 503

Ala Arg Gly Arg Arg Gln Pro Ile Pro Lys Glx
 1               5                  10

<210> SEQ ID NO 504
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 504

Ala Gly Arg Arg Gln Pro Ile Pro Lys Val Glx
 1               5                  10

<210> SEQ ID NO 505
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 505

Ala Arg Arg Gln Pro Ile Pro Lys Val Arg Glx
 1               5                  10

<210> SEQ ID NO 506
<211> LENGTH: 11
```

```
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 506

Ala Pro Ile Pro Lys Val Arg Arg Pro Glu Glx
 1               5                  10

<210> SEQ ID NO 507
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 507

Ala Pro Glu Gly Arg Thr Trp Ala Gln Pro Glx
 1               5                  10

<210> SEQ ID NO 508
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 508

Ala Glu Gly Arg Thr Trp Ala Gln Pro Gly Glx
 1               5                  10

<210> SEQ ID NO 509
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 509

Ala Gly Arg Thr Trp Ala Gln Pro Gly Tyr Glx
```

```
<210> SEQ ID NO 510
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 510

Ala Arg Thr Trp Ala Gln Pro Gly Tyr Pro Glx
 1               5                  10

<210> SEQ ID NO 511
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 511

Ala Thr Trp Ala Gln Pro Gly Tyr Pro Trp Glx
 1               5                  10

<210> SEQ ID NO 512
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 512

Ala Trp Ala Gln Pro Gly Tyr Pro Trp Pro Glx
 1               5                  10

<210> SEQ ID NO 513
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
``` two groups

<400> SEQUENCE: 513

Ala Ala Gln Pro Gly Tyr Pro Trp Pro Leu Glx
 1               5                   10

<210> SEQ ID NO 514
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 514

Ala Gln Pro Gly Tyr Pro Trp Pro Leu Tyr Glx
 1               5                   10

<210> SEQ ID NO 515
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 515

Ala Leu Ser Gly Lys Pro Ala Ile Ile Pro Glx
 1               5                   10

<210> SEQ ID NO 516
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 516

Ala Gly Lys Pro Ala Ile Ile Pro Asp Arg Glx
 1               5                   10

<210> SEQ ID NO 517
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents

```
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 517

Ala Pro Ala Ile Ile Pro Asp Arg Glu Val Glx
 1               5                  10

<210> SEQ ID NO 518
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 518

Ala Ala Ile Ile Pro Asp Arg Glu Val Leu Glx
 1               5                  10

<210> SEQ ID NO 519
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 519

Ala Ile Ile Pro Asp Arg Glu Val Leu Tyr Glx
 1               5                  10

<210> SEQ ID NO 520
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 520

Ala Ile Pro Asp Arg Glu Val Leu Tyr Arg Glx
 1               5                  10

<210> SEQ ID NO 521
<211> LENGTH: 11
<212> TYPE: PRT
```

<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 521

Ala Pro Asp Arg Glu Val Leu Tyr Arg Glu Glx
 1               5                  10

<210> SEQ ID NO 522
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 522

Ala Asp Arg Glu Val Leu Tyr Arg Glu Phe Glx
 1               5                  10

<210> SEQ ID NO 523
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 523

Ala Cys Ser Gln His Leu Pro Tyr Ile Glu Glx
 1               5                  10

<210> SEQ ID NO 524
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 524

Ala Ser Gln His Leu Pro Tyr Ile Glu Gln Glx
 1               5                  10

```
<210> SEQ ID NO 525
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 525

Ala Gln His Leu Pro Tyr Ile Glu Gln Gly Glx
 1               5                  10

<210> SEQ ID NO 526
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 526

Ala His Leu Pro Tyr Ile Glu Gln Gly Met Glx
 1               5                  10

<210> SEQ ID NO 527
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 527

Ala Leu Pro Tyr Ile Glu Gln Gly Met Met Glx
 1               5                  10

<210> SEQ ID NO 528
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups
```

```
<400> SEQUENCE: 528

Ala Pro Tyr Ile Glu Gln Gly Met Met Leu Glx
  1               5                  10

<210> SEQ ID NO 529
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 529

Ala Tyr Ile Glu Gln Gly Met Met Leu Ala Glx
  1               5                  10

<210> SEQ ID NO 530
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 530

Ala Ile Glu Gln Gly Met Met Leu Ala Glu Glx
  1               5                  10

<210> SEQ ID NO 531
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 531

Ala Met Met Leu Ala Glu Gln Phe Lys Gln Glx
  1               5                  10

<210> SEQ ID NO 532
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
```

```
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 532

Ala Met Leu Ala Glu Gln Phe Lys Gln Lys Glx
 1               5                  10

<210> SEQ ID NO 533
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 533

Ala Leu Ala Glu Gln Phe Lys Gln Lys Ala Glx
 1               5                  10

<210> SEQ ID NO 534
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 534

Ala Ala Glu Gln Phe Lys Gln Lys Ala Leu Glx
 1               5                  10

<210> SEQ ID NO 535
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 535

Ala Glu Gln Phe Lys Gln Lys Ala Leu Gly Glx
 1               5                  10

<210> SEQ ID NO 536
<211> LENGTH: 11
<212> TYPE: PRT
<213> ORGANISM: Hepatitis C virus
```

```
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 536

Ala Gln Phe Lys Gln Lys Ala Leu Gly Leu Glx
 1               5                  10

<210> SEQ ID NO 537
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 537

Ala Phe Lys Gln Lys Ala Leu Gly Leu Leu Glx
 1               5                  10

<210> SEQ ID NO 538
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 538

Ala Lys Gln Lys Ala Leu Gly Leu Leu Gln Glx
 1               5                  10

<210> SEQ ID NO 539
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 539

Ala Gln Lys Ala Leu Gly Leu Leu Gln Thr Glx
 1               5                  10
```

```
<210> SEQ ID NO 540
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 540

Ala Lys Ala Leu Gly Leu Leu Gln Thr Ala Glx
 1               5                  10

<210> SEQ ID NO 541
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 541

Ala Ala Leu Gly Leu Leu Gln Thr Ala Ser Glx
 1               5                  10

<210> SEQ ID NO 542
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 542

Ala Leu Gly Leu Leu Gln Thr Ala Ser Arg Glx
 1               5                  10

<210> SEQ ID NO 543
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups
```

<400> SEQUENCE: 543

Ala Gly Leu Leu Gln Thr Ala Ser Arg Gln Glx
 1               5                  10

<210> SEQ ID NO 544
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 544

Ala Leu Leu Gln Thr Ala Ser Arg Gln Ala Glx
 1               5                  10

<210> SEQ ID NO 545
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 545

Ala Ser Val Pro Ala Glu Ile Leu Arg Lys Glx
 1               5                  10

<210> SEQ ID NO 546
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 546

Ala Val Pro Ala Glu Ile Leu Arg Lys Ser Glx
 1               5                  10

<210> SEQ ID NO 547
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT

```
<222> LOCATION: (11)
<223> OTHER INFORMATION: Xaa = modified site : when present, represents
      an amino acid, OH-group, NH2-group, or a linkage involving these
      two groups

<400> SEQUENCE: 547

Ala Pro Ala Glu Ile Leu Arg Lys Ser Arg Glx
 1               5                  10

<210> SEQ ID NO 548
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 548

Ala Ala Glu Ile Leu Arg Lys Ser Arg Arg Glx
 1               5                  10

<210> SEQ ID NO 549
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 549

Ala Glu Ile Leu Arg Lys Ser Arg Arg Phe Glx
 1               5                  10

<210> SEQ ID NO 550
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 550

Ala Phe Ala Gln Ala Leu Pro Val Trp Ala Glx
 1               5                  10

<210> SEQ ID NO 551
<211> LENGTH: 11
<212> TYPE: PRT
<213> ORGANISM: Hepatitis C virus
<220> FEATURE:
```

```
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 551

Ala Ala Gln Ala Leu Pro Val Trp Ala Arg Glx
 1               5                  10

<210> SEQ ID NO 552
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 552

Ala Gln Ala Leu Pro Val Trp Ala Arg Pro Glx
 1               5                  10

<210> SEQ ID NO 553
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 553

Ala Ala Leu Pro Val Trp Ala Arg Pro Asp Glx
 1               5                  10

<210> SEQ ID NO 554
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 554

Ala Val Trp Ala Arg Pro Asp Tyr Asn Pro Glx
 1               5                  10
```

```
<210> SEQ ID NO 555
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 555

Ala Trp Ala Arg Pro Asp Tyr Asn Pro Pro Glx
 1               5                  10

<210> SEQ ID NO 556
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 556

Ala Ala Arg Pro Asp Tyr Asn Pro Pro Leu Glx
 1               5                  10

<210> SEQ ID NO 557
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 557

Ala Arg Pro Asp Tyr Asn Pro Pro Leu Val Glx
 1               5                  10

<210> SEQ ID NO 558
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 558
```

Ala Pro Asp Tyr Asn Pro Pro Leu Val Glu Glx
 1               5                  10

<210> SEQ ID NO 559
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 559

Ala Pro Pro Leu Val Glu Thr Trp Lys Lys Glx
 1               5                  10

<210> SEQ ID NO 560
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 560

Ala Pro Leu Val Glu Thr Trp Lys Lys Pro Glx
 1               5                  10

<210> SEQ ID NO 561
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 561

Ala Leu Val Glu Thr Trp Lys Lys Pro Asp Glx
 1               5                  10

<210> SEQ ID NO 562
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)

```
<223> OTHER INFORMATION: Xaa = modified site : when present, represents
      an amino acid, OH-group, NH2-group, or a linkage involving these
      two groups

<400> SEQUENCE: 562

Ala Trp Glu Thr Trp Lys Lys Pro Asp Tyr Glx
 1               5                  10

<210> SEQ ID NO 563
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 563

Ala Glu Thr Trp Lys Lys Pro Asp Tyr Glu Glx
 1               5                  10

<210> SEQ ID NO 564
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 564

Ala Thr Trp Lys Lys Pro Asp Tyr Glu Pro Glx
 1               5                  10

<210> SEQ ID NO 565
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 565

Ala Trp Lys Lys Pro Asp Tyr Glu Pro Pro Glx
 1               5                  10

<210> SEQ ID NO 566
<211> LENGTH: 11
<212> TYPE: PRT
<213> ORGANISM: Hepatitis C virus
<220> FEATURE:
<221> NAME/KEY: VARIANT
```

```
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 566

Ala Lys Lys Pro Asp Tyr Glu Pro Pro Val Glx
 1               5                  10

<210> SEQ ID NO 567
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 567

Ala Lys Pro Asp Tyr Glu Pro Pro Val Val Glx
 1               5                  10

<210> SEQ ID NO 568
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 568

Ala Pro Asp Tyr Glu Pro Pro Val Val His Glx
 1               5                  10

<210> SEQ ID NO 569
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 569

Ala Asp Tyr Glu Pro Pro Val Val His Gly Glx
 1               5                  10

<210> SEQ ID NO 570
```

```
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 570

Ala Tyr Glu Pro Pro Val Val His Gly Cys Glx
 1               5                  10

<210> SEQ ID NO 571
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 571

Ala Pro Pro Val Val His Gly Cys Pro Leu Glx
 1               5                  10

<210> SEQ ID NO 572
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 572

Ala Pro Val Val His Gly Cys Pro Leu Pro Glx
 1               5                  10

<210> SEQ ID NO 573
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 573
```

```
Ala Val Val His Gly Cys Pro Leu Pro Pro Glx
 1               5                   10

<210> SEQ ID NO 574
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 574

Ala Val His Gly Cys Pro Leu Pro Pro Lys Glx
 1               5                   10

<210> SEQ ID NO 575
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 575

Ala His Gly Cys Pro Leu Pro Pro Lys Ser Glx
 1               5                   10

<210> SEQ ID NO 576
<211> LENGTH: 11
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (11)
<223> OTHER INFORMATION: Xaa = modified site : when present, represents
      an amino acid, OH-group, NH2-group, or a linkage involving these
      two groups

<400> SEQUENCE: 576

Ala Ser Pro Pro Val Pro Pro Pro Arg Lys Glx
 1               5                   10

<210> SEQ ID NO 577
<211> LENGTH: 8
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (8)
<223> OTHER INFORMATION: Xaa = modified site : when present, represents
``` an amino acid, OH-group, NH2-group, or a linkage involving these
two groups

<400> SEQUENCE: 577

Ala Pro Gln Arg Lys Thr Lys Glx
 1               5

<210> SEQ ID NO 578
<211> LENGTH: 8
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (8)
<223> OTHER INFORMATION: Xaa = modified site : when present, represents
      an amino acid, OH-group, NH2-group, or a linkage involving these
      two groups

<400> SEQUENCE: 578

Ala Pro Gln Arg Lys Thr Lys Glx
 1               5

<210> SEQ ID NO 579
<211> LENGTH: 9
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (9)
<223> OTHER INFORMATION: Xaa = modified site : when present, represents
      an amino acid, OH-group, NH2-group, or a linkage involving these
      two groups

<400> SEQUENCE: 579

Ala Pro Gln Asp Val Lys Phe Pro Glx
 1               5

<210> SEQ ID NO 580
<211> LENGTH: 8
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (8)
<223> OTHER INFORMATION: Xaa = modified site : when present, represents
      an amino acid, OH-group, NH2-group, or a linkage involving these
      two groups

<400> SEQUENCE: 580

Ala Tyr Leu Leu Pro Arg Arg Glx
 1               5

<210> SEQ ID NO 581
<211> LENGTH: 9
<212> TYPE: PRT
<213> ORGANISM: Hepatitis C virus
<220> FEATURE:
<221> NAME/KEY: VARIANT
<222> LOCATION: (1)

```
<223> OTHER INFORMATION: Xaa = modified site : when present, represents
      an amino acid, amino group, or chemically modified amino terminus
<221> NAME/KEY: VARIANT
<222> LOCATION: (9)
<223> OTHER INFORMATION: Xaa = modified site : when present, represents
      an amino acid, OH-group, NH2-group, or a linkage involving these
      two groups

<400> SEQUENCE: 581

Ala Pro Arg Arg Gly Pro Arg Leu Glx
  1               5

<210> SEQ ID NO 582
<211> LENGTH: 9
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (9)
<223> OTHER INFORMATION: Xaa = modified site : when present, represents
      an amino acid, OH-group, NH2-group, or a linkage involving these
      two groups

<400> SEQUENCE: 582

Ala Arg Leu Gly Val Arg Ala Thr Glx
  1               5

<210> SEQ ID NO 583
<211> LENGTH: 9
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (9)
<223> OTHER INFORMATION: Xaa = modified site : when present, represents
      an amino acid, OH-group, NH2-group, or a linkage involving these
      two groups

<400> SEQUENCE: 583

Ala Ser Gln Pro Arg Gly Arg Arg Glx
  1               5

<210> SEQ ID NO 584
<211> LENGTH: 9
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (9)
<223> OTHER INFORMATION: Xaa = modified site : when present, represents
      an amino acid, OH-group, NH2-group, or a linkage involving these
      two groups

<400> SEQUENCE: 584

Ala Arg Arg Gln Pro Ile Pro Lys Glx
  1               5

<210> SEQ ID NO 585
<211> LENGTH: 8
```

```
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (8)
<223> OTHER INFORMATION: Xaa = modified site : when present, represents
      an amino acid, OH-group, NH2-group, or a linkage involving these
      two groups

<400> SEQUENCE: 585

Ala Arg Thr Trp Ala Gln Pro Glx
 1               5

<210> SEQ ID NO 586
<211> LENGTH: 10
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (10)
<223> OTHER INFORMATION: Xaa = modified site : when present, represents
      an amino acid, OH-group, NH2-group, or a linkage involving these
      two groups

<400> SEQUENCE: 586

Ala Gln Pro Gly Tyr Pro Trp Pro Leu Glx
 1               5                  10

<210> SEQ ID NO 587
<211> LENGTH: 8
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (8)
<223> OTHER INFORMATION: Xaa = modified site : when present, represents
      an amino acid, OH-group, NH2-group, or a linkage involving these
      two groups

<400> SEQUENCE: 587

Ala Pro Asp Arg Glu Val Leu Glx
 1               5

<210> SEQ ID NO 588
<211> LENGTH: 8
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (8)
<223> OTHER INFORMATION: Xaa = modified site : when present, represents
      an amino acid, OH-group, NH2-group, or a linkage involving these
      two groups

<400> SEQUENCE: 588

Ala His Leu Pro Tyr Ile Glu Glx
```

<210> SEQ ID NO 589
<211> LENGTH: 10
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (10)
<223> OTHER INFORMATION: Xaa = modified site : when present, represents
      an amino acid, OH-group, NH2-group, or a linkage involving these
      two groups

<400> SEQUENCE: 589

Ala Tyr Ile Glu Gln Gly Met Met Leu Glx
 1               5                  10

<210> SEQ ID NO 590
<211> LENGTH: 9
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (9)
<223> OTHER INFORMATION: Xaa = modified site : when present, represents
      an amino acid, OH-group, NH2-group, or a linkage involving these
      two groups

<400> SEQUENCE: 590

Ala Ala Glu Gln Phe Lys Gln Lys Glx
 1               5

<210> SEQ ID NO 591
<211> LENGTH: 8
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (8)
<223> OTHER INFORMATION: Xaa = modified site : when present, represents
      an amino acid, OH-group, NH2-group, or a linkage involving these
      two groups

<400> SEQUENCE: 591

Ala Lys Gln Lys Ala Leu Gly Glx
 1               5

<210> SEQ ID NO 592
<211> LENGTH: 9
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (9)
<223> OTHER INFORMATION: Xaa = modified site : when present, represents
      an amino acid, OH-group, NH2-group, or a linkage involving these two groups

<400> SEQUENCE: 592

Ala Leu Gly Leu Leu Gln Thr Ala Glx
 1               5

<210> SEQ ID NO 593
<211> LENGTH: 9
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (9)
<223> OTHER INFORMATION: Xaa = modified site : when present, represents
      an amino acid, OH-group, NH2-group, or a linkage involving these
      two groups

<400> SEQUENCE: 593

Ala Pro Ala Glu Ile Leu Arg Lys Glx
 1               5

<210> SEQ ID NO 594
<211> LENGTH: 9
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (9)
<223> OTHER INFORMATION: Xaa = modified site : when present, represents
      an amino acid, OH-group, NH2-group, or a linkage involving these
      two groups

<400> SEQUENCE: 594

Ala Glu Ile Leu Arg Lys Ser Arg Glx
 1               5

<210> SEQ ID NO 595
<211> LENGTH: 9
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (9)
<223> OTHER INFORMATION: Xaa = modified site : when present, represents
      an amino acid, OH-group, NH2-group, or a linkage involving these
      two groups

<400> SEQUENCE: 595

Ala Gln Ala Leu Pro Val Trp Ala Glx
 1               5

<210> SEQ ID NO 596
<211> LENGTH: 8
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents

```
      an amino acid, amino group, or chemically modified amino terminus
<221> NAME/KEY: VARIANT
<222> LOCATION: (8)
<223> OTHER INFORMATION: Xaa = modified site : when present, represents
      an amino acid, OH-group, NH2-group, or a linkage involving these
      two groups

<400> SEQUENCE: 596

Ala Pro Asp Tyr Asn Pro Pro Glx
  1               5

<210> SEQ ID NO 597
<211> LENGTH: 9
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (9)
<223> OTHER INFORMATION: Xaa = modified site : when present, represents
      an amino acid, OH-group, NH2-group, or a linkage involving these
      two groups

<400> SEQUENCE: 597

Ala Leu Val Glu Thr Trp Lys Lys Glx
  1               5

<210> SEQ ID NO 598
<211> LENGTH: 8
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (8)
<223> OTHER INFORMATION: Xaa = modified site : when present, represents
      an amino acid, OH-group, NH2-group, or a linkage involving these
      two groups

<400> SEQUENCE: 598

Ala Asp Tyr Glu Pro Pro Val Glx
  1               5

<210> SEQ ID NO 599
<211> LENGTH: 7
<212> TYPE: PRT
<213> ORGANISM: Hepatitis C virus
<220> FEATURE:
<221> NAME/KEY: VARIANT
<222> LOCATION: (1)
<223> OTHER INFORMATION: Xaa = modified site : when present, represents
      an amino acid, amino group, or chemically modified amino terminus
<221> NAME/KEY: VARIANT
<222> LOCATION: (7)
<223> OTHER INFORMATION: Xaa = modified site : when present, represents
      an amino acid, OH-group, NH2-group, or a linkage involving these
      two groups

<400> SEQUENCE: 599

Ala His Gly Cys Pro Leu Glx
  1               5

<210> SEQ ID NO 600
<211> LENGTH: 20
<212> TYPE: PRT
```

```
-continued

<213> ORGANISM: Hepatitis C virus

<400> SEQUENCE: 600

Gly Arg Thr Trp Ala Gln Pro Gly Tyr Pro Trp Pro Leu Tyr Gly Asn
 1               5                  10                  15

Glu Gly Cys Gly
            20
```

HCV CORE PEPTIDES

This is a divisional of application Ser. No. 08/723,425, filed Sep. 30, 1996, now pending, which is a divisional of application Ser. No. 08/146,028, filed Nov. 22, 1993, which is a 371 application of PCT/EP93/00517 filed Mar. 6, 1992, the entire content of which is hereby incorporated by reference in this application.

The technical problem underlying the present invention is to provide peptides corresponding to immunologically important epitopes on bacterial and viral proteins, as well as the use of said peptides in diagnostic or immunogenic compositions.

Recent developments in genetic engineering as well as the chemistry of solid phase peptide synthesis have led to the increasingly wider use of synthetic peptides in biochemistry and immunology. Protein sequences which become available as a result of molecular cloning techniques can be synthesized chemically in large quantities for structural, functional, and immunological studies. Peptides corresponding to immunologically important epitopes found on viral and bacterial proteins have also proven to be highly specific reagents which can be used for antibody detection and the diagnosis of infection.

Despite the many advantages synthetic peptides offer, there are a number of disadvantages associated with their use. Because of their relatively short size (generally less than 50 amino acids in length), their structure may fluctuate between many different conformations in the absence of the stabilizing influence of intramolecular interactions present in the full-length protein. Furthermore, the small size of these peptides means that their chemical properties and solubilities will frequently be quite different from those of the full-length protein and that the contribution of individual amino acids in the peptide sequence toward determining the overall chemical properties of the peptide will be proportionally greater.

Many immunological assays require that the antigen used for antibody detection be immobilized on a solid support. Most enzyme-linked immunosorbent assays (ELISA) make use of polystyrene as the solid phase. Many proteins can be stably adsorbed to the solid phase and present sequences which are accessible for subsequent interactions with antibodies. Because of their small size, direct adsorption of peptides to the solid phase frequently gives rise to unsatisfactory results for any of a number of reasons.

Firstly, the peptide may not possess the correct overall charge or amino acid composition which would enable the peptide to bind to the solid phase. Secondly, the same amino acid residues which are required for binding to the solid phase may also be required for antibody recognition and therefore not available for antibody binding. Thirdly, the peptide may become fixed in an unfavorable conformation upon binding to the solid phase which renders it unrecognizable to antibody molecules. In many cases, it is neither possible nor necessary to distinguish between these possibilities. Binding to the solid phase can be increased and made less sensitive to the specific chemical properties of a peptide by first coupling the peptide to a large carrier molecule. Typically, the carrier molecule is a protein. While the amount of peptide bound to the solid phase, albeit indirectly, can in some cases be increased by this method, this approach suffers from the fact that the linkage between the peptide and the carrier protein frequently involves the side chains of internal trifunctional amino acids whose integrity may be indispensable for recognition by antibodies. The binding avidity of antisera for the internally modified peptide is frequently very much reduced relative to the unmodified peptide or the native protein.

The production of antisera to synthetic peptides also requires in most cases that the peptide be coupled to a carrier. Again, the coupling reaction between an internal trifunctional amino acid of the peptide and the carrier is likely to alter the immunogenic properties of the peptide.

There exist many methods for performing coupling reactions and most of the procedures in current use are discussed in detail in Van Regenmortel, M. H. V., Briand, J. P., Muller, S., and Plaue, S.; Laboratory Techniques in Biochemistry and Molecular Biology, vol. 19, Synthetic Polypeptides as Antigens, Elsevier Press, Amsterdam, New York, Oxford, 1988. In addition to these procedures, unprotected peptides can also be biotinylated using commercially available reagents such as N-hydroxysuccinimidobiotin or biotinamidocaproate N-hydroxysuccinimide ester. Many of these reagents are discussed in Billingsley, M. L., Pennypacker, K. R., Hoover, C. G., and Kincaid, R. L., Biotechniques (1987) 5(1):22–31. Biotinylated peptides are capable of being bound by the proteins streptavidin and avidin, two proteins which exhibit extraordinarily high affinity binding to biotin.

In certain instances, it is possible to selectively couple biotin to an unprotected peptide or an unprotected peptide to a carrier. This may be accomplished by synthesizing the peptide with an additional trifunctional amino acid added to one of the ends which is capable of participating in the coupling reaction. This approach will only be successful, however, as long as this amino acid is not a critical residue in the immunogenic sequence of interest and as long as the coupling agent chosen is sufficiently selective. No single technique is applicable to all unprotected peptides regardless of their amino acid composition.

The etiological agent responsible for non-A, non-B hepatitis has been identified and termed hepatitis C virus (HCV). Patent application EP-A-0 318 216 discloses sequences corresponding to approximately 80% of the viral genome. The availability of these sequences rapidly led to the elucidation of the remainder of the coding sequences, particularly those located in the 5' end of the genome (Okamoto; J. Exp. Med. 60, 167–177, 1990). The HCV genome is a linear, positive-stranded RNA molecule with a length of approximately 9400 nucleotides. With the exception of rather short untranslated regions at the termini, the genome consists of one large, uninterrupted, open reading frame encoding a polyprotein of approximately 3000 amino acids. This polyprotein has been shown to be cleaved co-translationally into individual viral structural and non-structural (NS) regions. The structural protein region is further divided into capsid (Core) and envelope(E1 and E2) proteins. The NS regions are divided into NS-1 to NS-5 regions.

A number of independent patent applications have employed a variety of strategies to determine the locations of diagnostically important amino acid sequences and many of these studies have led to the identification of similar regions of the HCV polyprotein.

The NS4 region has mainly been studied in EP-A-0 318 216, EP-A-0 442 394, U.S. Pat. No. 5,106,726, EP-A-0 489 986, EP-A-0 484 787, and EP-A-0 445 801. Unfortunately only 70% of HCV-infected individuals produce antibodies to NS4, neither the synthetic nor recombinant proteins containing sequences from this region are adequate for identifying all infected serum samples. The nucleocapsid or Core region has been studied in patent applications EP-A-0 442 394, U.S. Pat. No. 5,106,726, EP-A-0 489 986, EP-A-0 445 801, EP-A-0 451 891 and EP-A-0 479 376. It was found that these peptides often used as mixtures, were more frequently recognized by antibodies (85–90%) in sera from chronically infected individuals than were the peptides derived from NS4. The NS5 region was studied in patent applications EP-A-0 489 986 and EP-A-0 468 527. Depending on the serum panel used, more than 60% of NANB hepatitis can be shown to contain antibodies directed against these peptides. The NS3 region was also studied in patent application EP-A-0 468 527. All available evidence suggests that the most dominant epitope of NS3 are discontinuous in nature and cannot be adequately represented by synthetic peptides. The E1 region which is potentially interesting as a region from the outer surface of the virus particles (possible immunogenic epitopes) was studied in both patent applications EP-A-0 468 527 and EP-A-0 507 615. The E2/NS1 region was studied for the same reason as E1. Comparisons of this region from different HCV variants elucidated that this protein contains variable region which are reminiscent of the HIV V3 loop region of gp120 envelope protein. Four peptides were found in EP-A-0 468 527 which were shown to contain relatively infrequently recognized epitopes. Finally, the NS2 region of HCV was analyzed in EP-A-0 486 527. However, the diagnostic value of this region is not clear yet. Virtually all patent applications concerning diagnostically useful synthetic peptides for antibody detection describe preferred combinations of peptides. Most of these include peptides from the HCV core protein and NS4. In some cases, peptides from NS5 (EP-A-0 489 968 and EP-A-0 468 527), and E1 and E2/NS1 are included (EP-A-0 507 615 and EO-A-0 468 527).

Different patent applications have addressed the problem of finding diagnostically useful epitopes of human immunodeficiency virus (HIV). An important immunodominant region containing cyclic HIV-1 and HIV-2 peptides was found in patent application EP-A-0 326 490. In EP-A-0 379 949, this region was asserted to be even more reactive with HIV-specific antibodies in case a biotin molecule was coupled to these cyclic HIV peptides. SU-A-161 22 64 also describes the use of a biotinylated peptide in a solid phase immunoassay for the detection of HIV antibodies.

Other applications have looked for useful HIV epitopes in the hypervariable V3 loop region of gp120 (such as EP-A-0 448 095 and EP-A-0 438 332).

U.S. Pat. No. 4,833,071 provides peptide compositions for detection of HTLV I antibodies.

Deciding whether or not an epitope is diagnostically useful is not always straightforward and depends to an extent on the specific configuration of the test into which it is incorporated. It should be ideally an immunodominant epitope which is recognized by a large percentage of true positive sera or should be able to complement other antigens in the test to increase the detection rate. Epitopes which are not frequently recognized may or may not be diagnostically useful depending on the contribution they make towards increasing the detection rate of antibodies in true positive sera and the extent to which incorporation of these epitopes has an adverse effect on the sensitivity of the test due to dilution of other stronger epitopes.

Peptides can thus be used to identify regions of proteins which are specifically recognized by antibodies produced as a result of infection or immunization. In general, there are two strategies which can be followed. One of these strategies has been described by Geysen, H. M., Meloen, R. H., and Barteling, S. J.; Proc. Natl. Acad. Sci. U.S.A. (1984) 81:3998–4002. This approach involves the synthesis of a large series of short, overlapping peptides on polyethylene rods derivatized with a noncleavable linker such that the entire length of the protein or protein fragment of interest is represented.

The rods are incubated with antisera and antibody binding is detected using an anti-immunoglobulin: enzyme conjugate. A positive reaction immediately identifies the location and sequence of epitopes present in the protein sequence. This technique has the advantage that all peptides are uniformly linked to the solid support through their carboxy-terminus. While this method allows for very accurate mapping of linear epitopes, the length of the peptides which can be reliably synthesized on the rods is limited. This may sometimes present problems if the length of the epitope exceeds the length of the peptides synthesized.

A second approach to epitope mapping involves the synthesis of larger peptides, generally between fifteen and thirty amino acids in length, along the sequence of the protein to be analyzed. Consecutive peptides may be contiguous but are preferably overlapping. Following cleavage, the evaluation of antibody binding to the individual peptides is assessed and the approximate positions of the epitopes can be identified. An example of this approach is given in Neurath, A. R., Strick, N., and Lee, E. S. Y.; J. Gen. Virol. (1990) 71:85–95. This approach has the advantage that longer peptides can be synthesized which presumably more closely resemble the homologous sequence in the native protein and which offer better targets for antibody binding. The disadvantage of this approach is that each peptide is chemically unique and that the conditions under which each peptide can be optimally coated onto a solid phase for immunological evaluation may vary widely in terms of such factors as pH, ionic strength, and buffer composition. The quantity of peptide which can be adsorbed onto the solid phase is also an uncontrolled factor which is unique for each peptide.

The main purpose of the present invention is to provide modified peptides corresponding to immunologically useful epitopes with said modified peptides having superior immunological properties over non-modified versions of these peptides.

Another aim of the present invention is to provide modified peptides corresponding to immunologically useful epitopes which could not be identified through classical epitope mapping techniques.

Another aim of the present invention is to provide a process for the in vitro determination of antibodies using said peptides, with said process being easy to perform and amenable to standardization.

Another aim of the invention is to provide a process for the determination of peptides corresponding to immunologically important epitopes on bacterial and viral proteins.

Another aim of the invention is to provide a method for preparing protein sequences used in any of said methods.

Another aim of the invention is to provide a method for preparing protein sequence which can be used in a process for the determination of their epitopes or in an in vitro method for the determination of antibodies.

Another aim of the invention is to provide intermediary compounds useful for the preparation of peptides used in the above-mentioned methods.

Another aim of the present invention is also to provide compositions containing peptides determined to correspond to immunologically important epitopes on proteins for diagnostic purposes.

Another aim of the present invention is also to provide compositions containing peptides determined to correspond to immunologically important epitopes on proteins for vaccine purposes.

According to the present invention, a series of biotinylated peptides representing immunologically important regions of viral proteins have been identified and prepared by solid phase peptide synthesis. These peptides have been identified to be very useful for (i) the detection of antibodies to HCV, and/or HIV, and/or HTLV-I or II. In some preferred arrangements, these peptides were also found or are at least expected, to be useful in stimulating the production of antibodies to HCV, and/or HIV, and/or HTLV-I or II in healthy animals such as BALB/C mice, and in a vaccine composition to prevent HCV and/or HIV, and/or HTLV-I or II infection.

As demonstrated in the Examples section of the present invention, the use of biotinylated peptides also allows the determination of immunologically important epitopes within a previously determined protein sequence. The determination of immunologically important epitopes using non-biotinylated peptides, which are covalently coupled to the solid phase, often fails to localize these epitopes. Especially in case of localization of structural epitopes, the use of biotinylated peptides seems to be quite successful.

(1) According to the present invention, a peptide composition useful for the detection of antibodies to HCV, and/or HIV, and/or HTLV-I or II comprise peptides corresponding to immunologically important epitopes being of the structure:

(A)-(B)-(X)-Y-[amino acids]$_n$-Y-(X)-Z where

[amino acids]$_n$ is meant to designate the length of the peptide chain where n is the number of residues, being an integer from about 4 to about 50, preferably less than about 35, more preferably less than about 30, and advantageously from about 4 to about 25;

B represents biotin;

X represents a biotinylated compound which is incorporated during the synthetic process;

Y represents a covalent bond or one or more chemical entities which singly or together form a linker arm separating the amino acids of the peptide proper from the biotinyl moiety B or X, the function of which is to minimize steric hindrance which may interfere with the binding of the biotinyl moiety B or X to avidin or streptavidin, wherein Y is not a covalent bond, it is advantageously at least one chemical entity and may consist of as many as 30 chemical entities but will consist most frequently of 1 to 10 chemical entities, which may be identical or different, more preferably glycine residues, β-alanine, 4-aminobutyric acid, 5-aminovaleric acid, or 6-aminohexanoic acid;

B and X being enclosed in parentheses to indicate that the presence of biotin or a biotinylated compound in these positions is optional, the only stipulation being that B or X be present in at least one of the positions shown;

A, when present, as indicated by parentheses, represents (an) amino acid(s), an amino group, or a chemical modification of the amino terminus of the peptide chain;

Z represents (an) amino acid(s), an OH-group, an NH2-group, or a linkage involving either of these two chemical groups wherein the amino acids are selectively chosen to be immunodominant epitopes which are recognized by a large percentage of true posistive sera or are able to complement other antigens in the test to increase the detection rate and B interacts with the selected amino acids to produce a compound with greater diagnostic senstivity.

The peptide composition comprises at least one and preferably a combination of two, three, four or more biotinylated peptides chosen from the following sequences:

1. Human immunodeficiency Virus type 1 Envelope Peptides:

a. gp41

1. (SEQ ID NO:1) gp41, isolate HTLV-IIIB
(A)-(B)-(X)-Y-Ile-Trp-Gly-Cys-Ser-Gly-Lys-Ile-Cys-Y-(X)-Z 2. (SEQ ID NO:2)
(A)-(B)-X)-Y-Ile-Trp-Gly-Cys-Ser-Gly-Lys-Leu-Ile-Cys-Thr-Thr-Ala-Val-Pro-Trp-Asn-Ala-Ser-Y-(X)-Z 3. (SEQ ID NO:3)
(A)-(B)-(X)-Y-Glu-Arg-Tyr-Leu-Lys-Asp-Gln-Gln-Leu-Leu-Gly-Ile-Trp-Gly-Cys-Ser-Gly-Lys-Leu-Ile-Y-(X)-Z 4. (SEQ ID NO:4)
(A)-(B)-(X)-Y-Leu-Gln-Ala-Arg-Ile-Leu-Ala-Val-Glu-Arg-Tyr-Leu-Lys-Asp-Gln-Gln-Leu-Y-(X)-Z 5. (SEQ ID NO:5) gp41, isolate Ant70
(A)-(B)-(X)-Y-Leu-Trp-Gly-Cys-Lys-Gly-Lys-Leu-Val-Cys-Y-(X)-Z 6. (SEQ ID NO:6) gp41, isolate ELI
(A)-(B)-(X)-Y-Asp-Gln-Gln-Leu-Leu-Gly-Ile-Trp-Gly-Cys-Ser-Gly-Lys-His-Ile-Cys-Thr-Thr-Asn-Val-Pro-Trp-Asn-Y-(X)-Z b. gp 120

1. (SEQ ID NO:7) Partial V3 loop sequence, consensus
(A)-(B)-(X)-Y-Asn-Asn-Thr-Arg-Lys-Ser-Ile-His-Ile-Gly-Pro-Gly-Arg-Ala-Phe-Tyr-Thr-Thr-Gly-Glu-Ile-Ile-Gly-Y-(X)-Z 1.a. (SEQ ID NO:8) Complete V3 loop sequence, consensus
(A)-(B)-(X)-Y-Cys-Thr-Arg-Pro-Asn-Asn-Asn-Thr-Arg-Lys-Ser-Ile-His-Ile-Gly-Pro-Gly-Arg-Ala-Phe-Tyr-Thr-Thr-Gly-Glu-Ile-Ile-Gly-Asp-Ile-Arg-Gln-Ala-His-Cys-Y-(X)-Z 2. (SEQ ID NO:9) Partial V3 loop sequence, isolate HIV-1 SF2
(A)-(B)-(X)-Y-Asn-Asn-Thr-Arg-Lys-Ser-Ile-Tyr-Ile-Gly-Pro-Gly-Arg-Ala-Phe-His-Thr-Thr-Gly-Arg-Ile-Ile-Gly-Y-(X)-Z 3. (SEQ ID NO:10) Partial V3 loop sequence, isolate HIV-1 SC
(A)-(B)-(X)-Y-Asn-Asn-Thr-Thr-Arg-Ser-Ile-His-Ile-Gly-Pro-Gly-Arg-Ala-Phe-Tyr-Ala-Thr-Gly-Asp-Ile-Ile-Gly-Y-(X)-Z 4. (SEQ ID NO:11) Partial V3 loop sequence, isolate HIV-1 MN
(A)-(B)-(X)-Y-Tyr-Asn-Lys-Arg-Lys-Arg-Ile-His-Ile-Gly-Pro-Gly-Arg-Ala-Phe-Tyr-Thr-Thr-Lys-Asn-Ile-Ile-Gly-Y-(X)-Z 5. Partial V3 loop sequence, isolate HIV-1 RF
(SEQ ID NO:12) (A)-(B)-(X)-Y-Asn-Asn-Thr-Arg-Lys-Ser-Ile-Thr-Lys-Gly-Pro-Gly-Arg-Val-Ile-Tyr-Ala-Thr-Gly-Gln-Ile-Ile-Gly-Y-(X)-Z 6. Partial V3 loop sequence, isolate HIV-1 mal
(SEQ ID NO:13) (A)-(B)-(X)-Y-Asn-Asn-Thr-Arg-Arg-Gly-Ile-His-Phe-Gly-Pro-Gly-Gln-Ala-Leu-Tyr-Thr-Thr-Gly-Ile-Val-Gly-Y-(X)-Z 7. Partial V3 loop sequence, isolate HTLV-IIIB
(SEQ ID NO:14) (A)-(B)-(X)-Y-Asn-Asn-Thr-Arg-Lys-Ser-Ile-Arg-Ile-Gln-Arg-Gly-Pro-Gly-Arg-Ala-Phe-Val-Thr-Ile-Gly-Lys-Ile-Gly-Y-(X)-Z 8. Partial V3 loop sequence, isolate HIV-1 ELI
(SEQ ID NO:15) (A)-(B)-(X)-Y-Gln-Asn-Thr-Arg-Gln-Arg-Thr-Pro-Ile-Gly-Leu-Gly-Gln-Ser-Leu-Tyr-Thr-Thr-Arg-Ser-Arg-Ser-Y-(X)-Z 9. Partial V3 loop sequence, isolate ANT70
(SEQ ID NO:16) (A)-(B)-(X)-Y-Gln-Ile-Asp-Ile-Gln-Glu-Met-Arg-Ile-Gly-Pro-Met-Ala-Trp-Tyr-Ser-Met-Gly-Ile-Gly-Gly-Y-(X)-Z 10. Partial V3 loop sequence, Brazilian isolate, Peptide V3-368
(SEQ ID NO:17) (A)-(B)-(X)-Y-Asn-Asn-Thr-Arg-Arg-Gly-Ile-His-Met-Gly-Trp-Gly-Arg-Thr-Phe-Tyr-Ala-Thr-Gly-Glu-Ile-Ile-Gly-Y-(X)-Z 11. Carboxy-terminus, HIV-1 gp120
(SEQ ID NO:18) (A)-(B)-(X)-Y-Arg-Asp-Asn-Trp-Arg-Ser-Glu-Leu-Tyr-Lys-Tyr-Lys-Val-Val-Lys-Ile-Glu-Pro-Leu-Gly-Val-Ala-Pro-Thr-Lys-Ala-Lys-Arg-Arg-Val-Val-Gln-Arg-Glu-Lys-Arg-Y-(X)-Z 2. Human immunodeficiency Virus type 2 Envelope Peptide
a. gp41, isolate HIV-2 rod
(SEQ ID NO:19) (A)-(B)-(X)-Y-Ser-Trp-Gly-Cys-Ala-Phe-Arg-Gln-Val-Cys-Y-(X)-Z
b.
(SEQ ID NO:20) (A)-(B)-(X)-Y-Lys-Tyr-Leu-Gln-Asp-Gln-Ala-Arg-Leu-Asn-Ser-Trp-Gly-Cys-Ala-Phe-Arg-Gln-Val-Cys-Y-(X)-Z
c. gp120, isolate HIV-2 NIHZ
(SEQ ID NO:21) (A)-(B)-(X)-Y-Asn-Lys-Thr-Val-Leu-Pro-Ile-Thr-Phe-Met-Ser-Gly-Phe-Lys-Phe-His-Ser-Gln-Pro-Val-Ile-Asn-Lys-Y-(X)-Z
d. Partial V3 loop sequence, Peptide V3-GB12
(SEQ ID NO:22) (A)-(B)-(X)-Y-Asn-Lys-Thr-Val-Val-Pro-Ile-Thr-Leu-Met-Ser-Gly-Leu-Val-Phe-His-Ser-Gln-Pro-Ile-Asn-Lys-Y-(X)-Z
e. Partial V3 loop sequence, Peptide V3-239
(SEQ ID NO:23) (A)-(B)-(X)-Y-Asn-Lys-Thr-Val-Leu-Pro-Val-Thr-Ile-Met-Ser-Gly-Leu-Val-Phe-His-Ser-Gln-Pro-Ile-Asn-Asp-Y-(X)-Z 3. Chimpanzee immunodeficiency Virus
a. gp41
(SEQ ID NO:24) (A)-(B)-(X)-Y-Leu-Trp-Gly-Cys-Ser-Gly-Lys-Ala-Val-Cys-Y-(X)-Z 4. Simian immunodeficiency Virus
a. Transmembrane protein, isolate SIVagm(TY01)
(SEQ ID NO:25) (A)-(B)-(X)-Y-Ser-Trp-Gly-Cys-Ala-Trp-Lys-Gln-Val-Cys-Y-(X)-Z.
b. Transmembrane protein, isolate SIVmnd
(SEQ ID NO:26) (A)-(B)-(X)-Y-Gln-Trp-Gly-Cys-Ser-Trp-Ala-Gln-Val-Cys-Y-(X)-Z 5. HTLV-I and HTLV-II Virus
Peptide I-gp46-3
(SEQ ID NO:27) (A)-(B)-(X)-Y-Val-Leu-Tyr-Ser-Pro-Asn-Val-Ser-Val-Pro-Ser-Ser-Ser-Ser-Thr-Leu-Leu-Tyr-Pro-Ser-Leu-Ala-Y-(X)-Z
Peptide I-gp46-5
(SEQ ID NO:28) (A)-(B)-(X)-Y-Tyr-Thr-Cys-Ile-Val-Cys-Ile-Asp-Arg-Ala-Ser-Leu-Ser-Thr-Trp-His-Val-Leu-Tyr-Ser-Pro-Y-(X)-Z
Peptide I-gp46-4
(SEQ ID NO:29) (A)-(B)-(X)-Y-Asn-Ser-Leu-Ile-Leu-Pro-Pro-Phe-Ser-Leu-Ser-Pro-Val-Pro-Thr-Leu-Gly-Ser-Arg-Ser-Arg-Arg-Y-(X)-Z
Peptide I-gp46-6
(SEQ ID NO:30) (A)-(B)-(X)-Y-Asp-Ala-Pro-Gly-Tyr-Asp-Pro-Ile-Trp-Phe-Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile-Leu-Glu-Y-(X)-Z
Peptide I-p21-2
(SEQ ID NO:31) (A)-(B)-(X)-Y-Gln-Tyr-Ala-Ala-Gln-Asn-Arg-Arg-Gly-Leu-Asp-Leu-Leu-Phe-Trp-Glu-Gln-Gly-Gly-Leu-Cys-Lys-Ala-Leu-Gln-Glu-Gln-Cys-Arg-Phe-Pro-Y-(X)-Z Peptide I-p19
(SEQ ID NO:32) (A)-(B)-(X)-Y-Pro-Pro-Pro-Pro-Ser-Ser-Pro-Thr-His-Asp-Pro-Pro-Asp-Ser-Asp-Pro-Gln-Ile-Pro-Pro-Pro-Tyr-Val-Glu-Pro-Thr-Ala-Pro-Gln-Val-Leu-Y-(X)-Z
Peptide II-gp52-1
(SEQ ID NO:33) (A)-(B)-(X)-Y-Lys-Lys-Pro-Asn-Arg-Gln-Gly-Leu-Gly-Tyr-Tyr-Ser-Pro-Ser-Tyr-Asn-Asp-Pro-Y-(X)-Z
Peptide II-gp52-2
(SEQ ID NO:34) (A)-(B)-(X)-Y-Asp-Ala-Pro-Gly-Tyr-Asp-Pro-Leu-Trp-Phe-Ile-Thr-Ser-Glu-Pro-Thr-Gln-Pro-Pro-Pro-Thr-Ser-Pro-Pro-Leu-Val-His-Asp-Ser-Asp-Leu-Glu-His-Val-Leu-Thr-Y-(X)-Z
Peptide II-gp52-3:
(SEQ ID NO:35) (A)-(B)-(X)-Y-Tyr-Ser-Cys-Met-Val-Cys-Val-Asp-Arg-Ser-Ser-Leu-Ser-Ser-Trp-His-Val-Leu-Tyr-Thr-Pro-Asn-Ile-Ser-Ile-Pro-Gln-Gln-Thr-Ser-Ser-Arg-Thr-Ile-Leu-Phe-Pro-Ser-Y-(X)-Z
Peptide II-p19
(SEQ ID NO:36) (A)-(B)-(X)-Y-Pro-Thr-Thr-Thr-Pro-Pro-Pro-Pro-Pro-Pro-Pro-Ser-Pro-Glu-Ala-His-Val-Pro-Pro-Pro-Tyr-Val-Glu-Pro-Thr-Thr-Thr-Gln-Cys-Phe-Y-(X)-Z These above-mentioned biotinylated peptides were synthesized and found to be specifically recognized by antisera from infected humans or primates are considered particularly advantageous. All these above-mentioned peptides are new.

The process of the invention enables to increase the antigenicity of these HIV peptides, which can however be bound to a support, even when they are not biotinylated.

The HCV peptide sequences which follow have been found to be specifically recognized by antisera from infected humans or primates and which are considered particularly advantageous. The non-biotinylated amino acid sequences can be synthesized according to classical methods.

The peptides of interest are intended to mimic immunologically proteins or domains of proteins encoded by HCV. Since sequence variability has been observed for HCV, it may be desirable to vary one or more amino acids so as to better mimic the epitopes of different strains. It should be understood that the peptides described need not be identical to any particular HCV sequence as long as the subject compounds are capable of providing for immunological competition with at least one strain of HCV. The peptides may therefore be subject to insertions, deletions and conservative as well as non-conservative amino acid substitutions where such changes might provide for certain advantages in their use. The peptides will preferably be as short as possible while still maintaining all of the sensitivity of the larger sequence. In certain cases, it may be desirable to join two or more peptides together into a single structure. The formation of such a composite may involve covalent or non-covalent linkages.

Of particular interest are biotinylated peptides of HCV into which cysteine, thioglycollic acid, or other thiol-containing compounds have been incorporated into the peptide chain for the purpose of providing mercapto-groups which can be used for cyclization of the peptides.

The following peptides from the Core region of HCV were determined as corresponding to immunologically important epitopes.

1. Peptide I or Core 1 (aa. 1–20) has the following amino acid sequence:
(I)
(SEQ ID NO:37) (A)-(B)-(X)-Y-Met-Ser-Thr-Ile-Pro-Lys-Pro-Gln-Arg-Lys-Thr-Lys-Arg-Asn-Thr-Asn-Arg-Arg-Pro-Gln-Y-(X)-Z 2. Peptide II or Core 2 (aa. 7–26) has the amino acid sequence:
(II)
(SEQ ID NO:38) (A)-(B)-(X)-Y-Pro-Gln-Arg-Lys-Thr-Lys-Arg-Asn-Thr-Asn-Arg-Arg-Pro-Gln-Asp-Val-Lys-Phe-Pro-Gly-Y-(X)-Z Of particular interest is the oligopeptide IIA (aa. 8 to 18):
(IIA)
(SEQ ID NO:39) (A)-(B)-(X)-Y-Gln-Arg-Lys-Thr-Lys-Arg-Asn-Thr-Asn-Arg-Arg-Y-(X)-Z.

3. Peptide III or Core 3 (aa 13–32) has the sequence:
(III)
(SEQ ID NO:40) (A)-(B)-(X)-Y-Arg-Asn-Thr-Asn-Arg-Arg-Pro-Gln-Asp-Val-Lys-Phe-Pro-Gly-Gly-Gly-Gln-Ile-Val-Gly-Y-(X)-Z 4. Peptide IV or Core 7 (aa 37–56) has the sequences:
(IV)
(SEQ ID NO:41) (A)-(B)-(X)-Y-Leu-Pro-Arg-Arg-Gly-Pro-Arg-Leu-Gly-Val-Arg-Ala-Thr-Arg-Lys-Thr-Ser-Glu-Arg-Ser-Y-(X)-Z Of particular interest is the oligopeptide IVa or Core 6 (aa. 31 to 50):
(IVa)
(SEQ ID NO:42) (A)-(B)-(X)-Y-Val-Gly-Gly-Val-Tyr-Leu-Leu-Pro-Arg-Arg-Gly-Pro-Arg-Leu-Gly-Val-Arg-Ala-Thr-Arg-Y-(X)-Z 5. Peptide V or Core 9 (aa 49–68) has the sequence:
(V)
(SEQ ID NO:43) (A)-(B)-(X)-Y-Thr-Arg-Lys-Thr-Ser-Glu-Arg-Ser-Gln-Pro-Arg-Gly-Arg-Arg-Gln-Pro-Ile-Pro-Lys-Val-Y-(X)-Z Of particular interest is the oligopeptide Va (aa. 55 to 74):
(Va)
(SEQ ID NO:44) (A)-(B)-(X)-Y-Arg-Ser-Gln-Pro-Arg-Gly-Arg-Arg-Gln-Pro-Ile-Pro-Lys-Val-Arg-Arg-Pro-Glu-Gly-Arg-Y-(X)-Z 6. Peptide VI or Core 11 (aa 61–80) has the following sequence:
(VI)
(SEQ ID NO:45) (A)-(B)-(X)-Y-Arg-Arg-Gln-Pro-Ile-Pro-Lys-Val-Arg-Arg-Pro-Glu-Gly-Arg-Thr-Trp-Ala-Gln-Pro-Gly-Y-(X)-Z 7. Peptide VII (aa 73–92) or core 13 has the sequence:
(VII)
(SEQ ID NO:46) (A)-(B)-(X)-Y-Gly-Arg-Thr-Trp-Ala-Gln-Pro-Gly-Tyr-Pro-Trp-Pro-Leu-Tyr-Gly-Asn-Glu-Gly-Cys-Gly-Y-(X)-Z 8. Peptide Core 123 (aa. 1–32):
(SEQ ID NO:47) (A)-(B)-(X)-Y-Met-Ser-Thr-Ile-Pro-Gln-Arg-Lys-Thr-Lys-Arg-Asn-Thr-Asn-Arg-Arg-Pro-Gln-Asp-Val-Lys-Phe-Pro-Gly-Gly-Gly-Gln-Ile-Val-Gly-Y-(X)-Z 9. Peptide Core 7910 (aa. 37–80):
(SEQ ID NO:48) (A)-(B)-(X)-Y-Gly-Gly-Val-Tyr-Leu-Leu-Pro-Arg-Arg-Gly-Pro-Arg-Leu-Gly-Val-Arg-Arg-Ala-Thr-Arg-Lys-Thr-Ser-Glu-Arg-Ser-Gln-Pro-Arg-Gly-Arg-Arg-Gln-Pro-Ile-Pro-Lys-Val-Arg-Arg-Y-(X)-Z The following peptides from the NS4 region of HCV were found to correspond to immunologically important epitopes.
Peptide VIII or NS4-1 or HCV1 (aa 1688–1707) has the sequence:
(VIII)
(SEQ ID NO:49) (A)-(B)-(X)-Y-Leu-Ser-Gly-Lys-Pro-Ala-Ile-Ile-Pro-Asp-Arg-Glu-Val-Leu-Tyr-Arg-Glu-Phe-Asp-Glu-Y-(X)-Z Peptide IX or HCV2 (aa 1694–1713) has the sequence:
(IX)
(SEQ ID NO:50) (A)-(B)-(X)-Y-Ile-Ile-Pro-Asp-Arg-Glu-Val-Leu-Tyr-Arg-Glu-Phe-Asp-Glu-Met-Glu-Glu-Cys-Ser-Gln-Y-(X)-Z Peptide HCV3
(SEQ ID NO:51) (A)-(B)-(X)-Y-Val-Leu-Tyr-Arg-Glu-Phe-Asp-Glu-Met-Glu-Glu-Cys-Ser-Gln-His-Leu-Pro-Tyr-Ile-Glu-Y-(X)-Z Peptide X or HCV4 (aa 1706–1725) has the sequence:
(X)
(SEQ ID NO:52) (A)-(B)-(X)-Y-Asp-Glu-Met-Glu-Glu-Cys-Ser-Gln-His-Leu-Pro-Tyr-Ile-Glu-Gln-Gly-Met-Met-Leu-Ala-Y-(X)-Z 11. Peptide XI or NS4-5 or HCV5 (aa 1712–1731) has the sequence:
(XI)
(SEQ ID NO:53) (A)-(B)-(X)-Y-Ser-Gln-His-Leu-Pro-Tyr-Ile-Glu-Gln-Gly-Met-Met-Leu-Ala-Glu-Gln-Phe-Lys-Gln-Lys-Y-(X)-Z 12. Peptide XII or HCV6 (aa 1718–1737) has the sequence:
(XII)
(SEQ ID NO:54) (A)-(B)-(X)-Y-Ile-Glu-Gln-Gly-Met-Met-Leu-Ala-Glu-Gln-Phe-Lys-Gln-Lys-Ala-Leu-Gly-Leu-Leu-Gln-Y-(X)-Z 13. Peptide XIII or NS4-7 or HCV7 (aa 1724–1743) has the sequence:
(XIII)
(SEQ ID NO:55) (A)-(B)-(X)-Y-Leu-Ala-Glu-Gln-Phe-Lys-Gln-Lys-Ala-Leu-Gly-Leu-Leu-Gln-Thr-Ala-Ser-Arg-Gln-Ala-Y-(X)-Z 14. Peptide XIV or HCV8 (aa 1730–1749) has the sequence:
(XIV)
(SEQ ID NO:56) (A)-(B)-(X)-Y-Gln-Lys-Ala-Leu-Gly-Leu-Leu-Gln-Thr-Ala-Ser-Arg-Gln-Ala-Glu-Val-Ile-Ala-Pro-Ala-Y-(X)-Z 15. Peptide NS4-27 or HCV9 (aa. 1712–1743):
(SEQ ID NO:57) (A)-(B)-(X)-Y-Ser-Gln-His-Leu-Pro-Tyr-Ile-Glu-Gln-Gly-Met-Leu-Ala-Glu-Gln-Phe-Lys-Gln-Lys-Ala-Leu-Gly-Leu-Leu-Gln-Thr-Ala-Ser-Arg-Gln-Ala-Y-(X)-Z 16. Peptide NS4e:
(SEQ ID NO:58) (A)-(B)-(X)-Y-Gly-Glu-Gly-Ala-Val-Gln-Trp-Met-Asn-Arg-Leu-Ile-Ala-Phe-Ala-Ser-Arg-Gly-Asn-His-Y-(X)-Z The following peptides of the NS5 region of HCV were found to correspond to immunologically important epitopes.
Peptide XV or NS5-25 (aa 2263–2282) has the sequence:
(XV)
(SEQ ID NO:59) (A)-(B)-(X)-Y-Glu-Asp-Glu-Arg-Glu-Ile-Ser-Val-Pro-Ala-Glu-Ile-Leu-Arg-Lys-Ser-Arg-Arg-Phe-Ala-Y-(X)-Z Peptide XVI or NS5-27 (aa 2275–2294) has the sequence:
(XVI)
(SEQ ID NO:60) (A)-(B)-(X)-Y-Leu-Arg-Lys-Ser-Arg-Arg-Phe-Ala-Gln-Ala-Leu-Pro-Val-Trp-Ala-Arg-Pro-Asp-Tyr-Asn-Y-(X)-Z Peptide XVII or NS5-29 (aa 2287–2306) has the sequence:
(XVII)
(SEQ ID NO:61) (A)-(B)-(X)-Y-Val-Trp-Ala-Arg-Pro-Asp-Tyr-Asn-Pro-Pro-Leu-Val-Glu-Thr-Trp-Lys-Lys-Pro-Asp-Tyr-Y-(X)-Z Peptide XVIII or NS5-31 (aa 2299–2318) has the sequence:
(XVIII)
(SEQ ID NO:62) (A)-(B)-(X)-Y-Glu-Thr-Trp-Lys-Lys-Pro-Asp-Tyr-Glu-Pro-Pro-Val-Val-His-Gly-Cys-Pro-Leu-Pro-Pro-Y-(X)-Z Peptide XIX or NS5-33(aa 2311–2330) has the sequence:
(XIX)
(SEQ ID NO:63) (A)-(B)-(X)-Y-Val-His-Gly-Cys-Pro-Leu-Pro-Pro-Pro-Lys-Ser-Pro-Pro-Val-Pro-Pro-Pro-Arg-Lys-Lys-Y-(X)-Z Peptide NS5-2527 (aa. 2263 to 2294):
(SEQ ID NO:64) (A)-(B)-(X)-Y-Glu-Asp-Glu-Arg-Glu-Ile-Ser-Val-Pro-Ala-Glu-Ile-Leu-Arg-Lys-Ser-Arg-Lys-Ser-Arg-Arg-Phe-Ala-Gln-Ala-Leu-Pro-Val-Trp-Ala-Arg-Pro-Asp-Tyr-Asp-Tyr-Asn-Y-(X)-Z The following peptides from the N-terminal region of the E2/NS1 region of HCV were found to correspond to immunologically important epitopes.

peptide XXa (aa. 383–416)
(SEQ ID NO:65) (A)-(B)-(X)-Y-Gly-Glu-Thr-Tyr-Thr-Ser-Gly-Gly-Ala-Ala-Ser-His-Thr-Thr-Ser-Thr-Leu-Ala-Ser-Leu-Phe-Ser-Pro-Gly-Ala-Ser-Gln-Arg-Ile-Gln-Leu-Val-Asn-Thr-Y-(X)-Z peptide XXa-1 (aa. 383–404)
(SEQ ID NO:66) (A)-(B)-(X)-Y-Gly-Glu-Thr-Tyr-Thr-Ser-Gly-Gly-Ala-Ala-Ser-His-Thr-Thr-Ser-Thr-Leu-Ala-Ser-Leu-Phe-Ser-Y-(X)-Z peptide XXa-2 (aa. 393–416)
(SEQ ID NO:67) (A)-(B)-(X)-Y-Ser-His-Thr-Thr-Ser-Thr-Leu-Ala-Ser-Leu-Phe-Ser-Pro-Gly-Ala-Ser-Gln-Arg-Ile-Gln-Leu-Val-Asn-Thr-Y-(X)-Z peptide XXb (aa. 383–416)
(SEQ ID NO:68) (A)-(B)-(X)-Y-Gly-His-Thr-Arg-Val-Ser-Gly-Gly-Ala-Ala-Ala-Ser-Asp-Thr-Arg-Gly-Leu-Val-Ser-Leu-Phe-Ser-Pro-Gly-Ser-Ala-Gln-Lys-Ile-Gln-Leu-Val-Asn-Thr-Y-(X)-Z peptide XXb-1 (aa. 383–404)
(SEQ ID NO:69) (A)-(B)-(X)-Y-Gly-His-Thr-Arg-Val-Ser-Gly-Gly-Ala-Ala-Ala-Ser-Asp-Thr-Arg-Gly-Leu-Val-Ser-Leu-Phe-Ser-Y-(X)-Z peptide XXb-2 (aa. 393–416)
(SEQ ID NO:70) (A)-(B)-(X)-Y-Ala-Ser-Asp-Thr-Arg-Gly-Leu-Val-Ser-Leu-Phe-Ser-Pro-Gly-Ser-Ala-Gln-Lys-Ile-Gln-Leu-Val-Asn-Thr-Y-(X)-Z peptide XXc (aa. 383–416)
(SEQ ID NO:71) (A)-(B)-(X)-Y-Gly-His-Thr-Arg-Val-Thr-Gly-Gly-Val-Gln-Gly-His-Val-Thr-Cys-Thr-Leu-Thr-Ser-Leu-Phe-Arg-Pro-Gly-Ala-Ser-Gln-Lys-Ile-Gln-Leu-Val-Asn-Thr-Y-(X)-Z peptide XXc-1 (aa. 383–404)
(SEQ ID NO:72) (A)-(B)-(X)-Y-Gly-His-Thr-Arg-Val-Thr-Gly-Gly-Val-Gln-Gly-His-Val-Thr-Cys-Thr-Leu-Thr-Ser-Leu-Phe-Arg-Y-(X)-Z peptide XXc-2 (aa. 393–416)
(SEQ ID NO:73) (A)-(B)-(X)-Y-Gly-His-Val-Thr-Cys-Thr-Leu-Thr-Ser-Leu-Phe-Arg-Pro-Gly-Ala-Ser-Gln-Lys-Ile-Gln-Leu-Val-Asn-Thr-Y-(X)-Z peptide XXd (aa. 383–416)
(SEQ ID NO:74) (A)-(B)-(X)-Y-Gly-His-Thr-His-Val-Thr-Gly-Gly-Arg-Val-Ala-Ser-Ser-Thr-Gln-Ser-Leu-Val-Ser-Trp-Leu-Ser-Gln-Gly-Pro-Ser-Gln-Lys-Ile-Gln-Leu-Val-Asn-Thr-Y-(X)-Z peptide XXd-1 (aa. 383–404)
(SEQ ID NO:75) (A)-(B)-(X)-Y-Gly-His-Thr-His-Val-Thr-Gly-Gly-Arg-Val-Ala-Ser-Ser-Thr-Gln-Ser-Leu-Val-Ser-Trp-Leu-Ser-Y-(X)-Z peptide XXd-2 (aa. 393–416)
(SEQ ID NO:76) (A)-(B)-(X)-Y-Ala-Ser-Ser-Thr-Gln-Ser-Leu-Val-Ser-Trp-Leu-Ser-Gln-Gly-Pro-Ser-Gln-Lys-Ile-Gln-Leu-Val-Asn-Thr-Y-(X)-Z peptide XXe (aa. 383–416)
(SEQ ID NO:77) (A)-(B)-(X)-Y-Gly-Asp-Thr-His-Val-Thr-Gly-Gly-Ala-Gln-Ala-Lys-Thr-Thr-Asn-Arg-Leu-Val-Ser-Met-Phe-Ala-Ser-Gly-Pro-Ser-Gln-Lys-Ile-Gln-Leu-Ile-Asn-Thr-Y-(X)-Z peptide XXe-1 (aa. 383–404)
(SEQ ID NO:78) (A)-(B)-(X)-Y-Gly-Asp-Thr-His-Val-Thr-Gly-Gly-Ala-Gln-Ala-Lys-Thr-Thr-Asn-Arg-Leu-Val-Ser-Met-Phe-Ala-Y-(X)-Z peptide XXe-2 (aa. 393–416)
(SEQ ID NO:79) (A)-(B)-(X)-Y-Ala-Lys-Thr-Thr-Asn-Arg-Leu-Val-Ser-Met-Phe-Ala-Ser-Gly-Pro-Ser-Gln-Lys-Ile-Gln-Leu-Ile-Asn-Thr-Y-(X)-Z peptide XXf (aa. 383–416)
(SEQ ID NO:80) (A)-(B)-(X)-Y-Ala-Glu-Thr-Tyr-Thr-Ser-Gly-Gly-Asn-Ala-Gly-His-Thr-Met-Thr-Gly-Ile-Val-Arg-Phe-Phe-Ala-Pro-Gly-Pro-Lys-Gln-Asn-Val-His-Leu-Ile-Asn-Thr-Y-(X)-Z peptide XXf-1 (aa. 383–404)
(SEQ ID NO:81) (A)-(B)-(X)-Y-Ala-Glu-Thr-Tyr-Thr-Ser-Gly-Gly-Asn-Ala-Gly-His-Thr-Met-Thr-Gly-Ile-Val-Arg-Phe-Phe-Ala-Y-(X)-Z peptide XXf-2 (aa. 393–416)
(SEQ ID NO:82) (A)-(B)-(X)-Y-Gly-His-Thr-Met-Thr-Gly-Ile-Val-Arg-Phe-Phe-Ala-Pro-Gly-Pro-Lys-Gln-Asn-Val-His-Leu-Ile-Asn-Thr-Y-(X)-Z peptide XXg (aa. 383–416)
(SEQ ID NO:83) (A)-(B)-(X)-Y-Ala-Glu-Thr-Ile-Val-Ser-Gly-Gly-Gln-Ala-Ala-Arg-Ala-Met-Ser-Gly-Leu-Val-Ser-Leu-Phe-Thr-Pro-Gly-Ala-Lys-Gln-Asn-Ile-Gln-Leu-Ile-Asn-Thr-Y-(X)-Z peptide XXg-1 (aa. 383–404)
(SEQ ID NO:84) (A)-(B)-(X)-Y-Ala-Glu-Thr-Ile-Val-Ser-Gly-Gly-Gln-Ala-Ala-Arg-Ala-Met-Ser-Gly-Leu-Val-Ser-Leu-Phe-Thr-Y-(X)-Z peptide XXg-2 (aa. 393–416)
(SEQ ID NO:85) (A)-(B)-(X)-Y-Ala-Arg-Ala-Met-Ser-Gly-Leu-Val-Ser-Leu-Phe-Thr-Pro-Gly-Ala-Lys-Gln-Asn-Ile-Gln-Leu-Ile-Asn-Thr-Y-(X)-Z peptide XXh (aa. 383–416)
(SEQ ID NO:86) (A)-(B)-(X)-Y-Ala-Glu-Thr-Tyr-Thr-Thr-Gly-Gly-Ser-Thr-Ala-Arg-Thr-Thr-Gln-Gly-Leu-Val-Ser-Leu-Phe-Ser-Arg-Gly-Ala-Lys-Gln-Asp-Ile-Gln-Leu-Ile-Asn-Thr-Y-(X)-Z peptide XXh-1 (aa. 383–404)
(SEQ ID NO:87) (A)-(B)-(X)-Y-Ala-Glu-Thr-Tyr-Thr-Thr-Gly-Gly-Ser-Thr-Ala-Arg-Thr-Thr-Gln-Gly-Leu-Val-Ser-Leu-Phe-Ser-Y-(X)-Z peptide XXh-2 (aa. 393–416)
(SEQ ID NO:88) (A)-(B)-(X)-Y-Ala-Arg-Thr-Thr-Gln-Gly-Leu-Val-Ser-Leu-Phe-Ser-Arg-Gly-Ala-Lys-Gln-Asp-Ile-Gln-Leu-Ile-Asn-Thr-Y-(X)-Z The above-mentioned sequences correspond to epitopes localized on the HCV type-1 isolate HCV-1 (Choo et al. Proc; Natl. Acad. Sci. 88, 2451–2455, 1991) and HC-J1 (Okamoto et al., Jap. J. Exp. Med. 60, 167–177, 1990) sequence. It is, however, to be understood that also peptides from other type-1 HCV isolate sequences which correspond to the above-mentioned immunologically important regions may also be comprised in the composition according to the invention. An example of variant HCV sequences also falling within the present invention may be derived from the HCV-J isolate (Kato et al., Proc. Natl. Acad. Sci. 87, 9524–9528).

The following peptides derived from the same regions as the above-cited peptide regions from the type 2 HCV sequences.

peptide XX/2
(SEQ ID NO:89) (A)-(B)-(X)-Y-Ala-Gln-Thr-His-Thr-Val-Gly-Gly-Ser-Thr-Ala-His-Asn-Ala-Arg-Thr-Leu-Thr-Gly-Met-Phe-Ser-Leu-Gly-Ala-Arg-Gln-Lys-Ile-Gln-Leu-Ile-Asn-Thr-Y-(X)-Z peptide XX/2-1
(SEQ ID NO:90) (A)-(B)-(X)-Y-Ala-Gln-Thr-His-Thr-Val-Gly-Gly-Ser-Thr-Ala-His-Asn-Ala-Arg-Thr-Leu-Thr-Gly-Met-Phe-Ser-Y-(X)-Z
peptide XX/2-2
(SEQ ID NO:91) (A)-(B)-(X)-Y-Ala-His-Asn-Ala-Arg-Thr-Leu-Thr-Gly-Met-Phe-Ser-Leu-Gly-Ala-Arg-Gln-Lys-Ile-Gln-Leu-Ile-Asn-Thr-Y-(X)-Z
peptide VIII-2 or NS4-1 (2)
(SEQ ID NO:92) (A)-(B)-(X)-Y-Val-Asn-Gln-Arg-Ala-Val-Val-Ala-Pro-Asp-Lys-Glu-Val-Leu-Tyr-Glu-Ala-Phe-Asp-Glu-Y-(X)-Z
peptide IX-2
(SEQ ID NO:93) (A)-(B)-(X)-Y-Val-Ala-Pro-Asp-Lys-Glu-Val-Leu-Tyr-Glu-Ala-Phe-Asp-Glu-Met-Glu-Glu-Cys-Ala-Ser-Y-(X)-Z
peptide X-2
(SEQ ID NO:94) (A)-(B)-(X)-Y-Asp-Glu-Met-Glu-Glu-Cys-Ala-Ser-Arg-Ala-Ala-Leu-Ile-Glu-Glu-Gly-Gln-Arg-Ile-Ala-Y-(X)-Z
peptide XI-2 or NS4-5 (2)
(SEQ ID NO:95) (A)-(B)-(X)-Y-Ala-Ser-Arg-Ala-Ala-Leu-Ile-Glu-Glu-Gly-Gln-Arg-Ile-Ala-Glu-Met-Leu-Lys-Ser-Lys-Y-(X)-Z
peptide XII-2
(SEQ ID NO:96) (A)-(B)-(X)-Y-Ile-Glu-Glu-Gly-Gln-Arg-Ile-Ala-Glu-Met-Leu-Lys-Ser-Lys-Ile-Gln-Gly-Leu-Leu-Gln-Y-(X)-Z
peptide XIII-2 or NS4-7(2)
(SEQ ID NO:97) (A)-(B)-(X)-Y-Ile-Ala-Glu-Met-Leu-Lys-Ser-Lys-Ile-Gln-Gly-Leu-Leu-Gln-Gln-Ala-Ser-Lys-Gln-Ala-Y-(X)-Z
peptide XIV-2
(SEQ ID NO:98) (A)-(B)-(X)-Y-Ser-Lys-Ile-Gln-Gly-Leu-Leu-Gln-Gln-Ala-Ser-Lys-Gln-Ala-Gln-Asp-Ile-Gln-Pro-Ala-Y-(X)-Z
peptide XV-2
(SEQ ID NO:99) (A)-(B)-(X)-Y-Arg-Ser-Asp-Leu-Glu-Pro-Ser-Ile-Pro-Ser-Glu-Tyr-Met-Leu-Pro-Lys-Lys-Arg-Phe-Pro-(X)-Y-Z
peptide XVI-2
(SEQ ID NO:100) (A)-(B)-(X)-Y-Met-Leu-Pro-Lys-Lys-Arg-Phe-Pro-Pro-Ala-Leu-Pro-Ala-Trp-Ala-Arg-Pro-Asp-Tyr-Asn-Y-(X)-Z
peptide XVII-2
(SEQ ID NO:101) (A)-(B)-(X)-Y-Ala-Trp-Ala-Arg-Pro-Asp-Tyr-Asn-Pro-Pro-Leu-Val-Glu-Ser-Trp-Lys-Arg-Pro-Asp-Tyr-Y-(X)-Z
peptide XVIII-2
(SEQ ID NO:102) (A)-(B)-(X)-Y-Glu-Ser-Trp-Lys-Arg-Pro-Asp-Tyr-Gln-Pro-Ala-Thr-Val-Ala-Gly-Cys-Ala-Leu-Pro-Pro-Y-(X)-Z
peptide XIX-2
(SEQ ID NO:103) (A)-(B)-(X)-Y-Val-Ala-Gly-Cys-Ala-Leu-Pro-Pro-Pro-Lys-Lys-Thr-Pro-Thr-Pro-Pro-Arg-Arg-Arg-Y-(X)-Z The above-mentioned sequences correspond to epitopes localized on the HCV type-2 isolate HC-J6 sequence (Okamoto et al., J. Gen. Virology 72, 2697–2704, 1991). It is, however, to be understood that also peptides from other type-2 HCV isolate sequences which correspond to the above-mentioned immunologically important regions may also be comprised in the composition according to the invention. Examples of variant sequences also falling within the present invention may be derived from HCV isolate HC-J8 (Okamato et al., Virology 188, 331–341, 1992).

The following peptides from the NS4 region of HCV type 3 are also preferred peptides according to the present invention:

Peptide NS4-1 (3)
(SEQ ID NO:104) (A)-(B)-(X)-Y-Leu-Gly-Gly-Lys-Pro-Ala-Ile-Val-Pro-Asp-Lys-Glu-Val-leu-Tyr-Gln-Gln-Tyr-Asp-Glu-Y-(X)-Z
Peptide NS4-5 (3)
(SEQ ID NO:5) (A)-(B)-(X)-Y-Ser-Gln-Ala-Ala-Pro-Tyr-Ile-Glu-Gln-Ala-Gln-Val-Ile-Ala-His-Gln-Phe-Lys-Glu-Lys-Y-(X)-Z
Peptide NS4-7 (3)
(SEQ ID NO:106) (A)-(B)-(X)-Y-Ile-Ala-His-Gln-His-Gln-Phe-Lys-Glu-Lys-Val-Leu-Gly-Leu-Leu-Gln-Arg-Ala-Thr-Gln-Gln-Gln-Y-(X)-Z It is to be understood that also other peptides corresponding to HCV type-3 isolate sequences which correspond to immunologically important regions as determined for HCV type-1 and type-2 may also be comprised in the composition according to the invention.

The composition according to the present invention may also comprise hybrid HCV peptide sequences consisting of combinations of the core epitopes of the HCV core (table 9) HCV NS4 (table 10) or the HCV NS5 (table 11) region separated by Gly and/or Ser residues, and preferentially the following hybrid HCV sequences:

Epi-152
(SEQ ID NO:107) (A)-(B)-(X)-Y-Ile-Pro-Asp-Arg-Glu-Val-Leu-Tyr-Arg-Gly-Gly-Lys-Lys-Pro-Asp-Tyr-Glu-Pro-Pro-Val-Gly-Gly-Arg-Arg-Pro-Gln-Asp-Val-Lys-Phe-Pro-Y-(X)-Z
Epi-33B3A
(SEQ ID NO:108) (A)-(B)-(X)-Y-Trp-Ala-Arg-Pro-Asp-Tyr-Asn-Pro-Pro-Gly-Gly-Gln-Phe-Lys-Gln-Lys-Ala-Leu-Gly-Leu-Gly-Ser-Gly-Val-Tyr-Leu-Leu-Pro-Arg-Arg-Gly-Y-(X)-Z
Epi-4B2A6
(SEQ ID NO:109) (A)-(B)-(X)-Y-Arg-Gly-Arg-Arg-Gln-Pro-Ile-Pro-Lys-Gly-Gly-Ser-Gln-His-Leu-Pro-Tyr-Ile-Glu-Gln-Ser-Gly-Pro-Val-Val-His-Gly-Cys-Pro-Leu-Pro-Y-(X)-Z

The composition according to the present invention may also comprise so called biotinylated mixotope sequences consisting of peptides containing at each position all the amino acids found in the naturally occurring isolates, with said peptides being derived from any of the above-mentioned immunologically important regions (see FIG. 14).

(2) A preferred mixture of biotinylated peptides for detecting and/or immunizing against Hepatitis C Virus, Human Immunodeficiency Virus type 1 and Human Immunodeficiency Virus type 2 consists of:

A. II, III, IVa, Va, IX, XI, XIII, XV, XVI, XVIII,
  1a.3, 1a.4, 1a.b, 1b.1a, 2b, 2d,
B. II, III, IVa, Va, IX, IX-2, XI, XI-2, XIII, XIII-2, XV, XV-2, XVI, XVI-2, XVIII, XVIII-2,
  1a.3, 1a.4, 1a.b, 1b.1a, 2b, 2d.

(3) A preferred mixture of biotinylated peptides for detecting and/or immunizing against Human Immunodeficiency Virus types 1 and 2 and Human Lymphotropic Virus types I and II consists of:
  1a.3, 1a.4, 1b.1, 2b, 2c, 2d, I-gp46-3, I-gp46-4, I-gp46-5, I-gp46-6, II-gp52-2, II-gp52-3, I-p21-2, I-p19, II-p19.

(4) Another preferred mixture of biotinylated peptides for detecting and/or immunizing against Hepatitis C Virus, Human Immunodeficiency Virus types 1 and 2 and Human Lymphotropic Virus types I and II consists of:
  1a.3, 1a.4, 1a.6, 1b.1a, 2d, II, III, IVa, Va, IX, XI, XIII, XV, XVI, XVIII, XXa-2, XXc-2, XXg-2, XXh-2, I-gp46-3, I-gp46-4, I-gp46-5, I-gp46-6, II-gp52-3, I-p21-2, I-p19, II-p19.

(5) The present invention relates also to compositions of biotinylated peptides which are considered particularly advantageous, for diagnostic as well as immunogenic purposes for Hepatitis C Virus, and which advantageously comprise the following mixtures:

A. I, III, IVa, Va,
B. II, III, IVa, Va,
C. IX, XI, XIII,
D. XV, XVI, XVIII, XIX,
E. XXc-2, XXa-1, XXa-2, XXh-1, XXh-2, XXg-2, XX/2-2,
F. IX-2, XI-2, XIII-2,
G. XV-2, XVI-2, XVIII-2, XIX-2,
H. IX, IX-2, XI, XI-2, XIII, XIII-2,
I. XV, XV-2, XVI, XVI-2, XVIII, XVIII-2, XIX, XIX-2,
J. II, III, IVa, Va, IX, IX-2, XI, XI-2, XIII, XIII-2, XV, XV-2, XVI, XVI-2, XVIII, XVIII-2,
K. II, III, IVa, Va, IX, XI, XIII, XV, XVI, XVIII,
L. II, III, IV, V, IX, XI, XIII, XV, XVI, XVIII,
M. II, III, IVa, Va, IX, XI, XIII, XV, XVI, XVIII, XXa-2, XXc-2, XXg-2, XXh-2.

(6) The present invention relates also to compositions of biotinylated peptides which are considered particularly advantageous, for diagnostic as well as immunogenic purposes for Human Immunodeficiency Virus, and which are advantageously selected from the following mixtures: for type 1:

A. 1a.3, 1a.4, 1a.5, 1a.b
B. 1a.3, 1a.4, 1b.1, 1b.3, 1b.6, 1b.10,
C. 1b.1, 1b.2, 1b.3, 1b.4, 1b.5, 1b.6, 1b.7, 1b.8, 1b.9, 1b.10
D. 1b.1, 1b.2, 1b.3, 1b.4, 1b.6, 1b.10,
E. 1a.3, 1a.4, 1a.5, 1a.b, 1b.1a.

for type 2:
A. 2b, 2c, 2d, 2e.

for types 1 and 2:
A. 1a.3, 1a.4, 1b.1, 2b, 2c, 2d,
B. 1a.3, 1a.4, 1b.1a, 2b, 2d.

(7) The present invention relates also to compositions comprising biotinylated peptides which are considered particularly advantageous, for diagnostic as well as immunogenic purposes for Human T-cell Lymphotropic Virus and are advantageously selected from the following mixtures:

for Human T-Lymphotropic virus type I:
Peptides I-gp46-3, I-gp46-4, I-gp46-5, I-gp46-6, I-p21-2, I-p19 for Human T-Lymphotropic virus type II:
Peptides II-gp52-1, II-gp52-2, II-gp52-3, I-gp46-4, II-p19, I-p21-2.

for Human lymphotropic virus types I and II:
Peptides I-gp46-3, I-gp46-4, I-gp46-5, I-gp46-6, II-gp52-1, IIgp52-2, II-gp52-3, I-p21-2, I-p19, II-p19.

The synthesis of the peptides may be achieved in solution or on a solid support. Synthesis protocols generally employ t-butyloxycarbonyl- or 9-fluorenylmethoxycarbonyl-protected activated amino acids. The procedures for carrying out the synthesis, the amino acid activation techniques, the types of side-chain production, and the cleavage procedures used are amply described in, for example, Stewart and Young, Solid Phase Peptide Synthesis, 2nd Edition, Pierce Chemical Company, 1984; and Atherton and Sheppard, Solid Phase Peptide Synthesis, IRL Press, 1989.

(8) The present invention also relates to a process for in vitro determination of antibodies using the above defined biotinylated peptides, wherein said biotinylated peptides are preferably in the form of streptavidin-biotinylated peptide complexes or avidin-biotinylated peptide complexes.

In the complex of streptavidin-biotinylated peptides or avidin-biotinylated peptides, the peptides may be biotinylated either N-terminally, C-terminally or internally.

This approach for the determination of antibodies is not limited with respect to peptide length and avoids the difficulties inherent in coating peptides directly onto the solid phase for immunological evaluation.

The use of biotinylated peptides, in the process of the invention, makes the anchorage of peptides to a solid support such that it leaves their essential amino acids free to be recognized by antibodies.

The expression anchoring peptide to a solid support means the attachment of the peptide to a support via covalent bonds or non-covalent interactions such that the peptide becomes immobilized.

The solid support can be nitrocellulose, polystyrene, nylon or any other natural or synthetic polymer.

The expression "their essential amino acids are left free to be recognized by antibodies" means that amino acid side chains of the peptide proper are neither chemically modified in any way nor involved in the interaction between the peptide and the solid phase.

The use of biotinylated peptides in the process of the invention enables said biotinylated peptides to be free to assume a wide range of conformations, among which at least one is appropriate for the binding of antibodies to said biotinylated peptides.

Any biotinylated peptide can be selected to be used in the process of the invention. However, some of them are able to be anchored on solid support and to react with antibodies specifically recognizing the epitope within this peptide even without being biotinylated and without being involved in a complex of avidin of streptavidin. In this case, the use of biotinylated peptides results in an apparent increase of the antigenicity of peptides with respect to the antigenicity observed when the peptides are not biotinylated. The expression "apparent" is meant to indicate an observed change obtained under similar test conditions without regard to the absolute cause of the observed change.

By "antigenicity" is meant the property of a peptide to be bound by an antibody.

By "increase of antigenicity" is meant that a positive signal is obtained for a dilution which is at least two times the dilution of the non-biotinylated peptides. Said positive signal is of the same magnitude as the one obtained for non-biotinylated peptides.

In other words, obtaining a positive signal can be obtained for a smaller amount of biotinylated peptide, compared to the amount of non-biotinylated peptide.

The present invention also illustrated a process for the identification of epitopes in a protein sequence comprises the following steps:

the preparation of peptides corresponding to portions of the amino acid sequence of the protein or polypeptide to be analyzed, said peptides being either contiguous, or preferably overlapping each other, the amount of overlapping being at least 3 amino acids, and preferably about 6 to about 12, the length of the peptides being at least about 5 amino acids and no more than about 50, preferably no more than about 40 amino acids, and more preferably from 9 to about 30 amino acids, with said peptides being characterized in that they are biotinylated;

binding the peptides to a solid phase through the interaction between the biotinyl group and streptavidin or avidin and measuring antibody binding to the individual peptides using classical methods.

(9) The present invention also relates to a process for the in vitro determination of antibodies to HIV or diagnosis of HIV infection by using a peptide composition as defined above in an immunoassay procedure, wherein the biotinylated peptides used are in the form of complexes of streptavidin-biotinylated or of avidin-biotinylated peptides.

(10) The present invention relates also to a process for the in vitro determination of antibodies to HCV or diagnosis of HCV infection by using a peptide composition as defined above in an immunoassay procedure, wherein the biotinylated peptides used are in the form of complexes of streptavidin-biotinylated or of avidin-biotinylated peptides.

(11) The present invention relates also to a process for the in vitro determination of antibodies to HTLV I or II or diagnosis of HTLV I or II infection by using a peptide composition as defined above in an immunoassay procedure, wherein the biotinylated peptides used are in the form of complexes of streptavidin-biotinylated or of avidin-biotinylated peptides.

A preferred method for carrying out the in vitro determination of antibodies is by means of an enzyme-linked immunosorbant assay (ELISA). This assay employs a solid phase which is generally a polystyrene microtiter plate or bead. The solid phase may, however, be any material which is capable of binding a protein, either chemically via a covalent linkage or by passive adsorption. In this regard, nylon-based membranes are also considered to be particularly advantageous. The solid phase is coated with streptavidin or avidin and after a suitable period, excess unbound protein is removed by washing. Any unoccupied binding sites on the solid phase are then blocked with an irrelevant protein such as bovine serum albumin or casein.

A solution containing the mixture or selection of biotinylated peptides is subsequently brought into contact with the streptavidin- or avidin-coated surface and allowed to bind. Unbound peptide is removed by washing. Alternatively, biotinylated peptides are allowed to form complexes with either avidin or streptavidin. The resulting complexes are used to coat the solid phase. After a suitable incubation period, unbound complex is removed by washing. An appropriate dilution of an antiserum or other body fluid is brought into contact with the solid phase to which the peptide is bound. The incubation is carried out for a time necessary to allow the binding reaction to occur. Subsequently, unbound components are removed by washing the solid phase. The detection of immune complexes is achieved by using heterologous antibodies which specifically bind to the antibodies present in the test serum and which have been conjugated with an enzyme, preferably but not limited to either horseradish peroxidase, alkaline phosphatase, or β-galactosidase, which is capable of converting a colorless or nearly colorless substrate or co-substrate into a highly colored product or a product capable of forming a colored complex with a chromogen which can be detected visually or measured spectrophotometrically.

Other detection systems known in the art may however be employed and include those in which the amount of product formed is measured electrochemically or luminometrically. The detection system may also employ radioactively labeled antibodies, in which case the amount of immune complex is quantified by scintillation counting or counting. In principle, any type of immunological test for the detection of antibodies may be used, as long as the test makes use of the complex between either streptavidin or avidin and (a) biotinylated peptide(s) synthesized as described.

Also included are competition assays in which streptavidin- or avidin- biotinylated peptide complexes in solution are permitted to compete with the solid phase-bound antigen for antibody binding or assays in which free peptide in solution is permitted to compete with solid phase-bound streptavidin or avidin: biotinylated peptide complexes. By way of example, the many types of immunological assays for the detection and quantitation of antibodies and antigen are discussed in detail (Tijssen, P., Practice and Theory of Enzyme Immunoassays, Elsevier Press, Amsterdam, Oxford, N.Y., 1985).

The immunological assays may be restricted to single biotinylated peptides. Preferably, however, a mixture of biotinylated peptides is used which includes more than one epitope derived from the infectious agent(s) to which the presence of specific antibodies is to be measured.

Another preferred method for carrying out the in vitro determination of antibody detection is the line immunoassay (LIA).

The method of antibody detection consists essentially of the following steps:

the antigens, in the form of biotinylated peptide: streptavidin or avidin complexes, to be tested or used are applied as parallel lines onto a membrane which is capable of binding, covalently or non-covalently, the antigen to be tested, unoccupied binding sites on the membrane are blocked with an irrelevant protein such as casein or bovine serum albumin, the membrane is cut into strips in a direction perpendicular to the direction in which the antigen (biotinylated peptide) lines are applied, an appropriate dilution of an antiserum or other body fluid (containing antibodies to be detected) is brought into contact with a strip to which the antigens are bound and allowed to incubate for a period of time sufficient to permit the binding reaction to occur, unbound components are removed by washing the strip, the detection of immune complexes is achieved by incubating the strip with heterologous antibodies which specifically bind to the antibodies in the test serum and which have been conjugated to an enzyme such as horseradish peroxidase, the incubation is carried out for a period sufficient to allow binding to occur, the presence of bound conjugate is detected by addition of the required substrate or co-substrates which are converted to a colored product by the action of the enzyme, the reactions are detected visually or may be quantified by densitometry.

(12) As demonstrated in the Examples section the present invention relates also the the use of a peptide composition as defined above, for immunization against HIV, and/or HCV, and/or HTLV I or II infection.

(13) The present invention also relates to a method for preparing the biotinylated peptides used in the invention involves the use of N-α-Fmoc-X (N-γ-biotin) or N-α-Fmoc-X (N-γ-biotin) derivative, wherein X represents

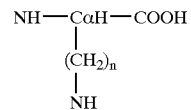

where n is at least 1 but less than 10 and is preferably between 2 and ε, one amino group being attached to the Cα atom while the other being attached to carbon Cγ, which is the most distal carbon in the side chain; or their esters obtained with alcohol ROH and more particularly pentafluorophenyl ester;

y representing position y with respect to the carbon atom carrying the COOH group in the radical.

This biotin derivative will be called intermediary product, and the above-defined intermediary products are new compounds determined according to the process of the invention.

(14) In an advantageous method for preparing the compounds of the invention, the intermediary product can be represented by one of the following formula:

N-α-Fmoc- (N-y-biotin) is N-α-Fmoc-lysine (ε-biotin) or N-α-Fmoc-ornithine (N-δ-biotin)

(15) The N-terminal biotinylated peptides can be prepared according to the method which comprises the following steps:

addition of the successive amino acids duly protected onto the resin to give:

Fmoc–AA$_n$ . . . AA$_1$–resin, deprotection of the NH$_2$-terminal for instance by means of piperidine, addition of the intermediary product:

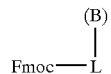

through its COOH onto the NH$_2$-terminal to obtain:

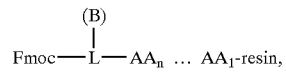

deprotection of the NH$_2$-terminal group of the compound obtained, cleavage from the resin, extraction and purification of the peptide obtained, biotinylated at its amino terminal, the steps of side chain deprotection and peptide cleavage being liable to be performed simultaneously or separately, and particularly deprotection of the NH$_2$-terminal group of the intermediary group, for instance by means of piperidine, cleavage from the resin for instance with an acid such as trifluoroacetic acid, in the presence of scavengers such as ethanedithiol, thioanisole, or anisole, extraction of the peptide with a solvent such as diethyl-ether to remove most the acid and scavengers, purification, such as with HPLC to obtain:

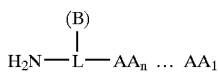

Biotin can be conveniently coupled to the free amino-terminus of an otherwise fully protected peptide chain using also conventional activation procedures. Since biotin possesses one carboxyl group and no amino groups, biotin essentially functions as a chain terminator. Preferred activating agents for in situ activation include but are not limited to benzotriazol-1-yl-oxy-tripyrrolidinophosphonium hexafluorophosphate (PyBOP) O-benzotriazol-1-yl-N,N,N', N'-tetramethyluronium hexafluorophosphate (HBTU), and O-(1H-benzotriazol-1-yl)-tetrafluoroborate (TBTU). The activation procedures employing these and related compounds are known to those versed in the art of solid phase peptide synthesis and the coupling of biotin does not entail a significant departure from standard coupling protocols.

Biotin in a pre-activated form may also be used. Either N-hydroxysuccinimidobiotin or biotinamidocaproate N-hydroxysuccinimide ester are conveniently employed and both are commercially available. This method of coupling has been described by Lobl, T. J., Deibel, M. R., and Yem, A. W., Anal. Biochem. (1988) 170(2):502–511. Following addition of the N-terminal biotin, the peptide is cleaved from the resin in the presence of scavengers, the choice of which will depend on the usual considerations of peptide amino acid composition and the nature of the protecting groups used.

(16) The carboxy terminal biotinylated peptides involved in the process of the invention can be prepared according to a method which comprises coupling of a carboxy-activated form of the intermediary product as defined above to a cleavable linker attached to the resin, for instance to obtain the following compound:

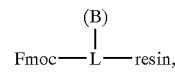

deprotection of the α amino group of the intermediary compound, for instance by means of piperidine to obtain:

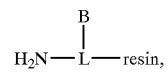

successive addition of the subsequent amino acids AA$_1$ . . . AA$_n$ dully protected onto

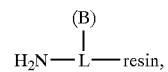

to obtain:

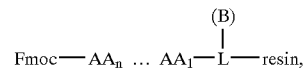

deprotection of the NH$_2$-terminal for instance by means of piperidine, deprotection of the compound obtained, cleavage from the resin, extraction and purification of the peptide obtained, biotinylated at its carboxy terminal end, the steps of side chain deprotection and peptide cleavage being liable to be performed simultaneously or separately, and particularly deprotection of the NH$_2$-terminal, for instance by means of piperidine, cleavage from the resin for instance with trifluoroacetic acid, in the presence of scavengers such as ethanedithiol, or thioanisole, or anisole, extraction of the peptide with a solvent such as diethyl-ether to remove most of the acid and scavengers, purification, such as with HPLC to obtain:

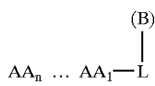

(17) The internally biotinylated peptides can be prepared according to a method which comprises the following steps:

addition of successive amino acids duly protected onto the resin to give:

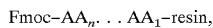

deprotection of the $NH_2$-terminal,
addition of the intermediary product:

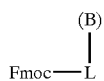

through its COOH onto the $NH_2$-terminal to obtain:

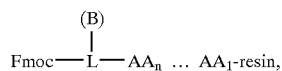

deprotection for the α amino group of the intermediary compound, for instance by means of piperidine to obtain:

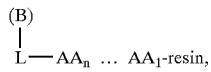

addition of the subsequent amino acids duly protected onto the resin to give:

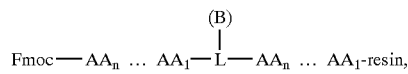

deprotection of the NH2 terminal group of the compound obtained, cleavage from the resin, extraction and purification of the peptide obtained, biotinylated at its amino-terminal, the steps of side chain deprotection and peptide cleavage being liable to be performed simultaneously or separately, and particularly, deprotection of the $NH_2$-terminus, for instance by means of piperidine, cleavage from the resin for instance with trifluoroacetic acid, in the presence of scavengers such as ethanedithiol, or thioanisole, or anisole, extraction of the peptide with a solvent such as diethyl-ether to remove most of the acid and scavengers, purification, such as with HPLC to obtain:

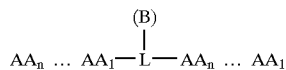

Under certain circumstances, it may prove particularly advantageous to be able to biotinylate a peptide internally or at its carboxy-terminus. Such instances arise, for example, when the amino acid sequence of a peptide corresponds to the amino-terminal sequence of a protein. Attachment of a biotin to the amino-terminus of such a peptide results in a structure which is significantly different from that found in the native protein and may, as a consequence, adversely affect the binding properties of biochemical properties of the peptide. It is also possible that even for peptides corresponding to internal protein sequences, their recognition by binding proteins or immunoglobulins may depend on which end of the peptide and the manner in which it is presented for binding. The importance of peptide orientation has been described by Dyrberg, T. and Oldstone, M. B. A., J. Exp. Med. (1986) 164:1344–1349.

In order to be able to incorporate a biotinyl moiety into a peptide in a position and sequence independent manner, efforts were made to synthesize a suitable reagent which can be coupled using conventional procedures. A convenient reagent for C-terminal or internal biotinylation is N-ε-biotinyl-lysine. Provided the α-amino group of this compound is suitably protected (Fmoc and tBoc), this reagent may be used to introduce a biotin anywhere in the peptide chain, including at the amino terminus, by the standard procedures used in solid phase peptide synthesis. The synthesis of the t-Boc-protected derivative has been described (Bodansky, M., and Fagan, DT., J. Am. Chem. Soc. (1977) 99:235–239) and was used to synthesize short peptides for use in studying the enzyme activities of certain transcarboxylases.

Unlike the t-Boc derivative, the synthesis of N-α-Fmoc-Lys (N-ε-biotin) has not been described and given the growing interest in Fmoc-based synthesis strategies, this compound is considered particularly advantageous.

There are a number of possible routes which can be taken to arrive at the desired Fmoc-protected compound. These are shown in FIG. 1. In the first approach, commercially available N-α-Fmoc-Lys (N-ε-tBoc) can be used as the starting material. The N-ε-tBoc protection is removed using trifluoroacetic acid and a scavenger such as water. A slight molar excess of the N-α-Fmoc-lysine so obtained is then reacted with carboxy-activated biotin. The resulting product can be readily purified by selective extractions and standard chromatographic techniques. In an alternative approach, N-α-Fmoc-Lys (N-ε-biotin) can be produced from commercially available N-ε-biotinyl lysine (biocytin) by reaction with fluorenylmethylsuccinimidyl carbonate. Numerous examples of these reactions which can be used as guidelines are given in Atherton and Sheppard, Solid Phase Peptide Synthesis, IRL Press, 1989.

The strategy shown in FIG. 1 (method A) may also be applied to synthesize N-α-Fmoc-ornithine (N-δ-biotin) from commercially available N-α-Fmoc-ornithine (N-δ-tBoc). The ornithine derivative differs from the lysine derivative only in the length of the side chain which, for the ornithine derivative, is shorter by one carbon atom. The N-α-Fmoc-Lys can be conveniently incorporated into the peptide chain using the same reagents for in situ activation described for free biotin.

Alternatively, N-α-Fmoc-Lys (N-ε-biotin)-O-pentafluorophenyl ester can be conveniently synthesized from N-α-Fmoc-Lys (N-ε-biotin) and pentafluorophenyl trifluoroacetate using the base-catalyzed transesterification reaction described by Green, M. and Berman, J., Tetrahedron Lett. (1990) 31:5851–5852, for the preparation of O-pentafluorophenyl esters of amino acids. This active ester can be used directly to incorporate N-α-Fmoc-Lys (N-ε-biotin) into the peptide chain. The class of above-defined intermediary products can be prepared according to a method which comprises the following steps:

reaction of a diamino-, monocarboxylic acid previously described with fluorenylmethysuccinimidylcarbonate or fluorenylmethyl chloroformate under conditions of carefully controlled pH to give the singly protected N-α-Fmoc derivative, or alternatively, use of commercially available N-α-Fmoc-protected diamino-monocarboxylic acids when the side chain amino group is provided with a protecting group which is different from the Fmoc group used to protect the α-amino group, the side chain amino group protection being liable to be selectively removed under conditions which leave the N-α-Fmoc group intact, purification of the mono-protected N-α-Fmoc-diamino-monocarboxylic acid derivative by selective extractions and chromatography, reaction of the derivative obtained with a carboxy-activated derivative of biotin, such as N-hydroxysuccinimide biotin, to obtain the (N-α-Fmoc)-(N-y-biotin) derivative which is the desired intermediary product, purification of the intermediary product by selective extractions, precipitations, or chromatography.

When the biotinylated peptides used in the process of the invention are to be provided with linker arms, these chemical entities may be conveniently attached to either the N- or C-terminus of a peptide sequence during solid phase synthesis using standard coupling protocols, as long as the amino groups of these compounds are provided with appropriate temporary amino group protection.

All these specific biotinylated peptides are new.

DESCRIPTION OF THE FIGURES

All the samples and sera mentioned in the figures and tables are randomly chosen samples and sera, containing antibodies produced as a result of naturally occurring infection by a viral agent.

More particularly:

Method A corresponds to the synthesis of (N-α-Fmoc-Lys (N-ε-biotin) from N-ε-Fmoc-Lys(N-ε-tBoc) and Method B corresponds to the synthesis of (N-α-Fmoc-Lys(N-ε-biotin) from N-ε-biotinyl lysine.

Figure 1A:
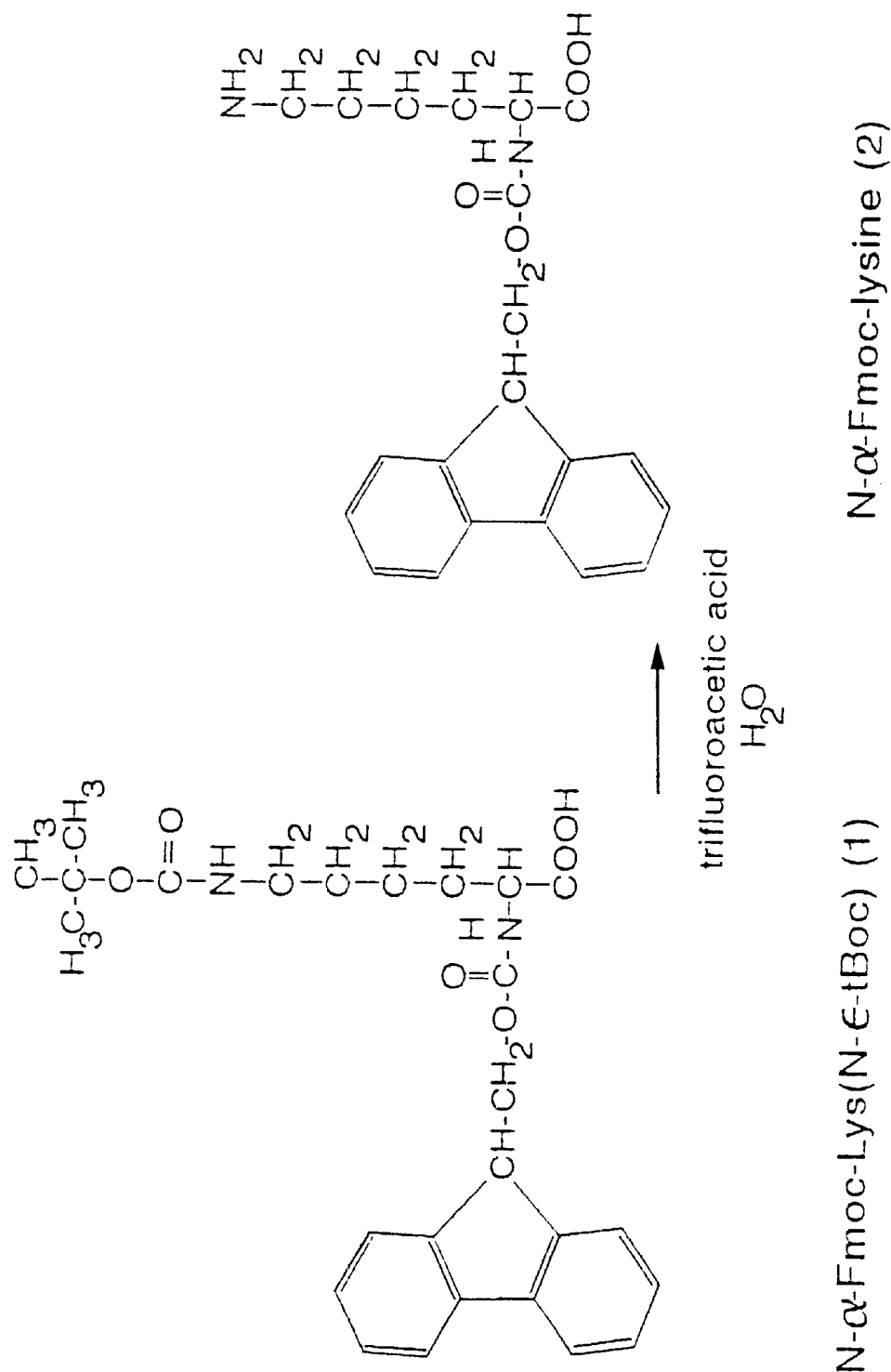
FIGS. 1a–1c represent the strategies for the synthesis of N-α-Fmoc-lysine (N-ε-Biotin).
Figure 1B:
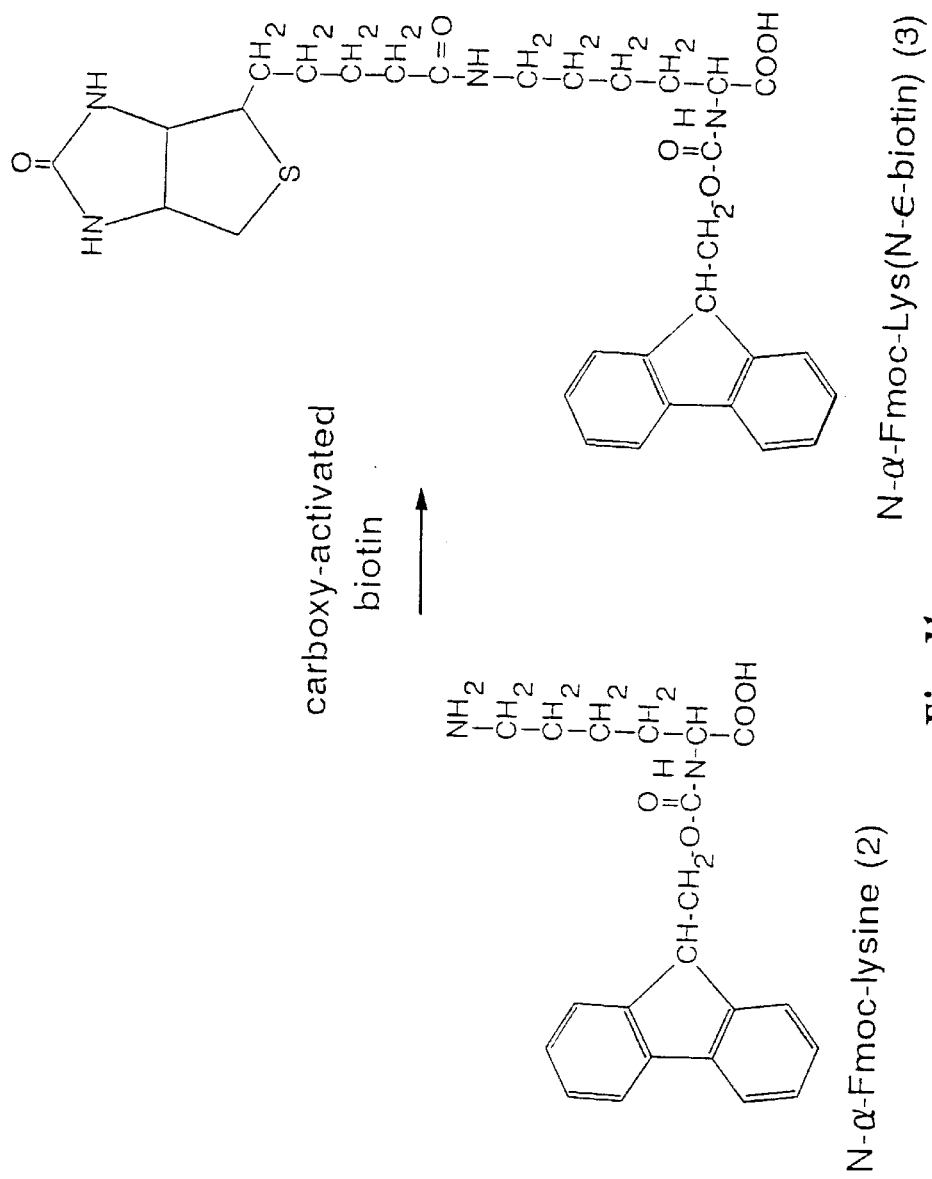
Figure 1C:
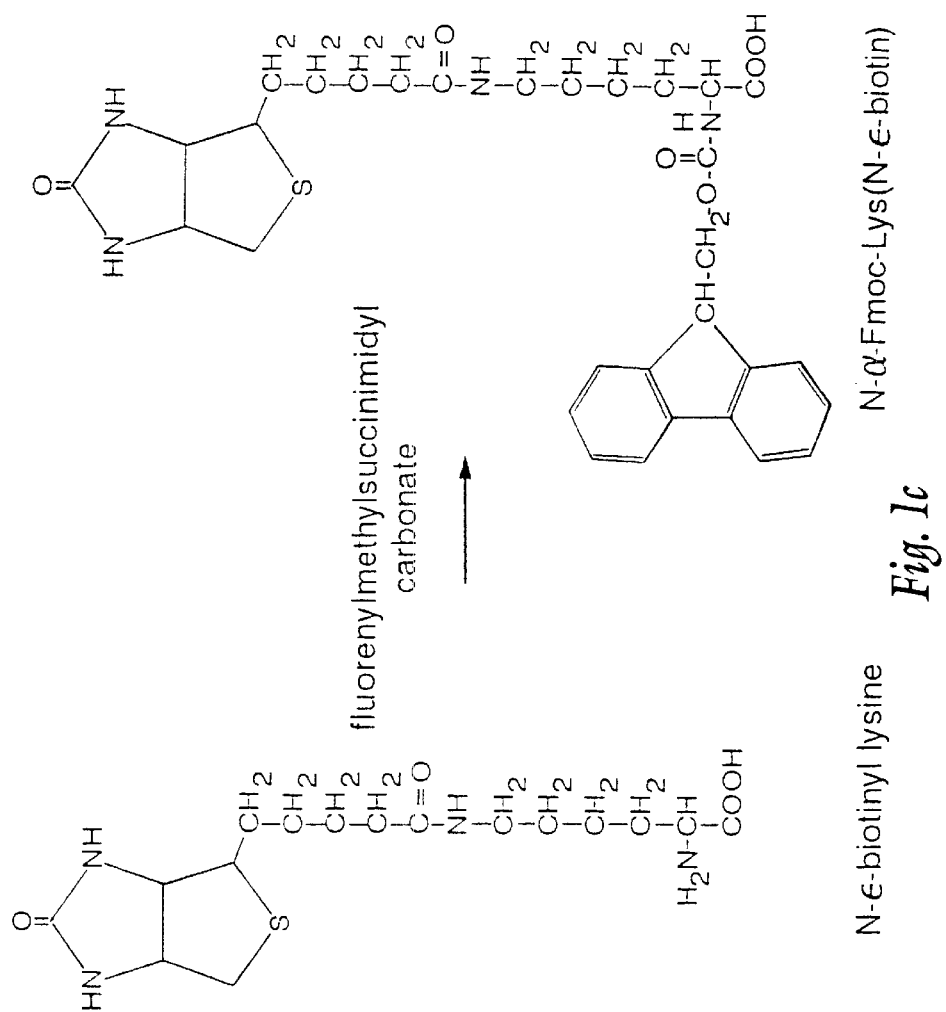
Figure 2A:
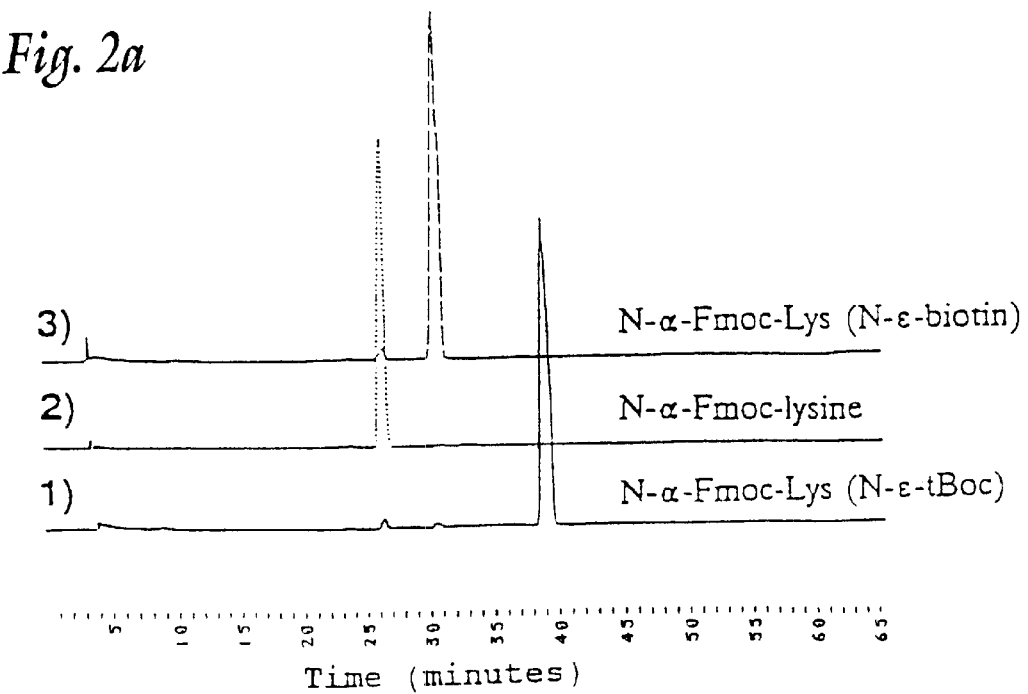
Figure 2B:
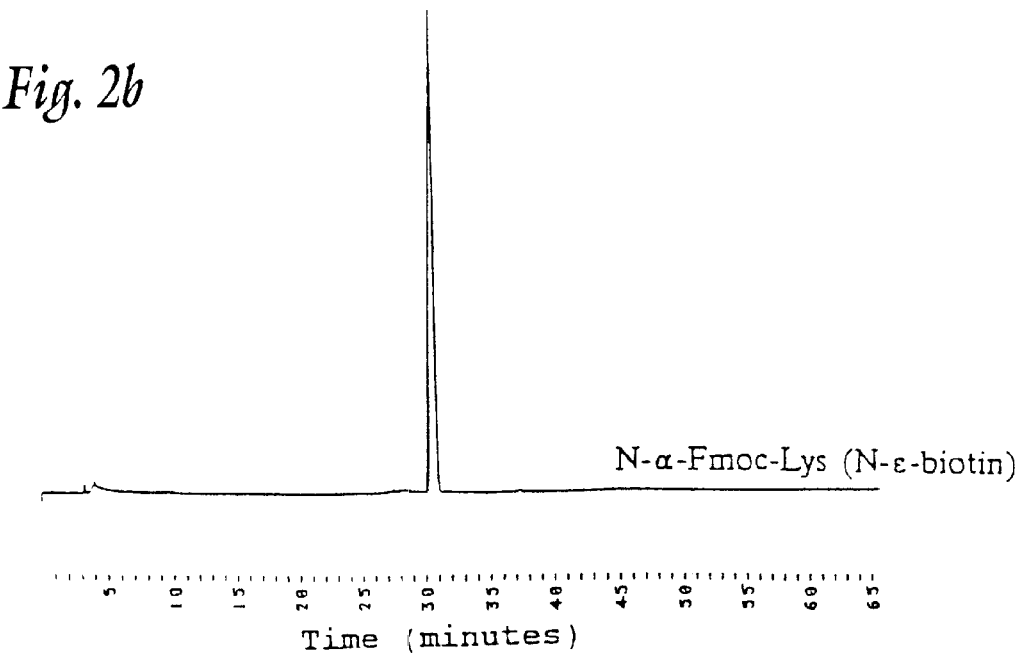

FIGS. 2a and 2b represent the diagram obtained in reverse phase chromatography of the precursors involved in the preparation of the intermediary products defined above, and of the intermediary compounds.

The reverse phase chromatography has been carried out in the following conditions:

gradient specifications:
  buffer A: 0.1% TFA in H2O,
  buffer B: 0.1% TFA in acetonitrile,
  column: C2/C18 reverse phase (Pharmacia, Pep-S),
    detection wavelength: 255 nanometers;
  gradient:
    0% B from 0 to 1 minute,
    0% B to 100% B from 1 minute to 60 minutes,
    0% B from 60 minutes to 70 minutes.

Figure 1:
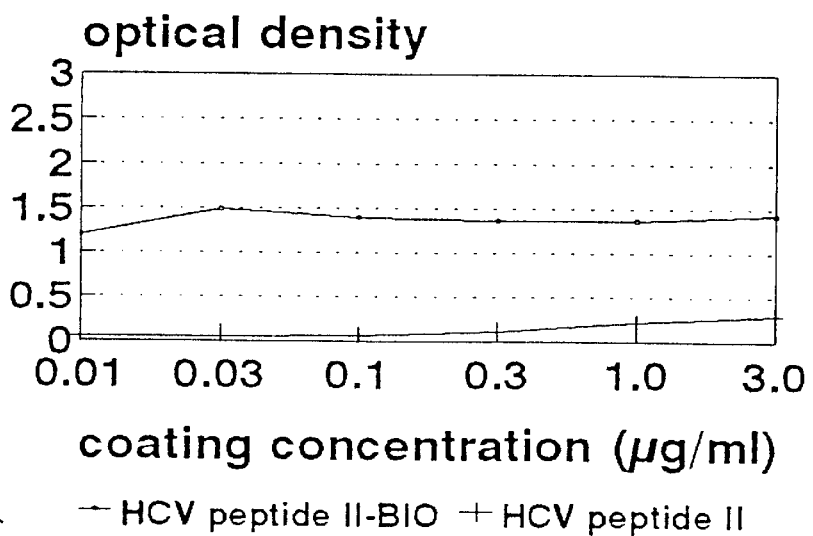
Figure 3A:
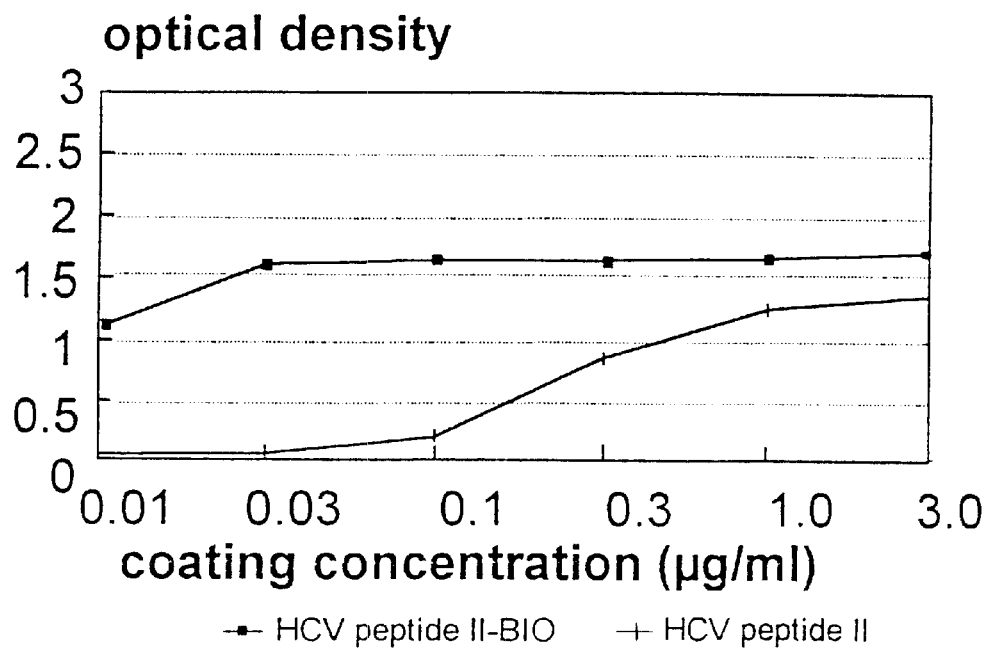

The first diagram corresponds to method A (see FIG. 1) and the second diagram corresponds to method B (see FIG. 1).

Figure 3A:
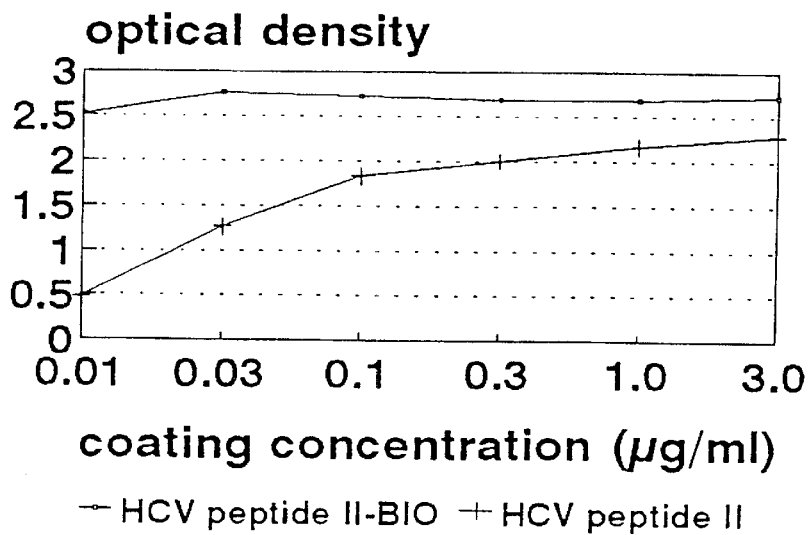
Figure 2:
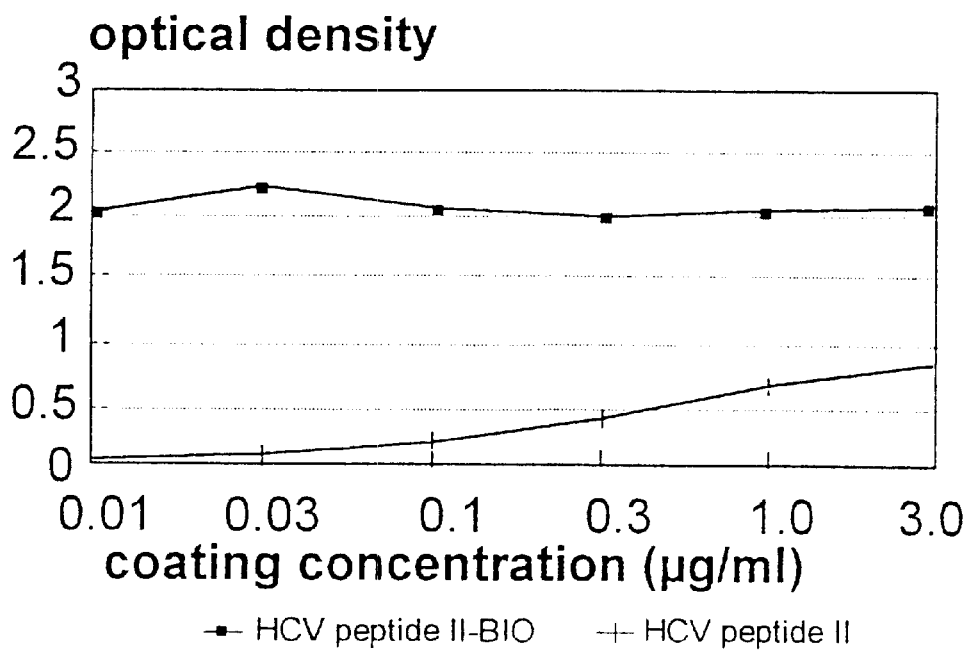

FIGS. 3A-1 and 3A-2 represents the antibody binding to HCV peptide II (in an ELISA).

The upper left curve corresponds to sample 8320.

The upper right curve corresponds to sample 8242.

The lower left curve corresponds to sample 8243.

The lower right curve corresponds to sample 8318.

In each of these samples, the optical density (at 450 nm) is plotted against the coating concentration expressed in μg/ml.

The curve with crosses corresponds to non-biotinylated HCV peptide II and the curve with dots corresponds to biotinylated HCV peptide II.

Figure 3B:
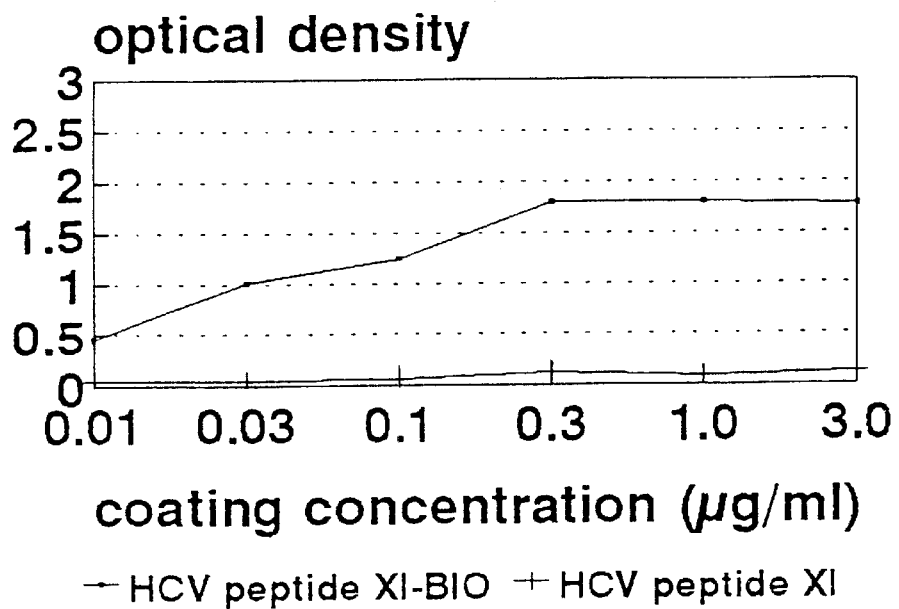
Figure 1:
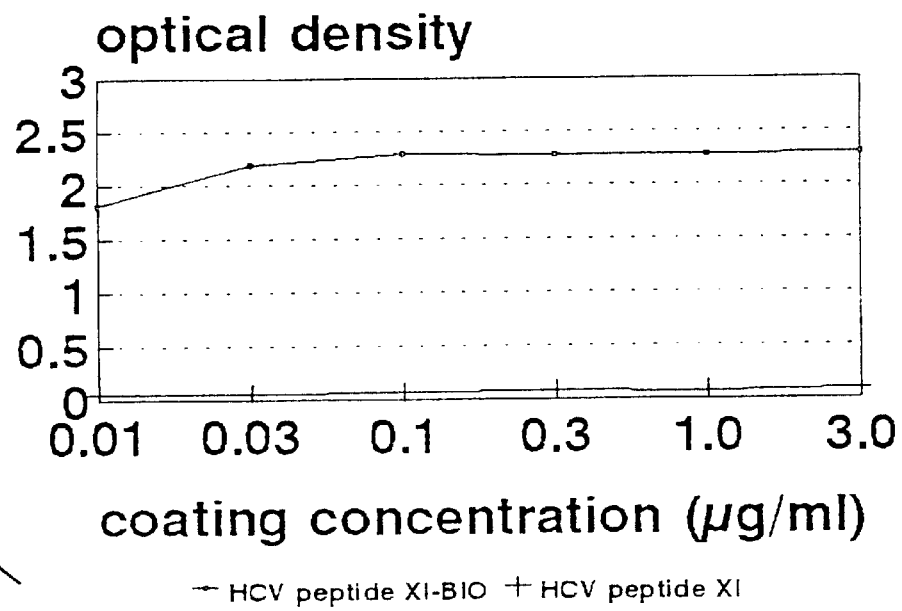
Figures 2, 3B:
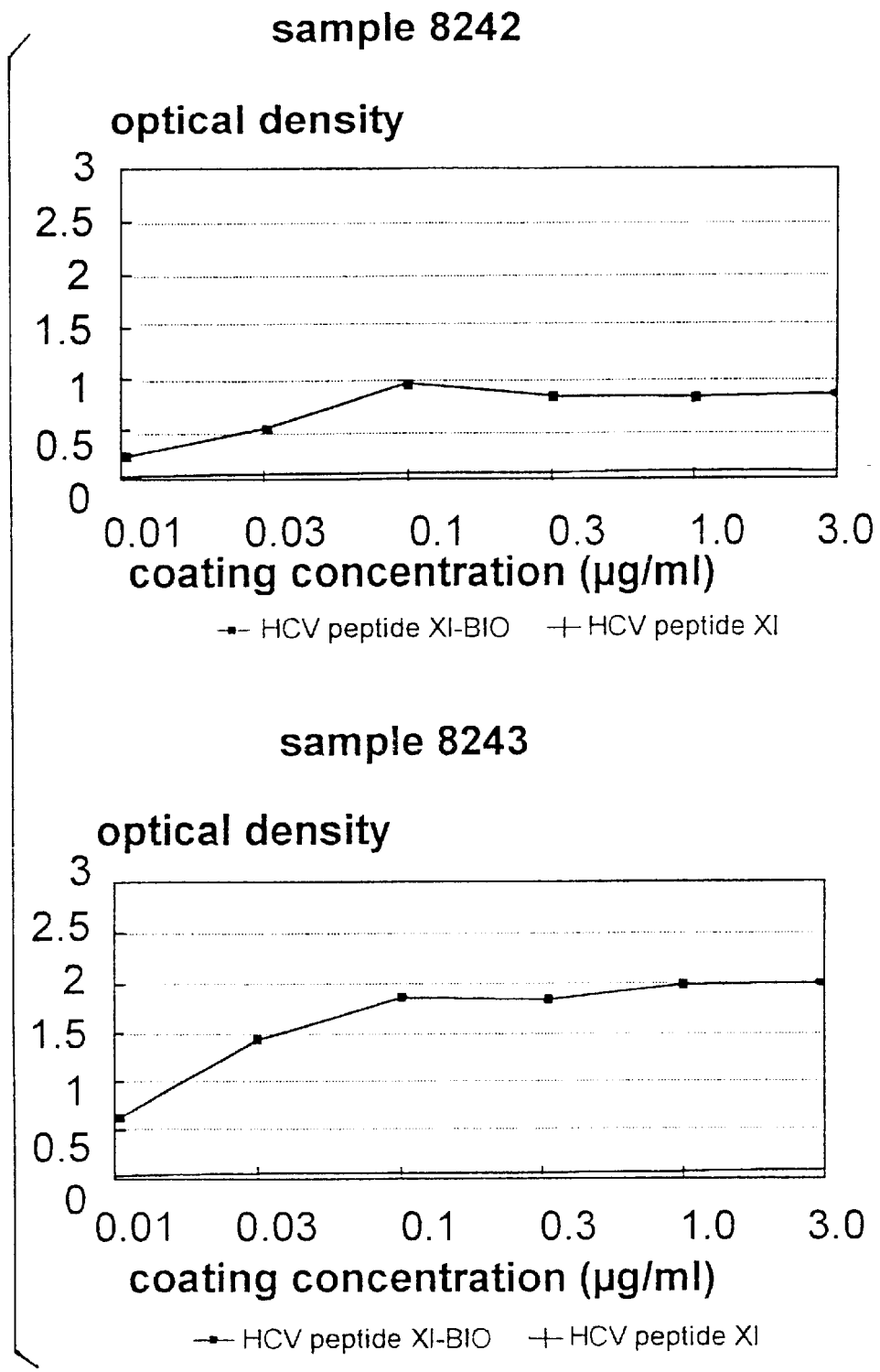

FIGS. 3b1 and 3b2 represent the antibody binding to HCV peptide XI (in an ELISA).

The upper left curve corresponds to sample 8320.

The upper right curve corresponds to sample 8326.

The lower left curve corresponds to sample 8242.

The lower right curve corresponds to sample 8243.

In each of these samples, the optical density (at 450 nm) is plotted against the coating concentration expressed in μg/ml.

The curve with crosses corresponds to non-biotinylated HCV peptide XI and the curve with dots corresponds to biotinylated HCV peptide XI.

Figure 3C:
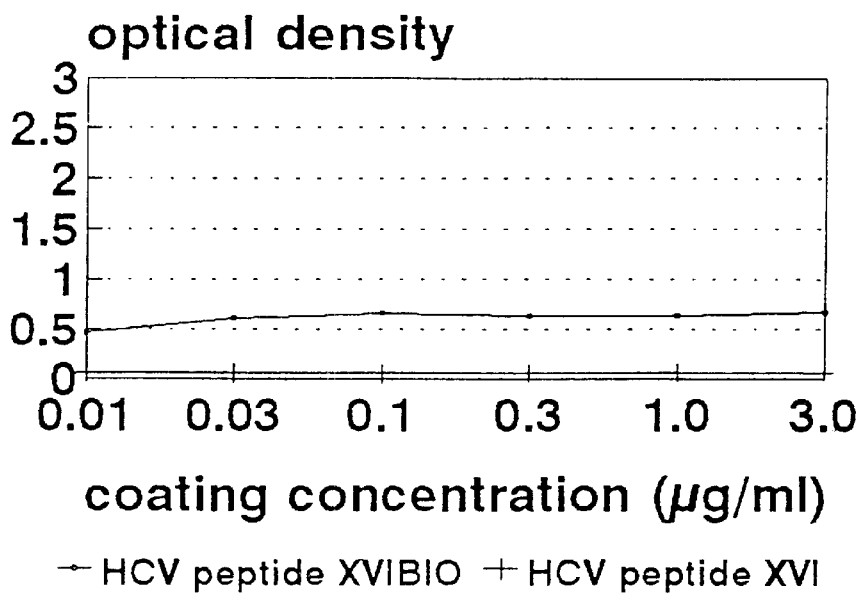
Figure 1:
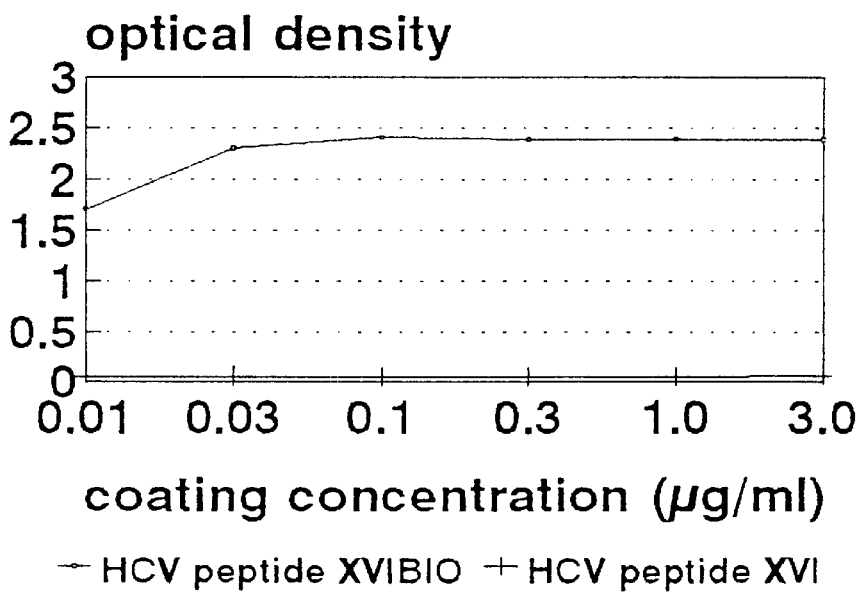
Figure 3C:
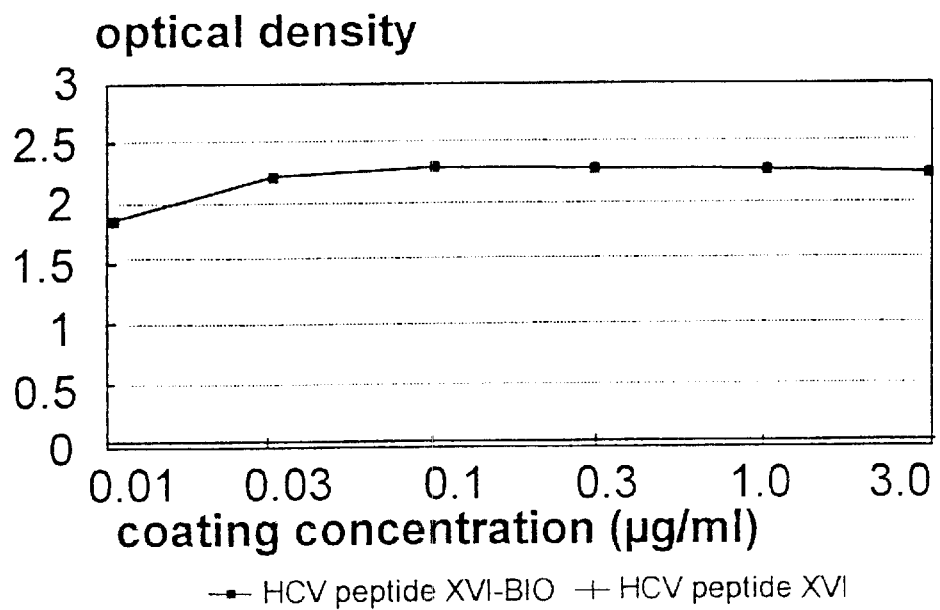
Figure 2:
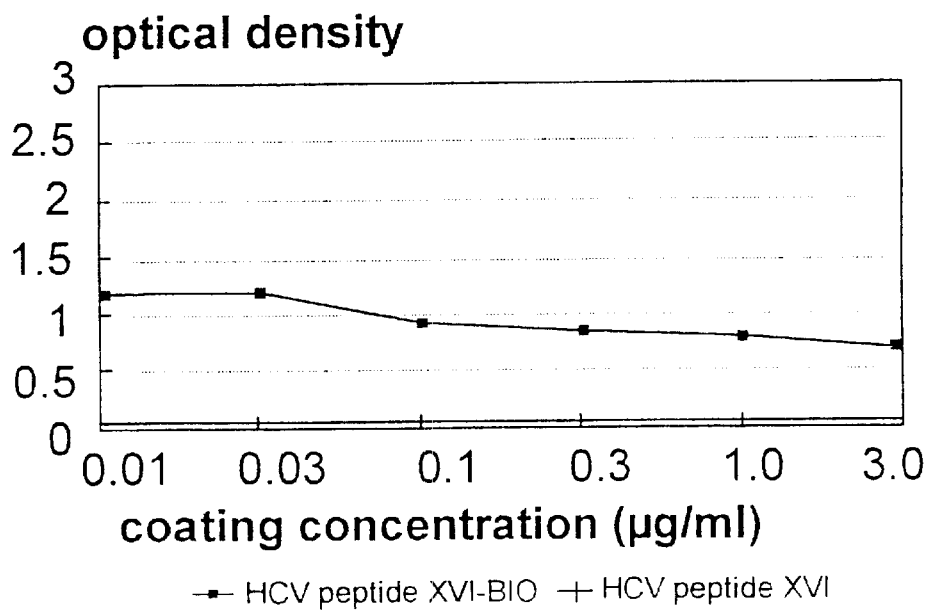

FIGS. 3c-1 and 3c-2 represent the antibody binding to HCV peptide XVI (in an ELISA).

The upper left curve corresponds to sample 8326.

The upper right curve corresponds to sample 8242.

The lower left curve corresponds to sample 8243.

The lower right curve corresponds to sample 8318.

In each of these samples, the optical density (at 450 nm) is plotted against the coating concentration expressed in μg/ml.

The curve with crosses corresponds to non-biotinylated HCV peptide XVI and the curve with dots corresponds to biotinylated HCV peptide XVI.

Figure 4A:
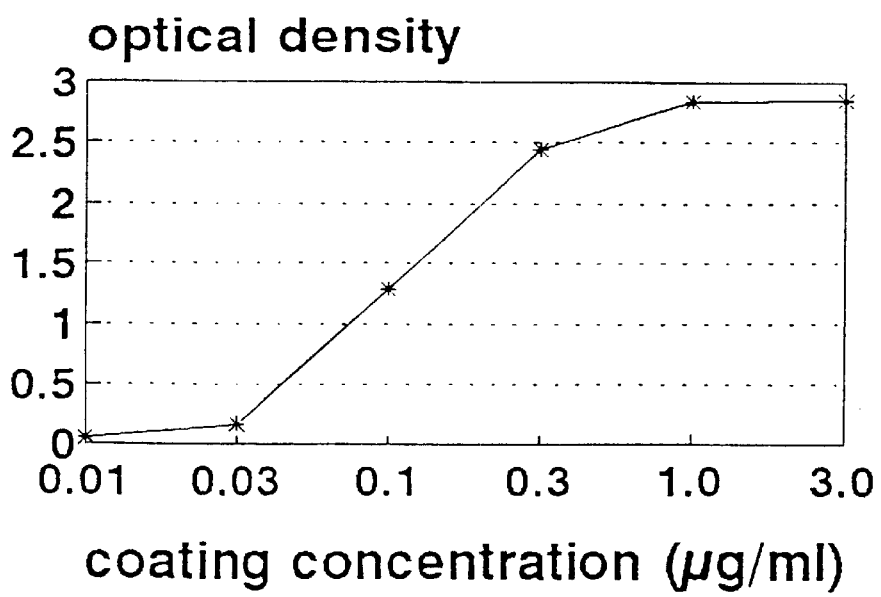
Figure 4A:
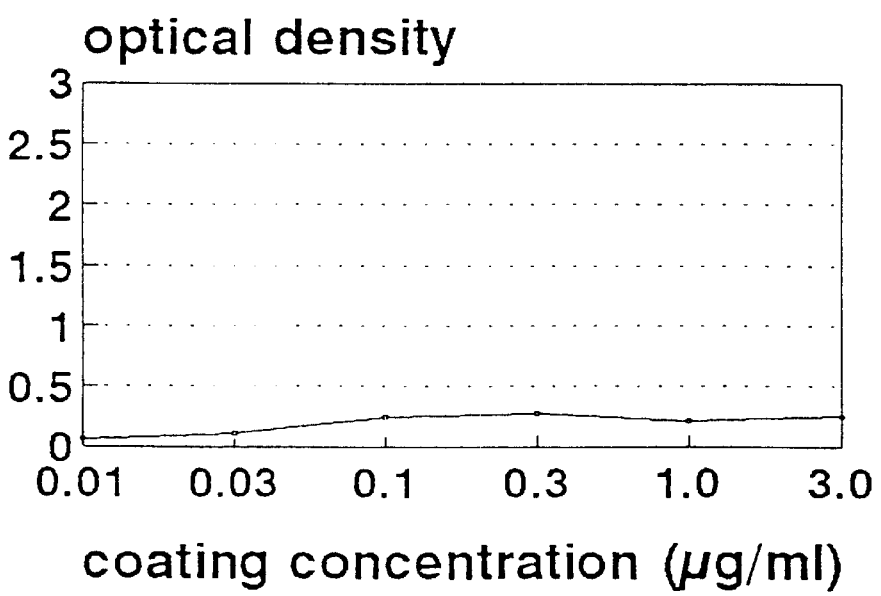
Figure 4B:
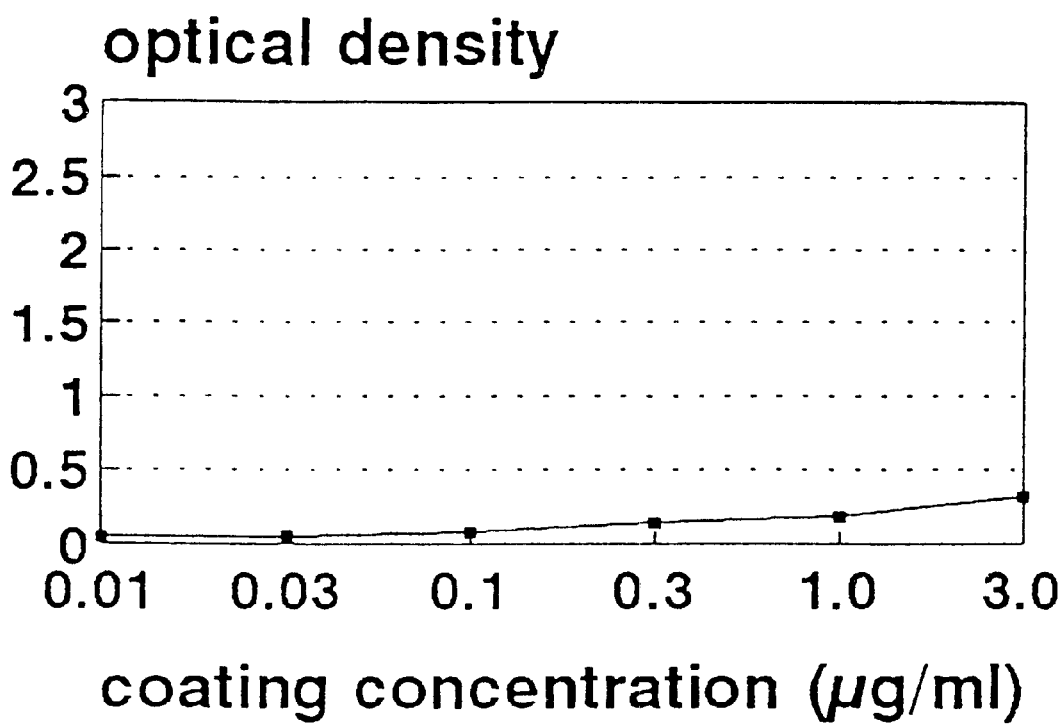

FIGS. 4a and 4b correspond to the detection of biotinylated peptides coated directly (in an ELISA).

The first curve corresponds to biotinylated HCV peptide II, the second curve to biotinylated HCV peptide XI and the third curve to biotinylated HCV peptide XVI.

In each of these samples, the optical density (at 450 nm) is plotted against the coating concentration expressed in μg/ml.

FIGS. 5A and 5b represent the structures of N- and C-terminally biotinylated HIV-1 peptides (hereabove designated by 1a.1) originating from the transmembrane (TM) protein of HIV-1.

Figures 1, 6A:
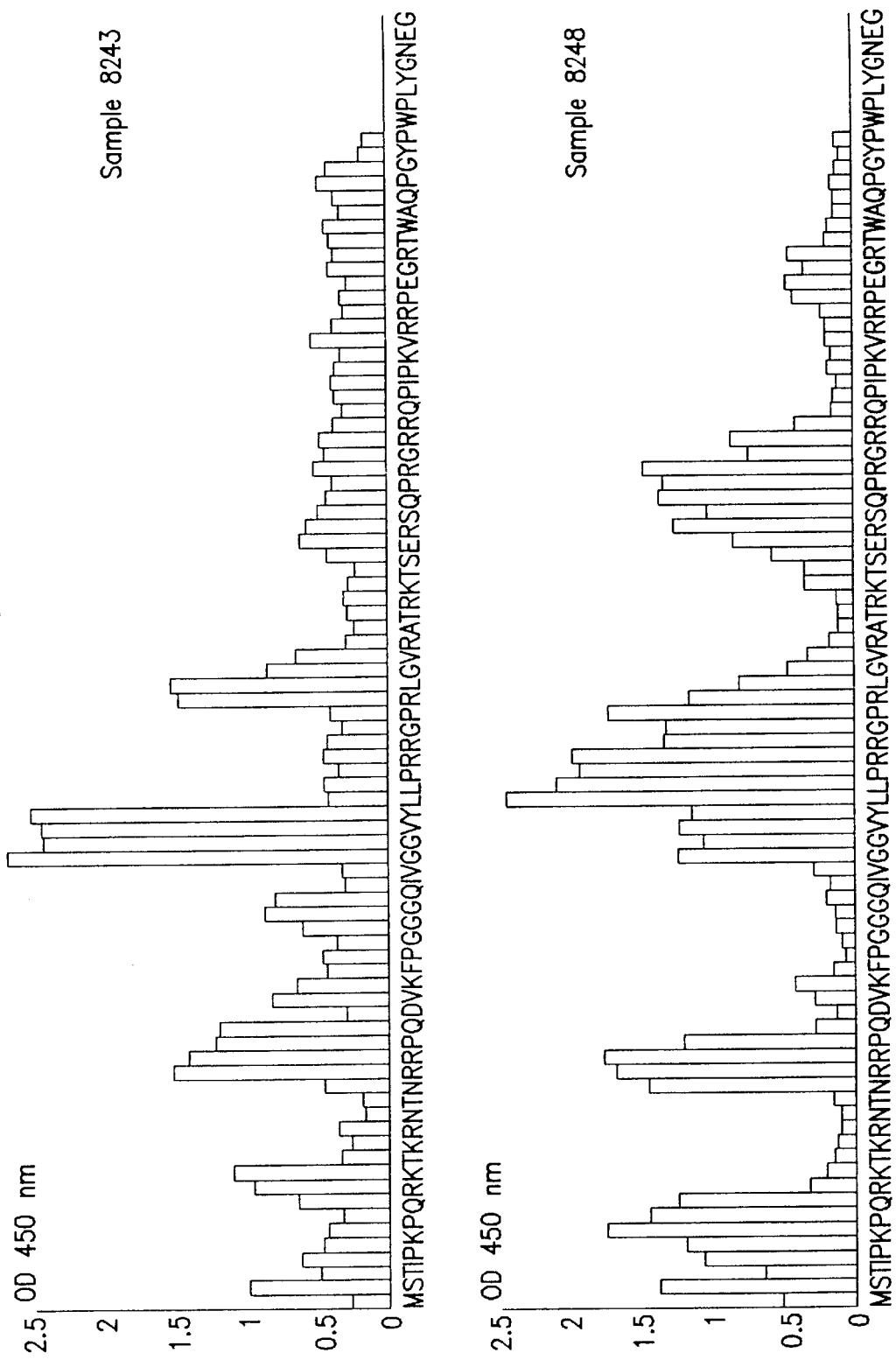
Figures 2, 6A:
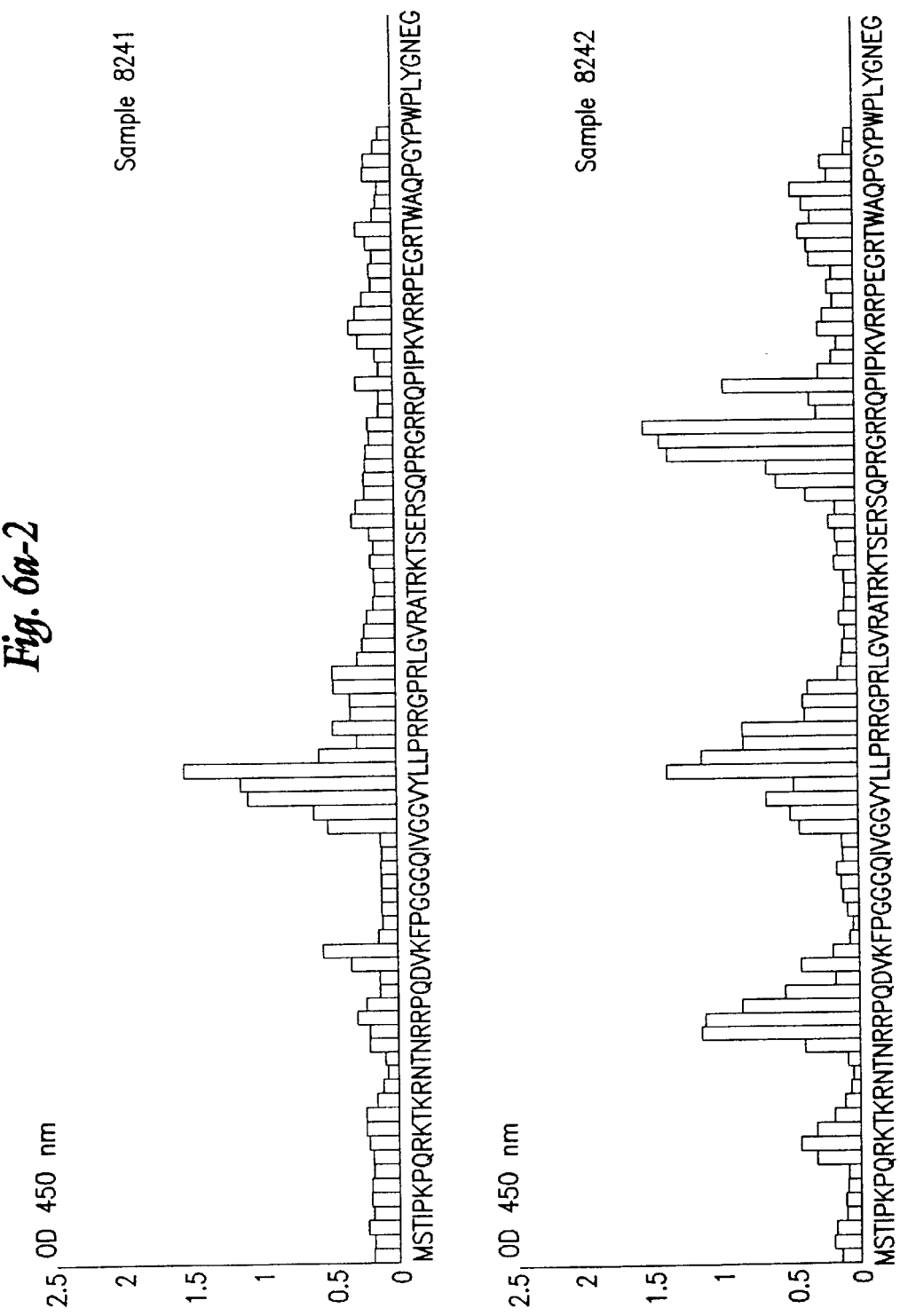
Figures 3, 6A:
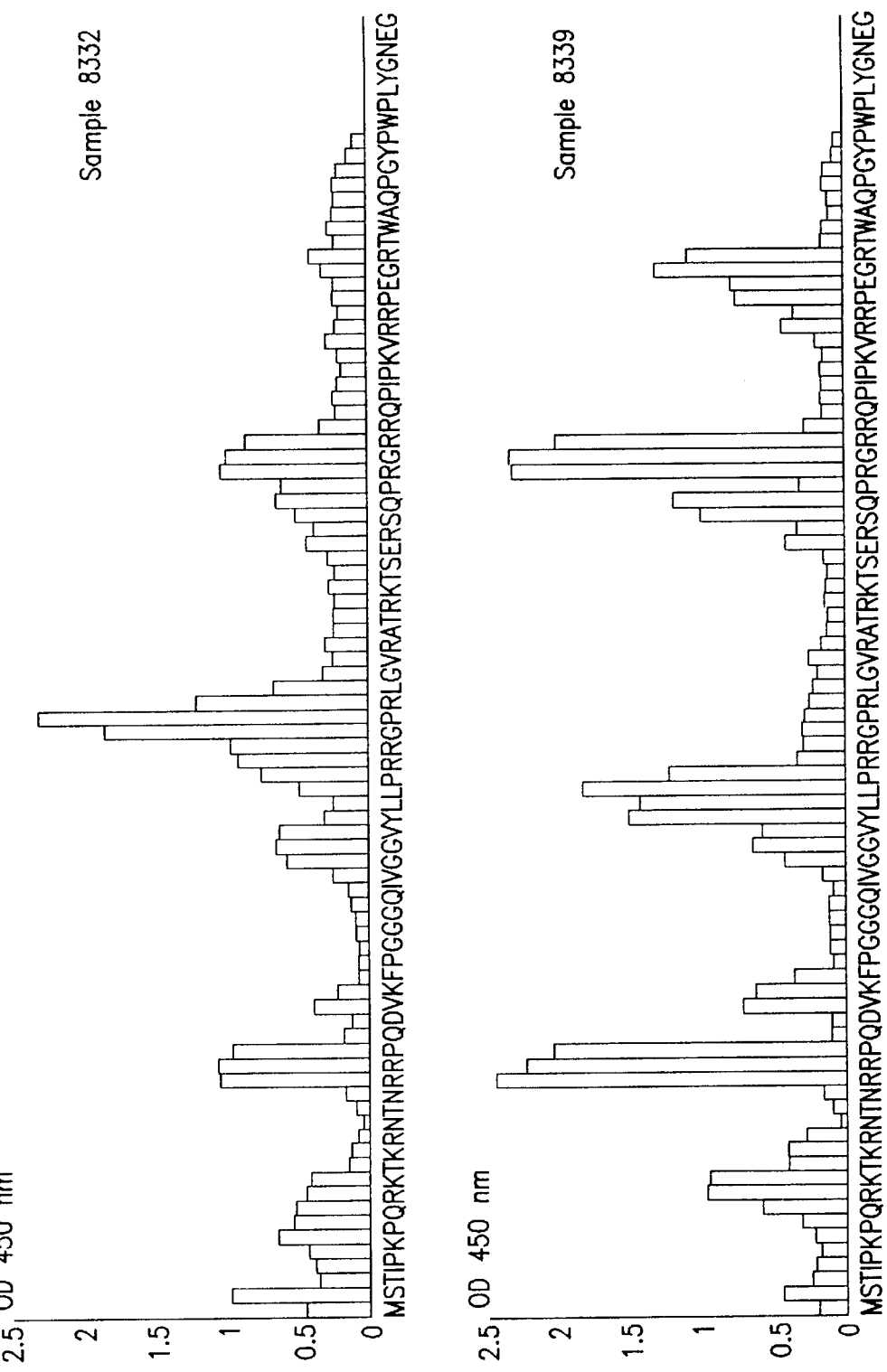
Figures 4, 6A:
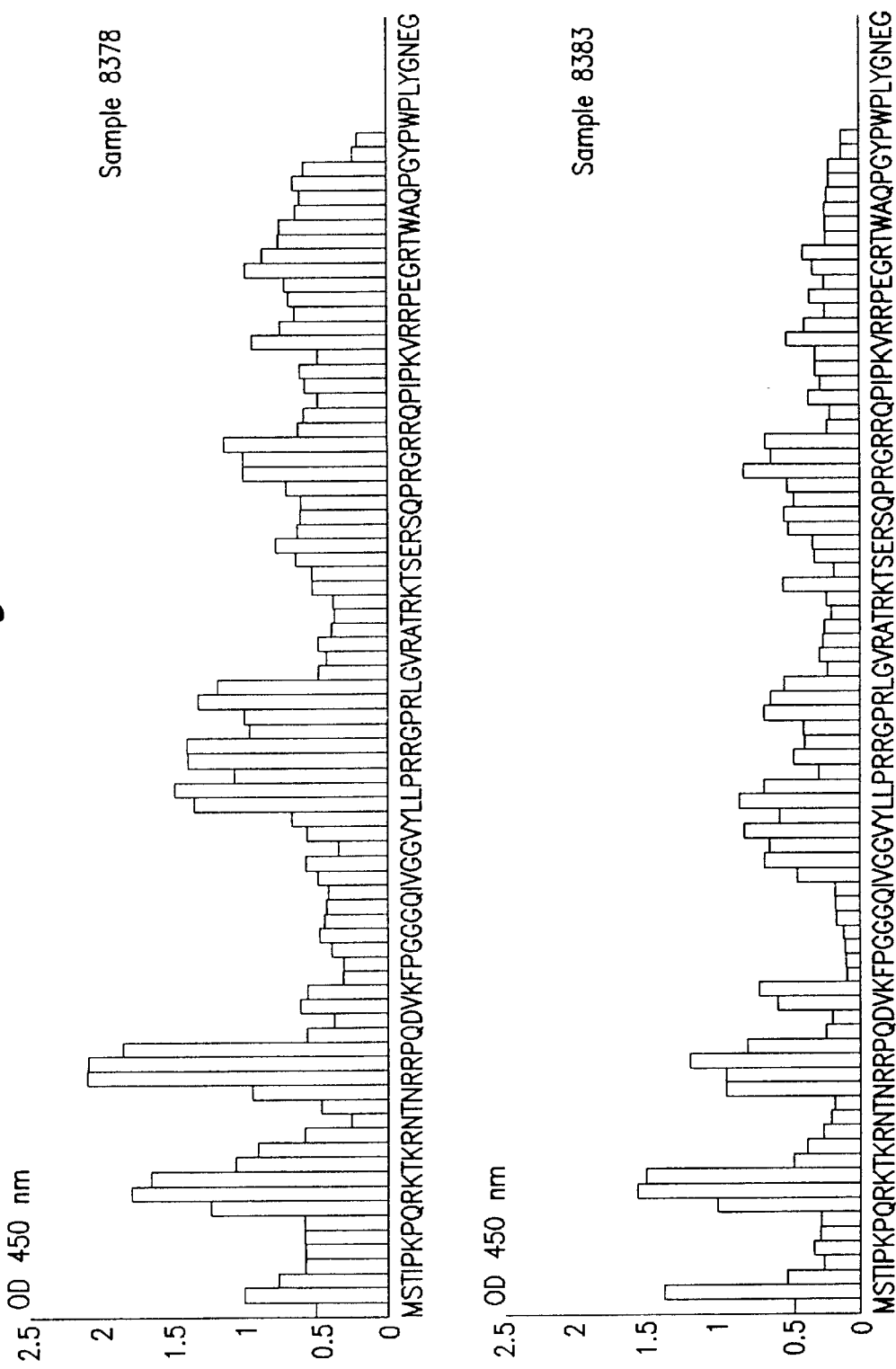
Figures 5, 6A:
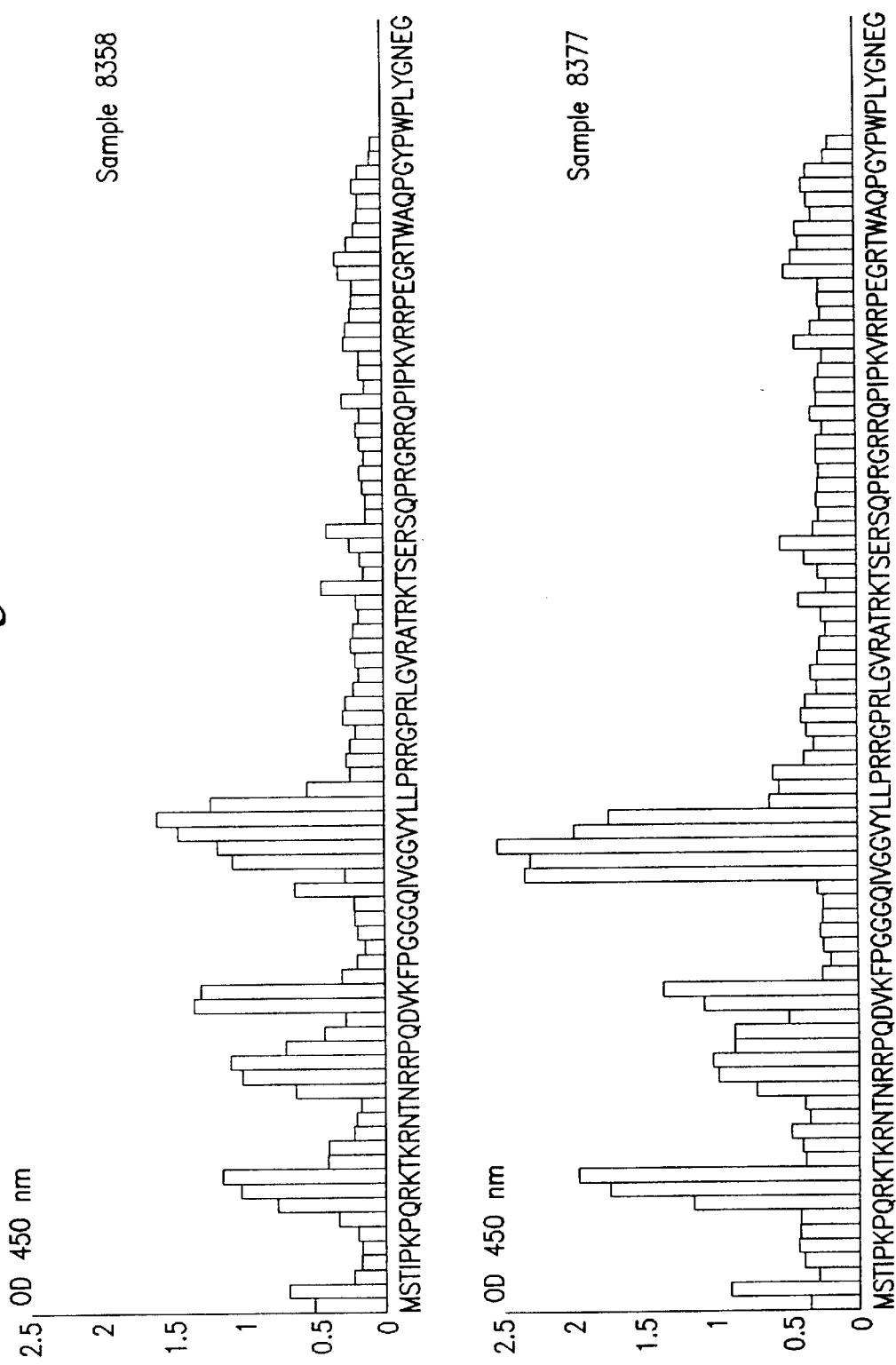

FIGS. 6a-1 through 6a-5 represent the detection of core epitopes in the Core region of HCV using overlapping 9-mers (in an ELISA).

The sera used are indicated above each diagram.

The ordinates correspond to the optical density at 450 nm.

The abscissae correspond to the sequence of the protein in which the location of the epitope(s) is to be determined. For purposes of graphic illustration, the optical density is assigned to the first amino acid in the respective nine-mer sequences.

Figures 1, 6B:
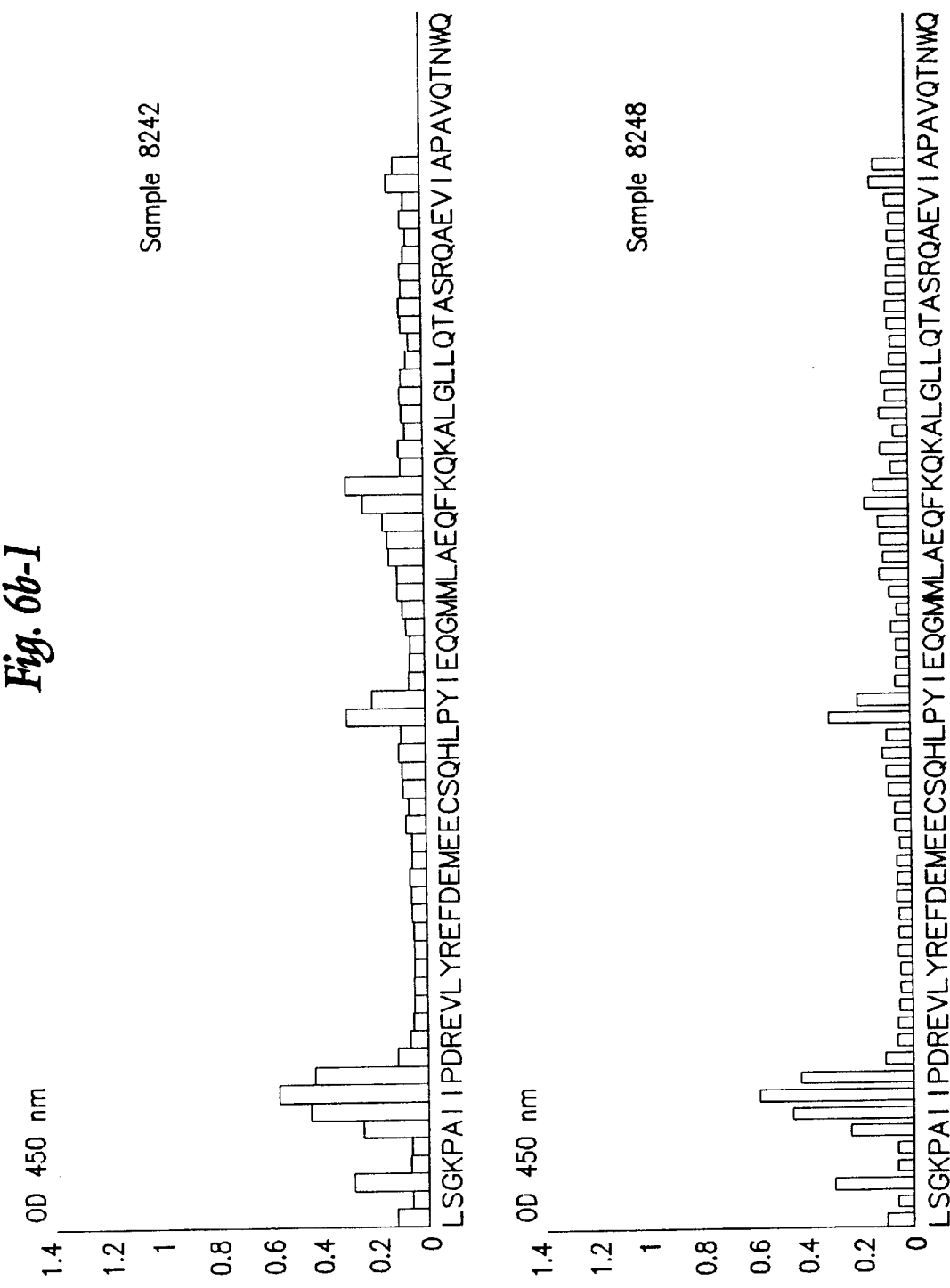
Figures 2, 6B:
Figures 3, 6B:
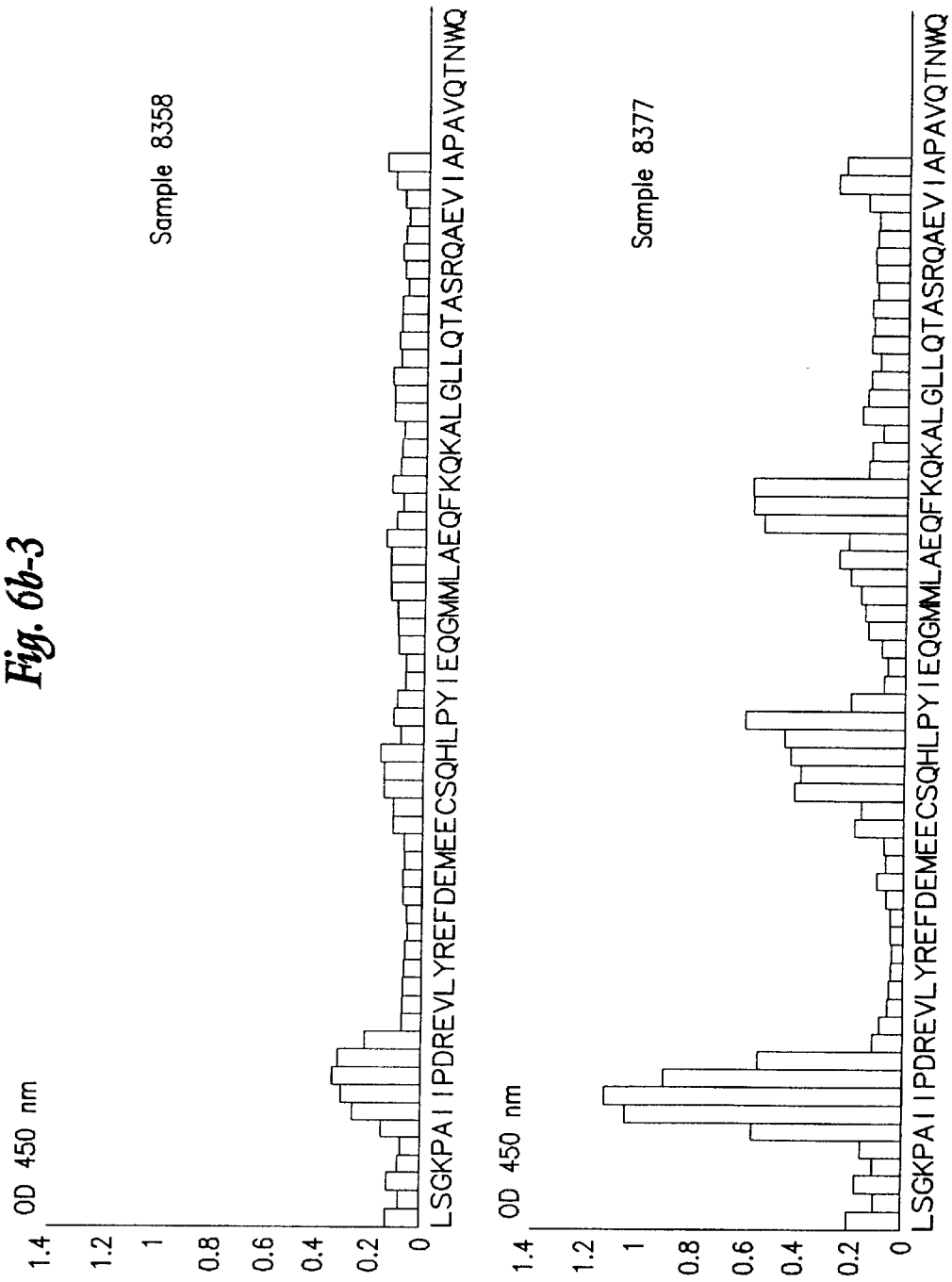
Figures 4, 6B:
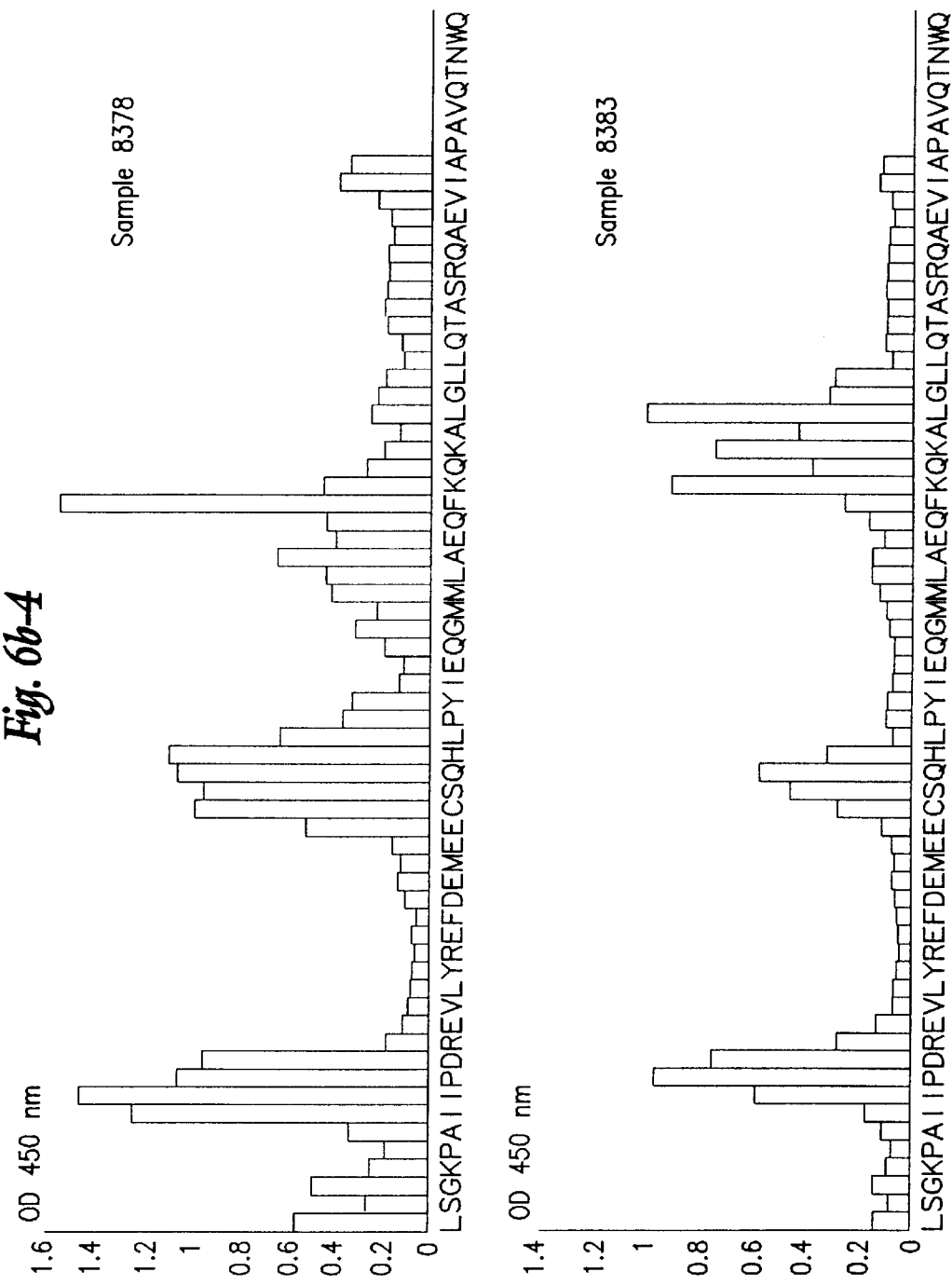
Figures 5, 6B:
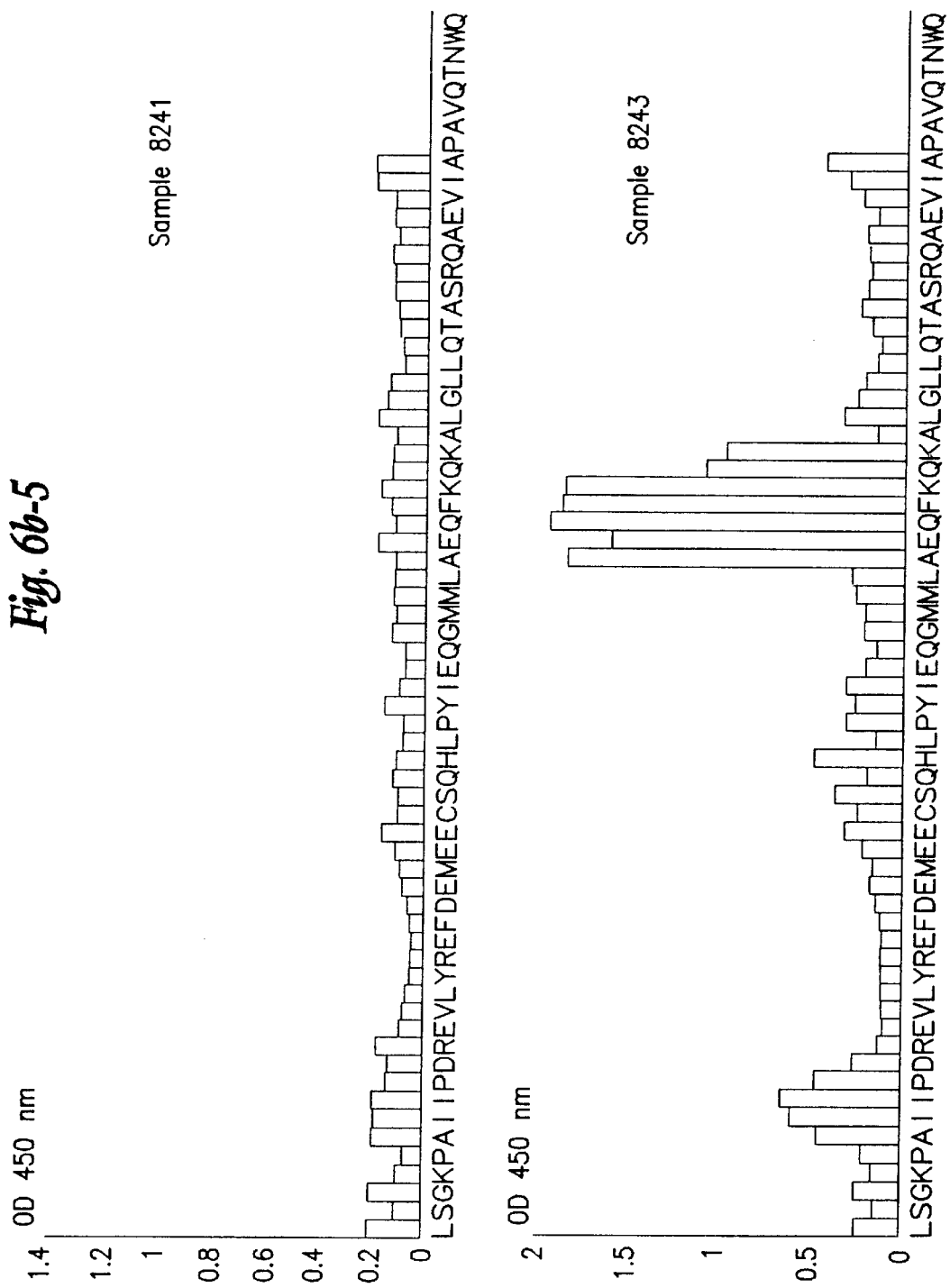

FIGS. 6b-1 through 6b-5 represent the detection of core epitopes in the NS4 region of HCV using overlapping 9-mers (in an ELISA).

The sera used are indicated above each diagram.

The ordinates correspond to the optical density at 450 nm.

The abscissae correspond to the sequence of the protein in which the location of the epitope(s) is to be determined. For purposes of graphic illustration, the optical density is assigned to the first amino acid in the respective nine-mer sequences.

Figures 3, 6C:
Figures 4, 6C:
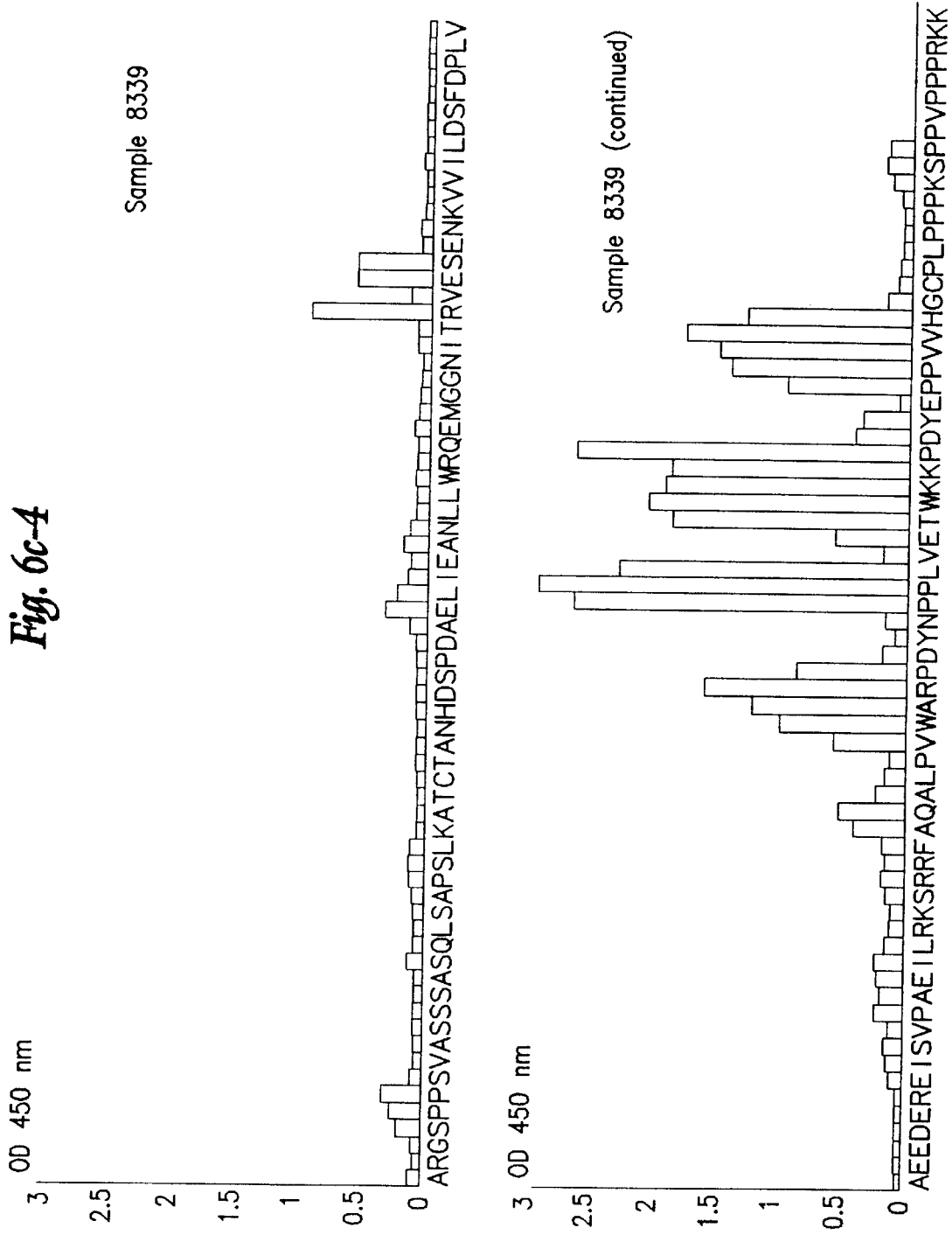
Figures 6, 6C, 7:
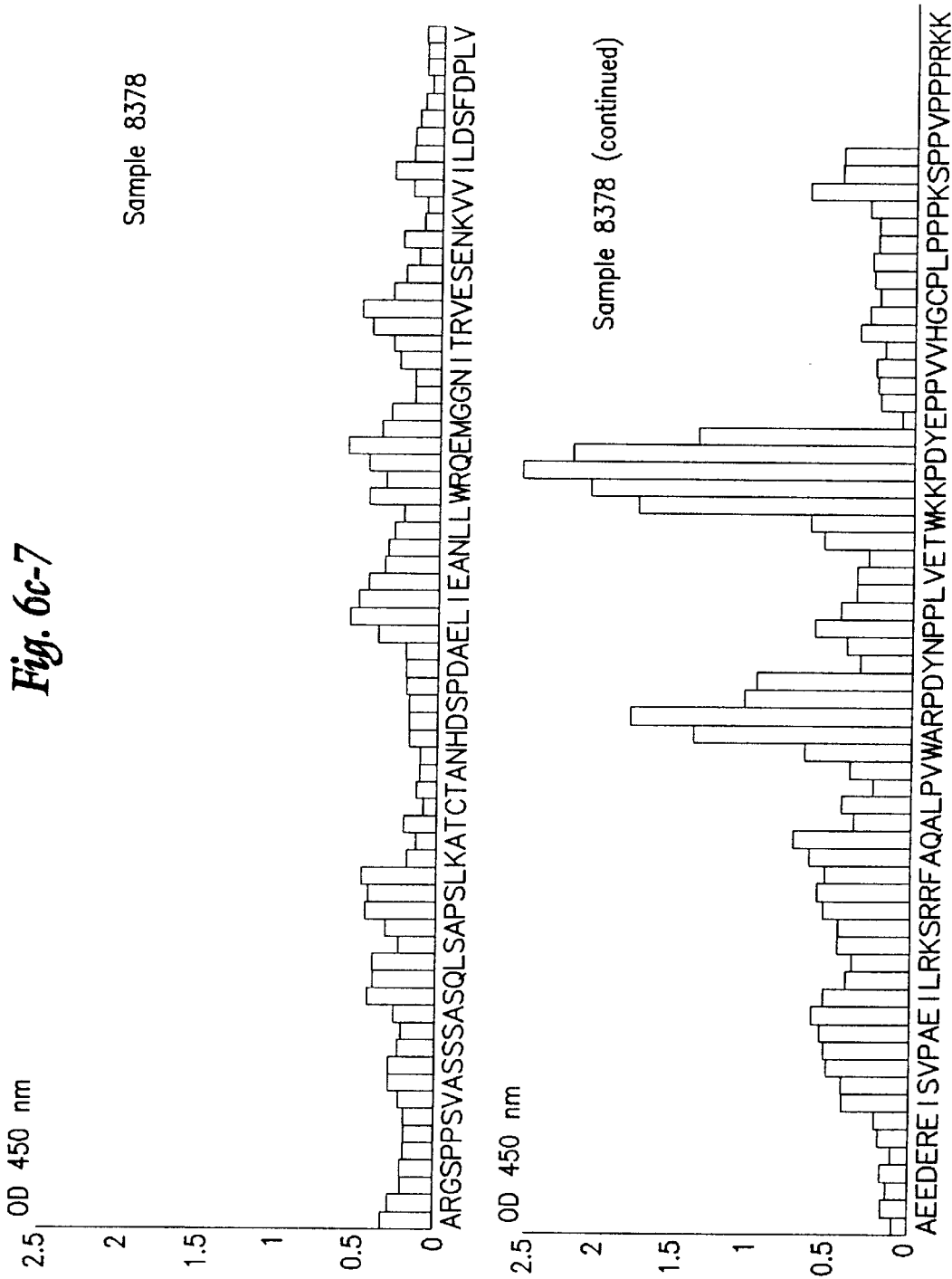
Figure 10:
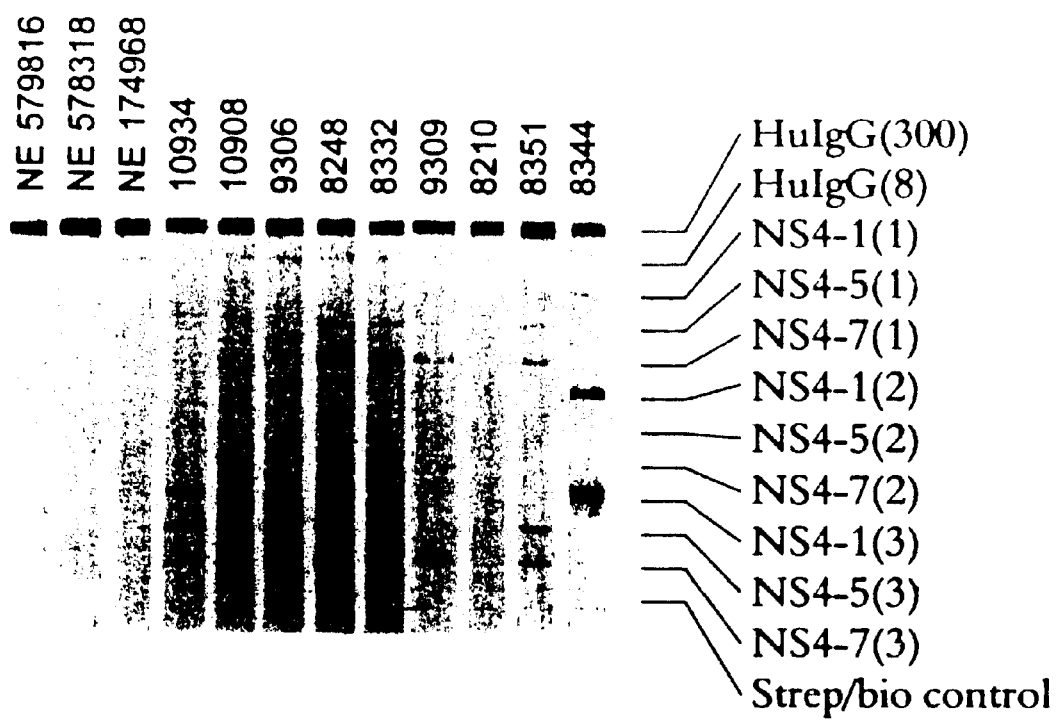

FIGS. 6c-1 through 6c10 represent the detection of core epitopes in the NS5 region of HCV using overlapping 9-mers (in an ELISA).

The sera used are indicated above each diagram.

The ordinates correspond to the optical density at 450 nm.

The abscissae correspond to the sequence of the protein in which the location of the epitope(s) is to be determined. For purposes of graphic illustration, the optical density is assigned to the first amino acid in the respective nine-mer sequences.

Figures 3, 7A:
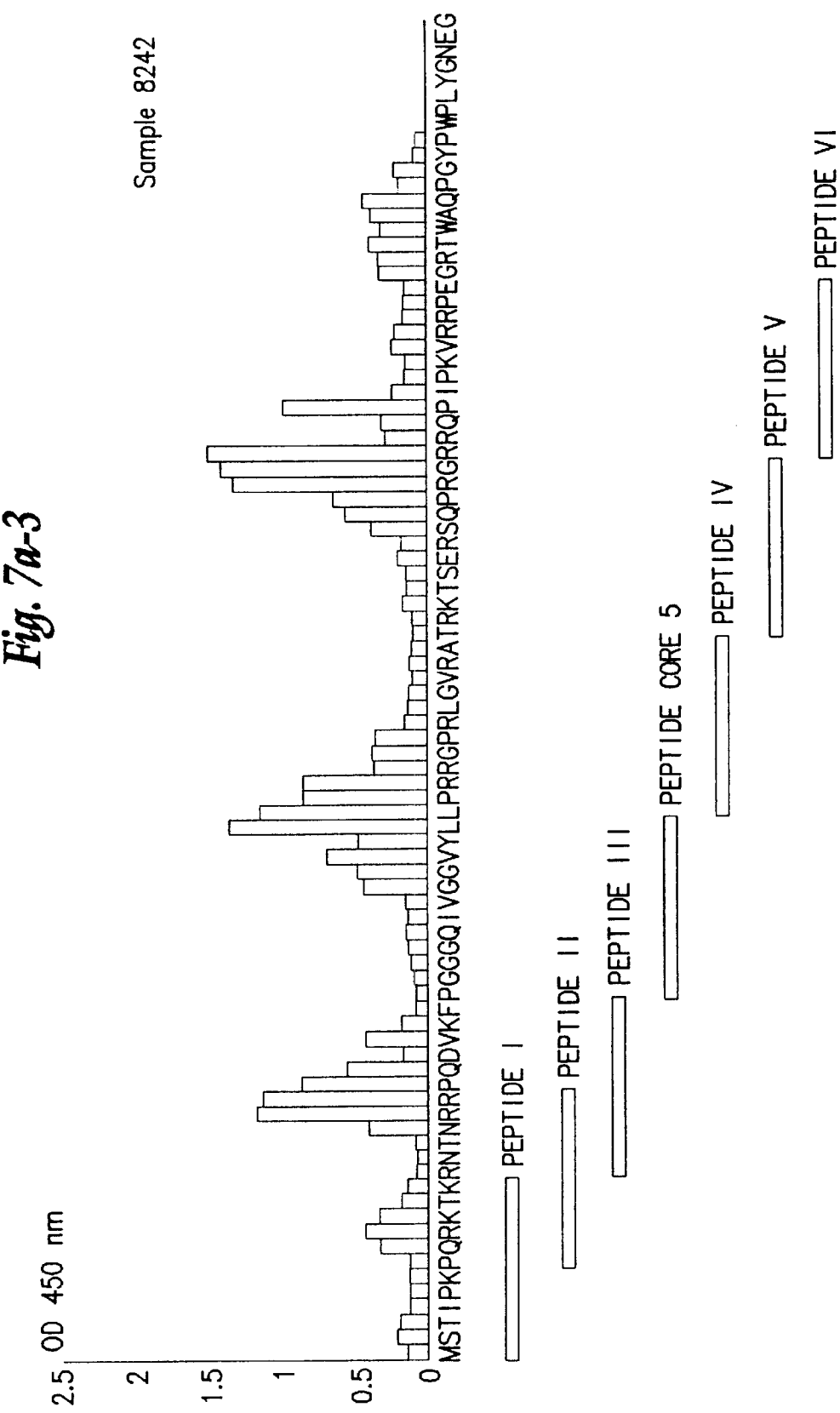

FIGS. 7a-1 through 7a-3 correspond to the positions of biotinylated 20-mers with respect to overlapping 9-mers (in an ELISA).

The abscissae corresponds to the protein sequence in which the epitope(s) is to be determined.

FIGS. 7b1 through 7b-3 correspond to the positions of biotinylated 20-mers with respect to overlapping 9-mers (in an ELISA).

The abscissae corresponds to the protein sequence in which the epitope(s) is to be determined.

Figures 3, 7C:
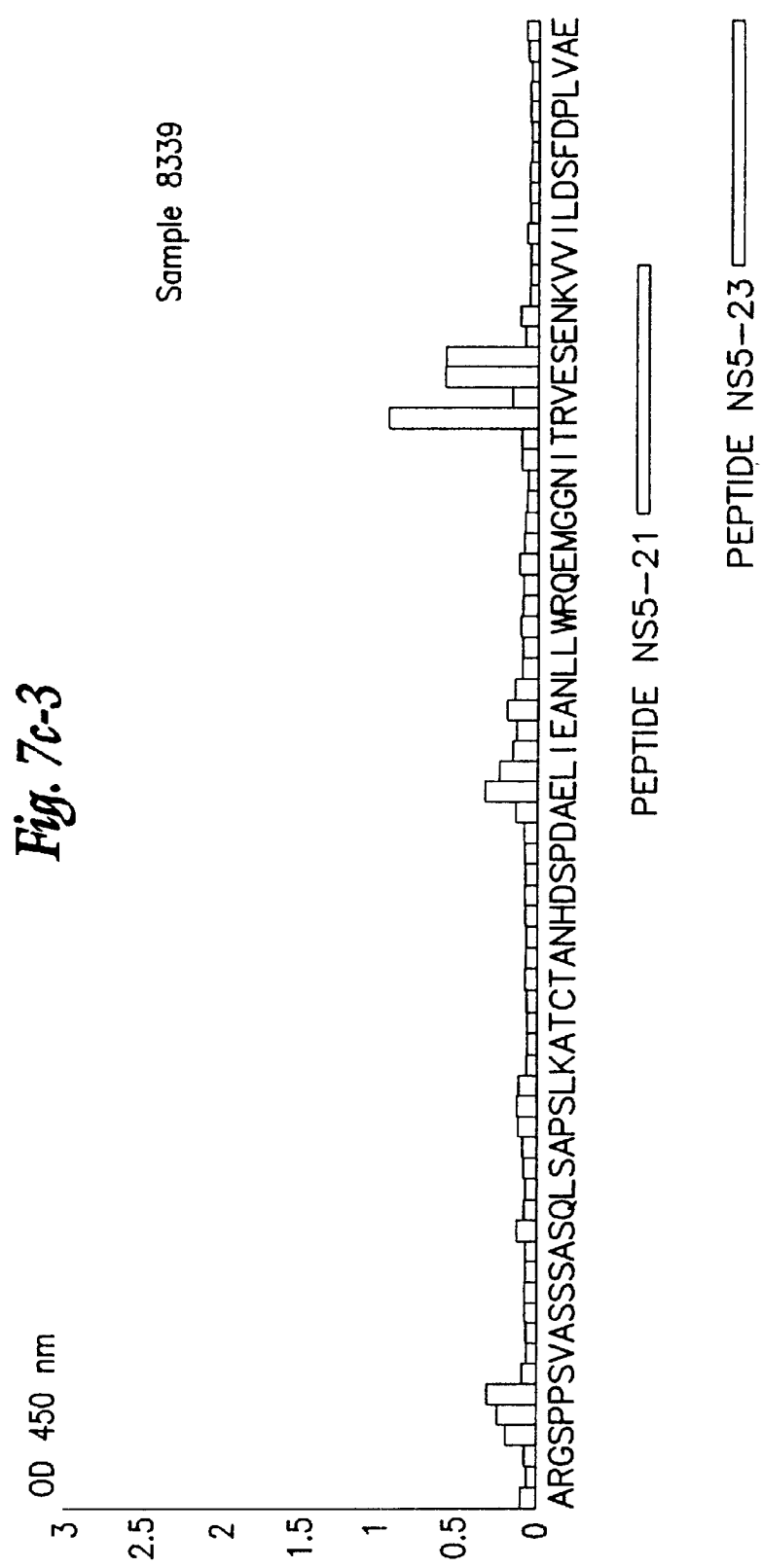
Figure 8:
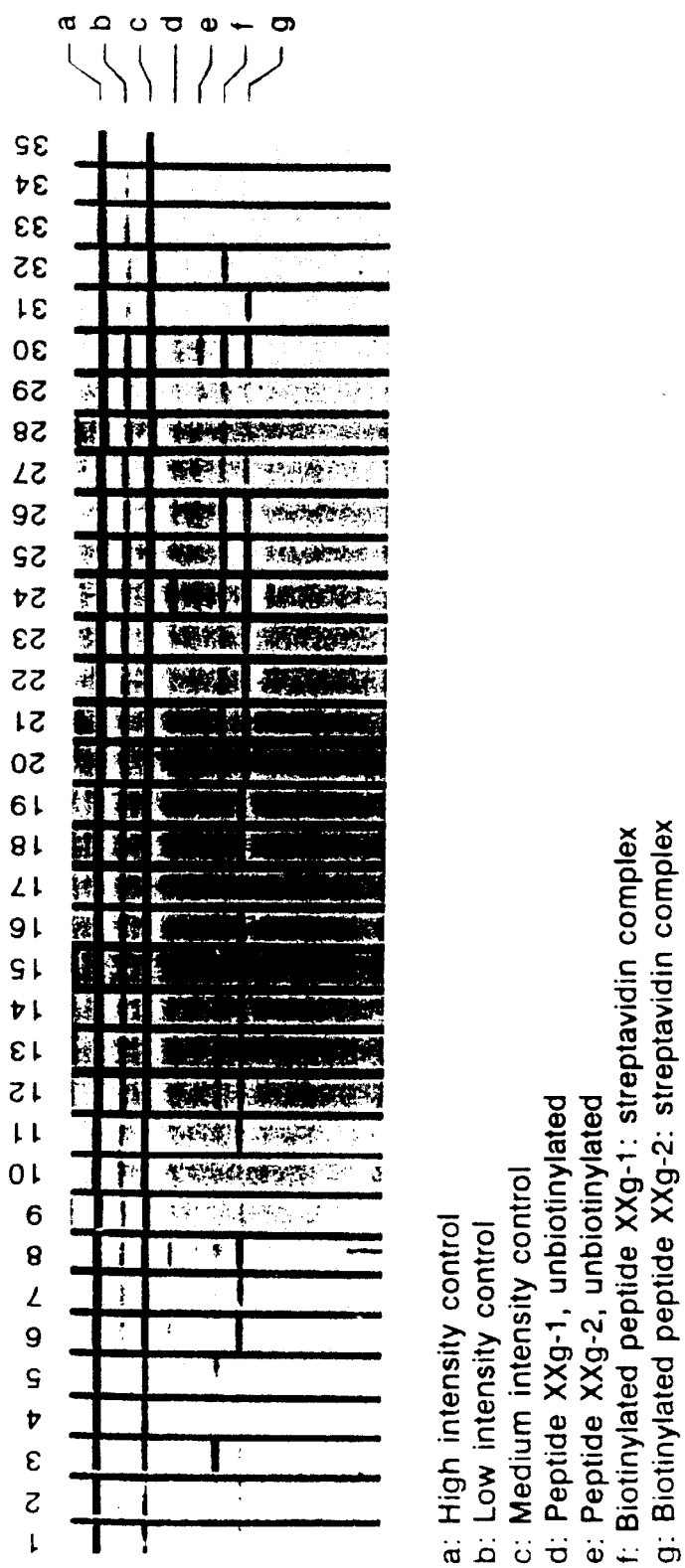

FIGS. 7c-1 through 7c-4 correspond to the positions of biotinylated 20-mers with respect to overlapping 9-mers (in an ELISA).

The abscissae corresponds to the protein sequence in which the epitope(s) is to be determined.

Figures 6, 6C, 7, 8:
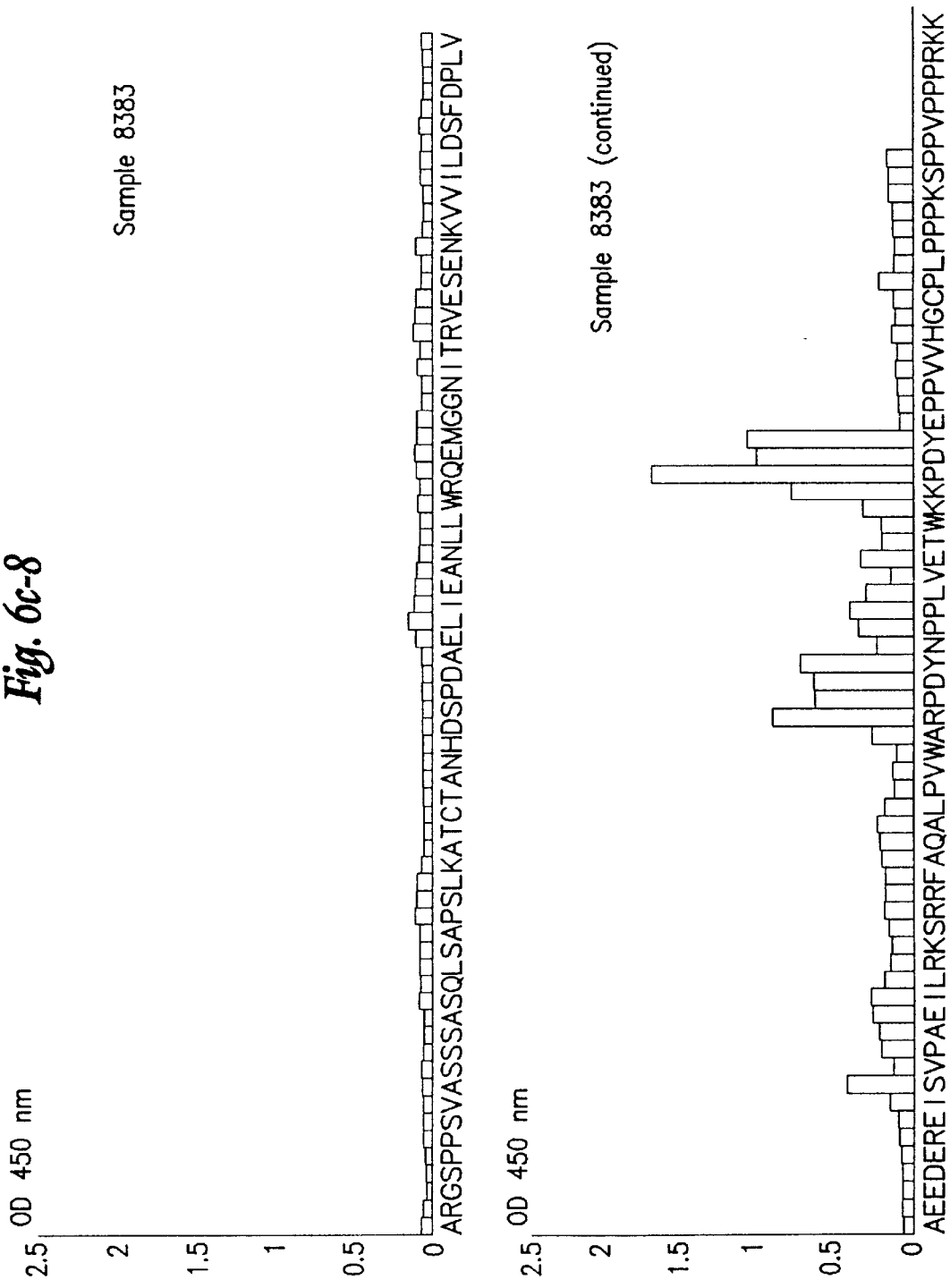

FIGS. 8 (SEQ ID NO: 176 and SEQ ID NO: 177) represents a comparison of antibody recognition of biotinylated and unbiotinylated HCV peptides by line immunoassay (LIA).

Figure 9:
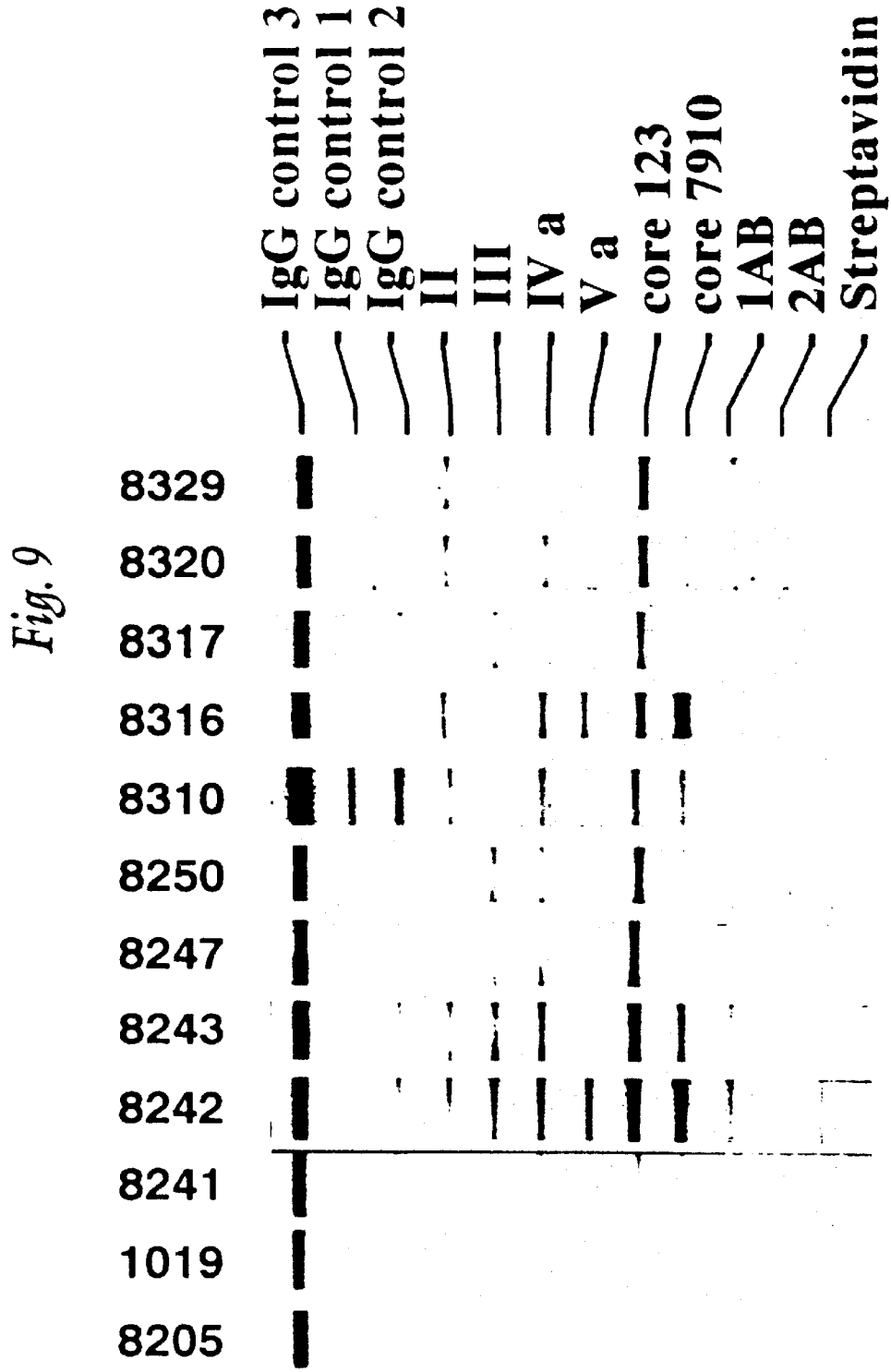

FIG. 9 represents a comparison of antibody recognition of biotinylated core peptides by line immunoassay (LIA).

The shorter and longer peptides are compared.

FIG. 10 represents an evaluation of type-specific HCV NS4 peptides by Line immunoassay (LIA).

FIG. 11 represents the amino acid sequence of peptides NS4-a to NS4-e.

FIG. 12 represents the composition of hybrid HCV peptides.

Figure 13:
Figures 14A, 14B:
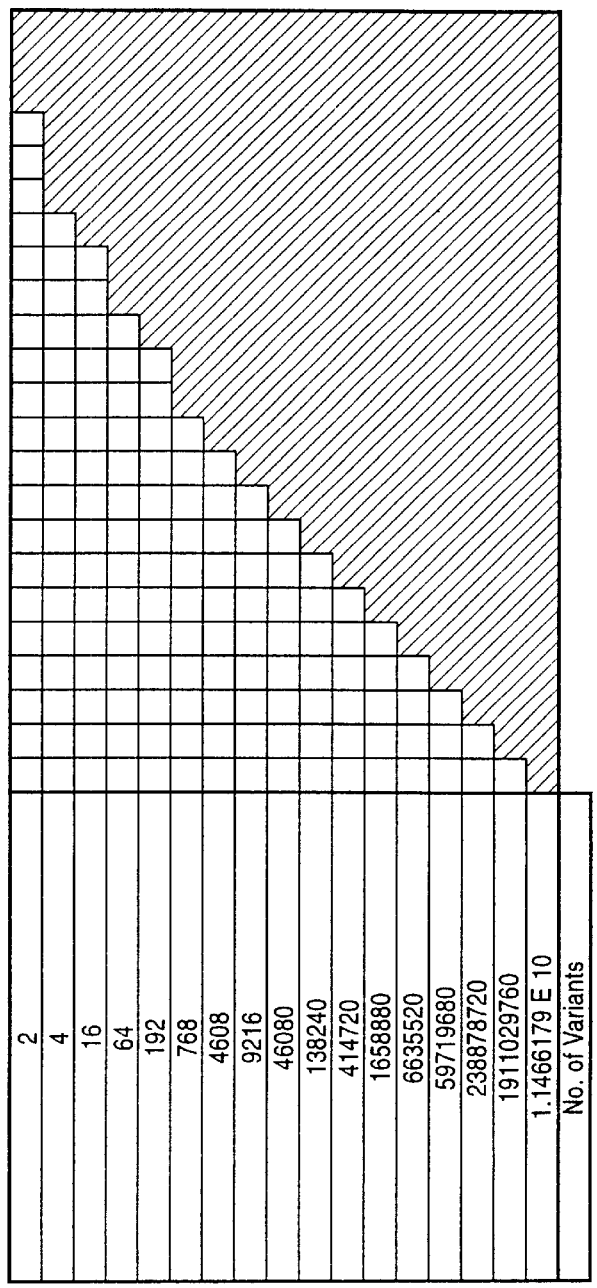
Figure 14C:
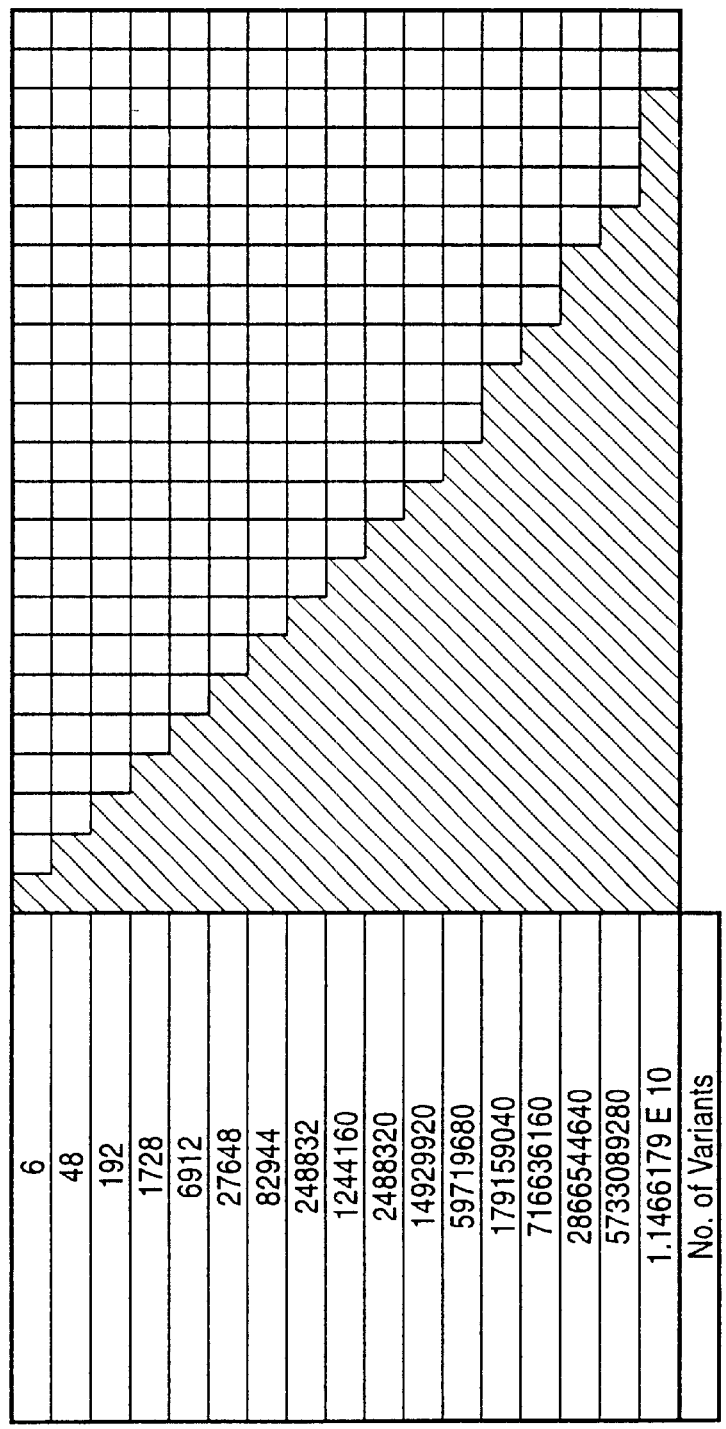
Figure 14D:
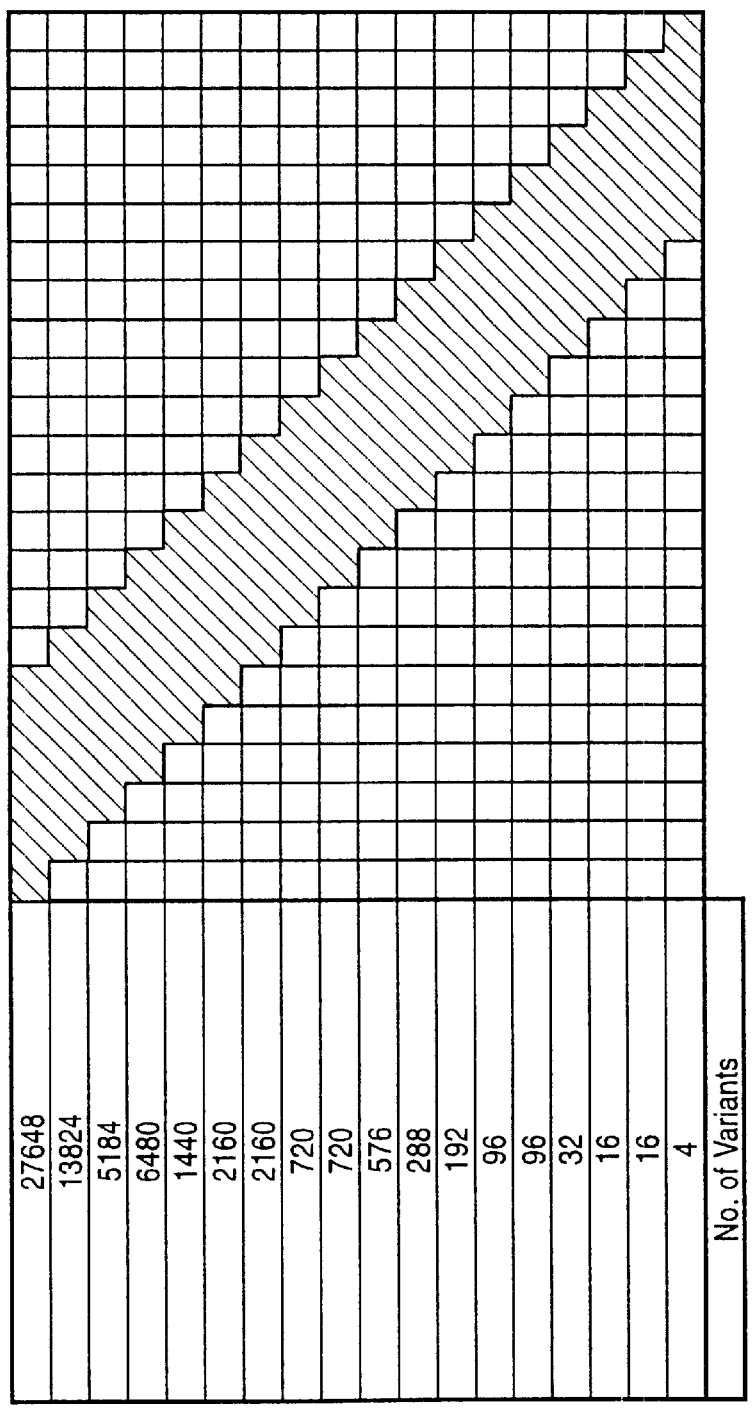

FIG. 13 represents the antibody recognition of hybrid HCV peptides.

FIGS. 14a–14d represents the construction scheme for mixotope peptides from the N-terminus of E2/HS1 of HCV type 1.

Figure 15:
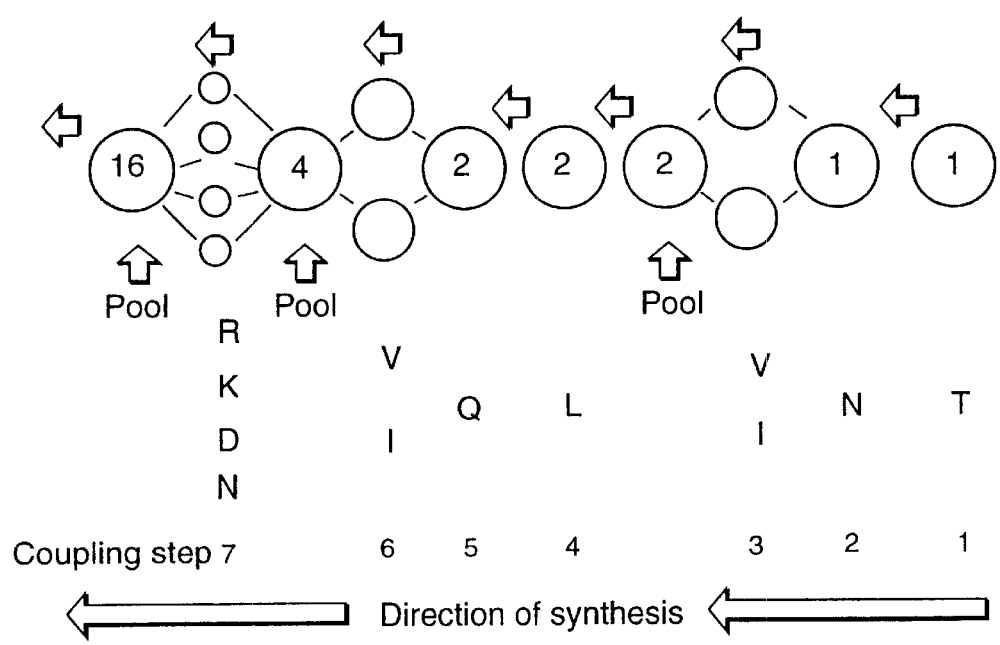

FIG. 15 (SEQ ID NO: 178 to SEQ ID NO: 261)represents the mixotope synthesis strategy.

Figure 16A:
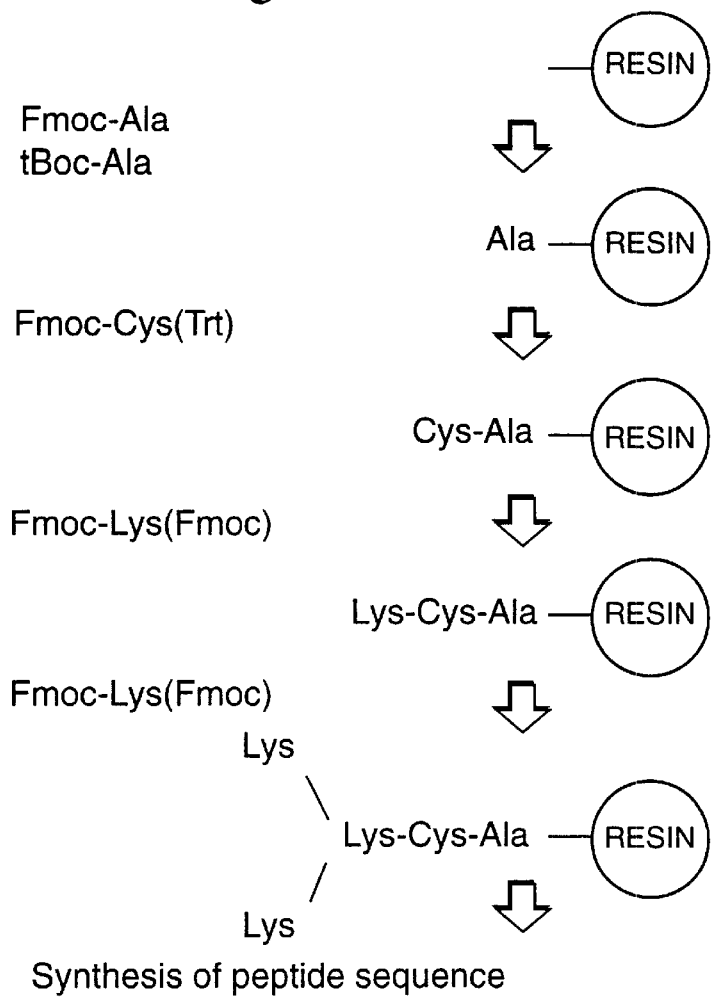
Figure 16A:
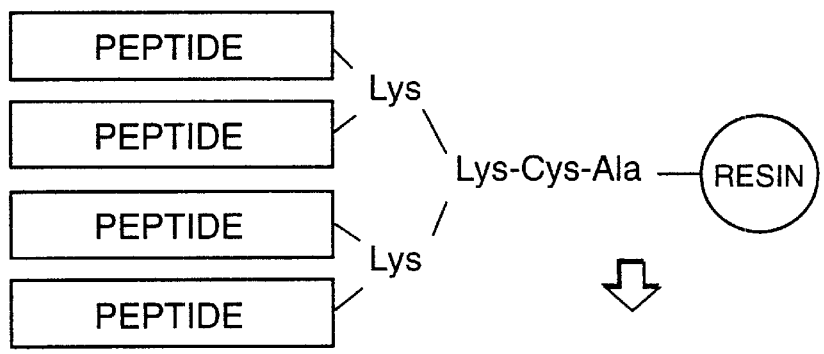
Figure 16B:
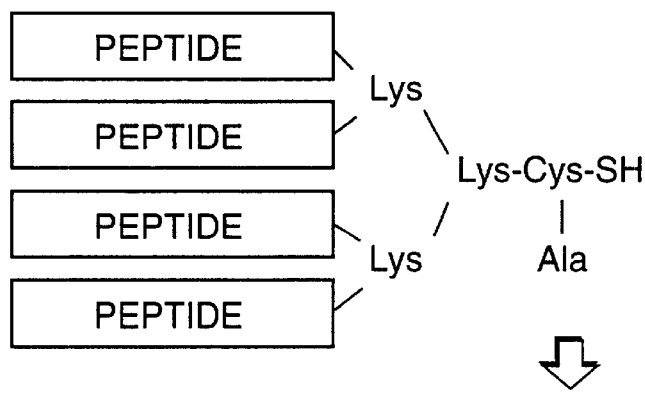
Figure 16B:
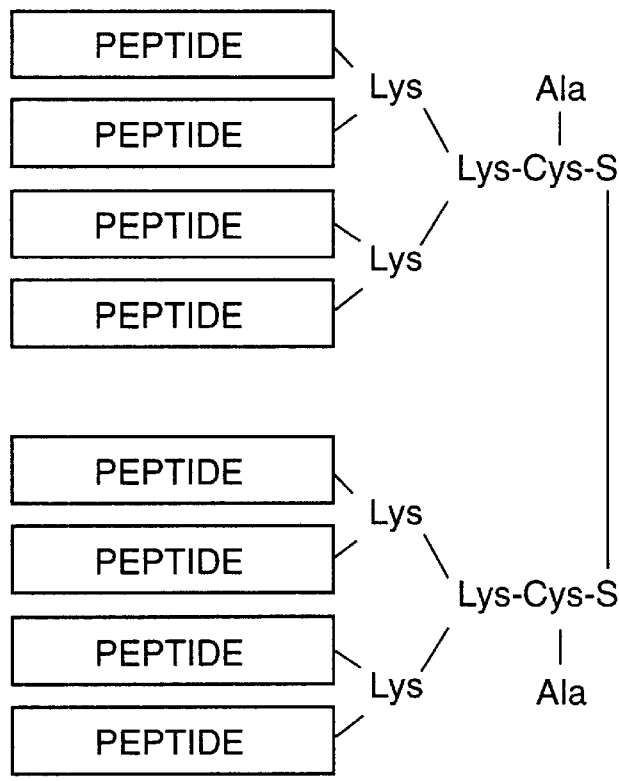

FIGS. 16A and 16B represent (SEQ ID NO: 262 to SEQ ID NO: 369) represents the synthesis of multiple antigen peptides (MAPs).

FIGS. 17A and 17B represent (SEQ ID NO: 370 to SEQ ID NO: 453) represents the recognition of E2/NS1 peptides by sera from rabbits immunized with E2/NS1 "b" peptide MAPs.

Figure 18:
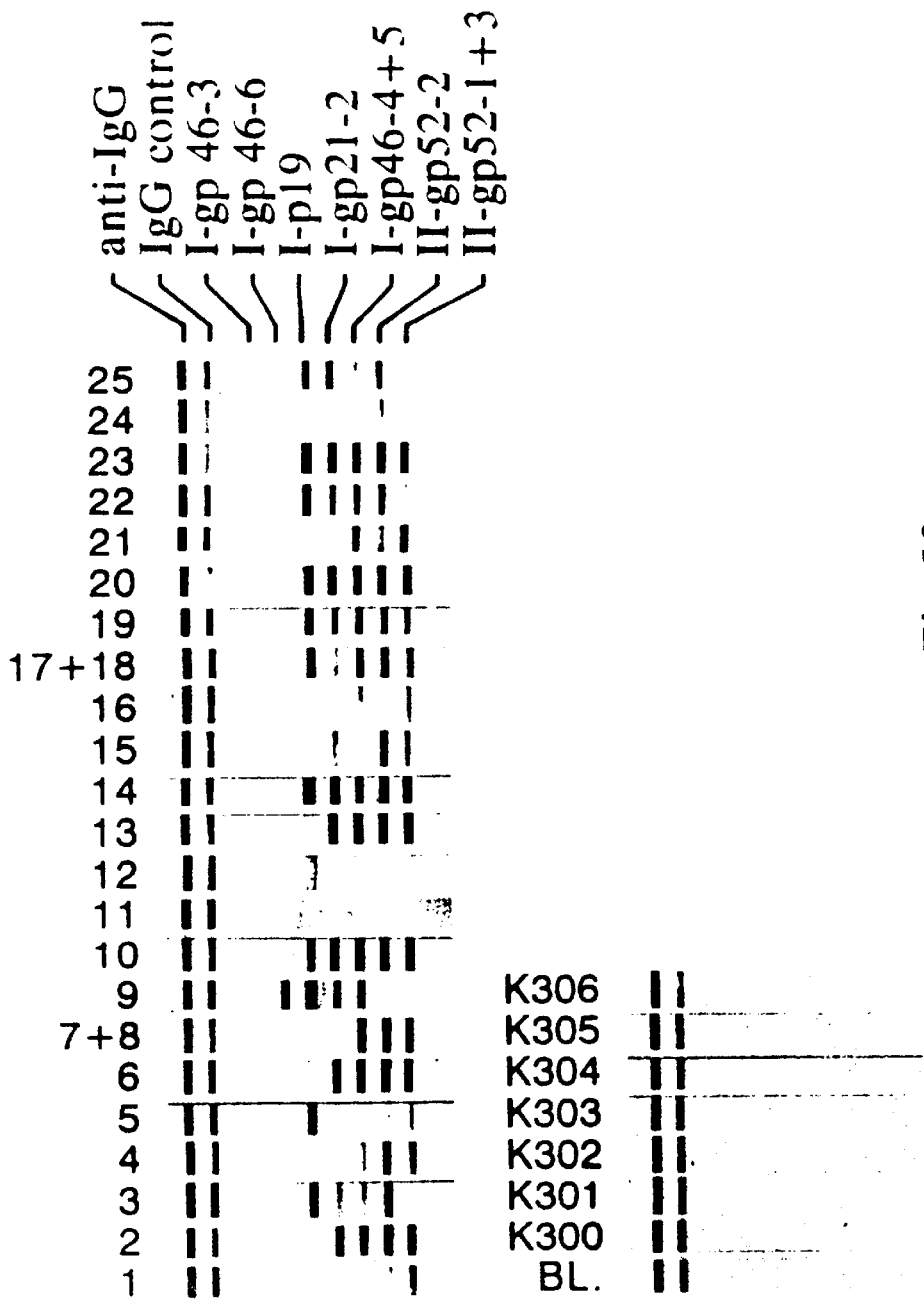

FIG. 18 represents the recognition of a commercially available serum panel with a number of biotinylated HTLV-I and HTLV-II peptides incorporated into LIA strips.

Table 1 represents the antibody recognition of unbiotinylated HIV-1 and HIV-2 peptides (designated by TM-HIV-1 and TM-HIV-2) and biotinylated HIV-1 and HIV-2 peptides (hereabove referred to as 1a.1 and 2a, and also designated by TM-HIV-1 Bio and TM-HIV-2 Bio) in an ELISA.

Table 2 represents the comparison of antibody recognition of unbiotinylated and biotinylated peptides from the V3 sequence of isolate HIV-1 mn (also referred as 1b.4) in an ELISA.

Table 3 represents the comparison of antibody recognition of the biotinylated V3-mn peptide (referred to as 1b.4) bound to streptavidin and avidin, in an ELISA.

Table 4 represents the comparison of antibody recognition of biotinylated and unbiotinylated HCV peptides, in an ELISA.

More particularly:

Table 4A corresponds to the antibody binding to HCV peptide XI.

Table 4B corresponds to the antibody binding to HCV peptide XVI.

Table 4C corresponds to the antibody binding to HCV peptide II.

Table 4D corresponds to the antibody binding to HCV peptide III.

Table 4E corresponds to the antibody binding to HCV peptide V.

Table 4F corresponds to the antibody binding to HCV peptide IX.

Table 4G corresponds to the antibody binding to HCV peptide XVIII.

Table 5 represents a comparison of antibody binding to biotinylated and non-biotinylated peptides, at different peptide coating concentrations, in an ELISA.

Table 6 represents the comparison of N- and C-terminally biotinylated TM-HIV-1 peptide (referred to as 1a.1), in an ELISA.

Table 7 represents a comparison of antibody recognition of unbiotinylated and carboxy-biotinylated HCV peptide I.

Table 8 represents the use of mixtures of biotinylated HIV and HCV peptides for antibody detection, in an ELISA.

Table 9 represents sequences of the core epitopes of the HCV Core protein.

Table 10 represents sequences of the core epitopes of the HCV NS4 protein.

Table 11 represents sequences of the core epitopes of the HCV NS5 protein.

Table 12 represents the antibody binding of various Core, NS4, and NS5 biotinylated 20-mers by 10 test sera.

Table 13 represents the antibody recognition of individual E2/NS1 peptides (percent of all sera giving a positive reaction).

Table 14 represents the overall recognition of HIV V3-loop peptides.

Table 15 represents the recognition of HIV peptides according to the geographical region.

Table 16 represents the recognition of European, African and Brazilian HIV-1-positive sera to HIV-I V3-loop peptides V3-con and V3-368.

Table 17 represents the recognition of HIV-2 positive sera to two HIV-2 V3 loop peptides.

Table 18 represents the antibody recognition of hybrid peptides.

Table 19 represents the antibody recognition of mixed HTLV I and II peptides.

All amino acid sequences are given in the conventional and universally accepted three-letter code and where indicated in the one-letter code. The peptide sequences are given left to right which, by convention, is the direction from the amino terminus to the carboxy-terminus.

A number of unconventional codes are also used to represent chemical groups or modifications and are defined as follows:

| Group | Code |
| --- | --- |
| Ac | acetyl |
| Bio | D-biotinyl |
| Fmoc | 9-fluorenylmethoxycarbonyl |
| tBoc | tertiary butyloxycarbonyl |

EXAMPLE 1

Peptide Synthesis

All of the peptides described were synthesized on Tenta-Gel S-RAM (Rapp Polymere, Tübingen, Germany), a polystyrene-polyoxyethylene graft copolymerfunctionalized with the acid-labile linker4-(α-Fmoc-amino-2',4'-dimethoxybenzyl) phenoxyaceticacid (Rink, Tetrahedron Lett. (1987) 28:3787) in order to generate peptide carboxyterminal amides upon cleavage. t-Butyl-based side chain protection and Fmoc-α-amino-protection was used. The quanidine-group of arginine was protected with the 2,2,5,7, 8-pentamethylchroman-6-sulfonyl moiety. The imidazole group of histidine was protected with either t-Boc or trityl and the sulfhydryl group of cysteine was protected with a trityl group. Couplings were carried out using preformed O-pentafluorophenyl esters except in the case of arginine where TBTU was used as the activating agent in the presence of 1.5 equivalents of the base N-methylmorpholine. Occasionally, glutamine and asparagine were also coupled using TBTU activation. In these cases, the trityl-protected derivatives of these amino acids were employed. Biotin was coupled using either TBTU or HBTU. All syntheses were carried out on a Milligen 9050 PepSynthesizer (Novato, Calif.) using continuous flow procedures. Following cleavage with trifluoroacetic acid in the presence of scavengers and extraction with diethylether, all peptides were analyzed by C18-reverse phase chromatography.

EXAMPLE 2

Synthesis of N-α-Fmoc-Lys (N-ε-biotin)

A. Method A

Commercially available N-α-Fmoc-L-lysine (N-ε-tBoc) (1.5 grams) was treated with 20 milliliters of 95% trifluoroacetic acid, 5% $H_2O$ for 2 hours at room temperature. Most of the acid was then evaporated under a stream of nitrogen. Ten milliliters of water was added and the solution was extracted 3 times with diethylether. The aqueous phase was then evaporated to dryness in vacuo over phosphorus pentoxide. The resulting powder (N-α-Fmoc-L-lysine) was analyzed by reverse phase chromatography and revealed a homogeneous product which was, an expected, more hydrophilic than the starting material.

N-α-Fmoc-lysine (190 mg, 0.49 mmol) was dissolved in 8 milliliters of 0.1 M borate buffer, pH 8.7. N-hydroxysuccinimidobiotin (162 mg, 0.47 mmol) was dissolved in 4 milliliters of dimethylformamide and added to the solution of N-α-Fmoc-lysine. The pH was monitored and titrated as necessary, with NaOH. After 2 hours, the solution was acidified with HCl to pH 2.0, at which time a white precipitate was obtained.

Following extraction with ethylacetate and centrifugation, the white precipitate was found at the H2O: ethylacetate interface. Both phases were removed and the precipitate extracted twice with 10 mM HCl, once with ethylacetate, followed by two extractions with diethylether. The precipitate was dissolved in DMF and precipitated by addition of diethylether. The crystalline powder was then dried in vacuo over phosphorus pentoxide. The resulting product was analyzed by reverse phase chromatography and revealed a major peak which, as expected, eluted later than N-α-Fmoc-Lys. A very small peak of N-α-Fmoc-Lys was also observed. (FIG. 2a).

B. Method B

Commercially available N-ε-biotinyl lysine (biocytin, Sigma, 249 mg, 0.67 mmol) was dissolved in 8 milliliters of 1 M Na2CO3 and cooled on ice. Fluorenylmethylsuccinimidyl carbonate (222 mg, 0.66 mmol) was dissolved in 2 milliliters of acetone and was added to the biotinyl lysine solution over a period of 30 minutes with vigorous stirring. Stirring was continued for 5 hours at room temperature. The pH was maintained between 8 and 9 by addition of 1 M $Na_2CO_3$ as necessary. The acetone was then evaporated off under vacuum, and 1.0 M HCl was added until the pH of the solution was approximately 2. Upon acidification of the solution, a white precipitate appeared which was washed twice with 10 mM HCl, twice with ethyl acetate, and twice with diethylether. The precipitate was dissolved in DMF and precipitated by addition of diethylether. The crystalline powder was then thoroughly dried in vacuo over prosphorus pentoxide. The resulting product was analyzed by reverse phase chromatography and revealed a major peak which eluted with the same retention time (30.5 minutes) as the product obtained using method 1 (FIG. 2b).

EXAMPLE 3

Methods for the Determination of Peptides Corresponding to Immunologically Important Epitopes in an Enzyme-Linked Immunosorbent Assay (ELISA) Using Specific Antibodies Where peptides were to be coated directly, stock solutions of the peptides were diluted in sodium carbonate buffer, pH 9.6 and used to coat polystyrene microtiter plates at a peptide concentration of 2 to 5 micrograms per milliliter for 1 hour at 37° C.

In cases where biotinylated peptides were to be evaluated, plates were first coated with streptavidin in sodium carbonate buffer, pH 9.6 at a concentration of 3 micrograms per milliliter for 1 hour at 37° C. The plates were then washed to remove excess, unbound protein. A working solution of the biotinylated peptide at 1 microgram per milliliter in sodium carbonate buffer was then added to the wells of the microtiter plate and incubated for 1 hours at 37° C.

Once the plates had been coated with antigen, any remaining free binding sites on the plastic were blocked with casein. After washing, a dilution of the appropriate antisera, usually 1:100, was added to the wells of the plates and incubated for 1 hour at 37° C.

After washing to remove unbound material, specific antibody binding was detected by incubating the plates with goat anti-human immunoglobulin antibodies conjugated to the enzyme horseradish peroxidase. Following removal of unbound conjugate by washing, a solution containing $H_2O_2$ and 3,3',5,5'-tetramethylbenzidine was added.

Reactions were stopped after a suitable interval by addition of sulfuric acid. Positive reactions gave rise to a yellow color which was quantified using a conventional microtiter plate reader. Absorbance measurements were made at a wavelength of 450 nanometers and all data are expressed as an optical density value at this wavelength.

EXAMPLE 4

Use of Biotinylated HIV Peptides for the Detection of HIV-Specific Antibodies

Experiments were performed to evaluate antibody recognition of short, 10 amino acid-long, N-acetylated peptides corresponding to other contained within the transmembrane proteins of HIV-1 and HIV-2. Direct coating of these peptides in the wells of microtiter plates gave very poor results when antibody binding was evaluated in an ELISA. Since it was suspected that the peptides did not bind well to the polystyrene solid phase, the peptides were resynthesized in the same way except that biotin was attached to the amino terminus of the peptides, separated from the decamer peptide sequence by three glycine residues whose function it was to service as a linker arm. The peptides used for the comparison were as follows:

TM-HIV-1:
(SEQ ID NO:110) Ac-Ile-Trp-Gly-Cys-Ser-Gly-Lys-Leu-Ile-Cys-NH2

TM-HIV-1 Bio
(SEQ ID NO:112) Bio-Gly-Gly-Gly-Ile-Trp-Gly-Cys-Ser-Gly-Lys-Leu-Ile-Cys-NH2

TM-HIV-2
(SEQ ID NO:112) Ac-Ser-Trp-Gly-Cys-Ala-Phe-Arg-Gln-Val-Cys-NH2

TM-HIV-2 Bio
(SEQ ID NO:113) Bio-Gly-Gly-Gly-Ser-Trp-Gly-Cys-Ala-Phe-Arg-Gln-Val-Cys-NH2

The biotinylated peptides were loaded onto microtiter plates which had been coated with streptavidin. Antibody binding to these peptides was compared to antibody binding to the unibiotinylated peptides which were coated directly onto microtiter plates. The results are shown in Table 1. It is evident that the biotinylated peptides from the HIV-1 or HIV-2 transmembrane proteins bound to streptavidin are recognized very well by antisera from HIV-1 or HIV-2 infected persons respectively. This is in contrast to the unbiotinylated versions of these peptides coated directly onto the polystyrene plates. Addition control experiments showed that the increase in antibody binding was the result of the specific interaction between the biotinylated peptide and streptavidin, since there was no difference in antibody recognition of the biotinylated or unbiotinylated peptides when both were coated directly onto the microtiter plate.

Some peptides, particularly ones which are 15 amino acids in length or longer, bind sufficiently to the solid phase to allow the detection of specific antibodies which recognize (an) epitope(s) present in the peptide sequence.

To ascertain whether biotinylation would also improve antibody recognition of longer peptides, both the biotinylated and unbiotinylated versions of the partial V3 loop sequence of isolate HIV-1 mn were synthesized. The sequence and method of synthesis of both peptides were identical except at the amino terminus. The unbiotinylated peptide was simply acetylated whereas in the biotinylated version, two glycine residues were added as a linker arm to separate the peptide from the biotinyl moiety.

The sequences of the two peptides used are as follows:
unbiotinylated V3 mn peptide
(SEQ ID NO: 114) Ac-Tyr-Asn-Lys-Arg-Lys-Arg-Ile-His-Ile-Gly-Pro-Gly-Arg-Ala-Phe-Tyr-Thr-Thr-Lys-Asn-Ile-Ile-Gly-NH2,
biotinylated V3 mn peptide (peptide 1b.4)
(SEQ ID NO: 115) Bio-Gly-Gly-Tyr-Asn-Lys-Arg-Lys-Arg-Ile-His-Ile-Gly-Pro-Gly-Arg-Ala-Phe-Tyr-Thr-Thr-Lys-Asn-Ile-Ile-Gly-NH2.

The unbiotinylated peptide was coated directly onto the wells of a polystyrene microtiter plate while the biotinylated peptide was bound to wells which had previously been coated with streptavidin. The results shown in Table 2 demonstrate that antibody binding to the biotinylated peptide is superior to antibody binding to peptide coated directly onto the plastic.

EXAMPLE 5

Use of Biotinylated Peptides—Avidin Complexes for Antibody Detection

Having demonstrated that antibody recognition of this peptide is improved when the peptide is biotinylated and bound to streptavidin, an additional experiment was performed to determine whether streptavidin could be substituted by avidin. The results shown in Table 3 indicate that this is the case and that biotinylated peptides bound to avidin are recognized very efficiently by specific antibodies.

EXAMPLE 6

Use of Biotinylated HCV Peptides for Detection of HCV Specific Antibodies

In order to determine whether the enhanced antibody recognition of biotinylated peptides was a general phenomenon, a number of additional twenty amino acid-long peptides were synthesized which correspond to sequences derived from the hepatatis C virus (HCV) polyprotein. The amino acid sequences evaluated were as follows:
a. HCV peptide XI
(SEQ ID NO: 116) Ser-Gln-His-Leu-Pro-Tyr-Ile-Glu-Gln-Gly-Met-Met-Leu-Ala-Glu-Gln-Phe-Lys-Gln-Lys
b. HCV peptide XVI
(SEQ ID NO: 116) Leu-Arg-Lys-Ser-Arg-Arg-Phe-Ala-Gln-Ala-Leu-Pro-Val-Trp-Ala-Arg-Pro-Asp-Tyr-Asn
c. HCV peptide II
(SEQ ID NO: 118) Pro-Gln-Arg-Lys-Thr-Lys-Arg-Asn-Thr-Asn-Arg-Arg-Pro-Gln-Asp-Val-Lys-Phe-Pro-Gly
d. HCV peptide III
(SEQ ID NO: 119) Arg-Asn-Thr-Asn-Arg-Arg-Pro-Gln-Asp-Val-Lys-Phe-Pro-Gly-Gly-Gly-Gln-Ile-Val-Gly
e. HCV peptide V
(SEQ ID NO: 120) Thr-Arg-Lys-Thr-Ser-Glu-Arg-Ser-Gln-Pro-Arg-Gly-Arg-Arg-Gln-Pro-Ile-Pro-Lys-Val
f. HCV peptide IX
(SEQ ID NO: 121) Ile-Ile-Pro-Asp-Arg-Glu-Val-Leu-Tyr-Arg-Glu-Phe-Asp-Glu-Met-Glu-Glu-Cys-Ser-Gln
g. HCV peptide XVIII
(SEQ ID NO: 122) Glu-Thr-Trp-Lys-Lys-Pro-Asp-Tyr-Glu-Pro-Pro-Val-Val-His-Gly-Cys-Pro-Leu-Pro-Pro In each case, two versions of the peptide were synthesized. In the unbiotinylated version, the peptide was acetylated at the amino terminus. The biotinylated versions were all N-terminally biotinylated. A linker arm consisting of two glycine residues separated the biotinyl moiety from the amino acids comprising the HCV sequence.

The unbiotinylated peptides were adsorbed onto the wells of polystyrene microtiter plates at a concentration of 3 micrograms per milliliter.

The biotinylated peptides were bound at a concentration of 1 microgram per milliliter to streptavidin-coated microtiter plates. Sera known to contain antibodies to these peptides were used for the evaluation and were tested at a 20-fold dilution. The results of these comparisons are shown in Table 4, a to g.

These results clearly indicate that antibody recognition of biotinylated peptides bound to streptavidin is enhanced relative to that of peptides coated directly onto the wells of the microtiter plate.

EXAMPLE 7

Influence of Coating Concentration of Antibody Detection

To investigate further the enhanced antibody recognition of biotinylated HCV peptides bound to streptavidin or avidin as compared to direct adsorption on plastic, the influence of peptide coating concentration was investigated. Three peptides (HCV peptides II, XI, and XVI) were coated in concentrations ranging from 10 nanograms per milliliter to 3 micrograms per milliliter in a volume of 200 microliters per microtiter plate well. For direct coating, the unbiotinylated versions of these peptides were used. The biotinylated versions of these peptides were used to coat wells to which streptavidin had previously been adsorbed. Sera known to contain antibodies to these peptides were used at a dilution of 1 to 100 to evaluate the magnitude of antibody binding.

The numerical results of this experiment are shown in Table 5 and are depicted graphically in FIG. 3, a–c.

It is evident that with few exceptions, the biotinylated peptide is recognized very well even at the lowest concentration tested (10 nanograms per milliliter, 2 nanograms per well). In many cases, optical density values close to the maximum attainable are observed at a peptide concentration of only 30 nanograms per milliliter (6 nanograms per well). In contrast, however, the unbiotinylated peptides absorbed directly onto the plastic are poorly bound by antibody, if at all.

EXAMPLE 8

Influence of Biotinylation of Peptides on Coating Efficiency of the Peptides on a Solid Phase To determine if the absence of a signal was due to lack of peptide adsorption when the peptides were coated directly, an additional experiment was performed. In this case, the biotinylated versions of the peptides were coated directly onto the plastic at the same concentrations used in the previous experiment for the unbiotinylated versions. To ascertain whether biotin-labeled peptide was bound, the microtiter plates were incubated with a streptavidin: horseradish peroxidase conjugate. Since each peptide contains a single biotinyl group, the resulting optical densities are a measure of the amount of peptide bound, although the absolute amount of bound peptide is not known. The results presented graphically in FIG. 4 demonstrate that plastic-bound peptide can be detected. As expected, the curves are different for each peptide which is a reflection of their chemical uniqueness. Two of the peptides, HCV peptides XI and XVI, appear to bind only weakly to the wells of the polystyrene microtiter plate and this poor binding is reflected in the low optical density values obtained in the ELISA. Since the binding of the biotinylated peptides to streptavidin-coated wells results in a very good antibody recognition, it is obvious that poor binding of the peptide to the solid phase is not a limitation when use is made of interaction between biotin and streptavidin.

On the other hand, one of the peptides, HCV peptide II, shows very significant binding to the solid phase, particularly at higher coating concentrations. However, at no coating concentration did the signal obtained when the peptide was coated directly ever equal the signal obtained when the biotinylated peptide was bound to streptavidin. Since even at the lowest concentration tested, the streptavidin-bound biotinylated versions of this peptide clearly gives a positive signal with the antisera tested, the results would seem to indicate either that the direct coating of this peptide is extraordinarily inefficient or that other factors are important besides the simple binding of peptide to the solid phase.

Although difficult to quantify, one of the factors almost certainly involves the manner in which the peptides is bound and available for antibody binding. In the case of peptides coated directly onto the solid phase, it is virtually inevitable that some proportion of the peptide molecules will interact with the solid phase through amino acid side chains which are also essential for antibody recognition. These peptide molecules will therefore be unable to participate in the binding reaction with antibodies. This problem is not encountered with the biotinylated peptides which are all bound to the solid phase through the interaction between biotin and the solid phase-bound streptavidin.

EXAMPLE 9

Use of C-Terminally Biotinylated HIV Peptides for Specific Antibody Recognition In order to determine whether the peptides biotinylated at their carboxy-terminus also give use to enhanced antibody recognition, a carboxy-biotinylated version of the TM-HIV-1 peptide was synthesized. N-α-Fmoc-Lys (N-ε-biotin) prepared by method A as described was coupled directly to resin functionalized with the acid labile linker 4-(α-Fmoc-amino-2',4'-dimethoxybenzyl) phenoxyacetic acid after removal of the linker-bound Fmoc group with 20 percent piperidine. The coupling was performed using a 3-fold molar excess of N-α-Fmoc-Lys (N-ε-biotin) relative to resin functional groups. Carboxyl group activation was achieved using one equivalent of HBTU, one equivalent of 1-hydroxybenzotriazole and 1.5 equivalents of N-methylmorpholine. N-methyl morpholine was dispensed as a 0.6 M solution indimethylformamide containing 40 percent dimethylsulfoxide which was necessary to achieve complete dissolution of the N-α-Fmoc-Lys (N-ε-biotin). Inspection of the Fmoc deprotection peak following coupling of the N-α-Fmoc-Lys (N-ε-biotin) indicated that coupling had proceeded smoothly and efficiently. Two glycine residues were coupled to separate the biotinyl lysine from the TM-HIV-1 amino acid sequence. Following synthesis of the peptide, the amino terminus was acetylated with acetic anhydride. The resulting structure of the carboxy-biotinylated peptide differs significantly from the peptide biotinylated at the amino terminus. A comparison of these structures is shown in FIG. 5.

In order to evaluate antibody recognition of these two peptides, the peptides were bound individually to streptavidin-coated microtiter plates and tested using a panel of antisera from HIV-1 seropositive donors. The results of this comparison is shown in Table 6. Clearly, antibody recognition of the C-terminally biotinylated peptide compares very favorably with that of the N-terminally biotinylated peptide. These results also confirm the utility of the reagent N-α-Fmoc-Lys (N-ε-biotin) for carboxy-terminal biotinylation.

EXAMPLE 10

Comparison of Antibody Recognition of HCV Peptide I, Coated Directly (Unbiotinylated) or Bound to Streptavidin-Coated Plated (Carboxy-Terminal Biotinylation)

A similar experiment was performed using a peptide which binds relatively well to polystyrene ELISA plates in order to determine whether the carboxy-biotinylated form of the peptide would result in superior antibody recognition relative to the unbiotinylated form of the peptide. The peptide chosen was HCV peptide I, which was synthesized in the following versions:

a. unbiotinylated version:
(SEQ ID NO: 123) H2N-Met-Ser-Thr-Ile-Pro-Lys-Pro-Gln-Arg-Lys-Thr-Lys-Arg-Asn-Thr-Asn-Arg-Arg-Pro-Gln-CONH2 b. carboxy-biotinylated version:
(SEQ ID NO: 124) H2N-Met-Ser-Thr-Ile-Pro-Lys-Pro-Gln-Arg-Lys-Thr-Lys-Arg-Asn-Thr-Asn-Arg-Arg-Pro-Gln-Gly-Gly-Lys (Bio)-CONH2.

A spacer consisting of two glycine residues was added at the carboxy-terminus to physically separate the HCV portion of the peptide proper from the Lys(N-ε-Bio). Synthesis was performed on resin functionalized with 4-(α-Fmoc-amino-2',4'-dimethoxybenzyl) phenoxyacetic acid linker in order to generate carboxy-terminal amides upon cleavage. Coupling of the N-α-Fmoc-Lys(N-ε-biotin) to the linker was performed using a 3-fold molar excess of the intermediate product relative to the linker. Activation of the N-α-Fmoc-Lys(N-ε-biotin) was achieved using one equivalent of TBTU, one equivalent of 1-hydroxybenzotriazole, and 1.5 equivalents of N-methylmorpholine. The coupling of all other amino acids was performed according to conventional protocols. Following cleavage of the peptides in trifluoroacetic acid in the presence of the appropriate scavengers, the peptides were precipitated and extracted with diethylether.

Unbiotinylated HCV peptide I was coated directly onto the wells of a polystyrene ELISA plate at a concentration of 3 micrograms per milliliter in sodium carbonate buffer, pH 9.6. Biotinylated HCV peptide I was bound to streptavidin-coated wells using a stock solution containing the peptide at a concentration of 1 microgram per milliliter. The resulting plates were then incubated in parallel with a panel of sera from HCV-seropositive donors. The results of this comparison are shown in Table 7. The biotinylated peptide clearly gives superior results relative to the unbiotinylated version of the same sequence. Two of the sera (8326 and 8244) recognize the biotinylated version of this peptide far better than the unbiotinylated version. The specificity of the antibody reaction is also reflected by the low optical density values obtained for 5 serum samples from uninfected donors (F88, F89, F76, F136, and F6).

EXAMPLE 11

Use of Mixtures of Biotinylated HIV and HCV Peptides

In many cases, the use of mixtures of peptides is required to give the desired result. Mixtures of peptides may be used for the detection of antibodies directed against one or more proteins of a single virus, or for the detection of antibodies directed against proteins of several viruses in a single test. Such tests are considered particularly advantageous for the screening of blood donations for their suitability for use in transfusions and as a source of blood products. In such cases, ELISA plates or other solid supports coated with suitable mixtures of peptides may be used to screen samples for the presence of antibodies to one or more infectious agents whose presence would render the sample unsuitable for use. For the diagnosis of specific infectious agents, appropriate mixtures of peptides are required in order to obtain accurate determinations. Antibodies to individual viral antigens derived from one or more infectious agents may be individually detected and identified simultaneously when use is made of test systems in which individual peptides or mixtures of peptides are bound to the solid phase but are physically separated as they are, for example, in the line immunoassay, such that individual reactions can be observed and evaluated. Such tests require the use of an appropriate combination of peptide mixtures to achieve the desired result.

It is frequently preferable to use mixtures of peptides rather than a single peptide for the diagnosis of ongoing or past infections. Since individual responses to single epitopes may be quite variable, more reliable results are often obtained when several immunologically important epitopes are present in the antibody test. However, since each peptide is chemically unique, it is frequently difficult to incorporate all of the desired peptides into one test, particularly when the peptides are to be coated directly onto the solid phase. Not all peptides are capable of binding to the solid phase and the peptides in the mixture may also exhibit very different optimal coating conditions in terms of pH, ionic strength, and buffer composition.

To determine how well biotinylated peptides would function in a mixture when bound to streptavidin- or avidin-coated plates, two mixtures were made of the N-terminally biotinylated versions of the HIV-1 peptides TM-HIV-1 (hereabove referred to as 1a.1) and V3-nm (hereabove referred to as 1b.4), the HIV-2 peptide TM-HIV-2 (hereabove referred to as 2a), and the hepatitis C virus peptides II, IX, and XVIII. Mixture A contained each of the six biotinylated peptides at a concentration of 1 microgram per milliliter (6 micrograms per milliliter peptide, total) while in mixture B, each peptide was present at a concentration of 0.1 microgram per milliliter (0.6 microgram per milliliter peptide, total). The individual peptides were coated at a concentration of 1 microgram per milliliter. For purposes of comparison, mixtures A and B were also coated directly onto the wells of a microtiter plate. Samples from HIV-1, HIV-2, and HCV-seropositive donors were tested and compared to sera from seronegative blood donors. A cut-off absorbance value of 0.250 was used to determine whether a reaction was positive or negative. Absorbance values equal or greater than 0.250 were considered positive while absorbance values below this value were considered negative. The results of this experiment are shown in Table 8.

Based on the reactions to the individual peptides, all of the HCV serum samples were negative for antibodies to either HIV-1 or HIV-2. One HIV-2 sample (no. 1400) had antibodies to HCV peptide XVIII. Of the HIV samples tested, there was no indication of cross reactivity and the ELISA based on individual peptides is specific.

Both mixtures A and B gave good results when bound to avidin-coated microtiter plates. As expected, these mixtures were recognized by HIV-1, HIV-2, and HCV-positive sera but not by sera from seronegative blood donors. In contrast, when these mixtures were coated directly onto the microtiter plates, the results were considerably less satisfactory, with many samples giving a reaction which fell below the cut-off value applied. These results serve to illustrate quite convincingly the enhanced immunological recognition of biotinylated peptides bound to avidin as compared to peptides coated directly onto the solid phase as well as the advantages of using mixtures of peptides for multiple antibody detection.

EXAMPLE 12

Use of Biotinylated Peptides for Mapping of Epitopes in Diagnostically Useful Regions of HCV It was demonstrated in Example 6 that several diagnostically important regions of the HCV polyprotein, such as Core, NS4, and NS5, can be identified using overlapping 20-mer biotinylated peptides. Extensive serological testing identified the most useful 20-mer biotinylated peptides which permitted to develop a line immunoassay utilizing these biotinylated peptides. However, it was desirable to know more exactly where in these 20 amino acid-long sequences that epitopes were located. One reason is that, if shorter sequences could be identified, it would be possible to make synthetic peptides containing two or three epitopes without the peptide becoming prohibitively long.

Epitopes present in a position of the putative HCV proteins were mapped using the method originally described by Geysen, H. M., Meloen, R. H., and Barteling, S. J.; Proc. Natl. Acad. Sci. USA (1984) 81:3998–4002. Consecutive peptides nine amino acids in length with an eight amino acid overlap were synthesized on polyethylene pins derivatized with a non-cleavable linker. This peptide length was chosen because it is larger than the size of typical linear epitopes which are generally between 5 and 7 amino acids in length. By synthesizing 9-mers, the probability that epitopes would be missed was minimized.

The regions in the HCV polyprotein which were scanned contain Core sequences (aa. 1 to 80), NS4 (aa. 1688 to 1755), and NS5 (aa. 2191 to 2330). These regions correspond to the previously determined 20-mers: Peptide I to VII (Core 1 to 13), Peptide VIII to XIV (NS4-1 to 9), and peptide XV to XIX (NS5-13 to 33).

Following synthesis, all peptides were N-acetylated prior to said chain deprotection in order to remove the unnatural positive charge at the amino terminus.

The peptides were then assayed for their ability to be recognized by antibodies present in sera from HCV seropositive donors. The results of these experiments are shown in FIGS. 6a to 6c. The optical density values shown are the average of duplicate determinations and have been assigned to the first amino acid of the 9-mer sequence.

The antibody binding profiles for 10 different HCV sera are shown in FIG. 6a. It is clear that the core protein of HCV presents well-defined linear epitopes which are readily stimulated by synthetic peptides. At least superficially, most sera appear to give very similar patterns. Closer inspection, however, reveals that there are individual differences. The various regions of the HCV core protein which are recognized by antibodies are perhaps more properly termed epitopic clusters rater than epitopes as such, since each region is undoubtedly composed of several overlapping epitopes which are difficult, if not impossible, to distinguish using polyclonal sera. An attempt was made to identify core epitopes in each of the epitopic clusters. Used in this sense, the word "core" refers to the minimal amino acid sequence recognizable by antibodies. It should be emphasized, however, that amino acids in addition to the core sequence may improve reactivity particularly in the case of polyclonal sera. An analysis of the epitopes is given in Table 9. By comparing the reactions of the various sera, subdomains of epitopic clusters could be identified. Some sera react predominantly with one subdomain and not with others, while other sera recognize all of the subdomains but still allow the subdomains to be distinguished because each forms a shoulder in the large peak which defines that particular epitopic clusters. Table 9 and FIG. 7a shows the locations of the core epitopes with respect to the sequences of the 20-mers.

The series of 9-mers corresponding to each of the 20-mer Core peptides are shown in FIG. 7a together with the placement of each of these sequences in relation to an antibody recognition profile for one of the antisera tested.

The antigenic profiles for the NS4 protein obtained with the 10 sera are shown in FIG. 6b. In general, the reaction of these sera with the 9-mers was less pronounced than with the peptides from the Core protein. It was, nevertheless, still possible to identify epitopic regions in the N-terminal sequences of the viral NS4 protein. The core sequences of these epitopes are analyzed in Table 10 and show their relation to the 20-mer synthetic peptides which are diagnostically important in this region. The 9-mers corresponding to the different 20-mers are shown in FIG. 7b together with their placement in relation to an example of an antigenic profile. It can be seen that the 20-mers correspond quite well to the epitopes in this region.

The portion of the NS5 protein which was scanned corresponds to the region covered by the 20-mer peptides 13 to 33. The antigenic profiles obtained in this region are shown in FIG. 6c. Again, an attempt was made to define core epitopes and these are listed in Table 11. Little antibody binding was observed in the amino terminal portion of this sequence. In FIG. 7c, the 9-mers corresponding to the 20-mer peptides NS5-21 to NS5-31 are listed and their positions are shown relative to one of the antigenic profiles.

In particular, it is apparent that, the importance of the sequence represented by HCV peptide XVI (NS5-27) would be severely underestimated based on the results obtained with the overlapping 9-mers. The importance of this sequence would also be underestimated if unbiotinylated HCV peptide XVI (NS5-27) were evaluated in an ELISA following direct coating onto the microtiter plate (see Table 4B). However, the biotinylated version of this peptide when bound to streptavidin- or avidin-coated plates reveals the presence of a very important epitope which is of diagnostic value.

In contrast to the often weak binding observed with the 9-mers, the binding with the 20-mers was frequently quite strong (see table 12). In several cases the differences are dramatic. For example, serum 8241 does not recognize any of the 9-mers, whereas the binding to the peptides HCV2 (peptide IX) and HCV5 (peptide XI) is very strong. Moderate binding was also observed to the peptide HCV7 (peptide XIII). This would seem to indicate that there is an important structural component to these epitopes which is present in the 20-mers but which is absent in the 9-mers.

EXAMPLE 13

Use of Biotinylated Peptides for Identification of Epitopes in the N-Terminus of NS1 Region of HCV Line Immunoassay Epitopes can also be identified using the line immunoassay (LIA). In general, unbiotinylated peptides bind better to nylon membranes than to polystyrene ELISA plates. Nevertheless, biotinylated peptides complexed with streptavidin or avidin give superior results in the line immunoassay than do their unbiotinylated counterparts bound directly to the membrane. In order to illustrate this, unbiotinylated and N-terminally biotinylated versions of HCV peptides XXg-1 and XXg-2 were synthesized. The unbiotinylated peptides were applied to the membrane as a stock solution containing 100 micrograms per milliliter peptide, whereas the biotinylated peptides were bound to streptavidin and applied as a stock solution of 100 micrograms per milliliter complex. The amount of biotinylated peptide in the stock solution was therefore approximately 10 micrograms per milliliter. Three human IgG control lines were also applied to the strips in order to assist in evaluating the intensity of the reactions.

Following application of the antigen lines, excess binding sites on the membrane were blocked with casein in phosphate-buffered saline. The membrane was subsequently cut into strips perpendicular to the direction in which the antigen lines were applied and the resulting strips were incubated with a panel of sera from HCV-seropositive donors. Bound antibody was detected visually using goat anti-human IgG antibodies conjugated to the enzyme alkaline phosphatase after addition of 5-bromo-4-chloro-3-indolylphosphate and Nitro Blue tetrazolium. The results are shown in FIG. 8.

The specificity of the reactions is demonstrated by the absence of detectable antibody binding to any of the HCV peptides by three sera (33, 34, and 35) obtained from HCV-seronegative donors. The reactions of sera 1 to 32 to the unbiotinylated HCV peptides XX-1 and XX-2 are generally absent or exceedingly weak. In contrast, many of the sera tested recognized the biotinylated versions of these peptides when complexed to streptavidin. The antibody reactions to the biotinylated peptides are significantly stronger in spite of the fact that only approximately one-tenth the amount of peptides was present in these stock solutions compared to the amount present in the stock solutions of the unbiotinylated peptides. The results obtained using the biotinylated peptides demonstrate the presence of a diagnostically useful epitope in these peptide sequences which is not evident when the unbiotinylated versions of the peptides are used.

A total of 8 sequences spanning the hypervariable N-terminus of the HCV E2-NS1 region (aa 383 to 416 of the HCV polyprotein) of different HCV isolates were chosen for further evaluation. These aligned sequences (One-letter code) are as following (SEQ ID NOs: 125–132, respectively):

XXa (SEQ ID NO:125) GETYTSGGAASHTTSTLASLF-SPGASQRIQLVNT (1)
XXb (SEQ ID NO:126) GHTRVSGGAAASDTRGLVSLF-SPGSAQKIQLVNT (2)
XXc (SEQ ID NO:127) GHTRVTGGVQGH-VTCTLTSLFRPGASQKIQLVNT (3)
XXd (SEQ ID NO:128) GHTHVTGGRVASSTQS-LVSWLSQGPSQKIQLVNT (4)
XXe (SEQ ID NO:129) GDTHVTGGAQAKTTNRLVSM-FASGPSQKIQLINT (5)
XXf (SEQ ID NO:130) AETYTSGGNAGHTMTGIVRF-FAPGPKQNVHLINT (6)
XXg (SEQ ID NO:131) AETIVSGGQAARAMSGLVS-LFTPGAKQNIQLINT (7)
XXh (SEQ ID NO:132) AETYTTGGSTARTTQGLVSLF-SRGAKQDIQLINT (8)

The sequences are derived from isolates described by the following groups:
(1) Hijikata et al., Biochem. Biophys. Res. Comm. 175:220–228, 1991.
(2) unpublished results
(3) Hijikata et al., Biochem. Biophys. Res. Comm. 175:220–228, 1991.
(4) Kato et al., Proc. Natl. Acad. sci. USA 87:9524–9528, 1990.
(5) Takamizawa et al., J. Virology 65:1105–1113, 1991.
(6) Weiner et al., Virology 180:842–848, 1991.
(7) Okamoto et al., Japan J. Exptl. Med. 60:167–177, 1990.
(8) Kremsdorfl et al., Abstract V64, Third International Symposium on HCV, Strasbourg, France, September, 1991.

Since the sequences are rather long and because secondary structure—related difficulties were predicted to occur during synthesis, it was decided to split the sequences into two overlapping parts ("a"=amino acid 383 to 404 and "b"= amino acid 393 and 416 of the HCV polyprotein). Subdividing the sequence also allows the position of the epitopes to be more accurately defined.

All of the peptides were N-terminally biotinylated, complexed with streptavidin and used to prepare LIA-strips (data not shown).

When only the LIA-positive samples are considered, the detection rate on the E2/NS1 peptides was found to be on the order of 90 percent. The correlations between recognition of the E2/NS1 peptides and LIA reactivity as well as the scores for the individual peptides are shown in Table 13. It was also clear from the observed reactions that the primary epitope in this sequence is located towards the carboxy-terminus of the hypervariable region. There were exceptions to this, however. Each serum appeared to have its own recognition pattern which underscores the importance of using a mixture of different sequences if this epitope is to be included as a line in the LIA. It would also appear that either there is a considerable degree of crossreactivity between the type 1a and type 1b sequences, or that most people are doubly infected. It is a simple matter to distinguish between these two possibilities by selectively removing the antibodies which bind to one sequence and looking to see what the effect is on antibody recognition of the other sequences. A number of samples gave a rather weak reaction to one or more E2/NS1 peptides but were LIA negative. While most probably false positive reactions, these sera may also be from people who where previously infected but who have resolved the infection.

EXAMPLE 14

Use of Combined HCV Peptides from the Core Region of HCV for the Detection of Antibodies by LIA In order to reduce the overall number of peptides in a HCV ELISA or LIA, biotinylated peptides can be synthesize which span other immunologically important peptides. Examples of such "combined" HCV peptides from the core protein NS3 region of HCV are given below: (SEQ ID NOs: 133–141, respectively)

| Peptide | Sequence |
|---|---|
| core 1 (I) | M S T I P K P Q R K T K R N T N R R P Q |
| core 2 (II) | P K P Q R K T K R N T N R R P |
| core 3 (III) | R N T N R R P Q D V K F P G G G Q I V G |
| core 110 | M S T I P K P Q R K T K R N T N R R P Q D V K F P G G G Q I V G |
| core 4 (IVa) | V G G V Y L L P R R G P R L G V R A T R |
| core 7 (IV) | L P R R G P R L G V R R T R K T S E R S |

-continued

| Peptide | Sequence |
|---|---|
| core 9 (V) | T R K T S E R S Q P R G R R Q P I P K V |
| core 10 (VI) | R S Q P R G R R Q P I P K V R R P E G A |
| core 2910 | G G V Y L L P R R G P R L G V R A T R K T S E R S Q P R G R R Q P I P E V R R |

All of these peptides have been provided with a Gly-Gly spacers and a biotin at the amino terminus. The peptides were evaluated in a line immunoassay experiment (LIA) and compared to the shorter core peptides. The results are shown in FIG. 9. The longer core peptides compare very favorably to the shorter peptides and consistently give a more intense reaction. This is could be explained if (i) the longer peptides incorporate two or more epitopes which were previously spread over two separate peptides and/or (2) there is any conformational contribution which may be more prominent in the longer peptides.

EXAMPLE 15

Use of Combined HCV Peptides from the NS4 and NS5 Regions of HCV for the Detection of Antibodies by LIA Other peptides combine sequences in NS4 and NS5 which are as follows: (SEQ ID NOs: 142–147, respectively):

| Peptide | Sequence |
|---|---|
| NS4-5 (XI) | S Q H L P Y I E Q G M M L A E Q F K Q K |
| NS4-7 (XIII) | L A E Q F K Q K A L G L L Q T A S R Q A |
| NS4-57 | S Q H L P Y I E Q G M M L A E Q F K Q K A L G L L Q T A S R Q A |
| NS5-25 (XV) | E D E R E I S V P A E I L R K S R R F A |
| NS5-27 (XVI) | L R K S R R F A Q A L P V W A R P D Y N |
| NS5-2527 | E D E R E I S V P A E I L R K S R R F A Q A L P V W A R P D Y N |

The general advantage in using the longer peptides lies in the fact that their use in an ELISA or LIA leaves more space for the incorporation of other peptides carrying immunologically important epitopes.

EXAMPLE 16

Use of Type-Specific HCV NS4 Peptides for the Detection of Antibodies by LIA

Equivalent peptides containing HCV type 2 and type 3 NS4 sequences which correspond to the type 1 peptides found to contain epitopes in NS4 were synthesized. The sequences of these peptides are shown below for comparison: (SEQ ID NOS: 148–153, respectively)

| Peptide | Sequence |
|---|---|
| NS4-1 (1) | L S G K P A I I P D R E V L Y R E F D E |
| NS4-1 (2) | V N Q R A V V A P D K E V L Y E A F D E |
| NS4-5 (1) | S Q H L P Y I E Q G M M L A E Q F K Q K |
| NS4-5 (2) | A S R A A L I E E G Q R I A E M L K S K |
| NS4-7 (1) | L A E Q F K Q K A L G L L Q T A S R Q A |
| NS4-7 (2) | I A E M L K S K I Q G L L Q Q A S K Q A |

LIA strips were prepared using these nine peptides which were subsequently incubated with different sera. The results are shown in FIG. 10. Two of the sera which were previously negative on type 1 NS4 peptides gave a positive reaction to the type 3 and type 2 peptides. This indicates that it is possible to increase the NS4 detection rate using these peptides.

EXAMPLE 17

Use of a Biotinylated Peptides From the V3 Loop Region of GP120 of Different HIV-1 Isolates in a Line Immunoassay for the Detection of HIV Antibodies In order to determine the general diagnostic value of the V3 loop region of gp120, nine peptides derived from this region of nine different HIV-1 isolates were synthesized and included in a LIA. All nine peptides were provided with a Gly-Gly spacer and an N-terminal biotin. The aligned peptides (one-letter amino acid code) sequences are as follows: (SEQ ID NOs: 154–162, respectively)

| | | |
|---|---|---|
| CON | NNTRKSIHI--GPGRAFYTTGEIIG | 23 |
| SF2 | NNTRKSIYI--GPGRAFHTTGRIIG | 23 |
| SC | NNTTRSIHI--GPGRAFYATGDIIG | 23 |
| MN | YNKRKRIHI--GPGRAFYTTKNIIG | 23 |
| RF | NNTRKSITK--GPGRVIYATGQIIG | 23 |
| MAL | NNTRRGIHF--GPGQALYTTG-IVG | 22 |
| BH | NNTRKSIRIQRGPGRAFVTIGKI-G | 24 |
| ELI | QNTRQRTPI--GLGQSLYTT-RSRS | 22 |
| ANT70 | QIDIQEMRI--GP-MAWYSMG-IGG | 21 |

The peptides were mixed with streptavidin in a slight molar excess over biotin binding sites and the peptide-:streptavidin complexes were separated from unbound material over Sephadex G-25. Material eluting in the void volume was used in the preparation of the LIA.

A total of 332 sera were tested which had been obtained from various geographical regions. Since it is known that virus strains isolated in Europe or North America exhibit less strain-to-strain variability than African isolates, geographical differences in the V3-loop sequence recognition were to be expected. The reactions of the various lines were evaluated as positive (i) or negative (o) (data not shown).

A complete evaluation of the sera is given in Table 14. In total, 307 of the 332 sera gave a reaction to at least one peptide on the V3-loop LIA. Those sera which failed to give a reaction to any peptide on the V3-loop LIA were tested by Western Blot to determine whether the sera were indeed positive for anti-HIV-I antibodies. It was found that 6 sera were in fact negative. The total number of positive sera tested was therefore 326. There were, however, 19 sera which contained antibodies to gp120 which failed to react with any of the V3-loop LIA, the percentage of sera giving a positive reaction was, in global terms, 94%. There were, however, significant geographical differences. These differences are shown in Table 15.

The total percentage of sera from the different geographical regions giving at least one positive reaction can be summarized as follows:

| | | |
|---|---|---|
| | European | 100% |
| | African | 94% |
| | Brazilian | 92% |

Additional evaluations with Europe samples indicate that this percentage is, in fact, some what less than 100% (data not shown). African samples which failed to give a reaction in the LIA have not been tested by Western Blot to confirm the presence of other HIV antibodies.

That the European sera would score well was expected. The lower score obtained for the African sera was also not totally unexpected, since it is known that there is more viral heterogeneity in Africa. Since V3-loop sequences of African strains of HIV have not been as extensively characterized as the European or North American strains, it is clear that we either do not have a representative sequence, or that attempting to characterize African strains in terms of a consensus sequence is not possible exercise since there is too much sequence divergence. The results obtained with the Brazilian sera were unexpected since nothing has ever been reported concerning HIV variability in Brazil. From these results, it appears that the situation in Brazil more closely resembles the situation in Africa and not the situation in North America or Europe.

EXAMPLE 18

Improved Detection of HIV-1 Anti-V3 Domain Antibodies in Brazilian Sera Using a V3 Sequence Derived from a Brazilian Isolate Brazilian serum samples which failed to recognize any HIV-1 V3 loop sequences present on the previously described LIA strips but which were positive for antibodies which recognized the HIV-1 gp120 protein on Western blots were selected for further study. In one of these samples, V3 loop sequences of virus present in the serum sample could be amplified using the polymerase chain reaction using primers derived from the more constant regions flanking the hypervariable domain. The resulting DNA fragment was subsequently cloned and the nucleotide sequence was determined. A peptide corresponding to the deduced amino acid sequence encoded by this fragment was synthesized and tested for its ability to be recognized by various HIV-1 antibody-positive sera. The sequence of this peptide was as follows:
Peptide V3-368:
(SEQ ID NO:163) Asn Asn Thr Arg Arg Gly Ile His Met Gly Trp Gly Arg Thr Phe Tyr Ala Thr Gly Glu Ile Ile Gly
A spacer consisting of two glycine residues was added to the amino terminus. Thereafter, the resulting N-terminal glycine residue was biotinylated. The ability of European, African, and Brazilian HIV-1 antibody-positive sera to recognize this peptide was investigated and compared to the ability of these same sera to recognize the consensus sequence peptide in an ELISA. The two peptides were also evaluated together as a mixture. These results are summarized in table 16. These results demonstrate that with sera of European or African origin, the V3-368 peptide does not result in an increased anti-V3 loop antibody detection over that which is observed with the V3con peptide. In contrast, the use of the V3-368 peptide results in a marked improvement in V3 antibody detection with Brazilian sera. Although this peptide is recognized less frequently than the V3con peptide, the two peptides complement each other to raise the detection rate from 83.3 percent using the V3con peptide alone to 97.2 percent when the two peptides are used together.

EXAMPLE 19

Antibody Recognition of HIV-2 V3 Loop Sequences

The outer membrane glycoprotein of HIV-2 (gp105) is similar to that of HIV-1 with respect to its organization. Like the gp120 protein of HIV-1, the gp105 protein of HIV-2 consists of domains of variable sequence flanked by domains of relatively conserved amino acid sequence. In order to detect antibodies specific for the V3 domain of HIV-2 produced in response to infection by this virus, biotinylated peptides were synthesized corresponding to the V3 sequences of the HIV-2/SIV isolates GB12 and isolate SIV mm 239 (Boeri, E., Giri, A., Lillo, F. et al.; J. Virol. (1992) 66(7):4546–4550). The sequences of the peptides synthesized are as follows:
V3-GB12:
(SEQ ID NO:164) Asn Lys Thr Val Val Pro Ile Thr Leu Met Ser Gly Leu Val Phe His Ser Gln Pro Ile Asn Lys
V3-239:
(SEQ ID NO:165) Asn Lys Thr Val Leu Pro Val Thr Ile Met Ser Gly Leu Val Phe His Ser Gln Pro Ile Asn Asp Two glycine residues were added at the N-terminus of each peptide to serve as a spacer and a biotin was coupled to the α-amino group of the resulting N-terminal glycine. The peptides were bound to streptavidin and coated in the wells of microwell plates. HIV-2 antibody-positive sera were used to evaluate these two peptides in an ELISA. These results are summarized in Table 17. The results clearly demonstrate the usefulness of these two peptide sequences for the diagnosis of HIV-2 infection.

EXAMPLE 20

Localization of the Epitope at the Carboxy Terminus of C-100 with Biotinylated Peptides There have been various reports of an epitope located towards the carboxy-terminal portion of the C-100 protein (EP-A-0 468 527, EP-A-0 484 787). Reactivity of certain sera toward this epitope and not to epitopes located within the 5-1-1 fragment could explain why these sera give a positive reaction on C-100 but not to the above-described peptides described in the above-mentioned examples. The five overlapping biotinylated peptides synthesized NS4-a, b, c, d and e are shown in FIG. 11 and cover the carboxy-terminus of C-100 except for the last three amino acids. LIA strips prepared with these peptides were tested using a series of HCV Ab-positive and negative sera. The results of this experiment (data not shown) are summarized below:

| Peptide | Nr. of reactive sera | Percentage |
|---|---|---|
| NS4-a | 0 | 0% |
| NS4-b | 2 | 3% |
| NS4-c | 0 | 0% |
| N54-d | 0 | 0% |
| NS4-e | 16 | 27% |

EXAMPLE 21

Use of Biotinylated Hybrid Peptides Containing Epitopes from Different HCV Proteins A fine mapping of the epitopes in the immunologically most important regions of the HCV polyprotein using 9-mers was performed as illustrated in Example 12. Using this information, 3 peptide sequences were devised which consisted of three 9-mer stretches of HCV sequence separated by 2 amino acid-long spacers. In general, Gly-Gly, Gly-Ser or Ser-Gly spacers were used to provide chain flexibility. The arrangement of the epitopes in the three hybrid peptides synthesized and their sequences are shown in FIG. 12. The three peptides were evaluated on a LIA strip. In the first evaluation, the sera originally used for the epitope fine mapping experiments were used since the precise interactions of these sera with the epitopes is known. These results are shown in FIG. 13 and are summarized in Table 16. The order in which the epitopes were incorporated into these three hybrid peptides was arbitrary. It is advantageous, however, to link the epitopes together in a limited number of peptide chains rather than attempting to develop a test based on individual 9-mers. The use of separate 9-mers would rapidly saturate the streptavidin binding sites on the plate (one biotin binding site/9-mer) whereas incorporating the 9-mers into a limited number of peptides as was done in these experiments would enable one to bind 3 times as much (one biotin binding site/three 9-mers).

EXAMPLE 22

E2/NS1 "b" Sequence Mixotope Peptides

The results using synthetic peptides (see Examples above) have indicated that most HCV seropositive sera contain antibodies directed towards the hypervariable N-terminus of E2/NS1. However, because of the hypervariable nature of this region of the protein, it is necessary to use a rather wide spectrum of sequences in order to detect these antibodies in an acceptably high percentage of sera. Analysis of available sequences revealed that the observed amino acid substitutions were not entirely random and that certain amino acids were preferred in certain positions within the sequence. Since the hypervariable sequence is rather long, this sequence who divided into two overlapping portions ("a" and "b") to improve the quality of the product and simplify the synthesis. Subdividing this region also permitted the determination of that the portion of this N-terminal segment of the E2/NS1 protein which was most frequently recognized by antibodies was located in the region encompassed by the "b" versions of these sequences. Given the sequence information shown in FIG. 14 a "mixotope" was synthesized which contains at each position all the amino acids found in the naturally occurring isolates examined. The strategy followed in the synthesis of the mixotope is depicted in FIG. 15. The strategy for designing mixotopes is reviewed in Gras-masse et al., Peptide Res. (1992) 5:211–216. The resin was divided into a number of portions equal to the number of amino acids to be coupled. The coupling reactions were carried out individually so as to avoid problems arising due to differences in coupling kinetics between the various amino acids. Following the coupling reactions, the resin portions were pooled and mixed thoroughly. The total number of variants obtained for this 23 amino acid-long sequence was +1.147×10$^{10}$. The increasing number of variants as a function of chain length as measured from the carboxy-terminus or amino-terminus is shown in FIG. 14. The rationale behind the mixotope approach is that epitopes are composed of amino acids whose contribution to antibody binding is not equal. Antibodies may recognize an epitope even though there may be a relatively large number of (generally not random) substitutions in certain positions. In this respect, the antigenic complexity of the mixotope should be substantially less than the number of variants comprising the mixture. For the sake of illustration, if it is assumed that an average epitope is 6 amino acids in length, it is possible to calculate the number variants for each successive 6 amino acid long segment in the sequence. The number of variants as a function of position in the sequence is shown in FIG. 14. The actual number of functional variant sequences will be equal to the number shown for any 6 amino acid-long sequence which happens to correspond to an epitope, divided by a degeneracy factor equal to the number if tolerated substitutions in each position of the epitope but modified to reflect the degree to which the particular substitutions are tolerated. Unfortunately, the exact position(s) of the epitope(s) are not known. It should be stated explicitly that this is not a random peptide library. Key positions in the total sequence which do not tolerate substitutions, as evidenced by the absence of amino acid variations in naturally occurring isolates, are preserved. One disadvantage to this synthetic approach is that rare amino acid substitutions are overrepresented and will tend to dilute out the more commonly encountered amino acids. On the other hand, the possibility existed that overrepresentation of rare substitutions might allow the detection of antibodies not detectable with epitope sequences comprised of more frequently encountered amino acids. Following completion of the synthesis of the mixotope, all peptide chains were provided with a (Gly)2 spacer and a biotin to facilitate immunological evaluation. A multiple antigen peptide (MAP) version of the mixotope may also be synthesized in parallel.

One result of previous studies was that while approximately 90 percent of HCV-positive sera could be shown to contain anti-E2/NS1 antibodies directed against the N-terminal hypervariable region with the 16 "a" and "b" sequences investigated. The apparent lack of these antibodies in the remaining 10 percent of HCV antibody-positive sera could be due to two factors: 1) these patients fail to produce antibodies against this portion of E2/NS1, or 2) has not yet been identified the correct sequence with which to detect these antibodies. Based on experiments with the HIV-1 V3 loop, this latter possibility did not seem at all unrealistic. LIA strips were prepared which contained the 8 "b" sequences previously used in addition to the mixotope. Sera were selected which previously scored positive on at least one of the eight defined sequences as well as sera which scored negative. In total, 60 sera were tested, of which 56 previously gave a positive reaction and 4 were previously found to be negative. Of the 56 sera which had previously scored positive, 21 reacted with only one or two of the peptides on the strip or only gave a very weak reaction. (data not shown) The mixotope was recognized by approximately one-third of all the sera tested. The reaction of some sera to the mixotope was surprisingly strong, however, it may be possible that the collection of E2/NS1 sequences on which the mixotope was based it not truly representative. It is expected that the mixotope MAP will elicit the production of broad specificity antisera directed against the amino-terminus of E2/NS1.

EXAMPLE 23

Use of Branched HCV N-Terminal E2/NS1 Region Peptides for Raising Antibodies Several sequences from the N-terminus of E2/NS1 were selected for synthesis as multiple antigen peptides (MAP's) using the technique described by Tam (Proc. Natl. Acad. Sci. USA 85:5409–5413,1988). The strategy used to synthesize the branched peptides is shown schematically in FIG. 16. Rabbits (two for each MAP) were given an initial injection and were boosted once before blood was drawn for a first evaluation of antibody production. The antisera were tested on LIA strips containing a total of 16 E2 peptides (sequences derived from 8 type 1 isolates, "a" and "b" versions of each). Examination of the LIA strips reveals that there is considerable cross-reaction between the antibodies raised in the rabbits and the various E2 peptides on the strips (FIG. 17). The fact that both "a" and "b" versions can be found which are recognized by the different antisera indicates that there is at least one epitope located in the region where these two versions overlap.

EXAMPLE 24

Diagnosis of HTLV Infection Using Biotinylated Synthetic Peptides

HTLV-I and II are antigenically related members of a family of oncogenic retroviruses. HTLV-I infection has been shown to be associated with two disease syndromes: HTLV-I-associated myelopathy/tropical spastic paraparesis (neurological disorders) and adult T-cell leukemia (ATL). In contrast, HTLV-II has not been conclusively linked to any known disease syndrome. This virus was originally isolated from a patient with hairy cell leukemia, however, no casual relationship between HTLV-II infection and the disease state could be established. Since HTLV-I infection has definitely been demonstrated to have the potential to result in human disease while HTLV-II infection has not, it is of clinical interest to be able to differentiate between these two infectious agents. Since these two viruses are antigenically highly related, it is difficult to discriminate between HTLV-I and HTLV-II infections when viral or recombinant antigens are used for antibody detection. A number of biotinylated peptides were synthesized and evaluated for their ability to detect antibodies raised in response to infection by either HTLV-I or HTLV-II. Some of the peptides were chosen because they contain epitopes which are highly conserved between HTLV-I and HTLV-II and should therefore be useful reagents for detecting HTLV infection without regard to virus type. Still other peptides were chosen because they contain epitopes which should allow HTLV-I and HTLV-II infections to be discriminated. The peptides synthesized are as follows:

I-gp46-3:
(SEQ ID NO:166) Bio Gly Gly Val Leu Tyr Ser Pro Asn Val Ser Val Pro Ser Ser Ser Thr Leu Leu Tyr Pro Ser Leu Ala

I-gp46-5:
(SEQ ID NO:167) Bio Gly Gly Tyr Thr Cys Ile Val Cys Ile Asp Arg Ala Ser Leu Ser Thr Trp His Val Leu Tyr Ser Pro

I-gp46-4:
(SEQ ID NO:168) Bio Gly Gly Asn Ser Leu Ile Leu Pro Pro Phe Ser Leu Ser Pro Val Pro Thr Leu Gly Ser Arg Ser Arg Arg

I-gp46-6:
(SEQ ID NO:169) Bio Gly Gly Asp Ala Pro Gly Tyr Asp Pro Ile Trp Phe Leu Asn Thr Glu Pro Ser Gln Leu Pro Pro Thr Ala Pro Pro Leu Leu Pro His Ser Asn Leu Asp His Ile Leu Glu

I-p21-2:
(SEQ ID NO:170) Bio Gly Gly Gln Tyr Ala Ala Gln Asn Arg Arg Gly Leu Asp Leu Leu Phe Trp Glu Gln Gly Gly Leu Cys Lys Ala Leu Gln Glu Gln Cys Arg Phe Pro

I-p19:
(SEQ ID NO:171) Bio Gly Gly Pro Pro Pro Pro Ser Ser Pro Thr His Asp Pro Pro Asp Ser Asp Pro Gln Ile Pro Pro Pro Tyr Val Glu Pro Thr Ala Pro Gln Val Leu

II-gp52-1:
(SEQ ID NO:172) Bio Gly Gly Lys Lys Pro Asn Arg Gln Gly Leu Gly Tyr Tyr Ser Pro Ser Tyr Asn Asp Pro

II-gp52-2:
(SEQ ID NO:173) Bio Gly Gly Asp Ala Pro Gly Tyr Asp Pro Leu Trp Phe Ile Thr Ser Glu Pro Thr Gln Pro Pro Pro Thr Ser Pro Pro Leu Val His Asp Ser Asp Leu Glu His Val Leu Thr

II-gp52-3:
(SEQ ID NO:174) Bio Gly Gly Tyr Ser Cys Met Val Cys Val Asp Arg Ser Ser Leu Ser Ser Trp His Val Leu Tyr Thr Pro Asn Ile Ser Ile Pro Gln Gln Thr Ser Ser Arg Thr Ile Leu Phe Pro Ser

II-p19:
(SEQ ID NO:175) Bio Gly Gly Pro Thr Thr Thr Pro Pro Pro Pro Pro Pro Ser Pro Glu Ala His Val Pro Pro Pro Tyr Val Glu Pro Thr Thr Thr Gln Cys Phe

A number of these peptides were used to prepare LIA strips for the detection of antibodies of HTLV. Several of the peptides, such as I-p19 and I-gp46-4, which are derived from regions of the HTLV-I p19 gag protein and envelope glycoprotein, respectively, are expected to be recognized by antibodies produced as a result of both HTLV-I and HTLV-II infection since these sequences are highly homologous in the two viruses. Others, such as I-gp46-3, I-gp46-6 for HTLV-I, and II-gp52-1, II-gp52-2 and II-gp52-3 for HTLV-II may be useful for detection of antibodies as well as discrimination. Since there is some homology between the HTLV-I and HTLV-II sequences, cross-reactions are to be expected. Nevertheless, the intensities of the reactions to the various peptides should reveal the identity of the virus to which the antibodies were produced.

An example of LIA strips prepared with a number of the biotinylated HTLV-I and HTLV-II peptides is shown in figure XXX. The LIA strips were evaluated using a commercially available serum panel (Boston Biomedia Inc., mixed titer panel, PRP203). The test results are in complete agreement with the analysis provided by distributor. Only one sample (nr. 9) is positive for HTLV-I. Sample nr.12 is detected as positive because of the positive reaction to the peptide I-p19. This sample could not be differentiated using these peptides, nor could this sample be differentiated by any other test used by the distributor of the serum panel. Sample nr. 11 was found to be negative and all other samples were found to be positive for HTLV-II. In an additional experiment, an ELISA was performed using all 10 of the biotinylated HTLV-I and HTLV-II peptides. The peptides were complexed with streptavidin individually and then mixed prior to coating. Some of the samples from the panel used to evaluate the LIA strips were used to evaluate the peptides in the ELISA. These results are shown in table. The ELISA in this configuration cannot be used to differentiate HTLV-I and -II infections but should identify HTLV-positive samples in general regardless of virus type. The results further demonstrate the utility of these peptides for the diagnosis of HTLV infection.

TABLE I

Antibody recognition of biotinylated and unbiotinylated HIV-1 and HIV-2 peptides

|  | Serum | TM-HIV-1 | TM-HIV-1 Bio | TM-HIV-2 | TM-HIV-2 Bio |
|---|---|---|---|---|---|
| HIV-1 positive | 0724 | 0.174 | 2.570 | 0.000 | 0.000 |
|  | mm | 0.051 | 2.579 | 0.000 | 0.000 |
|  | YEMO | 0.162 | 2.357 | 0.000 | 0.000 |
|  | PL | 0.000 | 1.559 | 0.000 | 0.000 |
|  | VE | 0.052 | 2.551 | 0.000 | 0.000 |
| HIV-2 positive | 1400 | 0.000 | 0.000 | 0.000 | 1.982 |
|  | AG | 0.000 | 0.000 | 0.000 | 2.323 |
|  | 53-3 | 0.000 | 0.000 | 0.000 | 2.365 |
| Seronegative donors | 194 | 0.000 | 0.000 | 0.000 | 0.000 |
|  | 195 | 0.000 | 0.000 | 0.000 | 0.000 |
|  | 180 | 0.000 | 0.005 | 0.000 | 0.000 |
|  | 204 | 0.000 | 0.001 | 0.000 | 0.000 |

TABLE 2

Comparison of antibody recognition of biotinylated and unbiotinylated peptides from the V3 sequence of isolate HIV-1 mn.

| Sample identity | V3-mn | V3-mn Bio |
|---|---|---|
| negative control | 0.063 | 0.069 |
| blank | 0.053 | 0.051 |
| YS | 1.442 | 2.784 |
| DV | 1.314 | 2.881 |
| VE | 1.717 | overflow* |
| OOST 6 | 1.025 | 2.355 |
| OOST 8 | 1 389 | overflow* |
| 3990 | 1.442 | overflow* |
| PL | 0.531 | 2.351 |
| MM | 0.791 | 2.542 |
| 4436 | 0.388 | 2.268 |
| 4438 | 0.736 | 2.554 |
| 266 | 0.951 | 2.591 |
| OOST 4 | 1.106 | overflow* |

*Absorbance value greater than 3.000

TABLE 3

Comparison of antibody recognition of the biotinylated V3-mn peptide bound to streptavidin and avidin

| Serum | Streptavidin | Avidin |
|---|---|---|
| YS | 1.236 | 1.721 |
| DV | 1.041 | 1.748 |
| PL | 0.222 | 0.983 |
| 3990 | 1.391 | 1.854 |
| VE | 1.526 | 1.908 |
| 4436 | 0.596 | 1.519 |
| Control | 0.050 | 0.063 |

TABLE 4

Comparison of antibody recognition of biotylated and unbiotinylated HCV peptides.

TABLE 4A
Antibody binding to HCV peptide XI

| Serum | Biotinylated peptide XI | Peptide XI |
|---|---|---|
| 2 | 0.090 | 1.971 |
| 3 | 0.443 | 2.086 |
| 4 | 0.473 | 1.976 |
| 6 | 0.053 | 0.518 |
| 8 | 1.275 | 2.624 |
| 10 | 0.764 | 2.321 |
| 11 | 0.569 | 2.378 |
| 23 | 0.775 | 2.503 |
| 31 | 0.497 | 2.104 |
| 77 | 0.093 | 0.159 |
| 33 | 0.832 | 1.857 |
| 49 | 0.515 | 2.180 |
| negative serum | 0.053 | 0.095 |

TABLE 4B
Antibody binding to HCV peptide XVI

| Serum | Unbiotinylated peptide XVI | Peptide XVI |
|---|---|---|
| 1 | 1.038 | 2.435 |
| 2 | 0.616 | 1.239 |
| 6 | 0.100 | 1.595 |
| 8 | 0.329 | 1.599 |
| 10 | 1.033 | 2.847 |
| 26 | 0.053 | 1.522 |
| 83 | 0.912 | 2.221 |
| 88 | 1.187 | 2.519 |
| 89 | 0.495 | 1.530 |
| 91 | 0.197 | 2.169 |
| 95 | 0.109 | 1.484 |
| 99 | 0.814 | 2.045 |
| 100 | 0.474 | 1.637 |
| 104 | 0.205 | 0.942 |
| 105 | 0.313 | 2.186 |
| 110 | 0.762 | 1.484 |
| 111 | 0.193 | 1.465 |
| 112 | 0.253 | 1.084 |
| 113 | 0.833 | 2.535 |
| 116 | 0.058 | 1.918 |
| 120 | 0.964 | 2.332 |
| 11476 | 0.068 | 2.197 |
| 24758 | 0.071 | 0.062 |
| 266 | 0.712 | 2.262 |
| 8247 | 0.059 | 0.618 |
| negative serum | 0.063 | 0.067 |

TABLE 4C

Antibody binding to HCV peptide II

| Serum | Unbiotinylated peptide II | Peptide II |
|---|---|---|
| 8241 | 0.444 | 0.545 |
| 8242 | 1.682 | 2.415 |
| 8243 | 2.181 | 2.306 |
| 8247 | 1.518 | 1.975 |
| 8250 | 0.110 | 0.357 |
| 8271 | 0.912 | 1.284 |
| 8273 | 2.468 | 2.769 |
| 8274 | 2.700 | 2.943 |
| 8275 | 1.489 | 2.030 |
| 8276 | 2.133 | 2.348 |
| 8277 | 1.771 | 2.572 |
| 8278 | 1.907 | 2.022 |
| negative serum | 0.047 | 0.070 |

TABLE 4D

Antibody binding to HCV peptide III

| Serum | Unbiotinylated peptide III | Peptide III |
|---|---|---|
| 8241 | 1.219 | 2.066 |
| 8242 | 1.976 | 2.197 |
| 8243 | 1.859 | 2.368 |
| 8247 | 1.072 | 2.398 |
| 8248 | 2.742 | 2.918 |
| 8250 | 2.471 | 2.626 |
| 8271 | 1.471 | 2.066 |
| 8272 | 2.471 | 2.638 |
| 8273 | 1.543 | 2.697 |
| 8274 | 2.503 | 2.905 |
| 8275 | 1.595 | 2.640 |
| 8276 | 1.976 | 2.674 |
| 8277 | 0.735 | 2.327 |
| negative serum | 0.050 | 0.06 |

TABLE 4E

Antibody binding to HCV peptide V

| Serum | Unbiotinylated peptide V | Peptide V |
|---|---|---|
| 8272 | 0.589 | 1.220 |
| 8273 | 0.294 | 1.026 |
| 8274 | 1.820 | 2.662 |
| 8275 | 1.728 | 1.724 |

TABLE 4E-continued

Antibody binding to HCV peptide V

| Serum | Unbiotinylated peptide V | Peptide V |
|---|---|---|
| 8276 | 2.194 | 2.616 |
| 8277 | 0.770 | 1.796 |
| 8278 | 1.391 | 1.746 |
| 8284 | 0.040 | 0.757 |
| negative serum | 0.047 | 0.070 |

TABLE 4F

Antibody binding to HCV peptide IX

| Serum | Unbiotinylated peptide IX | Peptide IX |
|---|---|---|
| 8315 | 2.614 | 2.672 |
| 8316 | 0.133 | 0.367 |
| 8317 | 0.855 | 1.634 |
| 8318 | 1.965 | 2.431 |
| 8320 | 0.721 | 0.896 |
| 8321 | 0.283 | 0.457 |
| 8326 | 2.219 | 2.540 |
| negative serum | 0.052 | 0.005 |

TABLE 4G

Antibody binding to HCV peptide XVIII

| Serum | Unbiotinylated peptide XVIII | Peptide XVIII |
|---|---|---|
| 79 | 1.739 | 2.105 |
| 83 | 1.121 | 1.232 |
| 88 | 0.972 | 1.858 |
| 89 | 2.079 | 2.309 |
| 91 | 2.202 | 1.132 |
| 99 | 1.253 | 1.526 |
| 104 | 1.864 | 1.998 |
| 105 | 1.522 | 2.053 |
| 110 | 1.981 | 2.065 |
| 111 | 1.363 | 1.542 |
| 112 | 1.172 | 1.408 |
| 116 | 1.534 | 1.978 |
| 120 | 1.599 | 2.031 |
| 1 | 2.523 | 2.691 |
| 33 | 1.463 | 1.813 |
| 39 | 0.068 | 0.213 |
| 47 | 2.117 | 2.611 |
| negative serum | 0.001 | 0.001 |

TABLE 5

| Peptide concentration* | 3.0 | | 1.0 | | 0.3 | | 0.1 | | 0.03 | | 0.01 | |
|---|---|---|---|---|---|---|---|---|---|---|---|---|
| coating method** | 1 | 2 | 1 | 2 | 1 | 2 | 1 | 2 | 1 | 2 | 1 | 2 |
| Unbiotinylated HCV peptide II and HCV peptide II | | | | | | | | | | | | |
| sample positive | | | | | | | | | | | | |
| 8320 | 2.718 | 2.278 | 2.684 | 2.163 | 2.684 | 2.004 | 2.718 | 1.828 | 2.757 | 1.272 | 2.519 | 0.479 |
| 8242 | 1.427 | 0.539 | 1.368 | 0.408 | 1.365 | 0.234 | 1.399 | 0.058 | 1.481 | 0.048 | 1.196 | 0.051 |
| 8243 | 1.668 | 1.341 | 1.652 | 1.221 | 1.608 | 0.831 | 1.639 | 0.181 | 1.597 | 0.057 | 1.088 | 0.056 |
| 8318 | 2.016 | 0.791 | 1.993 | 0.626 | 1.958 | 0.347 | 2.001 | 0.181 | 2.181 | 0.095 | 2.002 | 0.048 |
| sample negative | | | | | | | | | | | | |
| 1747 | 0.064 | 0.049 | 0.071 | 0.046 | 0.046 | 0.041 | 0.045 | 0.044 | 0.045 | 0.043 | 0.045 | 0.041 |
| 1781 | 0.057 | 0.053 | 0.055 | 0.053 | 0.051 | 0.045 | 0.047 | 0.046 | 0.049 | 0.053 | 0.053 | 0.046 |

TABLE 5-continued

| Peptide concentration* | 3.0 | | 1.0 | | 0.3 | | 0.1 | | 0.03 | | 0.01 | |
|---|---|---|---|---|---|---|---|---|---|---|---|---|
| coating method** | 1 | 2 | 1 | 2 | 1 | 2 | 1 | 2 | 1 | 2 | 1 | 2 |
| Unbiotinylated HCV peptide IX and HCV peptide IX | | | | | | | | | | | | |
| sample positive | | | | | | | | | | | | |
| 8320 | 1.779 | 0.129 | 0.802 | 0.093 | 1.798 | 0.122 | 1.244 | 0.063 | 1.007 | 0.057 | 0.461 | 0.059 |
| 8326 | 2.284 | 0.084 | 2.271 | 0.068 | 2.271 | 0.078 | 2.284 | 0.068 | 2.193 | 0.051 | 1.812 | 0.049 |
| 8242 | 0.791 | 0.059 | 0.777 | 0.052 | 0.795 | 0.048 | 0.911 | 0.046 | 0.496 | 0.047 | 0.215 | 0.049 |
| 8243 | 1.959 | 0.063 | 1.953 | 0.053 | 1.892 | 0.051 | 1.834 | 0.051 | 1.421 | 0.051 | 0.639 | 0.054 |
| sample negative | | | | | | | | | | | | |
| 1747 | 0.051 | 0.046 | 0.049 | 0.046 | 0.046 | 0.044 | 0.042 | 0.045 | 0.044 | 0.045 | 0.043 | 0.045 |
| 1781 | 0.053 | 0.053 | 0.051 | 0.052 | 0.051 | 0.051 | 0.047 | 0.052 | 0.048 | 0.049 | 0.049 | 0.051 |
| Unbiotinylated HCV peptide XVIII and HCV peptide XVIII | | | | | | | | | | | | |
| sample positive | | | | | | | | | | | | |
| 8326 | 2.315 | 0.052 | 2.331 | 0.053 | 2.331 | 0.053 | 2.331 | 0.049 | 2.219 | 0.051 | 1.848 | 0.051 |
| 8242 | 0.749 | 0.053 | 0.839 | 0.049 | 0.873 | 0.048 | 0.946 | 0.047 | 1.188 | 0.049 | 1.185 | 0.048 |
| 8243 | 0.671 | 0.057 | 0.627 | 0.053 | 0.629 | 0.054 | 0.661 | 0.051 | 0.611 | 0.053 | 0.462 | 0.053 |
| 8318 | 2.391 | 0.051 | 2.396 | 0.045 | 2.392 | 0.047 | 2.409 | 0.047 | 2.308 | 0.047 | 1.711 | 0.048 |
| sample negative | | | | | | | | | | | | |
| 1747 | 0.047 | 0.048 | 0.042 | 0.045 | 0.061 | 0.046 | 0.044 | 0.045 | 0.058 | 0.044 | 0.042 | 0.047 |
| 1781 | 0.053 | 0.055 | 0.048 | 0.054 | 0.048 | 0.051 | 0.048 | 0.051 | 0.051 | 0.051 | 0.045 | 0.053 |

*in micrograms per milliliters
**1 biotinylated peptide on streptabiden coated plate
2 unbiotinylated peptide coated directly

TABLE 6

Comparison of N— and C-terminally biotinylated TM-HIV-1 peptide.

| | Serum | TM-HIV-I C-terminal biotin | TM-HIV-1 N-terminal biotin |
|---|---|---|---|
| HIV positive | VE | 2.079 | 2.240 |
| | OOST 6 | 1.992 | 2.003 |
| | MM | 2.097 | 2.308 |
| | 0724 | 2.322 | 2.291 |
| | DV | 0.903 | 1.579 |
| | PL | 1.893 | 1.849 |
| | 2049 | 1.780 | 2.058 |
| | 3990 | 1.959 | 1.870 |
| | 4438 | 1.622 | 1.697 |
| | 4436 | 2.190 | 2.110 |
| | OOST 7 | 1.728 | 2.027 |
| | OOST 8 | 2.117 | 2.237 |
| | OOST 9 | 2.119 | 2.222 |
| | VCM | 2.131 | 2.263 |
| | 1164 | 1.865 | 1.919 |
| | 1252 | 2.244 | 2.356 |
| | 0369/87 | 2.059 | 2.042 |
| Seronegative blood donors | 1784 | 0.000 | 0.000 |
| | 1747 | 0.000 | 0.000 |
| | 1733 | 0.014 | 0.000 |

TABLE 7

| HCV antibody-positive sera | HCV peptide I (coated directly) | HCV peptide I carboxy-biotinylated (bound to streptavidin-coated wells) |
|---|---|---|
| 8316 | 2.394 | 2.541 |
| 8318 | 2.385 | 2.404 |
| 8320 | 2.760 | 2.762 |
| 8326 | 0.525 | 1.775 |
| 8329 | 2.633 | 2.672 |
| 8333 | 2.143 | 2.545 |
| 8334 | 2.271 | 2.549 |
| 8336 | 1.558 | 2.016 |
| 8344 | 1.878 | 2.010 |
| 8248 | 2.042 | 2.493 |
| 8244 | 0.077 | 1.399 |
| 8243 | 2.211 | 2.541 |
| 8242 | 1.367 | 2.389 |
| 8364 | 2.705 | 2.705 |
| 8374 | 1.070 | 2.151 |
| 6378 | 2.161 | 2.531 |
| 8330 | 1.985 | 2.651 |
| 8387 | 1.427 | 2.628 |
| HCV antibody-negative sera | | |
| F88 | 0.000 | 0.026 |
| F89 | 0.017 | 0.001 |
| F76 | 0.000 | 0.022 |
| F136 | 0.006 | 0.002 |
| F8 | 0.000 | 0.000 |

TABLE 8

Use of mixtures of biotinylated peptides for antibody detection.

| | Serum | TM-HIV-1-BIO Avidin | TM-HIV-2-BIO Avidin | V3-mn-BIO Avidin | HCV peptide II-BIO Avidin | HCV peptide IX-BIO Avidin | HCV peptide XVIII-BIO Avidin | Mixture A Avidin | Mixture B Avidin | Mixture A Direct coating | Mixture B Direct coating |
|---|---|---|---|---|---|---|---|---|---|---|---|
| HCV | 8243 | 0.108 | 0.109 | 0.114 | 1.430 | 1.213 | 0.118 | 1.590 | 1.638 | 0.542 | 0.184 |
| | 8247 | 0.042 | 0.048 | 0.052 | 1.356 | 0.756 | 0.046 | 0.840 | 1.149 | 0.049 | 0.049 |
| | 8248 | 0.043 | 0.046 | 0.048 | 2.287 | 0.047 | 0.905 | 1.859 | 2.154 | 0.407 | 0.064 |
| | 8269 | 0.053 | 0.049 | 0.056 | 1.213 | 0.051 | 1.513 | 0.923 | 1.268 | 0.078 | 0.067 |
| | 8290 | 0.045 | 0.047 | 0.050 | 0.060 | 0.048 | 2.323 | 1.210 | 1.761 | 0.559 | 0.717 |
| | 8278 | 0.046 | 0.045 | 0.053 | 1.878 | 0.074 | 0.052 | 1.806 | 1.944 | 0.540 | 0.152 |
| | 8273 | 0.053 | 0.050 | 0.056 | 2.017 | 0.053 | 0.052 | 2.037 | 2.113 | 0.773 | 0.185 |
| | 8285 | 0.134 | 0.163 | 0.143 | 1.592 | 0.270 | 0.146 | 1.746 | 1.822 | 0.908 | 0.401 |
| | 8291 | 0.048 | 0.050 | 0.053 | 1.539 | 0.052 | 0.049 | 1.591 | 1.809 | 0.335 | 0.098 |
| HIV-2 | AG | 0.054 | 2.065 | 0.068 | 0.081 | 0.064 | 0.058 | 1.833 | 1.880 | 0.054 | 0.056 |
| | 1400 | 0.051 | 1.781 | 0.055 | 0.121 | 0.052 | 1.362 | 1.692 | 2.031 | 0.214 | 0.326 |
| HIV-1 | YS | 0.046 | 0.046 | 2.201 | 0.048 | 0.049 | 0.049 | 2.045 | 1.845 | 0.200 | 0.052 |
| | PL | 1.974 | 0.051 | 1.321 | 0.052 | 0.056 | 0.052 | 1.587 | 1.776 | 0.052 | 0.055 |
| | DV | 1.329 | 0.048 | 2.340 | 0.047 | 0.049 | 0.047 | 1.969 | 1.742 | 0.100 | 0.049 |
| | 3990 | 1.602 | 0.054 | 2.319 | 0.054 | 0.066 | 0.056 | 2.217 | 1.926 | 0.390 | 0.081 |
| Blood donor | 1785 | 0.046 | 0.047 | 0.048 | 0.045 | 0.050 | 0.047 | 0.047 | 0.049 | 0.045 | 0.049 |
| | 1794 | 0.124 | 0.090 | 0.091 | 0.153 | 0.098 | 0.104 | 0.152 | 0.161 | 0.050 | 0.058 |
| | 1784 | 0.044 | 0.046 | 0.046 | 0.045 | 0.050 | 0.047 | 0.047 | 0.047 | 0.045 | 0.048 |
| | 1782 | 0.052 | 0.057 | 0.059 | 0.057 | 0.062 | 0.053 | 0.057 | 0.059 | 0.049 | 0.056 |

TABLE 9

Sequences of the Core Epitopes of the HCV Core Protein
HCV CORE PROTEIN AMINO ACIDS T-90
Positions of core epitopes

```
Epitope   I P K P O R K T K                                              CORE
1A:         P K P O R K T K R    M S T I P K P O R K T K R N T N R R P O  1
              K P O R K T K R N          P O R K T K R N T N R R P O D V K F P G  CORE
                P O R K T K R N T                                         2

Epitope   O P K T K R N T N                                              CORE
1B:         R K T K R N T N R    M S T I P K P O R K T K R N T N R R P O  1
              K T K R N T N R R          P O R K T K R N T N R R P O D V K F P G  CORE
                                                                          2

Epitope   R R P O D V K F P                                              CORE
2:          R P O D V K F P G    P O R K T K R N T N R R P O D V K F P G  2
              P O D V K F P G G          R N T N R R P O D V K F P G G G O I V G  CORE
                                                                          2

Epitope   G G V T L L P R R                                              CORE
2A:         G V T L L P R R G    P G G G O I V G G V T L L P R R G P R L  5
              V T L L P R R G P
                T L L P R R G P R Epitope   L L P R R G P R L                                              CORE
2B:         L P R R G P R L G    P G G G O I V G G V T L L P R R G P R L  5
              P R R G P R L G V          L P R R G P R L G V R A T R K I S E R S  CORE
                                                                          7

Epitope   G P R L G V R A T                                              CORE
3C:         P R L G V R A T R    L P R R G P R L G V D A T R K T G E R S  7
              R L G V R A T R K Epitope   E R S O P R G R G                                              CORE
4A:         R S O P R G R G O    T R K T S E R S O P R G R R O P I P K Y  9
              S O P R G R G O P Epitope   R G R R O P I P K                                              CORE
4B:         G R R O P I P K Y    T R K T S E R S O P R G R R O P I P K Y  9
              R R O P I P K Y R          R R O P I P K V R R P E G R T W A O P G  CORE
                                                                          11
```

TABLE 9-continued

Sequences of the Core Epitopes of the HCV Core Protein
HCV CORE PROTEIN AMINO ACIDS T-90
Positions of core epitopes

| Epitope 5A: | P E G R T W A O P <br> E G R T W A O P G <br> G R T W A O P G T <br> R T W A O P G T P | R R O P I P K Y R R P E G R T W A O P G <br> G R T W A O P G T P W P L T G N E G G G | CORE 11 <br> CORE 13 |
|---|---|---|---|
| Epitope 5B: runner 1 | A O P G T P W P L <br> O P G T P W P L T | G R T W A O P G T P W P L T G N E G G G | CORE 13 |

TABLE 10

Sequences of the Core Epitopes of the HCV NS4 Protein
HCV NS4 PROTEIN
Positions of core epitopes

| Epitope 1: | A I I P D R E V L <br> I I P D R E V L T <br> I P D R E V L T R <br> P D R E V L T R E | L S G K P A I I P D R E V L Y R E F D E <br> I I P D R E V L Y R E F D E M E E C S O | HCV1 <br> HCV2 |
|---|---|---|---|
| Epitope 2A: | O S O M L P T I E <br> S O M L P T I E O <br> O M L P T I E O G <br> M L P T I E O G M | V L T R E F D E M E E C S O M L P V L E <br> D E M E E C S O M L P V L E O G M M L A <br> S O M L P V L E O G M M L A E O F K O K | HCV3 <br> HCV4 <br> HCV5 |
| Epitope 2B: runner 1 | P T I E O G M M L <br> T I E O G M M L A | D E M E E C S O M L P T I E O G M M L A <br> S O M L P T I E O G M M L A E O F K O K | HCV4 <br> HCV5 |
| Epitope 3A: | M L A E G F K O K <br> L A E G F K O K A <br> A E G F K O K A L | S O M L P Y I E O G M M L A E O E K O K <br> I E O G M M L A E O E K O K A L G L L O <br> L A E O E K O K A L G L L O T A S R O A | HCV5 <br> HCV6 <br> HCV7 |
| Epitope 3B: | E O F K O K A L O <br> O F K O K A L O L <br> F K O K A L O L L <br> K O K A L O L L O | I E O C M M L A E O F K O K A L O L L O <br> L A E O F K O K A L O L L O T A S R O A | HCV6 <br> HCV7 |
| Epitope 4: | K A L G L L O T A <br> A L G L L O T A S <br> L G L L O T A S R | L A E O F K O K A L O L L O T A S R O A <br> O K A L O L L O T A S R O A E V I A P A | HCV7 <br> HCV8 |

TABLE 11

Sequences of the Core Epitopes of the HCV NSS Protein
-31 NSS PROTEIN
Positions of the core epitopes

| Epitope 1A: | S V P A E I L R K <br> V P A E I L R K S | E D E R E I S V P A E I L P M S R R F A | NSS-25 |
|---|---|---|---|
| Epitope 1B: | F A E I L R K S R <br> A E I L R K S R R <br> E I L R K S R R F | E D E R E I S V P A E I L P M S R R F A | NSS-25 |
| Epitope 2: | F A O A L P V W A <br> A O A L P V W A R <br> O A L P V W A R P | L R K S R R F A G A L P V W L R P D Y N | NSS-27 |

TABLE 11-continued

Sequences of the Core Epitopes of the HCV NS5 Protein
-31 NS5 PROTEIN
Positions of the core epitopes Epitope 3:
```
W A P P D T N P P
  A P P D T N P P L
    P P D T N P P L Y
      P D T N P P L Y E
```
V W A S <u>P S T M P P L</u> V E T W K K P D T    NS5-29

Epitope 4: runner 1
```
F F L V E T W K K
  F L V E T W K K P
    L V E T W K K P P
```
V W A S P S T M P P L V E T W K K P D T    NS5-29

Epitope 5:
```
K K P O Y E P P V
  K P O Y E P P V V
    P O Y E P P V V M
      O Y E P P V V M G
```
E T K K K P <u>D T E P P V</u> V M G C P L P P    NS5-31

Epitope 6:
```
P P V V M G C P L
  P V V M G C P L P
    V V M G C P L P P
      V M G C P L P P P
        M G C P L P P P K
```
E T K K K P D T E P P V V <u>M G C P L</u> P P    NS5-31
V <u>M G C P L</u> P P P K S P P V P P P R K K    NS5-33

TABLE 12

Antibody Binding of Various Core NS4 and NS5 Biotinylated 20-mers by the 10 Test Sera

PEPTIDE ELISA (O.D.)

| SERUM | Core-2 | Core-3 | Core-7 | Core-9 | HCV-2 | HCV-5 | HCV-7 | NS5-25 | NS5-27 | NS5-31 |
|---|---|---|---|---|---|---|---|---|---|---|
| 8242 | 2.415 | 2.197 | 0.632 | 2.315 | 2.114 | 1.625 | 1.252 | 0.260 | 2.318 | 2.453 |
| 8240 | 2.441 | 2.918 | 1.529 | 2.021 | 0.142 | 0.182 | 1.963 | 0.054 | 0.388 | 1.511 |
| 8332 | 1.977 | 2.054 | 1.387 | 1.455 | 0.392 | 0.575 | 0.945 | 0.047 | 2.130 | 2.290 |
| 8339 | 2.030 | 2.765 | 0.166 | 2.598 | 2.497 | 0.043 | 0.041 | 1.495 | 2.859 | 2.757 |
| 8350 | 1.982 | 2.135 | 0.357 | 0.685 | 1.779 | 0.623 | 0.598 | 0.069 | 2.249 | 0.182 |
| 8377 | 2.181 | 2.368 | 0.221 | 0.076 | 2.360 | 2.227 | 1.829 | 1.092 | 2.336 | 1.378 |
| 8378 | 2.140 | 2.369 | 1.089 | 1.228 | 1.859 | 1.449 | 2.006 | 0.279 | 1.602 | 2.337 |
| 8388 | 2.463 | 2.463 | 0.970 | 2.162 | 2.300 | 1.018 | 2.504 | 0.055 | 0.390 | 2.358 |
| 8241 | 0.545 | 2.066 | 0.448 | 0.274 | 0.421 | 2.280 | 0.968 | 0.050 | 2.456 | 0.273 |
| 0843 | 2.306 | 2.368 | 1.251 | 1.378 | 2.206 | 2.268 | 2.251 | 0.062 | 1.444 | 0.127 |

TABLE 13

Antibody recognition of individual E2/NS1 peptides.
(percent of all sera giving a positive reaction.)

| | | |
|---|---|---|
| CL14-A | 7 (51) | 13.7% |
| B | 36 (51) | 70.6% |
| KATO-A | 2 (51) | 3.92% |
| B | 26 (51) | 50.98% |
| HCJ4-A | 32 (51) | 62.74% |
| B | 41 (51) | 80.39% |
| FRENCH-A | 30 (51) | 58.8% |
| B | 42 (51) | 82.35% |
| YEK-A | 7 (51) | 13.72% |
| B | 49 (51) | 96.07% |
| TAMI-A | 12 (51) | 23.52% |
| B | 36 (51) | 70.58% |
| 18CH1-A | 5 (51) | 9.8% |
| B | 30 (51) | 58.82% |
| CHIR-A | 32 (51) | 62.7% |
| B | 40 (51) | 78.43% |

TABLE 14

Overall Recognition of V3-Loop Peptides

|  | CON | SC | MN | SF2 | BH | RF | MAL | ELI | 70 |
|---|---|---|---|---|---|---|---|---|---|
| Total SUM | 287 | 361 | 275 | 258 | 108 | 146 | 140 | 24 | 6 |
| COUNT gp120 positive | 326 | 326 | 326 | 326 | 326 | 326 | 326 | 326 | 326 |
| % Reactive | 88 | 80 | 84 | 79 | 33 | 45 | 43 | 7 | 2 |
| Total SUM COUNT | 287 | 261 | 275 | 258 | 108 | 146 | 140 | 24 | 6 |
| HIV-V3 positive | 307 | 307 | 307 | 307 | 307 | 307 | 307 | 307 | 307 |
| % Reactive | 93 | 85 | 90 | 84 | 35 | 48 | 46 | 8 | 2 |

TABLE 15

Recognition of Peptides According to Geographical Region

| EUROPEAN | % | AFRICAN | % | BRAZILIAN | % |
|---|---|---|---|---|---|
| Consensus | 98 | Consensus | 89 | Consensus | 82 |
| HIV-1 (SC) | 98 | HIV-1 (MN) | 85 | HIV-1 (MN) | 78 |
| HIV-1 (SF2) | 98 | HIV-1 (SF2) | 79 | HIV-1 (SC) | 75 |
| HIV-1 (MN) | 97 | HIV-1 (SC) | 73 | HIV-1 (SF2) | 72 |
| HIV-1 (RF) | 75 | HIV-1 (MAL) | 60 | HIV-1 (RF) | 38 |
| HIV-1 (MAL) | 68 | HIV-1 (RF) | 34 | HIV-1 (MAL) | 30 |
| HIV-1 (IIIB) | 61 | HIV-1 (IIIB) | 27 | HIV-1 (IIIB) | 26 |
| HIV-1 (ELI) | 8 | HIV-1 (ELI) | 13 | HIV-1 (ELI) | 5 |
| ANT 70 | 2 | ANT 70 | 2 | ANT 70 | 2 |

TABLE 16

Recognition of European, African and Brazilian HIV-1 antibody-positive sera to HIV-1 V3 loop peptides V3-con and V3-368

|  | V3-con | V3-368 | V3con-V3-368 |
|---|---|---|---|
| European sera | | | |
| number tested | 36 | 36 | 36 |
| number positive | 33 | 4 | 33 |
| number negative | 0 | 12 | 0 |
| number borderline | 3 | 20 | 3 |
| percent positive | 92 | 11 | 92 |
| percent negative | 0 | 33 | 0 |
| percent borderline | 8 | 56 | 8 |
| African sera | | | |
| number tested | 45 | 45 | 45 |
| number positive | 40 | 5 | 40 |
| number negative | 4 | 31 | 2 |
| number borderline | 1 | 9 | 3 |
| percent positive | 89 | 11 | 89 |
| percent negative | 9 | 69 | 4 |
| percent borderline | 2 | 20 | 7 |
| Brazilian sera | | | |
| number tested | 36 | 36 | 36 |
| number positive | 30 | 16 | 35 |
| number negative | 1 | 5 | 1 |
| number borderline | 5 | 15 | 0 |
| percent positive | 83.3 | 44.4 | 97.2 |
| percent negative | 2.8 | 13.9 | 2.8 |
| percent borderline | 13.9 | 41.7 | 0 |

TABLE 17

Recognition of HIV-2 positive sera to peptides from the V2 loop region of HIV-2

|  | V3-GB12 | V2-239 |
|---|---|---|
| number tested | 21 | 21 |
| number positive | 21 | 19 |
| number negative | 0 | 0 |
| number borderline | 0 | 2 |
| percent positive | 100 | 90.5 |
| percent negative | 0 | 0 |
| percent borderline | 0 | 9.5 |

TABLE 18

Antibody recognition of hybrid peptides

A.

| Serum | NS4 Epitope 1 | NS5 Epitope 5 | Core Epitope 2 | MA Epi-152 | Discrepancies |
|---|---|---|---|---|---|
| B241 | – | – | – | – | weak |
| B242 | – | – | – | – | |
| B243 | – | – | – | – | |
| B248 | – | – | – | – | |
| B332 | – | – | – | – | |
| B339 | – | – | – | – | |
| B368 | – | – | – | – | |
| B377 | – | – | – | – | |
| B378 | – | – | – | – | |
| B383 | – | – | – | – | |

B.

| Serum | NS5 Epitope 3 | NS4 Epitope 3B | Core Epitope 3A | MA Epi-3383A | Discrepancies |
|---|---|---|---|---|---|
| B241 | – | – | – | – | – |
| B242 | – | – | – | – | |
| B248 | – | – | – | – | |
| B245 | – | – | – | – | |
| B332 | – | –– | – | – | |
| B339 | – | – | – | – | |
| B368 | – | – | – | – | |
| B377 | – | – | – | – | |
| B378 | – | – | – | – | |
| B383 | – | – | – | – | |

TABLE 18-continued

Antibody recognition of hybrid peptides

C.

| Serum | Core Epitope 4B | NS4 Epitope 2A | NS5 Epitope 5 | MA Epi-4B245 | Discrepancies |
|---|---|---|---|---|---|
| B241 | – | – | – | – | |
| B242 | – | – | – | – | |
| B243 | – | –– | – | – | ––– |
| B248 | – | – | – | – | |
| B332 | – | –– | – | – | – weak |
| B339 | – | – | – | – | |
| B368 | – | – | – | –– | ? |
| B377 | – | – | – | – | – |
| B378 | – | – | – | – | |
| B383 | – | – | – | – | |

TABLE 19

ANTIBODY RECOGNITION OF HTLV PEPTIDES

| Serum number | Optical density |
|---|---|
| 1 | 0.303 |
| 2 | 3.001 |
| 3 | 0.644 |
| 4 | 1.262 |
| 6 | 3.001 |
| 7 | 2.623 |
| 9 | 2.607 |
|  | (HTLV-1) |
| 10 | 3.001 |
| 11 | 0.058 |
|  | (negative) |
| 13 | 3.001 |
| 14 | 3.001 |
| 15 | 0.850 |
| 16 | 0.278 |
| 19 | 1.048 |
| 20 | 3.001 |
| 21 | 0.805 |
| 22 | 0.812 |
| 23 | 3.001 |
| 24 | 0.405 |
| 25 | 1.521 |

What is claimed is:

1. A peptide consisting of an amino acid sequence of SEQ ID NO 403
   (A)-GGVYLLPRRGPRLGVRATRKTSERSQPRGRR-QPIPKVRR-(Z) (SEQ ID NO 403),
   wherein A, when present, represents an amino acid, amino group, or chemically modified amino terminus of the peptide, and wherein Z, when present, represents an amino acid, OH-group, NH2-group, or a linkage involving an OH-group or an NH2-group;
   or a peptide fragment of said peptide consisting of at least 5 contiguous amino acids of SEQ ID NO: 403 which is immunologically reactive with HCV antisera.

2. A peptide consisting of an amino acid sequence of SEQ ID NO 403
   (A)-GGVYLLPRRGPRLGVRATRKTSERSQPRGRR-QPIPKVRR-(Z) (SEQ ID NO 403),
   wherein A, when present, represents an amino acid, amino group, or chemically modified amino terminus of the peptide, and wherein Z, when present, represents an amino acid, OH-group, NH2-group, or a linkage involving an OH-group or an NH2-group;
   or a peptide fragment of said peptide consisting of at least 5 contiguous amino acids of SEQ ID NO: 403 which is immunologically reactive with HCV antisera; and
   said peptide or peptide fragment containing at least one N-terminal biotin group, C-terminal biotin group or biotin group attached to an internal amino acid;
   said biotin group attached directly to the peptide or peptide fragment or attached to the peptide or peptide fragment through a linker Y;
   said linker Y consisting of 1 to 10 chemical entities selected from the group consisting of a glycine residue, beta-alanine, 4-aminobutyric acid, 5-aminovaleric acid and 6-aminohexanoic acid.

3. A peptide complex comprising the peptide or peptide fragment according to claim 2 coupled to at least one streptavidin molecule or avidin molecule.

4. The peptide complex according to claim 3 wherein said streptavidin molecule or avidin molecule is coupled to a solid phase.

5. A solid phase comprising a peptide or peptide fragment according to claim 1 or 2 and a solid support wherein the solid support is anchored to the peptide via at least one covalent or non-covalent bond.

6. A solid phase according to claim 5, wherein said solid support is a nylon membrane and said peptide or peptide fragment is anchored via a biotin group to streptavidin present on the nylon membrane.

7. The solid phase according to claim 5 wherein said solid support is a nylon membrane.

8. An immunological assay kit for detecting antibodies to HCV comprising at least one peptide or peptide fragment according to claims 1 or 2, or a peptide complex of claim 3.

9. A Line Immunoassay kit for detecting antibodies to HCV comprising at lest one peptide or peptide fragment according to claim 1 or 2, or a peptide complex of claim 3.

10. An immunological assay kit for detecting antibodies to HCV present in a biological sample comprising at least one peptide or peptide fragment according to any of claims 1 or 2, or a peptide complex of claim 3.

11. A Line Immunoassay kit for detecting antibodies to HCV present in a biological sample comprising at least one peptide or peptide fragment according to any of claims 1 or 2, or a peptide complex of claim 3.

12. A peptide or peptide fragment of claim 1 or 2 wherein A and Z are not present.

13. A peptide complex of claim 3 wherein A and Z are not present.

14. A peptide complex according to claim 13 wherein said streptavidin molecule or avidin molecule is coupled to a solid phase.

15. A solid phase comprising a peptide or peptide fragment according to claim 12 and a solid support wherein the solid support is anchored to the peptide via at least one covalent or non-covalent bond.

16. A solid phase according to claim 15, wherein said solid support is a nylon membrane and said peptide or peptide fragment is anchored via a biotin group to streptavidin present on the nylon membrane.

17. The solid phase according to claim 15 wherein said solid support is a nylon membrane.

18. An immunological assay kit for detecting antibodies to HCV comprising at least one peptide or peptide fragment according to claim 12.

19. A Line Immunoassay kit for detecting antibodies to HCV comprising at least one peptide or peptide fragment according to claim 12.

20. An immunological assay kit for detecting antibodies to HCV present in a biological sample comprising at least one peptide or peptide fragment according to claim 12.

21. A Line Immunoassay kit for detecting antibodies to HCV present in a biological sample comprising at least one peptide or peptide fragment according to claim 12.

22. An immunological assay kit for detecting antibodies to HCV comprising a peptide complex of claim 13.

23. A Line Immunoassay kit for detecting antibodies to HCV comprising a peptide complex of claim 13.

24. An immunological assay kit for detecting antibodies to HCV present in a biological sample comprising a peptide complex of claim 13.

25. A Line Immunoassay kit for detecting antibodies to HCV present in a biological sample comprising a peptide complex of claim 13.

26. A peptide consisting of an amino acid sequence of SEQ ID NO 403
   (A)-GGVYLLPRRGPRLGVRATRKTSERSQPRGRR-QPIPKVRR-(Z) (SEQ ID NO 403),
   wherein A, when present, represents an amino acid, amino group, or chemically modified amino terminus of the peptide, and wherein Z, when present, represents an amino acid, OH-group, NH2-group, or a linkage involving an OH-group or an NH2-group;

or a peptide fragment of said peptide consisting of at least 5 contiguous amino acids of SEQ ID NO: 403.

27. A peptide consisting of an amino acid sequence of SEQ ID NO 403

(A)-GGVYLLPRRGPRLGVRATRKTSERSQPRGRR-QPIPKVRR-(Z) (SEQ ID NO 403), wherein A, when present, represents an amino acid, amino group, or chemically modified amino terminus of the peptide, and wherein Z, when present, represents an amino acid, OH-group, NH2-group, or a linkage involving an OH-group or an NH2-group;

or a peptide fragment of said peptide consisting of at least 5 contiguous amino acids of SEQ ID NO: 403; and said peptide or peptide fragment containing at least one N-terminal biotin group, C-terminal biotin group or biotin group attached to an internal amino acid;

said biotin group attached directly to the peptide or peptide fragment or attached to the peptide or peptide fragment through a linker Y;

said linker Y consisting of 1 to 10 chemical entities selected from the group consisting of a glycine residue, beta-alanine, 4-aminobutyric acid, 5-aminovaleric acid and 6-aminohexanoic acid.

28. A peptide complex comprising the peptide or peptide fragment according to claim 27 coupled to at least one streptavidin molecule or avidin molecule.

29. The peptide complex according to claim 28 wherein said streptavidin molecule or avidin molecule is coupled to a solid phase.

30. A solid phase comprising a peptide or peptide fragment according to claim 26 or 27 and a solid support wherein the solid support is anchored to the peptide via at least one covalent or non-covalent bond.

31. A solid phase according to claim 30, wherein said solid support is a nylon membrane and said peptide or peptide fragment is anchored via a biotin group to streptavidin present on the nylon membrane.

32. The solid phase according to claim 30 wherein said solid support is a nylon membrane.

33. An immunological assay kit for detecting antibodies to HCV comprising at least one peptide or peptide fragment according to any of claims 26 or 27, or a peptide complex of claim 28.

34. A Line Immunoassay kit for detecting antibodies to HCV comprising at least one peptide or peptide fragment according to any of claims 26 or 27, or a peptide complex of claim 28.

35. An immunological assay kit for detecting antibodies to HCV present in a biological sample comprising at least one peptide or peptide fragment according to any of claims 26 or 27, or a peptide complex of claim 28.

36. A Line Immunoassay kit for detecting antibodies to HCV present in a biological sample comprising at least one peptide or peptide fragment according to any of claims 26 or 27, or a peptide complex of claim 28.

37. A peptide or peptide fragment of claim 26 or 27 wherein A and Z are not present.

38. A peptide complex of claim 28 wherein A and Z are not present.

39. The peptide complex according to claim 38 wherein said streptavidin molecule or avidin molecule is coupled to a solid phase.

40. A solid phase comprising a peptide or peptide fragment according to claim 37 and a solid support wherein the solid support is anchored to the peptide via at least one covalent or non-covalent bond.

41. A solid phase according to claim 40, wherein said solid support is a nylon membrane and said peptide or peptide fragment is anchored via a biotin group to streptavidin present on the nylon membrane.

42. The solid phase according to claim 40 wherein said solid support is a nylon membrane.

43. An immunological assay kit for detecting antibodies to HCV comprising at least one peptide or peptide fragment according to claim 37.

44. A Line Immunoassay kit for detecting antibodies to HCV comprising at least one peptide or peptide fragment according to claim 37.

45. An immunological assay kit for detecting antibodies to HCV present in a biological sample comprising at least one peptide or peptide fragment according to claim 37.

46. A Line Immunoassay kit for detecting antibodies to HCV present in a biological sample comprising at least one peptide or peptide fragment according to claim 37.

47. An immunological assay kit for detecting antibodies to HCV comprising a peptide complex of claim 38.

48. A Line Immunoassay kit for detecting antibodies to HCV comprising a peptide complex of claim 38.

49. An immunological assay kit for detecting antibodies to HCV present in a biological sample comprising a peptide complex of claim 38.

50. A Line Immunoassay kit for detecting antibodies to HCV present in a biological sample comprising a peptide complex of claim 38.

* * * * *

UNITED STATES PATENT AND TRADEMARK OFFICE
CERTIFICATE OF CORRECTION

PATENT NO.    : 6,667,387 B1  
DATED         : December 23, 2003  
INVENTOR(S)   : De Leys, Robert Page 1 of 1

It is certified that error appears in the above-identified patent and that said Letters Patent is hereby corrected as shown below:

<u>Title page,</u>  
Item [57], ABSTRACT,  
Delete the ABSTRACT, and insert the following therefor:

-- This invention is directed toward a peptide corresponding to an immunologically important viral epitope. Specifically, the peptide corresponds to Core region of the hepatitis C virus (HCV). This peptide has the following amino acid sequence: (A) -GGVYLLPRRGPRLGVRATRKTSERSQPRGRRQPIPKVRR-(Z), wherein A, when present, represents an amino acid, amino group, or chemically modified amino terminus of the peptide, and wherein Z, when present, represents an amino acid, OH-group, $NH_2$-group, or a linkage involving an OH-group or an $NH_2$-group. The invention also relates to the use of this peptide, particularly when biotinylated in the form of complexes of streptavidin-biotinylated peptides or of avidin-biotinylated peptides, for the in vitro determination of HCV specific antibodies. --

Signed and Sealed this

Eleventh Day of May, 2004

JON W. DUDAS  
*Acting Director of the United States Patent and Trademark Office*